US008932558B2

(12) United States Patent
Madasamy

(10) Patent No.: US 8,932,558 B2
(45) Date of Patent: Jan. 13, 2015

(54) MULTI-SUBUNIT BIOLOGICAL COMPLEXES FOR TREATMENT OF PLAQUE-ASSOCIATED DISEASES

(75) Inventor: Shanmugavel Madasamy, Cupertino, CA (US)

(73) Assignee: Plaxgen Inc, Sunnyvale, CA (US)

(*) Notice: Subject to any disclaimer, the term of this patent is extended or adjusted under 35 U.S.C. 154(b) by 339 days.

(21) Appl. No.: 12/286,368

(22) Filed: Sep. 29, 2008

(65) Prior Publication Data

US 2009/0104121 A1 Apr. 23, 2009

Related U.S. Application Data

(60) Provisional application No. 60/978,093, filed on Oct. 5, 2007, provisional application No. 60/985,144, filed on Nov. 2, 2007, provisional application No. 61/019,212, filed on Jan. 4, 2008, provisional application No. 61/188,823, filed on Aug. 12, 2008.

(51) Int. Cl.
*A61K 51/00* (2006.01)
*A61M 36/14* (2006.01)
*A61K 49/00* (2006.01)
*A61K 51/04* (2006.01)
*G01N 33/68* (2006.01)

(52) U.S. Cl.
CPC .......... *A61K 49/0008* (2013.01); *A61K 51/0408* (2013.01); *A61K 51/0493* (2013.01); *A61K 51/0404* (2013.01); *G01N 33/6896* (2013.01)
USPC ........ 424/1.73; 424/1.11; 424/1.65; 424/1.77

(58) Field of Classification Search
CPC ........... A61K 51/0408; A61K 51/0493; A61K 51/0497; A61K 51/06; A61K 51/081; A61K 51/00; A61K 51/08; A61K 51/088; A61K 51/04; A61K 51/0404; A61K 2123/00; A61K 2121/00; A61K 49/00; A61K 49/0008; A61K 49/12; A61K 49/14; A61K 38/00; A61K 38/01; A61K 38/02; A61K 38/03; A61K 38/04; C07K 2/00; C07K 4/00; C07K 14/00; G01N 33/6896
USPC ........... 424/1.11, 1.41, 1.45, 1.49, 1.53, 1.65, 424/1.69, 1.73, 9.1, 9.5, 9.51, 9.52, 417, 424/418, 419, 420, 450, 455, 458, 459, 460, 424/461, 462, 1.77; 530/350, 359; 514/1, 514/1.1
See application file for complete search history.

(56) References Cited

U.S. PATENT DOCUMENTS

| | | | |
|---|---|---|---|
| 3,625,214 A | 12/1971 | Higuchi et al. | |
| 4,789,734 A | 12/1988 | Pierschbacher | |
| 4,897,268 A | 1/1990 | Tice et al. | |
| 4,906,474 A | 3/1990 | Langer et al. | |
| 4,925,673 A | 5/1990 | Steiner et al. | |
| 5,075,109 A | 12/1991 | Tice et al. | |
| 5,811,128 A | 9/1998 | Tice et al. | |
| 5,814,344 A | 9/1998 | Tice et al. | |
| 5,820,883 A | 10/1998 | Tice et al. | |
| 5,853,763 A | 12/1998 | Tice et al. | |
| 5,928,647 A | 7/1999 | Rock | |
| 5,942,252 A | 8/1999 | Tice et al. | |
| 6,025,477 A | 2/2000 | Calenoff | |
| 6,214,569 B1 | 4/2001 | Potter | |
| 6,218,506 B1 | 4/2001 | Krafft et al. | |
| 7,087,722 B1 | 8/2006 | Vogel et al. | |
| 7,138,255 B2 | 11/2006 | Vodyanoy et al. | |
| 7,172,875 B2 | 2/2007 | Kuret et al. | |
| 7,179,463 B2 | 2/2007 | Lannfelt et al. | |
| 7,595,047 B2* | 9/2009 | Moser et al. | 424/141.1 |
| 2002/0157122 A1* | 10/2002 | Wong et al. | 800/12 |
| 2005/0181386 A1 | 8/2005 | Diamond et al. | |
| 2006/0257396 A1 | 11/2006 | Jacobsen | |
| 2006/0257904 A1 | 11/2006 | Grossman et al. | |
| 2007/0059702 A1 | 3/2007 | Wanker et al. | |
| 2007/0111947 A1 | 5/2007 | McMurray et al. | |

OTHER PUBLICATIONS

International search report dated Dec. 12, 2008 for PCT Application No. US2008/11323.
Anderson, et al. The human plasma proteome. Mol Cell Proteomics. 2002; 1.11: 845-867.
Annex, et al. Differential expression of tissue factor protein in directional atherectomy specimens from patients with stable and unstable coronary syndromes. Circulation. 1995; 91:619-22.
Atwood, et al. Dramatic aggregation of Alzheimer Aβ by Cu (II) is induced by conditions representing physiological acidosis. J Biol Chem. 1998; 273:12817-12826.
Beckmann, et al. Age-dependent cerebrovascular abnormalities and blood flow disturbances in APP23 mice modeling Alzheimer's disease. J Neurosci 2003; 23:8453-9.
Bini, et al. Noncollagenous bone matrix proteins, calcification, and thrombosis in carotid artery atherosclerosis. Arterioscler Thromb Vasc Biol. 1999; 19:1852-61.
Bose, et al. "Nature-inspired" drug-protein complexes as inhibitors of Abeta aggregation. Biochem Soc Trans. 2005; 33:543-7.
Burke, et al. Healed plaque ruptures and sudden coronary death: evidence that subclinical rupture has a role in plaque progression. Circulation. 2001; 103:934-940.
Carmena, et al. Atherogenic lipoprotein particles in atherosclerosis. Circulation. 2004; 109:(suppl III-2-III-7).

(Continued)

*Primary Examiner* — D L Jones
(74) *Attorney, Agent, or Firm* — Geeta Kadambi Riddhi IP LLC

(57) ABSTRACT

Provided herein are methods and compositions for the in vitro formation of multi subunit biological platforms. The biological platforms may be used to screen chemical or biological compounds, in particular compounds that may disrupt or otherwise affect the formation of the multi subunit complexes, or disrupt already-formed in vitro assembled multi subunit complexes. Also provided herein are methods and compositions for the in vivo formation of multi-subunit biological complexes. The methods and compositions described herein may be used to develop animal models of diseases or disorders.

8 Claims, 58 Drawing Sheets

(56) References Cited

OTHER PUBLICATIONS

Carson, D. An infectious origin of extraskeletal calcification. Proc Natl Acad Sci. 1998; 95: 7846-7847.
Chang,. The structures and proteolytic specificities of autolysed human thrombin. Biochem. J. 1986; 240:797-802.
Davignon, et al. Role of Endothelial Dysfunction in Atherosclerosis. Circulation. 2004; 109:III-27-III-32.
Doherty, et al. Molecular, endocrine and genetic mechanisms of arterial calcification. Endocrine reviews. 2003; 25:629-672.
Ehara, et al. Spotty calcification typifies the culprit plaque in patients with acute myocardial infarction: an intravascular ultrasound study. Circulation. 2004; 30:3424-9.
Engel, et al. Conformation and orientation of a protein folding intermediate trapped by adsorption. Proc Natl Acad Sci USA. 2004; 101:11316-11321.
Fayad, et al. Clinical imaging of the high-risk or vulnerable atherosclerotic plaque. Circ. Res. 2001; 89:305-316.
Festa, et al. Low-density lipoprotein particle size is inversely related to plasminogen inhibitor-1 levels. Arterioscler.Thromb Vasc Biol. 1998; 19:605-610.
Gaeta, et al. The crucial role of metal ions in neurodegeneration: the basis for a promising therapeutic strategy. Br J Pharmacol. 2005; 146:1041-1059.
Gandy. The role of cerebral amyloid β accumulation in common forms of Alzheimer's disease. J Clin Invest. 2005; 115;1121-1129.
Grover, et al. Inhibition of CO crystal growth and aggregation by FII and its fragments in vitro. Eur. J. Biochem. 1999; 263:50-56.
Guo, et al. Quantitation in situ of crystalline cholesterol and calcium phosphate hydroxyapatite in human atherosclerotic plaques by solid state magic angle spinning NMR. Arterioscler Thromb Vasc Biol. 2000; 20:1630-1636.
Guyton, et al. Development of the lipid-rich core in human atherosclerosis. Arterioscler Thromb Vasc Biol. 1996; 16:4-11.
Higgins, et al. Quantification of calcification in atherosclerotic lesions. Arterioscler Thromb Vasc Biol. 2005; 25:1567-76.
Jennette. The role of metals in carcinogenesis: biochemistry and metabolism. Environ Health Prospect. 1981; 40:233-52.
Ke, et al. Optimal subsite occupancy and design of a selective inhibitor of urokinase. J Biol Chem. 1997; 272:20456-20462.
Kuusela, et al. Binding and activation of plasminogen at the surface of *Staphylococcus aureus*. Increase in affinity after conversion to the Lys form of the ligand. Eur J Biochem. 1990; 193:759-65.
Lalla, et al. Oral infection with a periodontal pathogen accelerates early atherosclerosis in apolipoprotein E-null mice. Arterioscler Thromb Vasc Biol. 2003; 23:1405-1411.
Liao, et al. Proteomic characterization of postmortem amyloid plaques isolated by laser capture micro dissection. J Biol Chem. 2004; 279:37061-37068.
Libby, et al. Roles of infectious agents in atherosclerosis and restinosis. Circulation. 1997; 96: 4095-4103.
Lindersson, et al. Proteasomal inhibition by α-synuclein filaments and oligomers. J Biol Chem. 2004; 279:12924-12934.
Lockhart, et al. Evidence for the presence of three distinct binding sites for the thioflavin T class of Alzheimer's disease PET imaging agents on the beta-amyloid peptides fibrils. J Biol Chem. 2005; 280:7677-84.
Lomashvili, et al. Phosphate-induced vascular calcification: Role of pyrophosphate and osteopontin. J Am Soc Nephrol. 2004; 15:1392-1401.
Margolis, et al. The diagnostic and prognostic significance of coronary artery calcification: a report of 800 cases. Radiology. 1980; 137:609-16.
McGeer, et al. Pathological proteins in senile plaques. Tohoku J Exp Med. 1994; 174:269-77.
Melchor, et al. The tissue plasminogen activator-plasminogen proteolytic cascade accelerates amyloid-beta (Abeta) degradation and inhibits Abeta-induced neurodegeneration. J Neurosci. 2003; 32:8867-8871.
Miao, et al. Reducing cerebral micro vascular amyloid-beta protein deposition diminishes regional neuroinflammation in vasculotrophic mutant amyloid precursor protein transgenic mice. J Neurosci. 2005; 25:6271-77.
Miao, et al. Cerebral micro vascular amyloid (beta) protein deposition induces vascular degeneration and neuroinflammation in transgenic mice expression human vasculotropic mutant amyloid (beta) precursor protein. Am J Pathol. 2005; 167:505-15.
Molinari, et al. Extracellular proteases and their inhibitors in genetic diseases of the central nervous system. Human Mol Gen. 2003; 12:195-200.
Monroe, et al. What does it take to make the perfect clot? Arterioscler Thromb Vasc Biol. 2005; 26:41-8.
Mykkanen, et al. LDL size and risk of coronary heart disease in elderly men and women. Arterioscler Thromb Vasc Biol. 1999; 19:2742-2748.
Mysorekar, et al. Mechanisms of uropathogenic *Escherichia coli* persistence and eradication from the urinary tract. Proc. Natl. Acad. Sci USA. 2006; 103:14170-141-75.
Nachtigal, et al. Atorvastatin has distinct effects on endothelial markers in different mouse models of atherosclerosis. J Pharm Pharmaceut Sci, 2006; 9(2):222-230.
Naghavi, et al. From vulnerable plaque to vulnerable patient: A call for new definitions and risk assessment strategies: part I. Circulation. 2003; 108:1664-1672.
Nelson, et al. Structure of the cross-beta spine of amyloid-like fibrils. Nature 2005; 435:773-778.
O'Nuallain, et al. Conformational Abs recognizing a generic amyloid fibril epitope. Proc Natl Acad Sci USA 99: 2002; 1485-1490.
Ofosu. The blood platelet as a model for regulating blood coagulation on cell surfaces and its consequences. Biochemistry (Mosc). 2002; 67, 47-55.
Peng, et al. Quantification of cholesteryl esters in human and rabbit atherosclerotic plaques by magic-angle spinning. Arterioscler Thromb Vasc Bio.l. 2000; 12:2682-8.
Piedrahita, et al. Generation of mice carrying a mutant apolipoprotein E gene inactivated by gene targeting in embryonic stem cells. Proc Natl Acad Sci USA. 1992; 89(10):4471-5.
Purandare, et al. Cerebral emboli as potential cause of Alzheimer's disease and vascular dementia: case-control study. B M J. 2006; 332:1119-1124.
Rauch, et al. Thrombus formation on atherosclerotic plaques: pathogenesis and clinical consequences. Ann. Intern. Med. 2001; 134:224-238.
Reilly, et al. Plasminogen activator inhibitor-1 binds to fibrin and inhibits tissue-type plasminogen activator-mediated fibrin dissolution. J Biol Chem. 1992; 267;17128-17135.
Ribeiro, et al. Cardiac valve calcification in haemodialysis patients: role of calcium-phosphate metabolism. Nephrol Dial Transplant. 1998; 8:2037-40.
Roy, et al. Recent advances in disorders of iron metabolism: mutations, mechanisms and modifiers. Human Mol Genetics. 2001; 10: 2181-2186.
Sarig, et al. Distribution of unesterified cholesterol-containing particles in human atherosclerotic lesions. Am. J. Pathol. 1994a; 146:139-147.
Schaar, et al. Terminology for high-risk and vulnerable coronary artery plaques. Eur Heart J. 2004; 25: 1077-82.
Schwartz, et al. Effects of Atorvastatin on Early Recurrent Ischemic Events in Acute Coronary Syndromes. JAMA. 2001; 285:1711-1718.
Serfaty, et al. Atherosclerotic plaques: Classification and characterization with T2-wieghted high-spacial-resolution MR imaging-an in vitro study. Radiology. 2001; 219:403-410.
Shah. Link between infection and atherosclerosis: who are the culprits: viruses, bacteria, both or neither? Circulation. 2000; 102: 2335-2340.
Sheng, et al. Crystal surface adhesion explains the pathological activity of calcium oxalate hydrates in kidney stone formation. J Am Soc Nephrol. 2005; 16:1904-8.
Silverman, et al. The serpins are an expanding superfamily of structurally similar but functionally diverse proteins. J Biol Chem. 2001; 276:33293-33296.

(56) References Cited

OTHER PUBLICATIONS

Silverstein, et al. Binding of Lys-Plasminogen to Monocytes/Macrophages. J Clin Invest. 1988; 82:1948-1955.
Sim, et al. Proteases of complement system. Biochem Soc Trans. 2004; 32:21-7.
Smith, et al. Iron accumulation in Alzheimer disease is a source of redox-generated free radicals. Proc Natl Acad Sci USA 1997; 94:9866-9868.
Stadler, et al. Direct detection and quantification of transition metal ions in human atherosclerosis plaques: Evidence for the presence of elevated levels of iron and copper. Arterioscler Thromb Vasc Biol. 2004; 24:949-54.
Syrovets, et al. Novel aspects and new roles for the serine protease plasmin. Cell Mol Life Sci. 2004; 8:873-85.
Thorpe et al. Improved antitumor effects of immunotoxins prepared with deglycosylated ricin A-chain and hindered disulfide linkages. Cancer Res. 1988; 48:6396-6403.
Tsuchihashi, et al. Mobile intracardiac calcinosis: a new risk of thromboembolism in patients with haemodialysed end stage renal disease. Heart. 1999; 82:638-40.
Uversky, et al. Metal-triggered structural transformations, aggregation, and fibrillation of human alpha-synuclein. A possible molecular NK between Parkinson's disease and heavy metal exposure. J Biol Chem. 2001; 276:44284-96.
Viles-Gonzalez, et al. Atherothrombosis: A widespread disease with unpredictable and life-threatening consequences. Eur. Heart Journal. 2004; 25:1197-1207.
Wang, et al. Association of inflammation and malnutrition with cardiac valve calcification in continuous ambulatory peritoneal dialysis patients. J Am Soc Nephrol.. 2001; 12:1927-36.
Xiao, et al. Fibrinogen deficiency is compatible with the development of atherosclerosis in mice. J Clin Invest. 1998; 101:1184-94.
Allen, et al. Surface-induced changes in protein adsorption and implications for cellular phenotypic responses to surface interaction. Biomaterials. 2006; 27:3096-3108.
Angles-Cano, et al. Effects of lipoprotein (a) on the binding of plasminogen to fibrin and its activation by fibrin-bound tissue-type plasminogen activator. Chem Phys Lipids. 1994; 67-68:369-80.
Angles-Cano. Overview on fibrinolysis: Plasminogen activation pathways on fibrin and cell surfaces. Chem Phys Lipids. 1994; 68:353-62.
Barrow, et al. Solution structures of β-peptide and its constituent fragments: Relation to amyloid deposition. Science 1995; 253:173-182.
Beeri, et al. Coronary artery disease is associated with Alzheimer disease neuropathology in APOE4 carriers. Neurology. 2006; 66:1399-404.
Bonifati, et al. Role of complement and neurodegeneration. Mol Immunol. 2007; 44(5):999-1010.
Brancaccio, et al. The mechanism of calcium deposition in soft tissues. Contrib Nephrol. 2005; 149: 279-86.
Brown, et al. Neurodegenerative diseases: an overview of environmental risk factors. Environ Health Perspect. 2005; 113;1250-56.
Bucciantini, et al. Inherent cytotoxicity of aggregates implies a common origin for protein misfolding diseases. Nature 2002; 416:507-511.
Burgermeister, et al. Mechanisms of cerebrovascular amyloid deposition. Lessons from mouse models. Ann N Y Acad Sci. 2000; 903:307-16.
Campean, et al. Atherosclerosis and vascular calcification in chronic renal failure. Kidney Blood Press Res. 2005; 28. 280-9.
Casserly, et al. Convergence of atherosclerosis and Alzheimer's disease: inflammation, cholesterol, and misfolded proteins. Lancet. 2004; 363:1139-46.
Castilla, et al. In vitro generation of infectious scrapie prions. 2005; Cell 121:195-206.
Collingwood, et al. In situ characterization and mapping of iron compounds in Alzheimer's disease tissue. J Alzheimers Dis 2005; 7:267-72.
Connar, et al. Is hemochromatosis a risk factor for Alzheimer's disease?. J Alzheimers Dis. 2001; 3:471-477.
Connor, et al. A histochemical study of iron, transferring, and ferritin in Alzheimer's diseased brain. J Neurosci Res. 1992; 31:75-83.
Corti, et al. Evolving concepts in the triad of atherosclerosis, inflammation and thrombosis. J Thromb Thrombolysis. 2005; 17:35-44.
Cullen, P., Rauterberg, J., Lorkowski, S. The pathogenesis of atherosclerosis. Handb Exp Pharmacol. 2005; 170:3-70.
Dahlback. Blood coagulation. Lancet. 355: 2000; 1627-32.
De La Torre. Alzheimer's disease is a vasocognopathy: a new term to describe its nature. Neurol Res. 2004; 26:517-24.
Dobson. Protein folding and misfolding. Nature 2003; 426:884-890.
Dornheim, et al. Preparation and characterization of an antithrombin III concentrate. Folia Haematol Int Mag Klin Morphol Blutforsch. 1982; 109:870-7.
Eikelenboom, et al. Cerebral amyloid plaques in Alzheimer's disease but not in scrapie-affected mice are closely associated with a local inflammatory process. Virchows Arch B Cell Pathol Incl Mol Pathol. 1991; 60:329-36.
Elliott, et al. Inhibitory conformation of the reactive loop of alpha 1-antitrypsin. Nat Sturct Biol. 1996; 8:676-681.
Esler, et al. In vitro growth of Alzheimer's disease β-amyloid plaques displays first-order kinetics. Biochemistry 1996; 23:749-757.
Evan, et al. Randall's plaque: pathogenesis and role in calcium oxalate nephrolithiasis. Kidney Int. 2006; 69:1313-8.
Falangola, et al. Histological co-localization of iron in Abeta plaques of PS/APP transgenic mice. Neurochem Res. 2005; 30.201-205.
Fenton, et al. Hepatocyte growth factor (HGF/SF) in Alzheimer's disease. Brain Res. 1998; 779:262-70.
Ferramosca, et al. Ethiopathogenesis, diagnosis and prevention of vascular calcification in end stage renal disease. Curr Med Chem Cardiovasc Hematol Agents. 2005; 3:165-71.
Finehout. Complement protein isoforms in CSF as possible biomarkers for neurodegenerative disease. Dis Markers. 2005; 21:93-101.
Fuster, et al. The serine proteases and their function in neuronal death process. Rev Neurol. 2004; 38:449-57.
Gaggelli, et al. Interaction of human prion PrP(106-126) sequence with copper(II), manganese(II) and zinc(II): NMR and EPR studies. J Am Chem Soc. 2005; 127:996-1006.
Garg, et al. Mutations in NOTCH1 cause aortic valve disease. Nature. 2005; 437:270-273.
Garzon-Rodriguez, et al. Binding of Zn(II), Cu(II), and Fe(II) ions to Alzheimer's Abeta peptide studied by fluorescence. Bioorg Med Chem Lett. 1999; 9:2243-8.
Gerhard, et al. Systemic nature of endothelial dysfunction in atherosclerosis. Am J Cardiol. 1995; 75:71B-74.
Gilbert, et al. Biofilsm in vitro and in vivo: do singular mechanisms imply cross-resistance? J. Appl. Microbiol. 2002; 92, 98-110.
Goodman. Vascular calcification in end-stage renal disease. J Nephrol. 2002; 6:82-85.
Grammas, et al. Thrombin and inflammatory proteins are elevated in Alzheimer's disease micro vessels: Implications for disease pathogenesis. J Alzheimers Dis. 2006; 9:51-58.
Greenland, et al. ACCF/AHA 2007 Clinical expert consensus document on coronary artery calcium scoring by computed tomography in global cardiovascular risk assessment and in evaluation of patients with chest pain. J. Amer. Col. Cardiology. 2007; 49:378-402.
Gregoriadis. Liposomes. Drug Carriers in Biology and Medicine. Academic Press 1979. Chapter 14: pp. 2.sup.87-341.
Haas, et al. Proteolysis of Alzheimer's disease beta-amyloid precursor protein by factor Xa. Biochim Biophys Acta. 1997; 1343:85-94.
Hannson, et al. Accumulation of IgG and complement factor C3 in human arterial endothelium and atherosclerotic lesions. Acta Path Microbiol Immunol Scan. Sec A. 1984; 92:429-435.
Hannson, et al. Fc-dependent binding of monocytes to areas with endothelial injury in the rabbit aorta. Experimental and Mol Pathol. 1981; 34, 264-280.
Hersh. Peptidases, proteases and amyloid beta-peptide catabolism. Curr Pharm Des. 2003; 9:449-54.
Higuchi, et al. Understanding molecular mechanisms of proteolysis in Alzheimer's disease: Progress toward therapeutic interventions. Biochim Biophys Acta. 2005; 175:60-67.

(56) References Cited

OTHER PUBLICATIONS

Hino, et al. Immunohistochemical localization of plasminogen activator inhibitor-1 in rat and human brain tissues. Neurosci Lett. 2001; 297:105-08.

Hirona, et al. Clinical significance of small dense low-density lipoprotein cholesterol levels determined by the simple precipitation method. Arterioscler Thromb Vasc Biol. 2004; 24:558-563.

Hirsch, et al. Colocalization of cholesterol and hydroxyapatite in human atherosclerotic lesions. Calcif Tissue Int. 1993; 52:94-98.

Hollander, et al. Soluble proteins in the human atherosclerotic plaque. With spectral reference to immunoglobulins, C3-complement component, alpha 1-antitrypsin and alpha 2-macroglobulin. Atherosclerosis. 1979; 34:391-405.

Huang, et al. The Aβ peptide of Alzheimer's disease directly produces hydrogen peroxide through metal ion reduction. Biochemistry. 1999; 38:7609-7616.

Huang, et al. Trace metal contamination initiates the apparent auto-aggregation, amyloidosis, and oligomerization of Alzheimer's abeta peptides. J Biol Inorg Chem. 2004; 9:954-60.

Jayaraman, et al. Effects of oxidation on the structure and stability of human low-density lipoprotein. Biochemistry. 2007; 46:5790-7.

Jein, K. Strategies and technologies for drug delivery systems. Trends in Pharmacological Sciences. 1998; 19:155-157.

Johnston, et al. Regression of poloxamer 407-induced atherosclerotic lesions in C57BL/6 mice using atorvastatin. Atherosclerosis. 2000; 149: 303-13.

Johnston, et al. Potential downregulation of HMG-CoA reductase after prolonged administration of P-407 in C57BL/6 mice. J Cardovasc Pharmacol, 1999; 34: 831-42.

Jono, et al. Vascular calcification in chronic kidney disease. J Bone Miner Metab. 2006; 24:176-81.

Kalaria. The blood-brain barrier and cerebrovascular pathology in Alzheimer's disease. Ann N Y Acad Sci. 1999; 893:113-25.

Kayed, et al. Common structure of soluble amyloid oligomers implies common mechanism of pathogenesis. Science 2003; 300:486-489.

Khan. Renal tubular damage/dysfunction: key to the formation of kidney stones. Urol Res. 2006; 11:1-6.

Kimchi, et al. Analysis of cerebral amyloid angiopathy in a transgenic mouse model of Alzheimer's disease using in vivo multiphoton microscopy. J Neuropathol Exp Neurol. 2001; 60:274-9.

Klein, et al. Interaction of some serum proteins with hydroxylapatite and other materials. J Biomed Mater Res. 1980; 14:705-12.

Kranenburg, et al. Amyloid-beta-stimulated plasminogen activation by tissue-type plasminogen activator results in processing of neuroendocrine factors. Neuroscience. 2005; 131:877-886.

Kruth. Filipin-positive, oil red O-negative particles in atherosclerotic lesions induced by cholesterol feeding. Lab invest. 1984; 50:87-93.

Lansbury. In pursuit of the molecular structure of amyloid plaque: New technology provides unexpected and critical information. Biochemistry. 1995; 31:6865-6870.

Le Vine. Iron deposits in multiple sclerosis and Alzheimer's disease brains. Brain Res. 1997; 760:298-303.

Leys. Atherothrombosis: a major health burden. Cerebrovasc Dis. 2001; 11: Suppl 2:1-4.

Liu, et al. Metal exposure and Alzheimer's pathogenesis. J Struct Biol. 2006; 155:45-51.

Lovell, et al. Copper, iron and zinc in Alzheimer's disease senile plaques. J Neurol Sci. 1998; 158: 47-52.

Lynch, et al. Detecting cryptic epitopes created by Nanoparticles. Sci STKE. 2006; 327:14.

Mandel, et al. Iron and alpha-synuclein in the substantia nigra of MPTP treated mice: effect of neuroprotective drugs R-apomorphine and green tea polyphenol(-)—epigallocatechin-3-gallate. J Mol Neurosci. 2004; 24:401-16.

Mathu, et al. Preclinical evaluation of atherosclerosis. Int J Diab Dev Ctries. 2006; 26:105-111.

Maynard, et al. Metals and amyloid-beta in Alzheimer's disease. Int J Exp Pathol. 2005; 86:147-59.

McAllister, et al. L. Protein interactions and misfolding analyzed by AFM force spectroscopy. J Mol Biol.. 2005; 354, 1028-42.

McAllister, et al. Protein interactions and misfolding analyzed by AFM force spectroscopy. J Mol Biol. 2005; 354:1028-1042.

McCullough, et al. Determinants of coronary vascular calcification in patients with chronic kidney disease and end-stage renal disease: a systemic review. J Nephrol. 2004; 17:205-15.

McGeer, et al. Inflammation and degenerative disease of aging. Ann N Y Acad Sci. 2004; 1033:104-16.

Meredith. Protein denaturation and aggregation: cellular responses to denatured and aggregated proteins. Ann N Y Acad Sci. 2006; 1066:181-221.

Molina, et al. A Proteomic Analysis of Human Hemodialysis Fluid. Mole Cell Proteomics. 2005;4.5:637-650.

Munger, et al. Atherothrombosis: epidemiology, pathophysiology, and prevention. J Am Pharm Assoc. 2004; 44:(2 Suppl 1):S5-12.

Murphy. Peptide aggregation in neurodegenerative disease. Annu Rev Biomed Eng. 2002; 4:155-174.

Nicholl, et al. Plasminogen activator system and vascular disease. Curr Vasc Pharmacol. 2006; 4:101-116.

O'Brian, et al. Antibody phage display. Methods and protocols. Humana press. 2002; 1-416.

Ohmori, et al. Concentration dependence of IgG-protein A affinity studied by wireless-electrodeless QCM. Biosens Bioelectron. 2007; 153238-42.

Ong, et al. Iron, atherosclerosis, and neurodegeneration: a key role for cholesterol in promoting iron-dependent oxidative damage?. Ann N Y Acad Sci. 2004; 1012:51-64.

Ong, et al. Iron, neuroinflammation, and Alzheimer's disease. J Alzheimers Dis. 2005; 8:183-200.

Parums, et al. Demonstration of immunoglobulin in the neighbourhood of advanced atherosclerotic plaques. Atherosclerosis 1981; 38, 211-216.

Peter, et al. Inflammation and Atherosclerosis. Circulation. 2002; 105:1135.

Purdey. Elevated levels of ferromagnetic metals in food chains supporting the Guam cluster of neurodegeneration: do metal nucleated crystal contaminants evoke magnetic fields that initiate the progressive pathogenesis of neurodegeneration?. Med Hypothesis. 2004; 63:793-809.

Quintana, et al. Study of the localization of iron, ferritin, and hemosderin in the Alzheimer's disease hippocampus by analytical microscopy at the sub cellular level. J Struct Biol. 2006; 153:42-54.

Raggi, et al. Cardiac calcification in adult hemodialysis patients. J. Amer. Col. Cardiology, 2002; 39:695-70.

Richardson. Novel chelators for central nervous system disorders that involve alterations in the metabolism of iron and other metal ions. Ann. N. Y. Acad. Sci. 2004; 1012:326-341.

Royal, et al. Intracrystalline proteins and urolithiasis: a comparison of the protein content and ultrastructure of urinary CO monohydrate and dihydrate crystals. Br J Urol. 2005; 96:654-663.

Sarig, et al. Detection of cholesterol associated with calcium mineral using confocal fluorescence microscopy. Lab Invest. 1994b; 71:782-787.

Schmiedl, et al. Nephrocalcinosis and hyperlipidemia in rats fed a cholesterol and fat-rich diet: association with hyperoxaluria, altered kidney and bone minerals, and renal tissue phospholipid-calcium interaction. Urol Res. 2000; 28:404-15.

Selkoe. Folding proteins in fatal ways. Nature 2003; 426:900-904.

Selkoe. Folding proteins in fatal ways. Nature. 2004; 426:900-4.

Small. Progression, and regression of atherosclerotic lesions: insights from lipid physical biochemistry. Arteriosclerosis, 1988; 8:103-129.

Stapleton, et al. Further evidence linking urolithiasis and blood coagulation: urinary FII fragment 1 is present in stone matrix. Kidney Int. 1996; 49:880-8.

Strohmeyer, et al. Detection of complement alternative pathway mRNA and proteins in the Alzheimer's disease brain. Brain Res Mol Brain Res. 2000; 81:7-18.

Tannir, et al. Age-related evolution of amyloid burden, iron load, and MT relaxation times in a transgenic mouse model of Alzheimer's disease. Neurobiol Dis. 2005.

(56) References Cited

OTHER PUBLICATIONS

Tanskanen, et al. Cerebral amyloid angiopathy in a 95+ cohort: complement activation and apolipoprotein E (ApoE) genotype. Neuropathol Appl Neurobiol. 2005; 31:589-99.

Thompson, et al. Predicting coronary heart disease. Lancet. 1994; 343:670-71.

Trojanowski, et al. Fatal attractions' of proteins. A comprehensive hypothetical mechanism underlying Alzheimer's disease and other neurodegenerative disorders. Ann N Y Acad Sci. 2000; 924:62-7.

Tsortos, et al. The dual role of FBN as inhibitor and nucleator of CP phases: The importance of structure. J Colloid Interface Sci. 1996; 177:257-262.

Van Nostrand, et al. Plasmin cleavage of the amyloid beta protein: alteration of secondary structure and stimulation of tissue plasminogen activator activity. Biochemistry. 1999; 38:11570-6.

Vu, et al. Domains specifying thrombin-receptor interaction. Nature. 1991; 353:674-7.

Walker, et al. Cerebrovascular amyloidosis: experimental analysis in vitro and in vivo. Histol Histopathol. 1999; 14:827-37.

White, et al. Metal homeostasis in Alzheimer's disease. Expert Rev Neurother. 2006; 6; 711-22.

Willens, et al. Mobile components associated with rapidly developing mitral annulus calcification in patients with chronic renal failure: review of mobile elements associated withmitral annulus calcification. Echocardiography. 2003: 20:363-7.

Young, et al. Predictors and consequences of altered mineral metabolism: the dialysis outcomes and practice patterns study. Kidney Int. 2005; 67:1179-87.

Ansel et al. Pharmaceutical Dosage Forms and Drug Delivery Systems. Lippencott Williams & Wilkins, Baltimore MD. $7^{th}$ edition. 1999, (pp. 1-4).

McCourt, et al. X-ray crystal structure of cytotoxic oxidized cholesterols: 7-ketocholesterol and 25-hydroxycholesterol. J Lipid Res. May 1997;38(5):1014-21.

Remington. The Science and Practice of Pharmacy. Lippincott Williams & Wilkins, Baltimore MD. $20^{th}$ Ed. 2000, (pp. 1-5).

Staprans, et al. Oxidized cholesterol in the diet is a source of oxidized lipoproteins in human serum. J Lipid Res. Apr. 2003;44(4):705-15. Epub Feb. 1, 2003.

* cited by examiner

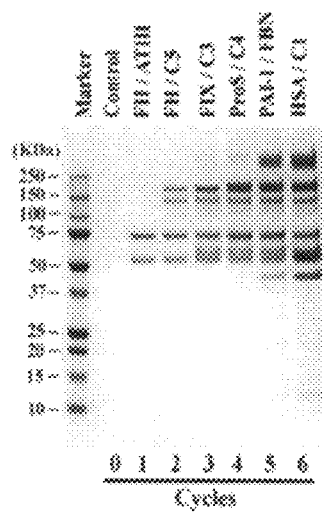
Fig. 5a
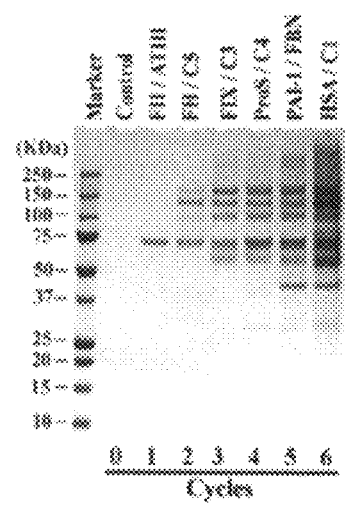
Fig. 5b
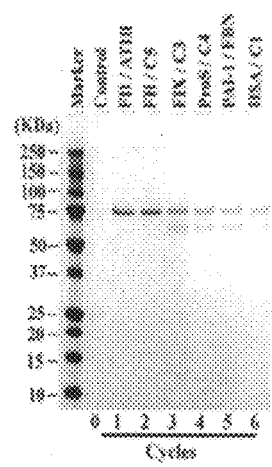
Fig. 5c
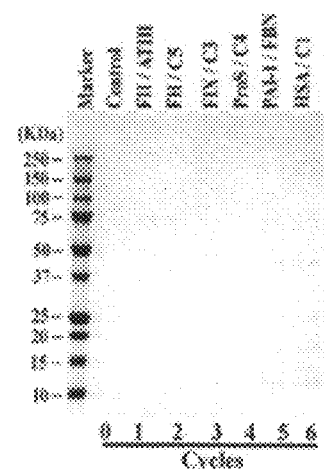
Fig. 5d
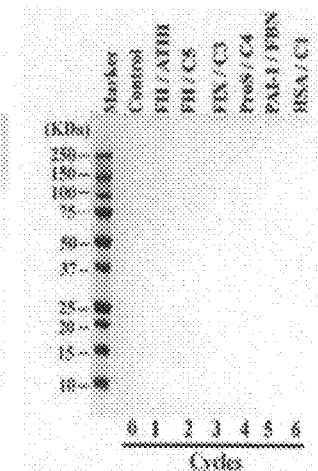
Fig. 5e
Fig. 5

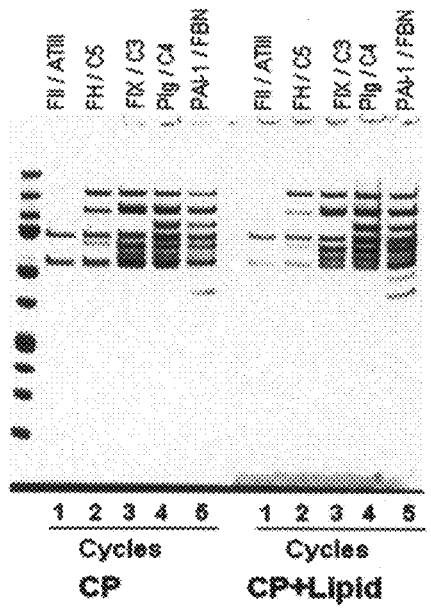
Fig. 8a
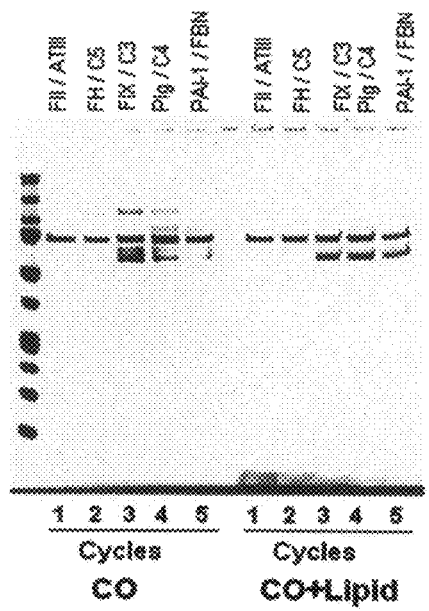
Fig. 8b
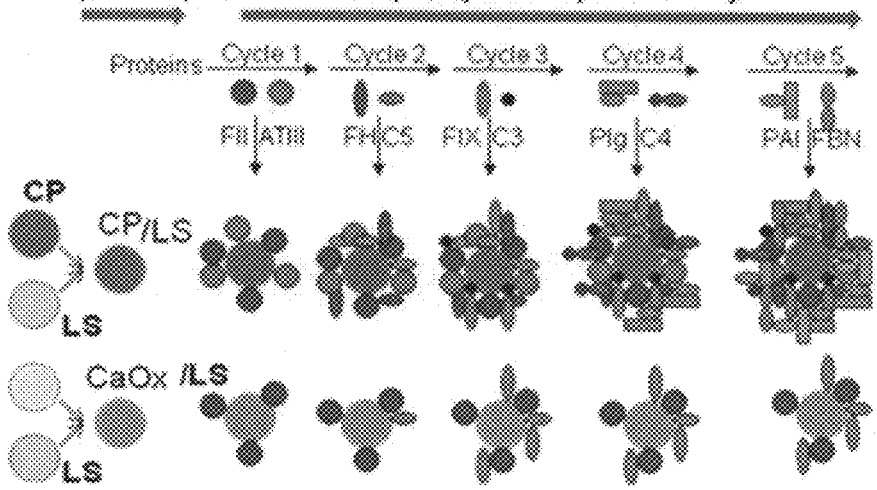
Fig. 8c.
Fig. 8

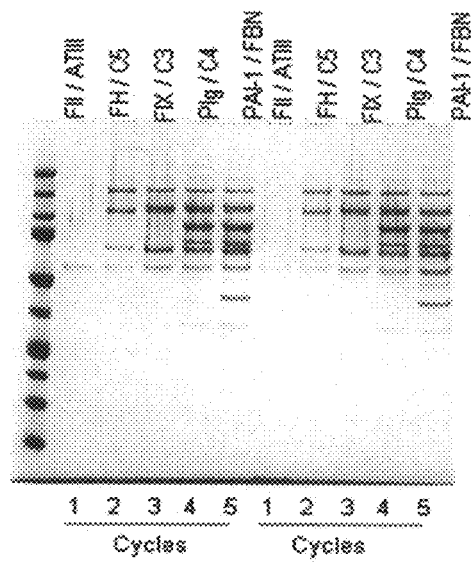
Fig. 9a
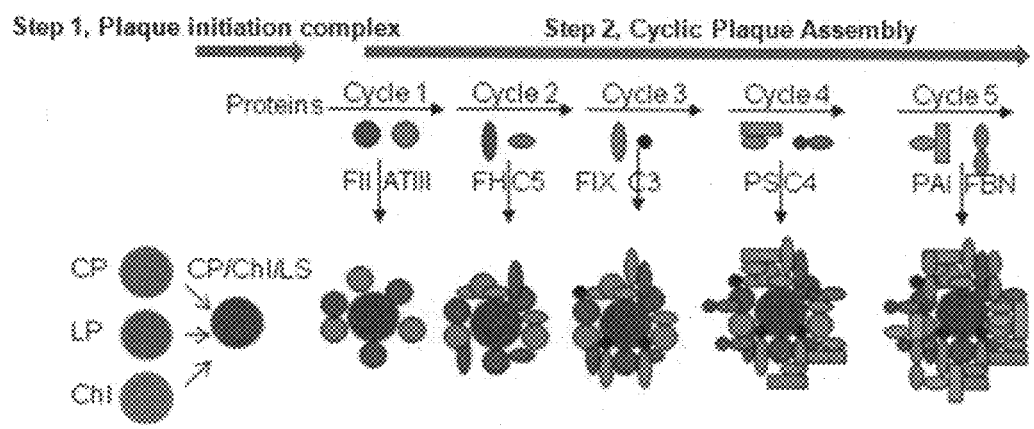
Fig. 9b
Fig. 9

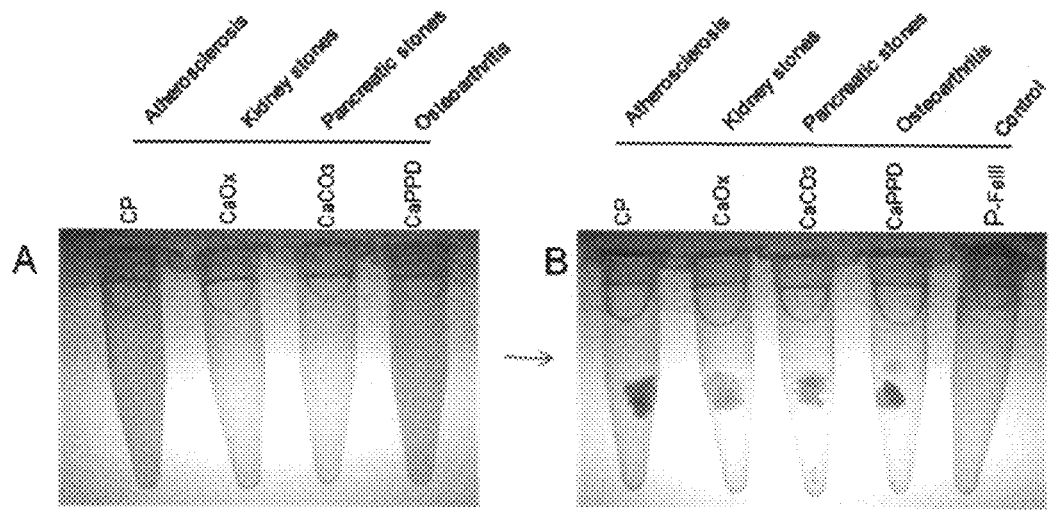
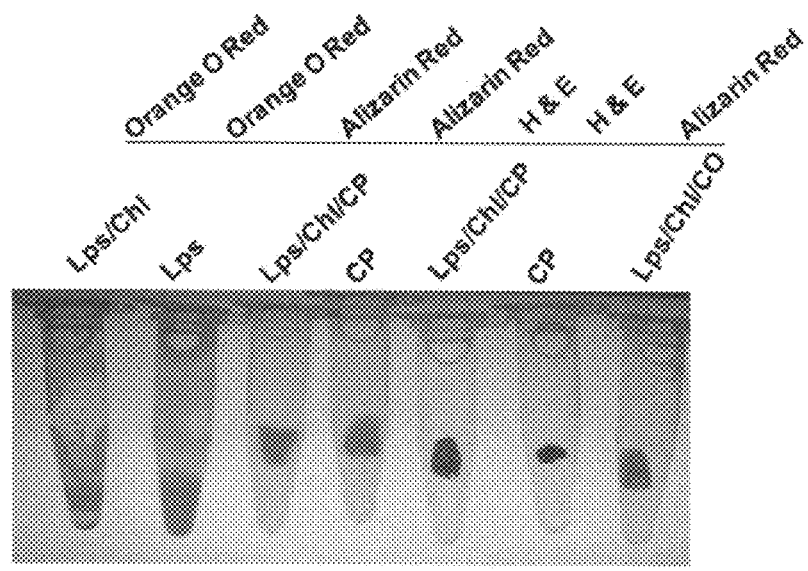
Fig. 11a
Fig. 11b
Fig. 11

Figs. 16a and b

Figs. 17a and b

Figs. 31 a and b.

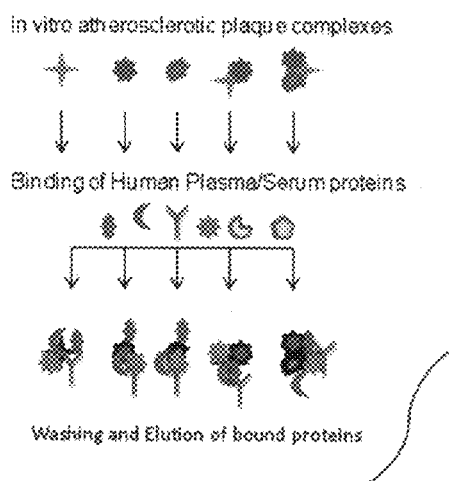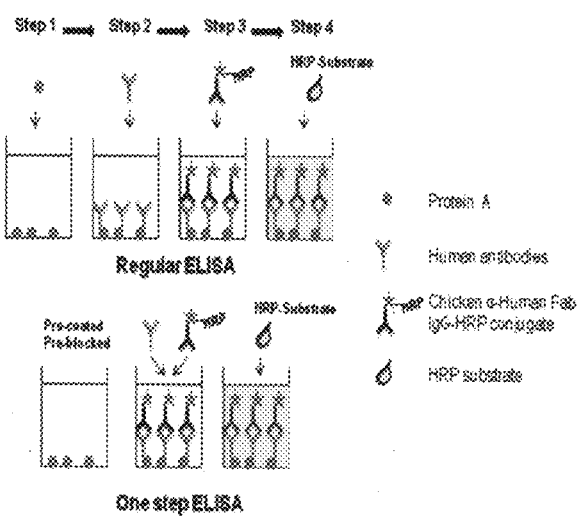
Fig 34a
Fig 34b
Fig. 34

A) Normal heart tissue 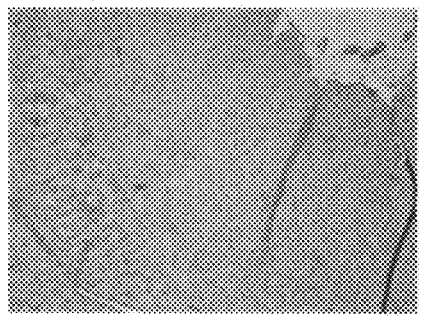
B) Plaque localization in heart tissue 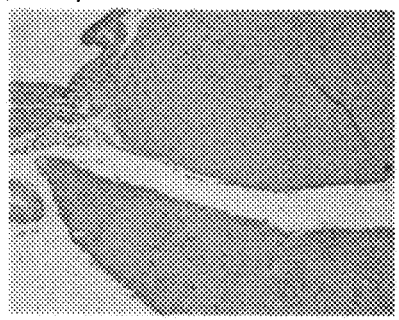
C) Plaque localization in heart tissue 
D) Plaque localization in heart tissue 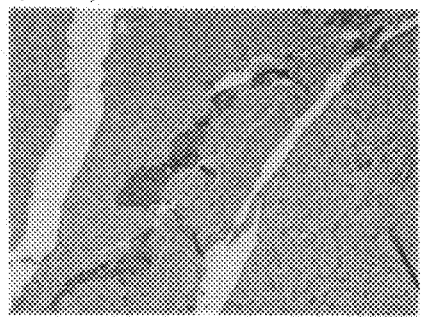
Figs. 38 A, B, C and D

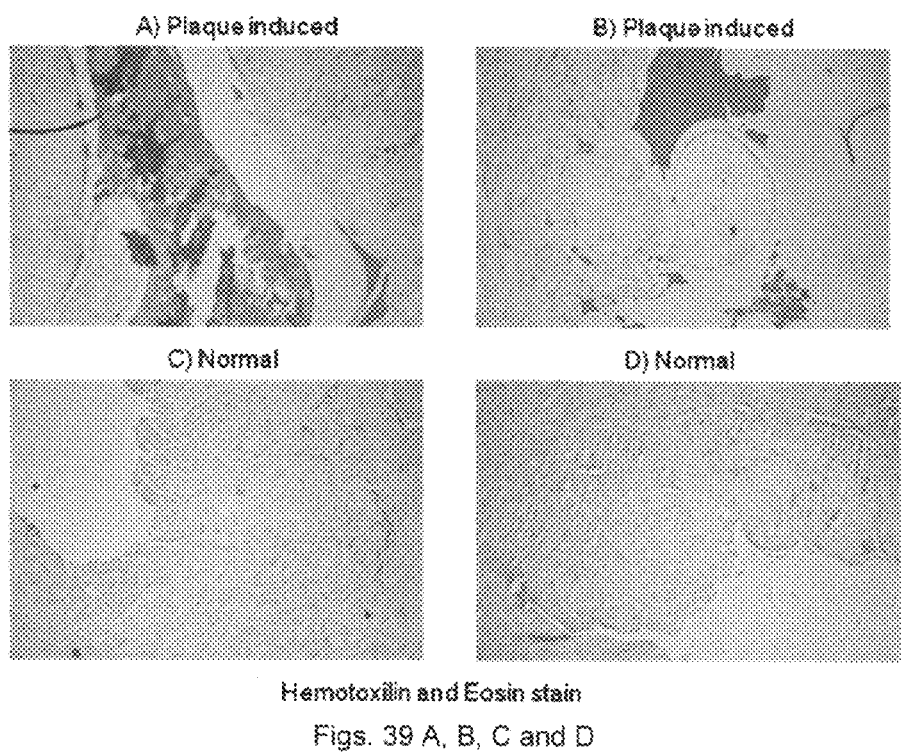
Figs. 39 A, B, C and D

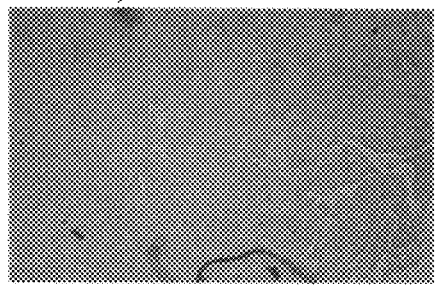 
A) Control-Alizarin Red B) Plaque induced-Alizarin Red
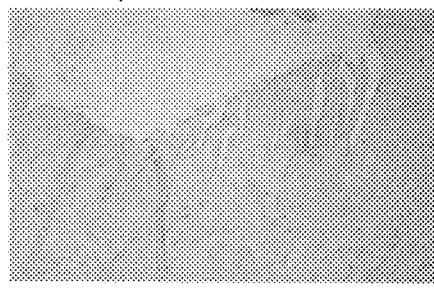 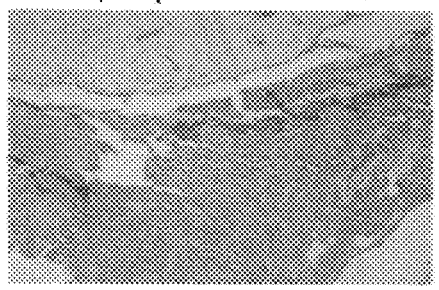
C) Control-Von Kosa D) Plaque induced-Von Kosa
Figs. 40A, B, C and D

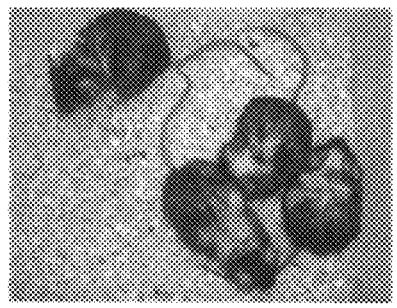 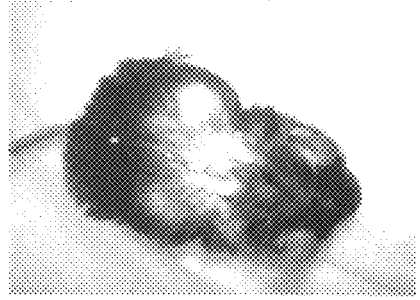
Fig. 41A — Atherosclerotic Mouse – Symptomatic Chronic Inflammation
Fig. 41B — Plaque induced chronic inflammatory mice
Fig. 41

Fig. 43 A, B, C

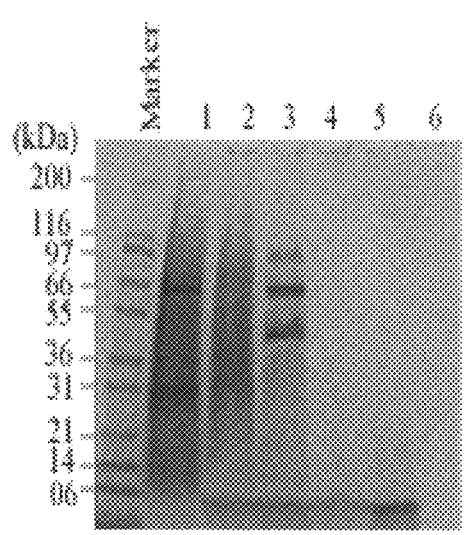 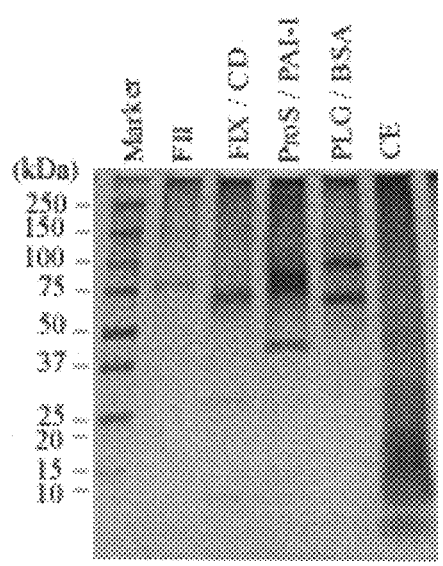
Fig. 46a          Fig. 46b
Fig. 46

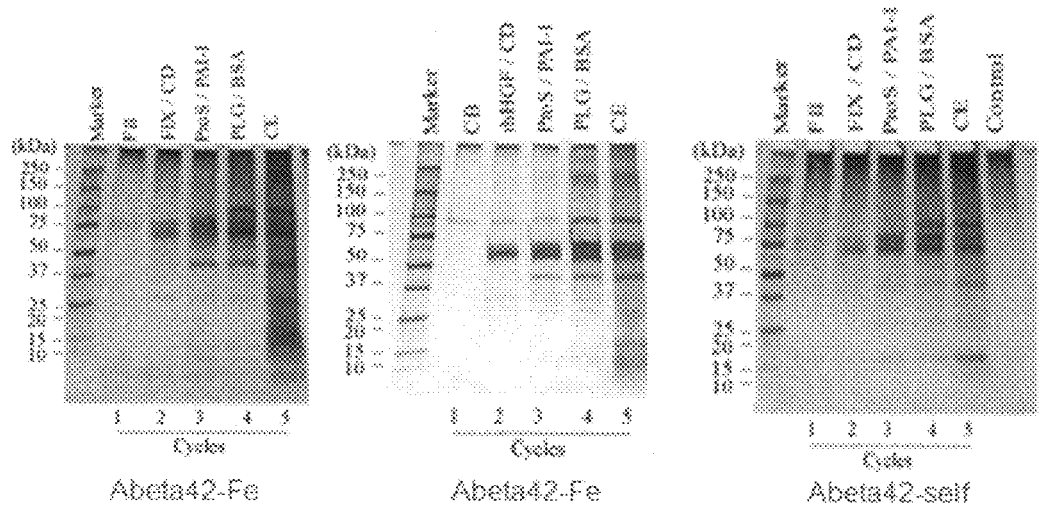
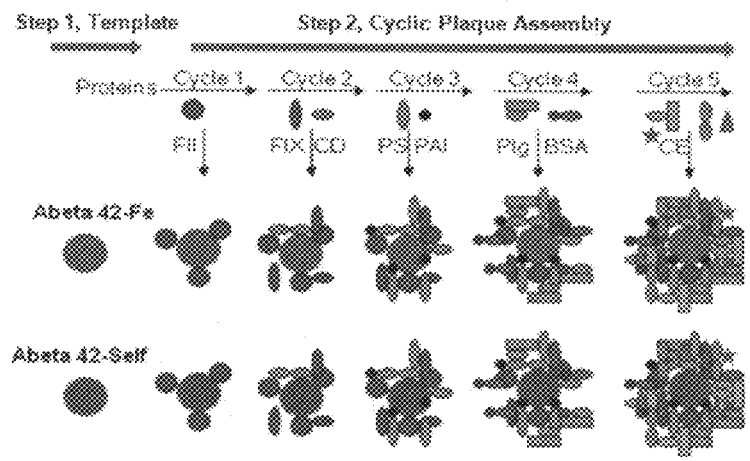
Fig. 47

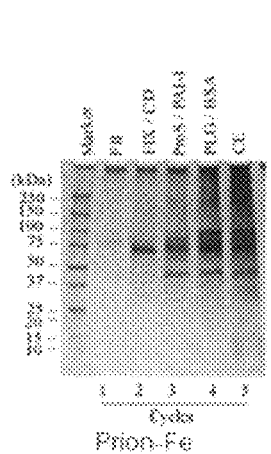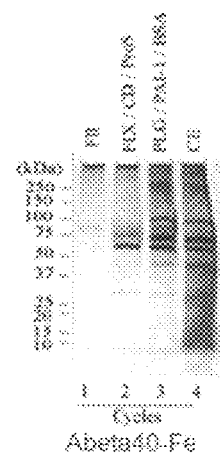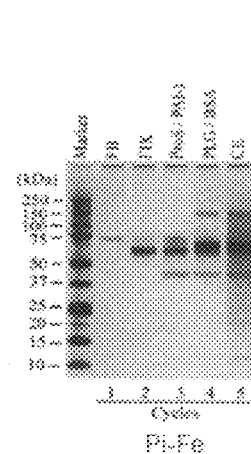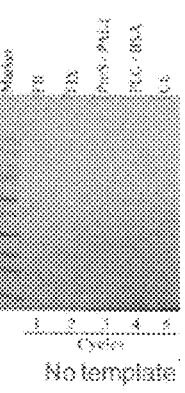
Fig. 48a   Fig. 48b   Fig. 48c   Fig. 48d
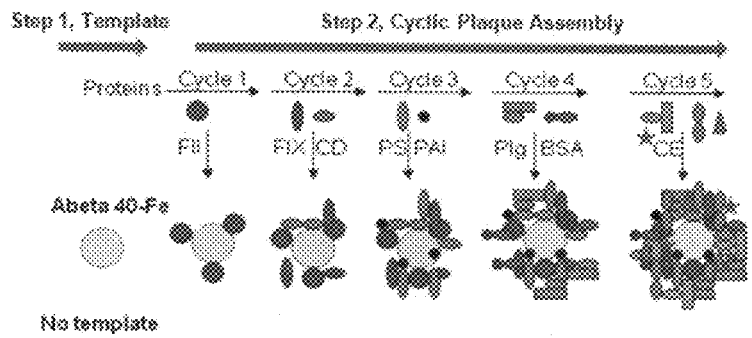
Fig. 48e
Fig. 48

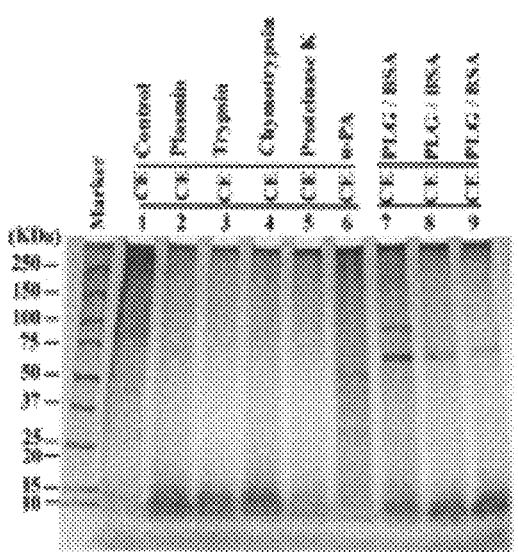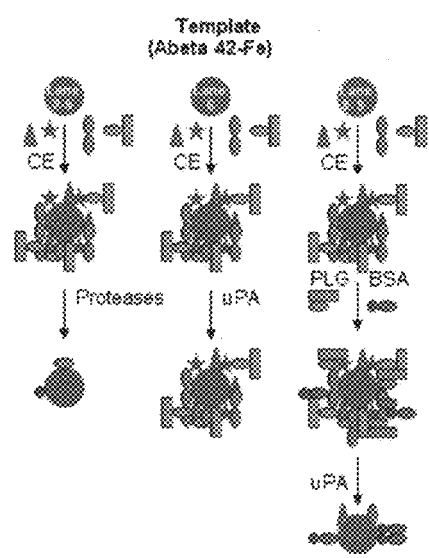
Fig. 50a    Fig. 50b
Fig. 50

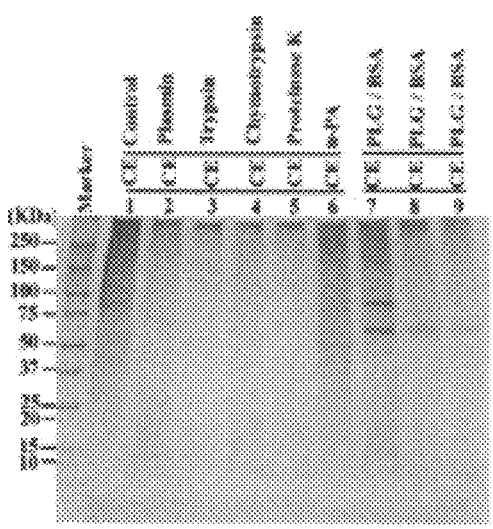 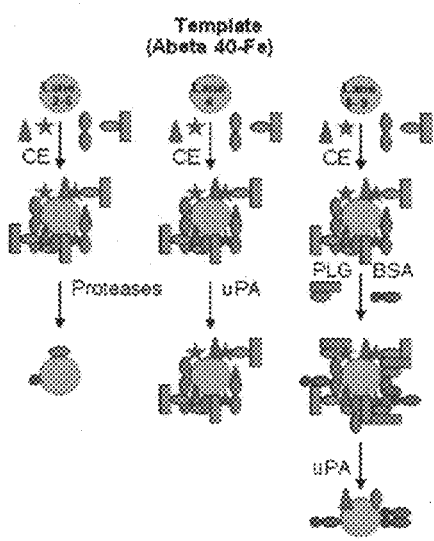
Fig. 51a  Fig. 51b
Fig. 51

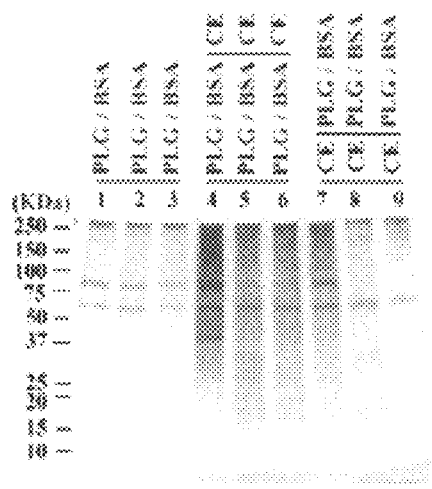 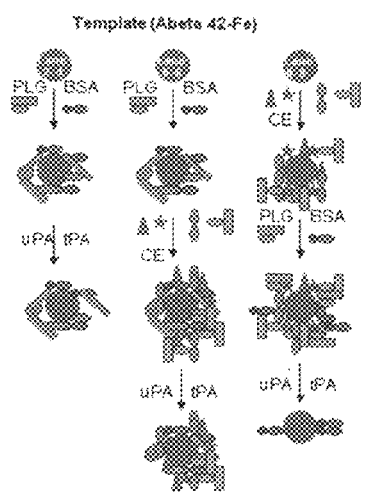
Fig. 52a        Fig. 52b
Fig. 52

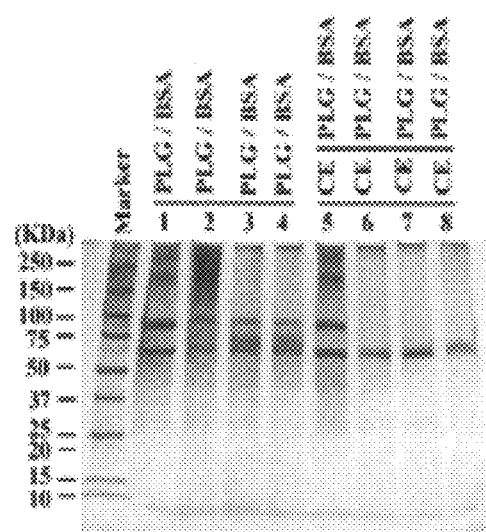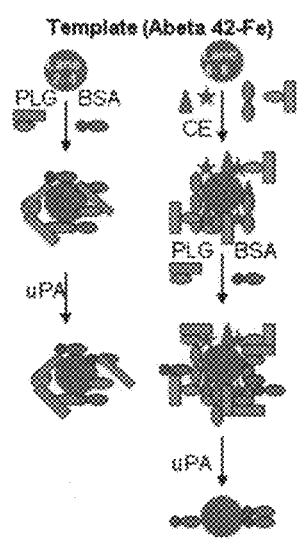
Fig. 53a  Fig. 53b
Fig. 53

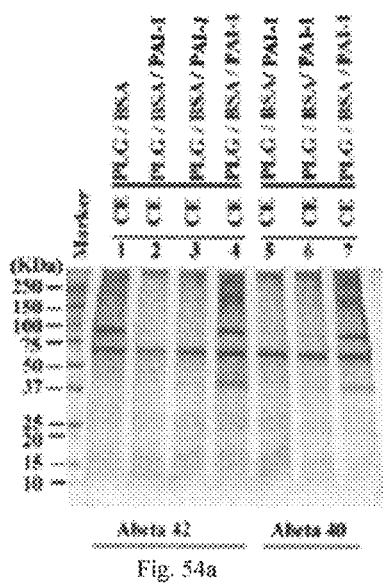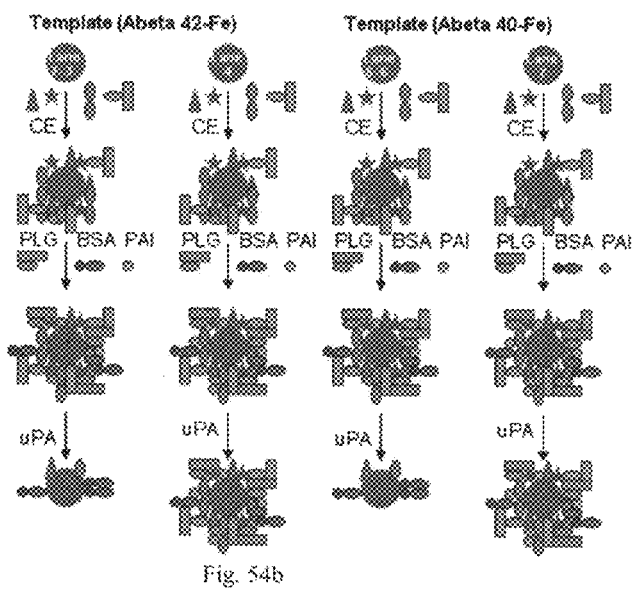
Fig. 54a    Fig. 54b
Fig. 54

Figs. 56a, b, c and d

Fig. 57 a, b, c and d

Fig. 57a to d.

MULTI-SUBUNIT BIOLOGICAL COMPLEXES FOR TREATMENT OF PLAQUE-ASSOCIATED DISEASES

CROSS REFERENCE

This application claims the benefit of U.S. Provisional Application No. 60/978,093, entitled "Methods and Compositions for the In Vitro Formation of Multi-Subunit Biological Platforms for Drug Discovery," filed Oct. 5, 2007; U.S. Provisional Application No. 60/985,144, entitled "Methods and Compositions for the In Vitro Formation of Multi-Subunit Amyloid Biological Platforms for Drug Discovery," filed Nov. 2, 2007; U.S. Provisional Application No. 61/019,212, entitled "Methods and Compositions for the In Vitro Formation of Multi-Subunit Biological Platforms for Drug Discovery," filed Jan. 4, 2008; and U.S. Provisional Application No. 61/188,823, entitled "Methods and Compositions for the In Vivo Formation of Multi-Subunit Biological Complexes," filed Aug. 12, 2008, each of which applications is incorporated herein in its entirety by reference.

FIELD OF THE INVENTION

The methods and compositions described herein relate to the formation of multi-subunit biochemical platforms for use in biological assays and drug discovery. More specifically, the embodiments described herein relate to the in vivo formation of biochemical plaques, in particular, atherosclerotic plaques. The plaque embodiments described may be used to enable rapid, sensitive and/or efficient drug discovery and medical diagnostics and analysis.

BACKGROUND OF THE INVENTION

Numerous fatal human diseases originate with the formation and progressive growth of deposits or "plaques" in tissues or organs. The materials for such plaques are generally organic or inorganic molecules that derive from the fluid bathing a particular organ. Progressive plaque build-up can occur in areas throughout the body, but organs particularly at risk are the heart, brain, kidney, gall bladder and vasculature.

Plaque development can be a gradual process, occurring over the course of years, or even decades. Likewise, the pathogenic consequences of such plaques can take a long time to appear. For example, atherosclerotic processes in blood vessels may begin in early childhood, continue without evident symptoms through middle age (Viles-Gonzalez J F et al, 2004), before developing into a potentially life-threatening cardiovascular condition later in the individual's life.

The American Heart Association classifies atherosclerotic processes based on the components of the plaques. The more fibrous stable preatheroma plaques (type I to III) have relatively lower extra cellular lipid content. In contrast atheromatic plaques (type IV and Va) typically contain higher levels of extra-cellular lipids, cholesterol, calcium crystals and thin fibrous caps, making them less stable and vulnerable to rupture (Serfaty J M et al, 2001). When unstable plaques rupture, they can generate thromboses accompanied by serious life-threatening conditions such as Myocardial Infarction, stroke and thromboembolic events (Rauch U et al, 2001).

Plaques also accumulate in other diseases including but not limited to Alzheimer's-disease, Parkinson's disease, and other amyloid protein aggregation diseases. These diseases are characterized by abnormal depositions of misfolded proteins in tissues and organs. These depositions often begin with the formation of insoluble aggregates consisting of amyloid proteins and/or peptides alone or in combination with certain metallic elements. Over the course of years, or even decades, amyloid aggregations can become pathogenic plaques; but the process of plaque development is not clearly understood. A better understanding of the assembly of amyloid plaque complexes and of the degree of their pathogenicity would enable the development of highly-targeted therapies.

Deposition of amyloid aggregates occurs on the walls of arteries, arterioles, cerebral vasculature, capillaries and veins of the cerebrovascular system of AD patients and normal aged individuals (Burgermeister et al, 2000; Walker L C et al, 1999). Epidemiological, pathological and clinical studies provide evidence that vascular factors may play a significant role in the pathogenesis of neurological diseases and particularly in the case of AD (de la Torre J C 2004; 2005). This hypothesis is reinforced by multiple studies carried out in transgenic animal models that relate over-expression of amyloid precursor protein (APP) to neuropathological conditions observed alike in the AD patients (Miao J et al, 2005). In addition, progressive accumulation of amyloid plaques on the sides of carotid and cerebral arteries could impair normal blood flow in the cerebrovascular system, eventually leading to the development of dementia and cerebral amyloid angiopathy (CAA) (Kimchi E Y et al, 2001; Beckmann N et al, 2003). Neuroinflammation is another related pathogenic event occurring in the cerebral vascular region of transgenic mice expressing human abeta42 peptides (Miao J et al, 2005).

Other methods for screening effective drugs for the treatment of Alzheimer's disease exist. One method, described in U.S. Pat. No. 6,214,569, concerns the screening of inhibitors of the formation of Alzheimer β-peptide filaments. The formation of such filaments in said invention involves incubating the Aβ peptide at room temperature, enabling the spontaneous formation of amyloid filaments.

Another method of screening for effective drugs for Alzheimer's disease is described in U.S. Pat. No. 6,218,506 B1. In this invention, amyloid β peptides first assemble into non-fibrillar structures after suspension in anhydrous DMSO and then, in certain embodiments, the assembled fibrils are used in animal studies, such as to evaluate the long-term potentiation response in animals.

A method for identifying and characterizing inhibitors of protein filament formation, including the formation of tau filaments in Alzheimer's patients and α-synuclein filaments in Parkinson's patients is described in U.S. Pat. No. 7,172,875 B2. In this invention, protein monomers are combined under physiological conditions with a fibrillization inducer in the presence or absence of a test agent.

A method of treating Alzheimer's Disease is described in U.S. Pat. No. 7,179,463 B2. In this invention a subject having or suspected of having Alzheimer's Disease is administered an antibody that had been raised against a protofibril containing Aβ-Arc peptide.

A method of isolating and assembling misfolded or partially misfolded proteins in blood and other biological materials is described in U.S. Pat. No. 7,138,255 B2. In some embodiments of this invention, "proteons" comprised of misfolded proteins present in the blood assemble on proteon nucleation centers.

However, drug discovery in this area is currently hindered by the absence of a biochemical model system that mimic the mature or late stage forms of amyloid plaque in vitro in a relatively short period of time. Accordingly, there is a great need to develop in vitro processes to synthesize physiologically relevant amyloid and amyloid-like plaque formations for testing and drug discovery purposes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In one embodiment of the present invention, the invention comprises a method of assembling in vitro multi-subunit complexes for use as a biochemical platform, comprising converting soluble organic or inorganic molecules into insoluble aggregates, wherein the insoluble aggregates bind to soluble molecules including proteins, lipids or carbohydrates to form a template complex, adding at least one substantially purified protein, lipid or carbohydrate to the template, wherein the substantially purified protein, lipid or carbohydrate has been pre-screened to test for binding to the insoluble aggregate template, incubating the template and substantially purified protein, lipid or carbohydrate at an elevated temperature to form a template complex, washing the template complex to remove the non-binding substantially purified protein, lipid or carbohydrate, adding at least one additional substantially purified protein, lipid or carbohydrate to the template-complex, wherein the additional substantially purified protein, lipid or carbohydrate has been pre-screened to test for binding to the template complex, repeating the washing and protein, lipid or carbohydrate addition steps with additional, pre-screened and identified proteins, lipids or carbohydrates that bind to the template complex after each template complex formation cycling step, and isolating the template complex after the final at least one substantially purified protein, lipid or carbohydrate is added by removing the added substantially purified proteins, lipids or carbohydrates from the template complex.

In another embodiment, the invention comprises a method of assembling in vitro atherosclerotic plaque-like complexes for use as a biochemical platform, the method comprising first converting soluble organic or inorganic molecules into insoluble aggregates, wherein the soluble organic or inorganic molecules is chosen from the group consisting of a cholesterol or its derivative, a lipid or its derivative, a calcium or its derivative, a lipoprotein or its derivative, or a mixture thereof, and wherein the insoluble aggregates bind to soluble molecules including proteins, lipids or carbohydrates to form a template complex, adding at least one substantially purified protein, lipid or carbohydrate to the template, wherein the substantially purified protein, lipid or carbohydrate has been pre-screened to test for binding to the insoluble aggregate template, incubating the template and substantially purified protein at an elevated temperature to form a template complex, washing the template complex to remove the non-binding substantially purified protein, lipid or carbohydrate, adding at least one additional substantially purified protein, lipid or carbohydrate to the template complex, wherein the additional substantially purified protein, lipid or carbohydrate has been pre-screened to test for binding to the template complex; repeating the washing and protein, lipid or carbohydrate addition steps with additional, pre-screened and identified proteins, lipids or carbohydrates that bind to the template complex after each template complex formation cycling step, and isolating the template complex after the final at least one substantially purified protein, lipid or carbohydrate is added by removing the added substantially purified proteins, lipids or carbohydrates from the template complex.

In another embodiment, the present invention relates to a method of assembling in vitro amyloid plaque-like complexes of varying compositions for use as a biochemical platform for the discovery of drugs, diagnostics, or vaccines, all of which aid patients with amyloid diseases or amyloid disease-like processes or patients at risk, or not, of developing such diseases or disease-like processes. The present invention is also directed to the composition of such amyloid plaque-like complexes. The drugs that could be identified by the biochemical platform in the present invention could be capable of preventing assembly of the plaque-like complexes or of disrupting plaque-like complexes that have already formed.

In yet another embodiment, the present invention discloses a method of assembling an in vitro thrombotic complex which is substantially free of blood platelet cells for use as a biochemical platform, comprising, converting soluble organic or inorganic molecules into insoluble aggregates, wherein the insoluble aggregates bind to soluble molecules including proteins, lipids or carbohydrates to form a template complex, adding at least one substantially purified protein to the template, wherein the substantially purified protein, lipid or carbohydrate has been pre-screened to test for binding to the insoluble aggregate template, incubating the template and substantially purified protein, lipid or carbohydrate at an elevated temperature to form a template complex, washing the template complex to remove the non-binding substantially purified protein, lipid or carbohydrate, adding at least one additional substantially purified protein, lipid or carbohydrate to the template-complex, wherein the additional substantially purified protein, lipid or carbohydrate has been pre-screened to test for binding to the template complex, repeating the washing and protein, lipid or carbohydrate addition steps with additional, pre-screened and identified proteins, lipids or carbohydrates that bind to the template complex after each template complex formation cycling step, isolating the template complex after the final at least one substantially purified protein, lipid or carbohydrate is added by removing the added substantially purified proteins, lipids or carbohydrates from the template complex, and inducing thrombosis of the insoluble aggregates by adding blood coagulation factors.

In another embodiment, the present invention describes a method of preventing or disrupting the formation of atherosclerotic plaques using the drug or chemical compounds identified in the disruption of in vitro assembled atherosclerotic plaques, the method comprising, screening in vitro assembled atherosclerotic plaques with a drug or chemical compound, wherein the drug, chemical or biological compound disrupts the in vitro assembled atherosclerotic plaque formation; and administering a therapeutically effective amount of the identified drug, chemical or biological compound to a patient to prevent or disrupt the formation of atherosclerotic plaques and atherothrombosis in the patient.

In another embodiment, the present invention comprises a multi-subunit complex formed by a process comprising the steps of a) converting a soluble molecule or a mixture of soluble molecules into an insoluble aggregate, wherein the insoluble aggregate binds to themselves and or to soluble molecules to form a template; b) adding cell extract or at least one substantially purified protein, lipid or carbohydrate to the template, wherein the substantially purified protein, lipid or carbohydrate binds to the template to form a template complex; c) removing unbound substantially purified protein, lipid or carbohydrate from the template complex; d) repeating the addition of at least one substantially purified protein, lipid or carbohydrate to the template complex, wherein the additional substantially purified protein, lipid or carbohydrate binds to the template complex to form a multi-subunit complex; e) obtaining a purified multi-subunit complex after cyclic plaque assembly (CPA) by removing unbound protein, lipid or carbohydrate from the multi-subunit complex. In some embodiments, the soluble molecule is a protein, lipid, or carbohydrate. In some embodiments, the soluble molecule is one or more of the following: Cholesterol, lipids, calcium chloride, sodium phosphate, sodium pyrophosphate, oxalic acid, sodium bicarbonate, iron sulfate, abeta40, abeta42, prion peptides, iron sulfate, iron phosphate, copper sulfate $CUSO_4$, zinc chloride $ZnCl_2$, aluminum chloride $AlCl_3$, iron III, iron III sulfate, sodium acetate, sodium butyrate, sodium bicarbonate, sodium phosphate, magnesium sulfate, sodium citrate, DNA, or RNA. In other embodiments, the substantially purified protein is human blood coagulation factor prothrombin, antithrombin III, factor H, a complement factor, protein S, plasminogen activator inhibitor 1(PAI-1), plasminogen (PLG), human FBN, serum albumin, blood coagulation factor II (FII), factor IX (FIX), or recombinant human hepatocyte growth factor. In some embodiments, the insoluble aggregate is formed from $\alpha$-synuclein, amyloid $\beta$ peptide, cystatin C, atrial natiuretic factor, procalcitonin, calcium bicarbonate, calcium oxalate, calcium pyrophosphate, cholesterol, lipid, iron phosphate, A-beta40-42, prion, amylin, tau, ammonium phosphate, phospholipids, cholesterol crystals, palmitic anhydrate, serum amyloid A protein, $\beta 2$ microglobulin, lysozyme, insulin, superoxide dismutase, transthyretin, immunoglobulin, fibrinogen $\alpha$-chain variants, apolipoprotein A-1, a fragment thereof, or a mixture thereof. In certain embodiments, a mixture of insoluble aggregates is used to form a hybrid insoluble aggregate. The hybrid insoluble aggregate is composed of calcium phosphate (CP)-lipids, calcium oxalate (CO)-lipids, CP-cholesterol (Chl)-lipids, CO-Chl, Chl-lipids, abeta40, abeta42, iron-abeta40, iron-abeta42, prion, iron-sodium-acetate, iron-(bi)carbonate, iron-phosphate, iron-magnesium-sulfate, aluminum-phosphate, copper-phosphate, or zinc-phosphate. In some embodiments, the multi-subunit complex formed in vitro resembles an atherosclerotic plaque. In other embodiments, the multi-subunit complex formed in vitro resembles an amyloid plaque. In still other embodiments, the multi-subunit complex formed in vitro resembles a plaque associated with atherosclerosis, atherothrombosis, Alzheimer's disease, Parkinson's disease, osteoarthritis, mad cow disease or spongiform encephalopathy, Huntington's disease, type II diabetes, dementia, atrial amyloidosis, systemic amyloidosis, dialysis-related amyloidosis, hemodialysis-related amyloidosis, fibrinogen chain amyloidosis, lysozyme amyloidosis, insulin-related amyloidosis, amyotrophic lateral sclerosis, familial amyloidotic polyneuropathy II, medullary carcinoma of the thyroid, kidney stone, gall bladder stone, pancreatic stone, or a calcification-related disease. In some embodiments, the multi-subunit complex further comprises a thrombotic complex formed by adding one or more blood coagulation factor to the multi-subunit complex. In some embodiments, the multi-subunit complex further comprises a physiologically acceptable carrier to form a pharmaceutical composition. In some embodiments, the pharmaceutical composition can be used to prevent or treat a plaque-associated disease including but not limited to atherosclerosis, atherothrombosis, Alzheimer's disease, Parkinson's disease, osteoarthritis, mad cow disease or spongiform encephalopathy, Huntington's disease, type II diabetes, dementia, atrial amyloidosis, systemic amyloidosis, dialysis-related amyloidosis, hemodialysis-related amyloidosis, fibrinogen $\alpha$-chain amyloidosis, lysozyme amyloidosis, insulin-related amyloidosis, amyotrophic lateral sclerosis, familial amyloidotic polyneuropathy II, medullary carcinoma of the thyroid, kidney stone, gall bladder stone, pancreatic stone, or a calcification-related disease.

In still another embodiment, the present invention comprises an in vitro-assembled thrombotic complex which is substantially free of blood platelet cells, the complex formed by, converting soluble organic or inorganic molecules into insoluble aggregates, wherein the insoluble aggregates form a template for binding of soluble molecules including proteins, lipids or carbohydrates to form a template complex, adding at least one substantially purified protein, lipid or carbohydrate to the template, wherein the substantially purified protein, lipid or carbohydrate has been pre-screened to test for binding to the insoluble aggregate template, incubating the template and substantially purified protein at an elevated temperature to form a template complex, washing the template complex to remove the non-binding substantially purified protein, lipid or carbohydrate, adding at least one additional substantially purified protein, lipid or carbohydrate to the template complex, wherein the additional substantially purified protein, lipid or carbohydrate has been pre-screened to test for binding to the template complex, repeating the washing and protein, lipid or carbohydrate addition steps with additional, pre-screened and identified proteins, lipids or carbohydrates that bind to the template complex after each template complex formation cycling step, isolating the template complex after the final at least one substantially purified protein, lipid or carbohydrate is added by removing the added substantially purified proteins, lipids or carbohydrates from the template complex, and inducing thrombosis of the insoluble aggregates by adding blood coagulation factors.

In yet another embodiment, the present invention discloses a method for screening anti-plaque agents, the method comprising exposing a multi-subunit complex of the present invention or an insoluble component thereof to an agent, and determining effect of the agent on the multi-subunit complex or the insoluble component. In one aspect, the screening is performed in vitro. In some embodiments, the in vitro screening comprises: a) contacting a cell with a multi-subunit complex of the invention; b) contacting the same cell with an agent; c) selecting an agent that prevents, reduces or inhibits assembly of the multi-subunit complex, or disrupts, destabilizes, or eliminates the multi-subunit complex in the cell. In some embodiments, the cell is a mammalian cell. In some embodiments, the mammalian cells express morphologic changes, pathological symptoms and or cell death upon exposure to the agent being screened. In another aspect, the screening is performed in vivo. In some embodiments, the in vivo screening comprises: a) introducing to a subject a multi-subunit complex of the invention or an insoluble component thereof; b) introducing to the same subject an agent; c) selecting an agent that prevents or alleviates one or more signs or pathological symptoms associated with exposure to the multi-subunit complex or the insoluble component in the subject. In some embodiments, the subject is an animal including but not limited to a human. In some embodiments, the method further comprises monitoring the subject for development of a plaque-related or plaque-induced disease in the subject. In some embodiments, the disease is an atherosclerotic plaque-related disease. In other embodiments, the disease is an amyloid plaque-related disease. In some embodiments, the disease is atherosclerosis, atherothrombosis, Alzheimer's disease, Parkinson's disease, osteoarthritis, mad cow disease or spongiform encephalopathy, Huntington's disease, type II diabetes, dementia, atrial amyloidosis, systemic amyloidosis, dialysis-related amyloidosis, hemodialysis-related amyloidosis, fibrinogen α-chain amyloidosis, lysozyme amyloidosis, insulin-related amyloidosis, amyotrophic lateral sclerosis, familial amyloidotic polyneuropathy II, medullary carcinoma of the thyroid, kidney stone, gall bladder stone, pancreatic stone, or a calcification-related disease. In some embodiments, the method further comprises introducing to the subject a second multi-subunit complex of the invention. In some embodiments, the agent is a small molecule, an antibody-based agent, or an RNA-based agent. In a specific embodiment, the agent is tetracycline chloride (PGN27) or any derivative or analog or conjugates of tetracycline. In other embodiments, the agent has effect on plasminogen activation. In a preferred embodiment, the agent is urokinase-type plasminogen activator (u-PA) (PGN54) or a variant of uPA. In some embodiments, the agent is selected to bind, penetrate, disassemble, prevent or disrupt a multi-subunit complex that resembles an atherosclerotic plaque. In other embodiments, the agent is selected to bind, penetrate, disassemble, digest, prevent or disrupt a multi-subunit complex that resembles an amyloid plaque. In some embodiments, the multi-subunit complex is labeled.

Another embodiment comprises a method for preventing or treating a plaque-related disease comprising administering to a subject in need thereof a therapeutically effective amount of an agent that binds, penetrates, disassembles, prevents or disrupts a plaque involved in the disease, wherein the plaque resembles the in vitro assembled multi-subunit complex of the invention. In some embodiments, the agent is a small molecule, an antibody-based agent, or an RNA-based agent. In a preferred embodiment, the agent is tetracycline chloride (PGN27) or any derivative or conjugates or analog of tetracycline. In another preferred embodiment, the agent is uPA (PGN54) or a variant of uPA. In some embodiments, the agent is labeled. In some embodiments, the plaque is an atherosclerotic plaque. In other embodiments, the plaque is an amyloid plaque. In certain embodiments, the disease is atherosclerosis, atherothrombosis, Alzheimer's disease, Parkinson's disease, osteoarthritis, mad cow disease or spongiform encephalopathy, Huntington's disease, type II diabetes, dementia, atrial amyloidosis, systemic amyloidosis, dialysis-related amyloidosis, hemodialysis-related amyloidosis, fibrinogen α-chain amyloidosis, lysozyme amyloidosis, insulin-related amyloidosis, amyotrophic lateral sclerosis, familial amyloidotic polyneuropathy II, medullary carcinoma of the thyroid, kidney stone, gall bladder stone, pancreatic stone, or a calcification-related disease.

Yet another embodiment comprises a method for profiling or categorizing the pathogenicity of nanomaterials, insoluble aggregates, plaque-like complexes or thrombotic complexes in a cell culture system the method comprising adding an in vitro-assembled insoluble aggregate, plaque-like complex, thrombotic-like complex, or a mixture thereof, to cultured mammalian cells, culturing mammalian cells with the insoluble aggregates, plaque-like complexes or thrombotic-like complexes or a mixture thereof; and evaluating the cultured mammalian cells, wherein express morphologic changes or pathological symptoms or cytokine expression, cell death indicate the pathogenicity of the insoluble aggregates, plaque-like complexes or thrombotic-like complexes.

Yet another embodiment comprises a method of diagnosing, categorizing, evaluating or predicting a plaque-related disease process in a subject, the method comprising: a) contacting a biological sample of a subject with one or more in vitro assembled plaque-like complexes or aggregates of the invention; b) detecting the binding of an antibody present in the biological sample of the subject to the in vitro assembled plaque-like complexes or aggregates. In some embodiments the plaque-related disease is atherosclerosis, atherothrombosis, Alzheimer's disease, Parkinson's disease, osteoarthritis, mad cow disease or spongiform encephalopathy, Huntington's disease, type II diabetes, dementia, atrial amyloidosis, systemic amyloidosis, dialysis-related amyloidosis, hemodialysis-related amyloidosis, fibrinogen α-chain amyloidosis, lysozyme amyloidosis, insulin-related amyloidosis, amyotrophic lateral sclerosis, familial amyloidotic polyneuropathy II, medullary carcinoma of the thyroid, kidney stone, gall bladder stone, pancreatic stone, or a calcification-related disease. In some embodiments, the subject is a human. In some embodiments, the biological sample is blood, plasma, serum, urine or tissue. In some embodiments, the antibody is an IgM, IgG, IgA or IgE. In some embodiments, the step of detecting involves an immunological assay. In a preferred embodiment, the immunologic assay is an Enzyme-Linked Immunosorbent Assay (ELISA).

Yet another embodiment comprises a method for developing an animal model of plaque disease comprising introducing to an animal one or more of the following: (1) an in vitro assembled insoluble aggregate comprising two or more: cholesterol, lipid and calcium; or (2) an in vitro-assembled multi-subunit complex (PGN32) comprising insoluble aggregates of cholesterol, lipids and calcium described herein. The method may comprise introducing a first in vitro assembled insoluble aggregate or a first in vitro-assembled multi-subunit complex, followed by introducing a second in vitro assembled insoluble aggregate or a second in vitro-assembled multi-subunit complex. In some aspects, the method comprises multiple introductions. In some aspects, the in vitro assembled insoluble aggregate is a hybrid insoluble aggregate that is generated by mixing two or more: a lipid aggregate, a cholesterol aggregate, and a calcium-containing aggregate. In some aspects, the calcium-containing aggregate comprises one or more: calcium phosphate (CP), calcium pyrophosphate (CPP), or calcium oxalate (CO). In some aspects, the hybrid insoluble aggregate comprises CP, cholesterol (Chl) and lipid. In other aspects the hybrid insoluble aggregate comprises two or more: CP—cholesterol-lipid (PGN32), e.g., CP and lipid, CO and lipid, CP and Chl, CO and Chl, Chl and lipid, and the like. In some embodiments, the method comprises introducing into the animal in vitro assembled insoluble aggregate or the in vitro assembled multi-subunit complex via intra-peritoneal, subcutaneous, or intravenous routes. In some embodiments, the method further comprises monitoring the animal for the development of a disease in said animal. In some aspects, the disease is inflammation, chronic inflammation, a plaque-related disease, a plaque-related disorder or atherosclerosis. In some embodiments, the method further comprises the step of monitoring the animal for the presence of the in-vitro assembled multi-subunit complex, or fragment thereof, or for the presence of the in vitro-assembled insoluble aggregate, in the system of said animal. In some aspects, the monitoring comprises detecting with a device the presence of the in vitro assembled insoluble aggregate or the in vitro assembled multi-subunit complex, or fragment thereof, in the system of said animal. In some aspects, the in vitro assembled insoluble aggregate or the in vitro assembled multi-subunit complex, or fragment thereof, is or has been labeled with a fluorophore, magnetic resonance imaging contrast reagent, positron emitting reagent, X-ray contrast reagent, radionuclide, or luminescent molecule; and wherein the monitoring comprises detecting the presence of the labeled in vitro assembled insoluble aggregate or the labeled in vitro assembled multi-subunit plaque complex, or fragment thereof. In some aspects, the fluorophore is a near infrared fluorophore or an infrared fluorophore; in some aspects, the device is a fluorometer, a magnetic resonance imaging machine, a positron emission tomography machine, an X-ray machine, a computerized tomography machine, a gamma counter, or a luminescent imager. In some embodiments, the method comprises testing blood or tissue sample for antibodies against the in vitro assembled insoluble aggregate or the in vitro assembled multi-subunit plaque complex, or fragment thereof, or testing blood or tissue samples for markers (e.g., cytokines) of plaque induced chronic inflammation. In some embodiments, the method further comprises histochemical analysis of tissue, such as cardiovascular tissue; and, in some aspects, the histochemical analysis comprises comprising staining the tissue with orange red, hemotoxilin, eosin, Von Kosa stain, or alizarin red.

In some embodiments, this disclosure comprises an animal for drug development, wherein said animal was previously treated with (1) an in vitro assembled complex or insoluble aggregate comprising two or more: cholesterol, lipid and calcium; or (2) an in vitro-assembled multi-subunit plaque complex (PGN32) described herein. In some aspects, the in vitro assembled insoluble aggregate comprises a hybrid insoluble aggregate that was generated by mixing a lipid aggregate, cholesterol aggregate with a calcium-containing aggregate. In some aspects, the calcium-containing aggregate comprises calcium phosphate, calcium pyrophosphate, calcium chloride, or calcium oxalate. In some aspects, the calcium-containing aggregate comprises one or more: calcium phosphate (CP), calcium pyrophosphate (CPP), calcium chloride, or calcium oxalate (CO). In some aspects, the hybrid insoluble aggregate comprises CP, cholesterol (Chl) and lipid. In other aspects the hybrid insoluble aggregate comprises two or more: CP, cholesterol and lipid, e.g., CP and lipid, CP-Chl-lipid (PGN32), CO and lipid, CP and Chl, CO and Chl, Chl and lipid, and the like. In some aspects, the disclosure provides an animal for drug development in which the treatment with said in vitro assembled multi-subunit complex resulted in, or contributed to, the formation or deposition of a plaque or plaque-like complex in the system of said animal. In some aspects, the treatment with the in vitro assembled multi-subunit complex resulted in, or contributed to, the development of one or more: atherosclerosis, inflammation, chronic inflammation, plaque-related disease, or plaque-related disorder in the animal for drug development. In some aspects, the animal is a mouse, rat, pig, horse, non human primate, guinea pig, hamster, chicken, a frog, cat, dog, sheep, or cow. In some aspects, the in vitro assembled multi-subunit complex introduced to the animal, or developed in the animal, resembles an atherosclerotic plaque. In some aspects, this disclosure provides an animal for drug development, wherein the in vitro assembled multi-subunit complex was introduced to the system of the animal via intra-peritoneal, subcutaneous, or intravenous routes. In further embodiments, the animal exhibits one or more signs or symptoms of a plaque-related disease, e.g., atherosclerosis, chronic inflammation or inflammation.

In some embodiments, the disclosure provides a method of drug screening comprising contacting an animal for drug development described herein (e.g., an animal that was previously treated with (1) an in vitro assembled complex or insoluble aggregate comprising two or more: cholesterol, lipid and calcium; or (2) an in vitro-assembled multi-subunit complex described herein) with a drug, chemical or biological compound (including a library of organic molecules; also including antibodies to the in vitro assembled multi-subunit complex) and monitoring the animal for pathological symptoms, death, morphological changes, or phenotypic changes.

In some embodiments, the disclosure provides a method of vaccinating a subject against a plaque-related disease, the method comprising administering into a subject an in vitro assembled multi-subunit complex, or a pharmaceutical composition thereof, to prevent or treat a plaque-related disease. In some embodiments, the subject is a mouse, a rat, a pig, a horse, a non human primate, a guinea pig, a hamster, a chicken, a frog, a dog, a sheep, a cow, or a human. In a preferred embodiment, the subject is a human. In some embodiments, the in vitro assembled multi-subunit complex is an atherosclerotic plaque-like complex. In other embodiments, the in vitro assembled multi-subunit complex is an amyloid plaque-like complex. In still other embodiments, the in vitro assembled multi-subunit complex comprises two or more cholesterol, lipid and calcium. In some embodiments, the in vitro assembled multi-subunit complex, upon administration into the subject, stimulates an immune response against a plaque involved in a plaque-related disease. In certain embodiments, the antibodies and cytokines elicited from the immune response against a plaque involved in the disease are administered to a subject to treat or prevent the disease. In some embodiments, the in vitro assembled multi-subunit complex (PGN32) is metabolic adjuvant or immune stimulator administered to a subject for the treatment of cancer, viral infection, bacterial infection, psoriasis, autoimmune diseases, inflammatory diseases, or immunodeficiency diseases. In some embodiments, the plaque-related disease is atherosclerosis, atherothrombosis, Alzheimer's disease, Parkinson's disease, osteoarthritis, mad cow disease or spongiform encephalopathy, Huntington's disease, type II diabetes, dementia, atrial amyloidosis, systemic amyloidosis, dialysis-related amyloidosis, hemodialysis-related amyloidosis, fibrinogen α-chain amyloidosis, lysozyme amyloidosis, insulin-related amyloidosis, amyotrophic lateral sclerosis, familial amyloidotic polyneuropathy II, medullary carcinoma of the thyroid, kidney stone, gall bladder stone, pancreatic stone, or a calcification-related disease. In some embodiments, the method further comprises introducing an additional antigen into the subject.

In some embodiments, the disclosure provides a method of treatment comprising contacting an animal suffering from cancer, viral infection, bacterial infection, psoriasis, autoimmune diseases, inflammatory diseases, or immunodeficiency diseases with: (1) an in vitro assembled insoluble aggregate comprising two or more: cholesterol, lipid and calcium; or (2) an vitro-assembled multi-subunit complex (PGN32) described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2a, b, c, d, e and 2f show picture of six insoluble aggregates (1000×) that are indicated on the top of each picture.

FIG. 5 SDS-PAGE analysis of the complexes assembled using cyclic plaque assembly (CPA) method. FIGS. 4a, b, c, d and e show CPA using CP, CC, CO, Calcium Pyrophosphate (CaPPD) templates and negative control respectively. Cycle 0 indicates templates before binding; Cycle 1, binding of FII and AT III to the templates; cycle 2, binding of FH and C5 proteins to the complexes-1; cycle 3, binding of FIX and C3 proteins to the complexes-2; cycle 4, binding of ProS and C4 proteins to the complexes-3; cycle 5, binding of PAI-1 and FBN proteins to the complexes-4 and cycle 6, binding of HAS and C1 proteins to the complexes-5. e, Analysis of complex formation performed without templates. Control, PBS buffer; Cycle 1, incubation of FII and AT III; cycle 2, binding of FH and C5 proteins to the complexes-1; cycle 3, binding of FIX and C3 proteins to the complexes-2; cycle 4, binding of ProS and C4 proteins to the complexes-3; cycle 5, binding of PAI-1 and FBN proteins to the complexes-4 and cycle 6, binding of HSA and C1 proteins to the complexes-5.

FIG. 8 SDS-PAGE analysis of the complexes assembled using the CPA method. FIG. 8a plaque like complexes assembled using CP and CP-Lipid templates. FIG. 8b plaque like complexes assembled using CO, CO-Lipid templates. Cycle 1, binding of the FII and AT III to the templates; cycle 2, binding of FH and C5 proteins to the complexes-1; cycle 3, binding of FIX and C3 proteins to the complexes-2; cycle 4, binding of PLG and C4 proteins to the complexes-3 and cycle 5, binding of PAI-1 and FBN proteins to the complexes-4. 8c, diagrammatic illustration of CPA.

FIG. 9 SDS-PAGE analysis of the complexes assembled using CPA method. FIG. 9a plaque like complexes assembled using CP-Cholesterol-Lipid templates. FIG. 9b Diagram showing assembly of complexes using CP-Cholesterol-Lipid templates. Cycle 1, binding of the FII and AT III to the templates; cycle 2, binding of FH and C5 proteins to the complexes-1; cycle 3, binding of FIX and C3 proteins to the complexes-2; cycle 4, binding of PLG and C4 proteins to the complexes-3 and cycle 5, binding of PAI-1 and FBN proteins to the complexes-4.

FIG. 11 Analysis of thrombosis of the plaque complexes. FIG. 11a shows the calcium containing aggregates and the thrombus generated from those aggregates. The label on top of the each tube indicates each calcium containing aggregates and their associated diseases. 11b, Staining of atherosclerotic plaque complexes/thromboses by Alizain red, orange O red and hemotoxilin & eosin stains. The label on top of the each tube indicates the specific plaque complexes and corresponding staining.

FIGS. 29a, b, c, d, e and f show picture of thrombosis assays (1000×) and the complexes used in the assays are indicated on the top of each picture.

FIGS. 30a, b, c, d, e and f show picture of thrombosis assays (1000×) and the complexes used in the assays are indicated on the top of each picture.

FIG. 34 Diagram showing purification and detection of antibodies using ELISA method. 34a, steps showing binding and purification proteins from plaque complexes. 34b, the top showing steps of regular ELISA for detecting antibodies using protein A and the bottom portion show one-step ELISA method for rapid detection and quantitation of human antibodies for atherosclerotic plaques.

FIG. 38 Microscopic (400×) observation of orange red stained heart tissues isolated from normal and induced atherosclerotic plaque mice for examining in vivo plaque formation FIG. 39 Microscopic (400×) observation of hemotoxilin and eosin stained heart tissues isolated from normal and induced atherosclerotic plaque mice for examining in vivo plaque formation FIG. 40. Microscopic (400×) observation of Alizarin red and Von Kosa stained heart tissues isolated from normal and induced atherosclerotic plaque mice for examining in vivo plaque formation FIG. 41. Visual examination of symptomatic Atherosclerotic mice models with morphological chronic plaque inflammation FIG. 42 Visual examination of symptomatic Atherosclerotic mice models showing reduction in morphological chronic plaque inflammation after treatment with PGN27 and ovastatin drugs FIG. 43. Microscopic (400×) observation of orange red stained heart tissues isolated from normal and induced atherosclerotic plaque mice for examining efficacy of PGN27 and ovastain treated mice for plaque regression FIG. 44. Microscopic (400×) observation of hemotoxilin and eosin stained heart tissues isolated from normal and induced atherosclerotic plaque mice for examining efficacy of PGN27 and ovastain treated mice for plaque regression FIG. 45. Design showing in vitro amyloid plaque assembly processes FIG. 46. SDS-PAGE analysis of binding between iron-loaded abeta42 templates and proteins. 46a, Detection of binding between the templates and proteins in coomassie blue stained gel. Lane1, loaded with 6.0 μg of total CE proteins as control; lane 2, binding of CE proteins to the templates; lane 3, binding of PLG, BSA and PAI-1 proteins together with the templates; lane 4, the iron loaded templates (5.0 μg) only; lane 5, monomer of abeta 42 (5.0 μg) loaded as control and lane 6, PLG, BSA and PAI-1 proteins processed without the templates. 46b, Detection of binding between the templates and proteins by silver staining method. Lane 1, binding of FII to the templates; lane 2, binding of both FIX and CD proteins to the templates; lane 3, binding of both ProS and PAI-1 proteins to the templates; lane 4, binding of both PLG and BSA proteins to the templates and lane 5, binding of CE proteins to the templates.

FIG. 47. Assembly of plaque complexes using abeta 42 as templates and SDS-PAGE analysis of the plaques complexes obtained after successive cycles. 47a, Cycle 1, binding of FII to the templates; cycle 2, binding of FIX and CD proteins to the complexes-1; cycle 3, binding of ProS and PAI-1 proteins to the complexes-2; cycle 4, binding of PLG and BSA proteins to the complexes-3 and cycle 5, binding of CE proteins to the complexes-4. 47b and c, cycle 1, binding of CB to the templates; cycle 2, binding of rhHGF and CD proteins to the complexes-1; cycle 3, binding of ProS and PAI-1 proteins to the complexes-2; cycle 4, binding of PLG and BSA proteins to the complexes-3 and cycle 5, binding of CE proteins to the complexes-4. d, Diagram showing assembly of amyloid plaque complexes using abeta42 as template.

FIG. 48a, cycle 1, binding of FII to the templates; cycle 2, binding of FIX and CD proteins to the complexes-1; cycle 3, binding of ProS and PAI-1 proteins to the complexes-2; cycle 4, binding of PLG and BSA proteins to the complexes-3; cycle 5, binding of CE proteins to the complexes-4 and control, the templates processed without proteins. FIG. 48b, c, cycle 1, binding of FII to the templates; cycle 2, binding of FIX to the complexes-1; cycle 3, binding of ProS and PAI-1 proteins to the complexes-2; cycle 4, binding of PLG and BSA proteins to the complexes-3 and cycle 5, binding of CE proteins to the complexes-4. d, cycle 1, FII processed without the templates; cycle 2, binding of FIX and CD proteins to samples of cycle 1; cycle 3, binding of ProS and PAI-1 proteins to samples of cycle 2; cycle 4, binding of PLG and BSA proteins to samples of cycle 3 and cycle 5, binding of CE proteins to samples of cycle 4. 48e, Diagram showing assembly of amyloid plaques using abeta40 template.

FIG. 50 Proteolysis analysis of the in vitro assembled plaque complexes. 50a, Lane 1, control complex that was not treated with protease; lanes 2 to 6, treatment of the complexes with different serine proteases (20 ng of each) that are indicated above each lane; lane 7, the control complex containing bound BSA and PLG proteins; lane 8, activation of the PLG bound to the complex by t-PA (20 ng) and lane 9, activation of the PLG bound to the complex by u-PA (20 ng). 50b, Diagram showing proteolytic analysis of amyloid like plaques complexes assembled using abeta42 template.

FIG. 51 Proteolysis analysis of in vitro assembled amyloid plaque complexes. 51a, Lane 1, control complex that was not treated with protease; lanes 2 to 6, treatment of the complexes with different serine proteases (20 ng of each) that are indicated above each lane; lane 7, the control complex containing bound BSA and PLG proteins; lane 8, activation of the PLG bound to the complex by t-PA (20 ng) and lane 9, activation of the PLG bound to the complex by u-PA (20 ng). 51b, Diagram showing proteolysis of amyloid plaques assembled using abeta40 templates.

FIG. 52 Analyzing functional state/s of PLG attached to the plaques complexes assembled with iron-loaded abeta42 aggregates. 52a, Activation of the PLG attached to complexes during first and second cycles of binding by its physiological activators. Lanes 1, 4 and 7 are the control complexes without treatment of PLG activators; lanes 2, 5 and 8 are the complexes treated with u-PA (20 ng) for PLG activation and lanes 3, 6 and 9 are the complexes treated with t-PA (20 ng) for the PLG activation. 52b, Diagram showing activation of PLG sandwiched between protein layers.

FIG. 53 Activation of the PLG attached to the complexes with increasing concentrations of u-PA. 53a, Lanes 1 and 5 are the control complexes without the u-PA treatment; lanes 2 and 6 are the complexes treated with 25 ng of u-PA; lanes 3 and 7 are the complexes treated with 50 ng of u-PA and lanes 4 and 8 are the complexes treated with 100 ng of u-PA. 53b, Diagram showing activation of PLG sandwiched between protein layers.

FIG. 54 Analyzing functional state/s of the PAI-1 attached to the complexes assembled using the iron-loaded abeta42 or abeta40 aggregates as templates. a, Lane 1, control complex without PAI-1 and u-PA treatment; lanes 2 and 5 are complexes attached with the PLG and PAI-1 (50 ng) proteins and treated with u-PA (20 ng); lanes 3 and 6 are the complexes attached with the PLG and PAI-1 (10 ng) proteins and treated with u-PA (20 ng) and lanes 4 and 7 are the complexes attached with the PLG and PAI-1 (200 ng) proteins treated with u-PA (20 ng).

DETAILED DESCRIPTION OF THE INVENTION

Figure 1:
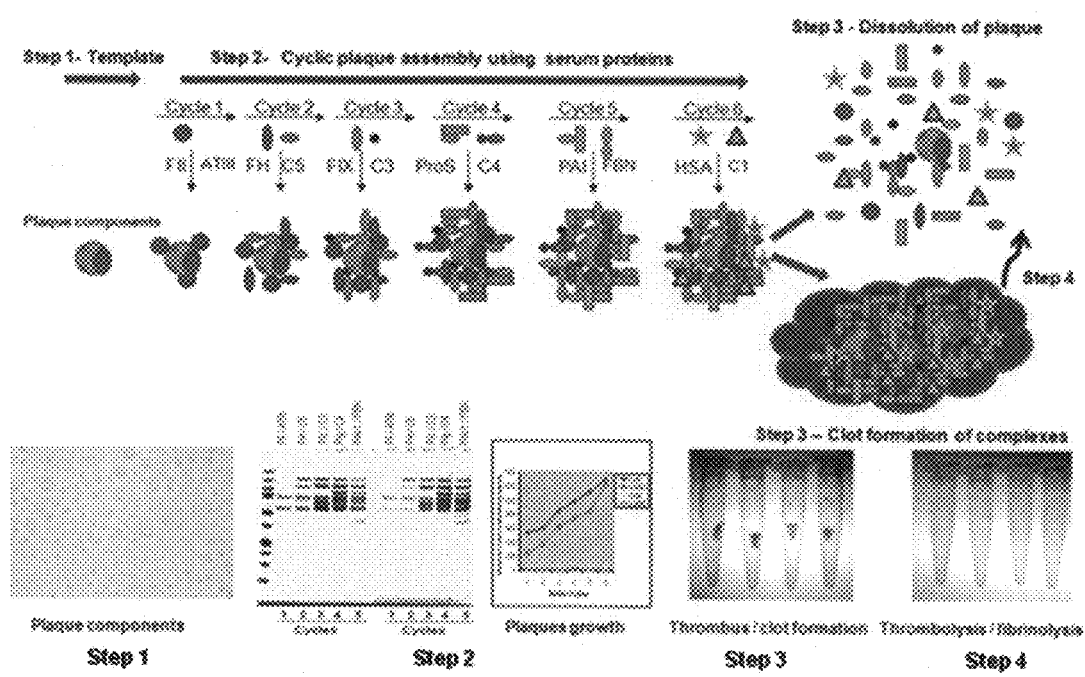
FIG. 1 shows the design and the results supporting the development of Plaque Engineering Technology (PET) platform. The top portion of the FIG. shows the design and the bottom portion shows the experimental data supporting the design of four steps of in vitro Atherosclerotic plaques assembly process.

The present invention provides the compositions and methods of generating multi-subunit biochemical platforms for use in biological plaque assays and drug discovery. More specifically, the embodiments described herein relate to the in vitro and in vivo formation of biochemical plaques, in particular, atherosclerotic plaques and amyloid plaques. The plaque embodiments described may be used to enable rapid, sensitive and/or efficient drug discovery and medical diagnostics and analysis.

I. Plaque-Related Diseases or Disorders

The present invention provides a method of assembling in vitro multi-subunit complexes for use as a biochemical platform to simulate a disease stage or process. Numerous types of diseases are associated with plaque formation, as listed in Table 1.

TABLE 1

| Amyloid aggregates | Chemical aggregates | Lipid aggregates | Protein aggregates |
|---|---|---|---|
| Abeta40-42 (Alzheimer's) | Calcium phosphate (Atherosclerosis) | Phospholipids (Atherosclerosis) | Serum Amyloid A (Systemic Amyloidosis) |
| Synuclein (Parkinson's)) | Calcium oxalate (Kidney Stones) | Cholesterol crystals (Atherosclerosis, Gall Bladder) | Beta Microglobulin (Dialysis related Amyloidosis) |
| Prion (Mad Cow Spongiform) | Calcium Pyrophosphate (Osteoarthritis) | Palmitic anhydrate (Gall bladder stone) | Lysozyme (Lysozyme Amyloidosis) |
| Amylin (Type II diabetes) | Calcium Bicarbonate (Pancreatic stones) | | Insulin (Insulin related Amyloidosis) |
| Tau (Dementia/parkinsonism) | Ammonium Phosphate (Kidney stone disease) | | Super dioxide dismutase (Amyotrophic Lateral sclerosis) |

Atherosclerosis

In one aspect of the present invention, a method for assembling atherosclerotic plaque-like complexes is provided. Atherosclerosis is a disease affecting arterial blood vessels. It is commonly referred to as a hardening of the arteries. It is caused by the formation of multiple plaques within the arteries. As used herein, the term "atherosclerotic plaque" refers to the build up of fatty plaque deposits within the wall of blood vessels. The major components present in atherosclerotic plaques are lipids, cholesterol, calcium crystals, proteins, blood platelets, fibrin, blood clots, macrophages, cell debris, microorganisms and minerals (Corti R et al, 2004). According to American Heart association, atherosclerosis-related cardiovascular diseases are responsible for annual fatalities of 1.2 million patients in U.S and 19 million worldwide. Drugs currently available on the market for treating patients with advanced atherosclerotic plaques are mainly statins, antithrombin and blood thinners and they do not prevent or cure these plaques. Although, the chemical and physical nature of a plaque's contents varies greatly, a common factor responsible for origin of the plaque diseases is formation of insoluble aggregates or materials. Examples of such insoluble aggregates that are implicated in the origin of many human diseases are listed in table 1. Insoluble aggregate formation takes place, under abnormal or pathological conditions, either as self aggregation of the homogeneous molecules or as by-products derived from interaction between two or more molecules. For example, cholesterol and calcium phosphate (CP) crystals represent two major components accumulated in the advanced atherosclerotic plaques and the accumulation of former is due to its self aggregation whereas the latter is a by-product resulted from interaction between inorganic calcium and phosphate. Numerous studies have reported the important role of cholesterol and CP either individually or in combination towards the development of atherosclerotic processes (Doherty, T M et al, 2004).

Plasma lipids and lipoproteins are associated with an increased risk of cardiovascular diseases. These lipid molecules exist both as low-density lipoprotein (LDL) particles and elevated plasma triglyceride. Further, studies have found heterogeneities in size, density and composition among LDL particles (Mkkanen L et al, 1999) and particularly the small LDL particles are found to be more atherogenic than the larger LDL particles (Carmena R et al, 2004). Cholesterol is a major lipid component present in the atherosclerotic plaques and specifically, the low-density cholesterol particles are found to be associated with increased risk of coronary heart diseases (Hirano T et al, 2003; Festa A et al, 1998). The formation of a lipid-rich lesion in the artery wall is considered to be a key event in the initiation and progression of atherosclerosis (Peng S et al, 2000). Continuous accumulation of lipids and cholesterol in an atherosclerotic plaque may cause progressive narrowing of the arterial lumen. It has been hypothesized that during the atherosclerotic process, cholesterol undergoes a structural transition from the initial esterified form to an intermediate un-esterified aggregates form and finally to an irreversible crystal form (Sarig S et al, 1994a). The plaque-containing major share of un-esterified cholesterol aggregates in the lipid core is considered vulnerable for rupture and thrombus formation (Small D M, et al, 1988).

In addition, the composition of the atherosclerotic plaques is an important factor in predicting the stability of the plaques. Apart from the presence of heterogenic chemical constituents in the atherosclerotic plaques, the physical nature of each component also exists in various forms. For example, the cholesterol is present in the atherosclerotic plaques as non-crystalline and crystalline monohydrate forms and the former is largely localized in the soft plaque core making it susceptible for rupture (Guyton, J R, 1996). Inside the atherosclerotic plaques core, the cholesterol particles are found to occur in three different sizes such as small spherulites (3-5 µm), elongated structures (10-30 µm) and large irregular deposits (100 µm) (Sarig S, et al, 1994b). Further, agglomeration of these un-esterified cholesterol particles along with granular CP is a common indication found in the advanced plaques (Kruth H S, 1984). However, the physical association between cholesterol and CP in the atherosclerotic plaques development need to be further elucidated (Hirsch D, 1993). Advanced analytical tools such as X-ray diffraction, optical microscopy and Raman spectroscopy are useful to identify and semi-quantitate the crystalline contents of cholesterol and CP in the matured atherosclerotic plaques (Guo W et al, 2000).

Atherosclerosis is a major cardiovascular complication and a leading cause of death among patients with the chronic kidney disease and end stage renal disease (ESRD) thus revealing casual association between kidney and heart diseases (Brancaccio D et al, 2005; McCullough P A et al, 2004; Higgins C L et al, 2005). Increasing evidence has shown that due to abnormal minerals metabolism, the serum concentrations of calcium and phosphate are present in elevated levels in patients with the chronic kidney disease and hemodialysis (Young E W et al, 2005; Wang A Y et al, 2001). The prevalence of extraskeletal calcium crystal depositions in the soft tissues of patients with chronic kidney diseases indicate defects in the metabolism of one or more minerals such as calcium, phosphate, oxalate, pyrophosphate and carbonate (Schmeidl A et al, 2000). The formation of disordered extra skeletal calcium crystals or stones is a common medical problem causing various chronic diseases such as atherosclerosis, kidney and bladder stones, dental pulp stones, some gall stones, salivary gland stones, chronic calculus prostatitis, scleroderma, pancreatic stones, several malignancies, pseudogout etc (Carson D A, 1998). The CP crystals are present in the approximately 82% of the advanced atherosclerotic plaques and remain co-localized with fibrin and cholesterol deposits (Bini A et al, 1999). These crystals deposited in the entire region of vascular system found to cause chronic cardiovascular pathologies such as stiffening of the arteries, stenosis, reduced blood flow, altered coronary perfusion and under acute conditions causes heart attack and stroke (Higgins C L et al, 2005). Although the initiation of the coronary calcification process takes place as an asymptomatic event in normal persons, it is prominently identified in dialysis and ESRD patients who are at the increased risk of atherosclerosis and related mortalities (Thompson G R et al, 1994).

According to the American heart association, the coronary calcification and particularly aortic valve calcification is the third leading cause of the heart diseases in adults (Garg V et al 2005). Further estimates show that approximately 40-50% of mortalities among patients with chronic kidney disease are due to cardiovascular complications such as atherosclerosis, valvular calcification, myocardial infarction etc (Campean V et al, 2005). Particularly, elderly patients with the chronic kidney disease and ESRD are vulnerable for the development of vascular calcification and atherosclerosis revealing the link between kidney and heart diseases (Brancaccio D et al, 2005; Cullen P et al, 2005). In addition, conditions such as hypercalcemia, hyperphosphatemia and injuries to blood vessels promote arterial and cardiac valve calcification (Ribeiro S et al, 1998; Lomashvili K A et al, 2004).

kidney disease and end stage renal disease thus revealing casual association between kidney and heart diseases (Brancaccio D et al, 2005; McCullough P A et al, 2004; Higgins C L et al, 2005). Both the calcium phosphate and cholesterol crystals, identified as major pathological constituents prevalent in the atherosclerotic plaques, found to be frequently associated with each other (Guo W et al, 2000).

1. Preclinical Diagnosis of Atherosclerosis

Approximately, 40 million people in US are believed to be at risk of atherosclerosis without noticeable clinical symptoms and among them only 6 million are symptomatic (Calenoff E, 2000). This suggests that a large number of people with the atherosclerotic disease remain undiagnosed until they show life threatening symptoms such as heart attacks, stroke and other thromboembolic events. Identifying these individuals at the early stage is a challenging task due to the fact that atherosclerosis is a multi-factorial disease. In general, traditional risk factors such as age, gender, smoking, family history of heart attacks, elevated cholesterol levels, elevated blood glucose levels and elevated blood pressure are evaluated to identify suspected individuals with the atherosclerosis disease (Madhu S V et al, 2006). To complement this process, a number of analytical methods and tools (table 2) are used to diagnose both symptomatic and asymptomatic patients of the atherosclerosis (Naghavi et al, 2003).

TABLE 2

| # | Diagnostic method/tools | Specific aim |
|---|---|---|
| 1 | Cardiac catheterization | to locate the narrowing, occlusions, and other abnormalities of specific arteries |
| 2 | Computed tomography | to diagnose and analyze the presence of calcified nodules in the atherosclerotic plaques |
| 3 | X-ray diffraction | to identify and analyze the presence of crystalline contents of cholesterol and calcium phosphate |
| 4 | Optical microscopy and/or Raman spectroscopy | to semi-quantitative analysis of crystalline contents of cholesterol and calcium in the plaques |
| 5 | Doppler sonography | a special transducer is used to direct sound waves into a blood vessel to evaluate blood flow |
| 6 | MUGA/radionuclide angiography | Nuclear scan to see how the heart wall moves and how much blood is expelled with each heartbeat |
| 7 | Homocysteine | an amino acid marker in the blood that, at high levels, may damage the lining of the arterial wall |
| 8 | Lipoprotein (a) | a unique lipid, or fat, often elevated in people who have a family history of early-onset atherosclerosis |
| 9 | Small LDL particles | a predominance of small particles of LDL, or "bad," cholesterol that may form plaque on the arteries, causing atherosclerosis more easily than larger LDL particles |
| 10 | C-reactive protein | a trace protein that is a marker for inflammation and is associated with higher risk of heart attack and stroke |
| 11 | Electrocardiogram | is a test that measures the electrical activity of the heartbeat |

Abnormal metabolisms of both lipids and minerals play significant roles in the atherosclerotic processes. The accumulation of lipid, cholesterol and calcium-containing crystals in the atherosclerotic plaques and the clinical consequences of their exposure to the hemostasis factors during plaques rupture are life threatening. In addition to abnormal lipid and mineral metabolisms, inappropriate activation of blood coagulation cascade, vascular injury, thrombosis and endothelial dysfunctions attributed to early events of atherosclerotic plaque formation (Xiao Q et al, 1998). Dyslipidemia plays important roles in the pathogenesis of atherosclerosis and specifically, the low-density cholesterol particles are found to be associated with increased risk of coronary heart diseases (Hirano T et al, 2003; Festa A et al, 1998). Improved understanding on "plaque assembly instructions" would significantly help to develop novel therapeutics to treat atherosclerosis and its related cardiovascular diseases.

Atherosclerosis is a major cardiovascular complication and a leading cause of death among patients with the chronic Amyloid Protein Aggregation Diseases Alzheimer's Disease, Parkinson's Disease, and other amyloid protein aggregation diseases, are characterized by abnormal depositions of misfolded proteins in tissues and organs. These depositions often begin with the formation of insoluble aggregates consisting of amyloid proteins and/or peptides alone or in combination with certain metallic elements. Over the course of years, or even decades, amyloid aggregations can become pathogenic plaques. For example, Alzheimer's disease has been identified as a protein misfolding disease due to the accumulation of abnormally folded A-beta and tau proteins in the brain. Plaques are made up of small peptides, beta-amyloid (also written as A-beta or Aβ). A beta-amyloid is a fragment from a larger protein called amyloid precursor protein (APP). APP is critical to neuron growth, survival and post-injury repair. In Alzheimer's disease, an unknown process causes APP to be divided into smaller fragments by enzymes through proteolysis. One of these fragments is fibrils of beta-amyloid, which form clumps that deposit outside neurons in dense formations known as senile plaques. A better understanding of the assembly of amyloid plaque complexes and of the degree of their pathogenicity would enable the development of highly-targeted therapies.

Drug discovery in this area is currently hindered by the absence of a biochemical model system capable of reproducing the amyloid plaque assembly process. Although amyloid proteins generally lack significant primary sequence homology, their aggregates possess similar features, including high beta-sheet content, fibrillar morphology, relative insolubility, and protease resistance (Murphy R M, 2002). The present invention utilizes some common traits exhibited by amyloid plaques in vivo, including high beta-sheet content, fibrillar morphology, relative insolubility, and protease resistance to direct the in vitro assembly of aggregates of amyloid proteins (Murphy R M 2002). Our current understanding of the plaque-assembly process and related diseases is mostly based on knowledge derived from the interactions between soluble molecules mediated by their native conformations. Little is known about the role contributed by insoluble molecules. The insoluble aggregates acquire novel conformations when the soluble molecule transform into insoluble forms (McAllister C et al, 2005). Combining metals with amyloid peptides or proteins and adding layers of proteins to the resulting aggregates will help us to unravel the mystery of amyloid-plaque growth as well as the mechanism underlying their pathogenicity. Accordingly, one embodiment of the present invention takes advantage of certain types of templates or template complexes formed from aggregates of physiologically relevant organic or inorganic molecules, including proteins, lipids, minerals and other types of molecules, including amyloid proteins. The focus on aggregates as opposed to soluble molecules gives the present invention two valuable features: (1) it enables the recapitulation of physiologically relevant forms of amyloid proteins and (2) it enables the study or use of a wide range of plaque-like complexes associated with a diverse array of amyloid diseases. A non-exhaustive list of such amyloid diseases and associated proteins is contained in Table 3.

TABLE 3

Listing different amyloid diseases and the causative proteins/peptides

| # | Disease | Protein/Peptide | Localization |
|---|---|---|---|
| 1 | Alzheimer's | Amyloid β-protein | Extracellular plaques in brain tissues and neuronal cytoplasm |
| 2 | Parkinson's | A-synuclein | Neuronal cytoplasm |
| 3 | Frontotemporal dementia with parkinsonism | Tau | Tangles in neuronal cytoplasm |
| 4 | Mad cow disease or Spongiform encephalopathies | Prion protein | Extracellular plaques with oligomers inside and outside the neurons |
| 5 | Huntington's | Long glutamine stretches within certain proteins | Neuronal nuclei and cytoplasm |
| 6 | Amyotrophic lateral sclerosis | Superoxide dismutase | Neuronal cytoplasm |
| 7 | Type II diabetes | Amylin | Extracellular |
| 8 | Cerebral hemorrhage with amyloidosis | Amyloid β-peptide or cystatin C | Extracellular brain tissues |
| 9 | Atrial amyloidoses | Atrial natriuretic factor | Extracellular |
| 10 | Medullary carcinoma of the thyroid | Procalcitonin | Extracellular |
| 11 | Hemodialysis related amyloidosis | $B_2$-Microglobulin | Extracellular |
| 12 | Senile systemic amyloidosis | Transthyretin | Extracellular |
| 13 | Insulin-related amyloid | Full-length insulin | Extracellular |
| 14 | Primary systemic amyloidosis | Light chain immunoglobulin | Extracellular |
| 15 | Fibrinogen a-chain amyloidosis | Fibrinogen a-chain variants | Extracellular |
| 16 | Secondary systemic amyloidosis | Fragments of serum amyloid A protein | Extracellular |
| 17 | Lysozyme amyloidosis | Full-length mutant lysozyme | Extracellular |
| 18 | Familial amyloidotic polyneuropathy II | Fragments of apolipoprotein A-1 | Extracellular |

II. Assembly of Multi-Subunit Complexes Resembling Plaques Involved in Diseases

The present invention generally relates to a plaque engineering technology (PET) method that has the advantage both of enabling rapid plaque assembly and of permitting the study of insoluble, native forms of plaques. The present invention also comprises the composition of in-vitro assembled plaques and plaque-like complexes and kits comprising such complexes that may be of diagnostic and therapeutic value. In addition the present invention comprises animal models for the study of in vitro assembled plaque-like complexes in vivo.

The present invention provides methods of assembling multi-subunit complexes mimicking disease-associated plaques such as atherosclerotic or amyloid plaques utilizing plaque engineering technology (PET). The innovative PET drug discovery platform is invented to mimic different stages of the in vivo atherosclerotic plaques assembly processes such as initiation, progression, maturation, thrombosis and thrombolysis in a few hours.

The assembly of PET platforms comprises the development of a novel cyclic plaque assembly method, for in vitro assembly of plaque like complexes, and discovery of a novel mechanism of blood platelet independent thrombosis of plaque complexes. Screening of known and unknown drugs molecules against the in vitro plaques assembly processes can lead to identification of drug candidates that inhibit different stages of the in vitro plaques assembling process. Such drug candidate may be a promising drug for treating patients with plaque-associated diseases including but not limited to advanced atherosclerosis, chronic kidney disease, end stage renal disease and hemodialysis.

In vitro plaques assembly process using the PET platform may reveal novel biochemical interactions among cholesterol, lipid, proteins, calcium, minerals, blood coagulation factors and fibrinolytic factors. Compounds that block these interactions would be successful leads to plaque-associated diseases such as atherosclerosis related cardiovascular diseases and plaque-related neurological diseases. The current invention provides powerful, innovative methods to rapidly discover and develop novel therapeutic modalities to treat atherosclerosis and other plaques related diseases.

This PET technology uses a novel cyclic plaque assembly method (CPA) to assemble and dissolve complex structures by applying nanotechnology approaches. The multiple proteins layering method inherent to CPA may permit discovery of novel mechanisms of plaque assembly and may enable the evaluation of the pathogenicity of plaques of varying composition. The CPA uses as building blocks materials normally present in advanced atherosclerotic plaques, including lipids, proteins, cholesterol, calcium, endothelial cells, bacteria, and minerals. These components are present in plaques in soluble insoluble and crystalline forms. When soluble molecules transition into insoluble aggregates, they may undergo new conformations (McAllister C et al, 2005). The advantage of the CPA system is that it permits the study of insoluble aggregates in their native conformations. In addition, it permits analysis of binding between different insoluble aggregates.

Notably, the PET platform permits in vitro assemble of plaque like complexes in four steps that imitate in vivo atherosclerotic processes such as initiation, progression, thrombosis and thrombolysis (FIG. 1). The four step process of the PET platform reproduces the initiation, progression, thrombosis and thrombolysis stages of in vivo atherosclerotic plaques developments.

In one aspect, the present invention comprises a method of assembling in vitro multi-subunit complexes for use as a biochemical platform. In certain embodiments, the method comprises a first step of producing template complex after converting soluble molecules into insoluble aggregates and then binding additional soluble molecules to the insoluble aggregates. Such additional soluble molecules may comprise one or more: proteins, lipids, or carbohydrates. Such method may further comprise the "addition step" of adding at least one substantially-purified protein, lipid, or carbohydrate to the template, wherein such protein, lipid or carbohydrate has been pre-screened for binding to the insoluble aggregate template. A further step may be incubating such template and substantially-purified protein, lipid, or carbohydrate at an elevated temperature to form a template complex. The method further comprises a removal step comprising washing of the template complex to remove the non-binding substantially-purified protein, lipid, or carbohydrate. A further step may be repeating the addition step described above with additional such substantially-purified protein, lipid, or carbohydrates, and repeating the removal step multiple times to form a multi-subunit complex. The method further includes isolating the multi-subunit complex after the cyclic addition and removal steps to obtain purified multi-subunit complex that resembles a plaque involved in a disease listed in Table 1.

A. Formation of Template

One aspect of the present invention provides a method of assembling a multi-subunit complex, wherein the first step includes converting soluble molecules into an insoluble aggregate to form a template. The soluble molecule may be a protein, a lipid, cholesterol or a carbohydrate. The soluble molecule may be organic or inorganic. One or more soluble molecules may be used to form the insoluble template.

In certain embodiments, the soluble organic molecules include one or more of the following: protein, protein derivative, cholesterol, cholesterol derivative, lipid, or lipid derivative. In further embodiments, the soluble molecules include but are not limited to calcium chloride, sodium phosphate, sodium pyrophosphate, oxalic acid, sodium bicarbonate, or iron sulfate. The insoluble aggregate may be composed of one or more of the following: calcium oxalate, calcium phosphate, cholesterol, lipid, iron phosphate, A-beta40-42, Synuclein, prion, Amylin, Tau, ammonium phosphate, phospholipids, cholesterol crystals, palmitic anhydrate, Serum Amyloid A, Beta Microglobulin, lysozyme, insulin, or super dioxide dismutase. In certain embodiments, the method comprises the use of insoluble aggregates that have been synthesized before the running of the CPA. In certain embodiments, the synthesis of the insoluble aggregate may occur in a remote location.

In some embodiments, the method includes a mixture of insoluble aggregates that form a hybrid insoluble aggregate. Examples of such hybrid insoluble aggregates include but are not limited to calcium-phosphate (CP)-lipids, calcium oxalate (CO)-lipids, CP-cholesterol (Chl), or CP-Chl-lipids or Chl-lipids.

In certain embodiments, the soluble proteins used to form the template include but are not limited to human blood coagulation factor prothrombin, factor H, complement factor C5, complement factor C3, complement factor C4, complement factor C1, protein S, plasminogen activator inhibitor 1, plasminogen, human FBN or human serum albumin.

In other embodiments, the components used to form the template or insoluble aggregates are components often found in mature amyloid plaques. Such components include but are not limited to amyloid peptides, proteins, metals, endothelial cells, minerals, lipids, carbohydrates or their derivatives. In a preferred embodiment, the soluble molecules are amyloid proteins, peptides or oligomers combined with one or more metals such as iron, copper or zinc. Such embodiments enable assessing the role of metals in the formation of amyloid aggregates. In another preferred embodiment, the soluble molecule is an amyloid protein/peptide abeta40 and/or abeta42 that are loaded with iron or an iron-derived compound. In other embodiments, the soluble molecule(s) is/are one or more of the following: abeta40, abeta42, prion peptides, copper sulfate ($CuSO_4$), Zinc Chloride ($ZnCl_2$), aluminum chloride ($AlCl_3$), iron III sulfate, sodium acetate, sodium butyrate, sodium bicarbonate, sodium phosphate, magnesium sulfate, sodium citrate, DNA, RNA, or other soluble molecules that are pre-screened for binding to the insoluble aggregate or template. In another embodiment, the soluble molecules are present in cellular extract.

An insoluble aggregate resulting from the combining of one or more soluble elements serves as the template for the cyclic plaque assembly (CPA) system described herein. Examples of such insoluble aggregate include, but are not limited to, abeta40, abeta42, iron-abeta40, iron-abeta42, prion, iron, and iron-phosphate. Pre-formed insoluble aggregates are also obtainable before use in the assay.

In general, the present invention is directed at a method of assembling multi-subunit complexes in vitro. In one embodiment, the method is a step-wise process involving the sequential addition of components to a template to enable formation of amyloid multi-subunit plaque complexes. The first step involves converting soluble amyloid proteins, peptides, organic molecules or inorganic molecules into insoluble aggregates to form a template. The first step may also involve obtaining a pre-formed template or plaque initiation complex.

B. Cyclic Plaque Assembly (CPA) and Formation of Template Complex

The second component of the method of assembling a multi-subunit complex as described herein includes cyclic plaque assembly and formation of a template complex. In one aspect, the present invention discloses the in vitro assembly of atherosclerotic plaque-like complexes using lipids, cholesterol, proteins, and carbohydrates, as a biochemical platform for identifying therapeutics for diseases including but not limited to atherosclerosis and atherothrombosis. In another aspect, the present invention discloses the in vitro assembly of amyloid plaque-like complexes by using amyloid peptides, proteins, and/or metals, as a biochemical platform for identifying therapeutics for amyloid plaque related diseases.

The method disclosed herein utilizes cyclic plaque assembly (CPA), which is a mechanism-based biochemical model system enabling rapid in vitro assembly of plaque-like complexes in a very short period of time (e.g. a few hours). The CPA method is based on both "bottom to top" and "top to bottom" nanotechnology principles, involving the assembly and disassembly of plaque-like complexes. In this system, the insoluble aggregate generated in step 1 as described hereinabove, is used as a template for iterative binding with various proteins, lipids, carbohydrates, molecules or components of a cellular extract, to form a template complex that resembles a physiological or pathological plaque present in vivo, such as an atherosclerotic plaque or an amyloid plaque. Individual or pools of molecules involved in critical biochemical pathways, such as blood coagulation, complement activation, or fibrinolysis are then introduced to the insoluble aggregate on a step-wise basis over many cycles.

Another aspect of the invention is the use of metals in forming the multi-subunit complex; in particular, the use of metals in the formation of insoluble aggregates for the formation of physiologically relevant amyloid plaques or plaque-like complexes. Metals may play a role both in facilitating protein-aggregate formation as well as in the production of reactive oxygen species (Maynard C J, et al, 2005). Metals such as Zn (II), Cu (II) and Fe (II) make complexes with abeta42 peptides, a prominent amyloid peptide implicated in the origin of Alzheimer's disease (AD), and accelerates the formation of aggregates (Garzon-Rodriguez et al, 1999). Also, the in vivo concentration of metals such as iron (Fe) (~1 mM), copper (Cu) and zinc (Zn) (~0.4 mM) may be elevated in the brain tissues of both normal-aging individuals and patients with AD (Smith, M A et al, 1997; Lovell, M A et al, 1998). Metals and their by-products might form complexes with a range of biological molecules, such as proteins, nucleic acids and other components, so as to compromise the natural functions of the biological molecules (Jennette K W, 1981). For example, the presence of even trace amounts of metals (0.8 μM) in solution suffices to induce amyloid peptides to form insoluble aggregates (Huang X et al, 2004; Maynard C J et al, 2005). Another amyloid peptide, prion peptide, responsible for the origin of prion disease also forms complexes with metals such as Cu (II), manganese (II) and Zn (II) (Gaggelli E, et al, 2005). The proteins and peptides capable of binding to the metals undergo certain conformational changes in their structure, as is in the case of alpha-synuclein (Uversky V N 2001). Further support for the role of metals in the formation of amyloid plaques or plaque-like complexes is found in the link between known disorders of metals, particularly of iron metabolism, and plaque-associated diseases. Impaired iron metabolism is associated with the development of devastating human diseases such as Friedreich's ataxia, Sideroblastic anemia, Aceruloplasminemia and neurodegenerative diseases including Alzheimer's disease (AD), Huntington's disease (HD) and Parkinson's disease (PD) (Roy C N et al, 2001; Richardson D R, 2004). In addition, iron accumulation in human arterial lesions is considered to be a contributing factor in the development and progression of cardiovascular diseases such as atherosclerosis (Ong W Y and Halliwell B, 2004; Ong W Y and Farooqui A A, 2005; Stadler N, et al, 2004). Iron also plays a significant role in the pathogenesis of AD and PD diseases by accelerating aggregation of Abeta42 peptides and asynuclein (Garzon-Rodriguez et al, 1999; Mandel S et al, 2004; Tannir E L et al, 2005).

The present invention comprises the further step of combining the template, or pre-formed template, with cell extracts or at least one substantially-purified protein, lipid or carbohydrate that has been pre-screened to test for binding to the template complex. Still another step involves incubating the template with cellular extract or at least one substantially-purified protein, lipid, or carbohydrate at an elevated temperature to form a template complex. Details are provided in Examples 5-8. The template complex is washed to remove the non-binding cell extract or substantially purified protein, lipid, or carbohydrate. The steps of adding cellular extract or at least one substantially-purified protein, lipid, or carbohydrate to the template complex followed by washing the non-binding cell extract or substantially purified protein, lipid or carbohydrate, is repeated over at least one cycle. Finally, the template complex is isolated by washing or removing the final cell extract or at-least-one added substantially-purified protein, lipid, or carbohydrate.

In some embodiments, the template complex is treated with a member of the plasminogen cascade in order to simulate a physiological process. In some embodiments, the template complex may or may not be treated with one or more of the following either simultaneously or sequentially: PLG, chymotrypsin, trypsin, proteinase K, urokinase, and/or other serine protease. In some embodiments, one or more of the following: PLG, BSA, or cytoplasmic extract proteins are added to the template complex over the course of several cycles.

In some embodiments, the present invention provides a method of identifying molecules that bind to the insoluble aggregate or template. A complex mixture of proteins or other molecules are combined with the template(s) or insoluble molecules and then subjected to CPA to form a multi-subunit complex. Then, the multi-subunit complex is evaluated to determine which molecules in the complex mixture bound to the template. In certain preferred embodiments, the complex mixture is a cell extract. In other embodiments, the complex mixture is a mixture of purified or partially purified proteins.

Soluble molecules that bind to the insoluble aggregate may be identified through known interactions. Although there appears to be no shared homology in the secondary structure of known proteins that bind the insoluble amyloid aggregates or templates, there may be some exposed domains, surface loops or residues in tertiary structure of proteins or other molecules, and correspondingly predictable binding or interactive behavior, that may be exploited to identify soluble molecules that bind to the insoluble amyloid aggregate or template. For example, the amino acid histidine has known affinity for metals. In addition, lysine, another amino acid, may interact specifically and non-specifically with proteins. Common conformations among insoluble aggregates may be predicted, and may be responsible for non-covalent interactions, such as hydrophobic interactions, hydrogen, Van der Waal, or electrostatic attractions, between the insoluble amyloid aggregates or templates and soluble molecules. Examples of substantially-purified proteins that may be added to the template to form a template complex include but are not limited to: bovine serum albumin (BSA), Factor IX, plasminogen (PLG), plasminogen activator inhibitor I (PAI-1), blood coagulation factor II (FII), Factor IX (FIX), protein S, complement factor D, complement factor B, recombinant human hepatocyte growth factor and cell extracts (CE).

In certain preferred embodiments, the in-vitro assembled plaque or plaque-like complex resembles atherosclerotic plaque or a plaque associated with an atherosclerotic disease-like process. In other embodiments, the template complex resembles a plaque associated with amyloid diseases or disease-like processes. Examples of plaque related diseases include but are not limited to atherosclerosis, atherothrombosis, coronary artery disease, Alzheimer's disease, Parkinson's disease, mad cow disease or spongiform encephalopathy, Huntington's disease, cerebral hemorrhage with amyloidosis, atrial amyloidosis, hemodialysis-related amyloidosis, senile systemic amyloidosis, systemic amyloidosis, primary systemic amyloidosis, secondary systemic amyloidosis, fibrinogen α-chain amyloidosis, lysozyme amyloidosis, dialysis-related amyloidosis, lysozyme amyloidosis, insulin-related amyloidosis, familial amyloidotic polyneuropathy II, Type II diabetes, dementia, medullary carcinoma of the thyroid, or amyotrophic lateral sclerosis.

The present invention is also directed at assembling complexes in vitro using the iterative process of CPA. In certain embodiments, proteins capable of binding to an iron-loaded abeta42 template are added step-wise to the templates for up to five cycles. In certain embodiments, CPA is also repeated using templates with new combinations of proteins to examine whether the binding of proteins to the template is an ordered versus a random process. Some embodiments also include proteins such as complement factor B, plasminogen activator inhibitor 1 (PAI-1) and hepatocyte growth factor (HGF), given that these proteins are shown to be present in brain tissues or plaques isolated from Alzheimer's patients (Fenton H, et al, 1998; Strohmeyer, R, 2000; Hino H, 2001). The present invention also provides a way of determining whether the presence of metal such as iron is necessary for plaque formation.

The multiple proteins layer formation method extends the CPA method in order to assemble multiple layers of proteins using insoluble aggregate as the template. A minimum of two to six cycles of binding is required in order to assemble multi-subunit complexes resembling mature in vivo plaques. In one embodiment, the assembly of in vitro amyloid plaques using the CPA method reveals that a wide range of proteins from cell extracts bind to the iron-loaded amyloid template. The conformation of these insoluble templates appear to be favorable for non-specific binding of these proteins that might lead to changes in the conformation of the proteins attached to these complexes. In addition, upon binding to the insoluble templates or materials, the cryptic domains of the attached proteins might be exposed due to their conformational changes. The exposed domains or residues of these complexes bound proteins may allow non-specific binding of other proteins, carbohydrates and lipids in a template independent mechanism contributing to the further growth of the amyloid plaques.

In other embodiments, proteins involved in the plasminogen (PLG) cascade, particularly PLG, and PAI-1, are used in the multi-subunit complex assembly processes and are sandwiched between amyloid template and protein layers in order to probe their functional and conformational properties. In certain embodiments, iron-loaded abeta42 aggregates are subjected to multiple protein layering involving three different sets of components. In one embodiment of the invention, both PLG and bovine serum albumin (BSA) proteins are mixed with the aggregates for complex formation. In a second embodiment, both PLG and BSA proteins are mixed with the aggregates in the first cycle but then the resulting complexes are mixed with CE proteins for another cycle of binding. In a third embodiment, the CE proteins are mixed with the templates for complex formation followed by another cycle of binding of the resulting complexes with both the PLG and BSA proteins. All three of these complexes are treated with either urokinase-type plasminogen activator (u-PA) or tissue-type plasminogen activator (t-PA) to examine activation of the PLG attached to these complexes. In a further embodiment, present invention is used to evaluate the susceptibility of different types of template complexes-bound to PLG to increasing concentrations of u-PA. In yet another embodiment, the conformational and functional states of PAI-1, an inhibitor of PLG activators, are evaluated when it is bound to various complexes.

C. Thrombosis

In certain embodiments, the present invention further includes a method of assembly of an in-vitro thrombotic complex for use as a biochemical platform. Such thrombotic complex may be substantially free of blood platelet cells. The method may comprise the steps outlined herein for the assembly of in-vitro multisubunit complexes with the further step of inducing thrombosis by adding blood coagulation factors. The blood coagulation factors may be supplied in whole or in part by biological samples. Examples of the blood coagulation factors that may be used in this invention include fibrinogen (FBN) and/or FII without excluding any other blood coagulation factor. In some embodiments, the biological sample is blood, plasma, serum, urine, or tissue from a subject. The present invention may also comprise a composition of such in-vitro assembled thrombotic complexes.

D. Thrombolysis/Dissolution of Plaque

The present invention also provides a method of testing and screening for agents that induce thrombolysis or dissolution of the multi-subunit complex described herein. Thrombolysis normally refers to the breakdown of blood clots by pharmacological means. It works by stimulating fibrinolysis by plasmin through infusion of analogs of tissue plasminogen activator.

In another aspect, the present invention provides a method of evaluating the susceptibility of a multi-subunit complex or components of the multi-subunit complex to degradation by various molecules, for example, proteases. In amyloid plaque related diseases, amyloid fibrils generally share the common feature of being resistant to the activity of proteases (Murphy R M, 2002; Castilla J, 2005). The present invention aids in evaluating not only the susceptibility of amyloid aggregates to proteases, but also the susceptibility of the proteins which are attached to the complexes. In one embodiment, a panel of serine proteases is employed to test the susceptibility to proteolytic degradation of proteins attached to template complexes. In another embodiment, iron-loaded abeta42 aggregates are mixed with cell extracts (CE) proteins. In another embodiment, serine proteases are tested for their effect on the multi-subunit complexes. In yet another embodiment, the serine proteases include but are not limited to plasmin, chymotrypsin, trypsin, proteinase K, urokinase plasminogen activator (u-PA), or tissue plasminogen activator (t-PA). In other embodiments, the serine proteases are used to evaluate the conformation of the proteins attached to the complexes.

Such proteins may be one or more of the serine proteases mentioned above. In another embodiment, the proteins are one or more serine protease activators. In still another embodiment, the proteins are one or more serine protease inhibitors. Examples of such proteins include but are not limited to PLG, u-PA, t-PA or PAI-1.

III. Multi-Subunit Complex

In one embodiment, the invention discloses an in vitro assembled multi-subunit complex, the complex formed by employing an insoluble chemical aggregate as a template for cyclic protein, lipid or carbohydrate binding, adding at least one substantially purified protein, lipid or carbohydrate to the template, wherein the substantially purified protein, lipid or carbohydrate has been pre-screened to test for binding to the insoluble aggregate template, incubating the template and substantially purified protein, lipid or carbohydrate at an elevated temperature to form a template complex, washing the template complex to remove the non-binding substantially purified protein, lipid or carbohydrate; adding at least one additional substantially purified protein, lipid or carbohydrate to the template complex, wherein the additional substantially purified protein, lipid or carbohydrate has been pre-screened to test for binding to the template complex; repeating the washing and protein addition steps with additional, pre-screened and identified proteins, lipids or carbohydrates that bind to the template complex after each template complex formation cycling step, and isolating the template complex after the final at least one substantially purified protein, lipid or carbohydrate is added by removing the added substantially purified proteins, lipids or carbohydrates from the template complex.

In another embodiment, the present invention provides an in vitro-assembled thrombotic complex which is substantially free of blood platelet cells, the complex formed by, converting soluble organic or inorganic molecules into insoluble aggregates, wherein the insoluble aggregates form a template for binding of soluble molecules including proteins, lipids or carbohydrates to form a template complex, adding at least one substantially purified protein, lipid or carbohydrate to the template, wherein the substantially purified protein, lipid or carbohydrate has been pre-screened to test for binding to the insoluble aggregate template, incubating the template and substantially purified protein at an elevated temperature to form a template complex, washing the template complex to remove the non-binding substantially purified protein, lipid or carbohydrate, adding at least one additional substantially purified protein, lipid or carbohydrate to the template complex, wherein the additional substantially purified protein, lipid or carbohydrate has been pre-screened to test for binding to the template complex, repeating the washing and protein, lipid or carbohydrate addition steps with additional, pre-screened and identified proteins, lipids or carbohydrates that bind to the template complex after each template complex formation cycling step, isolating the template complex after the final at least one substantially purified protein, lipid or carbohydrate is added by removing the added substantially purified proteins, lipids or carbohydrates from the template complex, and inducing thrombosis of the insoluble aggregates by adding blood coagulation factors.

In yet another embodiment of the present invention, there is provided an in vitro assembled multi-subunit amyloid complex, the complex formed by generating or obtaining a substantially purified amyloid template, wherein the amyloid template comprises an insoluble aggregate of amyloid peptides, organic molecules or inorganic molecules; adding at least one cell extract or substantially purified protein, lipid or carbohydrate to the template complex, wherein the cell extract or substantially purified protein, lipid or carbohydrate has been pre-screened to test for binding to the insoluble aggregate template; incubating the template and cell extract or substantially purified protein, lipid or carbohydrate at an elevated temperature to form a template complex; washing the template complex to remove the non-binding cell extract or substantially purified protein, lipid or carbohydrate; adding at least one additional cell extract or substantially purified protein, lipid or carbohydrate to the template-complex, wherein the additional cell extract or substantially purified protein, lipid or carbohydrate has been pre-screened to test for binding to the template complex; repeating the washing and cell extract or protein, lipid or carbohydrate addition steps with additional cell extract or pre-screened and identified proteins, lipids or carbohydrates that bind to the template complex after each template complex formation cycling step; and isolating the template complex after the final cell extract or at least one substantially purified protein, lipid or carbohydrate is added by removing the added substantially purified proteins, lipids or carbohydrates from the template complex.

In still another embodiment, the present invention provides a pharmaceutical composition comprising a multi-subunit complex described herein and a pharmaceutically acceptable carrier. Such pharmaceutical compositions can be used as a vaccine to treat or prevent plaque related or plaque induced diseases including but not limited to atherosclerosis, atherothrombosis, coronary artery disease, Alzheimer's disease, Parkinson's disease, mad cow disease or spongiform encephalopathy, Huntington's disease, cerebral hemorrhage with amyloidosis, atrial amyloidosis, hemodialysis-related amyloidosis, senile systemic amyloidosis, systemic amyloidosis, primary systemic amyloidosis, secondary systemic amyloidosis, fibrinogen α-chain amyloidosis, lysozyme amyloidosis, dialysis-related amyloidosis, lysozyme amyloidosis, insulin-related amyloidosis, familial amyloidotic polyneuropathy II, Type II diabetes, dementia, medullary carcinoma of the thyroid, or amyotrophic lateral sclerosis.

IV. In Vivo Animal Model

Yet another embodiment comprises a method for developing an animal model of plaque-related disease comprising introducing to an animal one or more of the following: (1) an in vitro assembled insoluble aggregate comprising two or more: cholesterol, lipid and calcium; or (2) an in vitro-assembled multi-subunit complex described herein. The method may comprise introducing a first in vitro assembled insoluble aggregate or a first in vitro-assembled multi-subunit complex, followed by introducing a second in vitro assembled insoluble aggregate or a second in vitro-assembled multi-subunit complex. In one embodiment, the method comprises multiple introductions. In another embodiment, the in vitro assembled insoluble aggregate is a hybrid insoluble aggregate that is generated by mixing two or more: a lipid aggregate, a cholesterol aggregate, and a calcium-containing aggregate. The calcium-containing aggregate may be composed of one or more of the following: calcium phosphate (CP), calcium pyrophosphate (CPP), calcium chloride (CC), or calcium oxalate (CO). In some aspects, the hybrid insoluble aggregate comprises CP, cholesterol (Chl) and lipid. In other aspects the hybrid insoluble aggregate comprises two or more: CP, cholesterol and lipid, e.g., CP and lipid, CO and lipid, CP and Chl, CO and Chl, Chl and lipid, and the like.

The method of the present invention provides introducing into the animal in vitro assembled insoluble aggregate or the in vitro assembled multi-subunit complex via intra-peritoneal, subcutaneous, or intravenous routes. In some embodiments, the method further comprises monitoring the animal for the development of a disease in said animal. Such methods include, but are not limited to, the injection, infusion or placement by other means, of the assembled multi-subunit complex formed in vitro, into brain or other tissues of an animal. Such animal models can be used to identify anti-plaque therapeutics for the treatment of disease including but not limited to inflammation, chronic inflammation, a plaque-related disease, a plaque-related disorder or atherosclerosis. In some embodiments, the method further comprises the step of monitoring the animal for the presence of the in-vitro assembled multi-subunit complex, or fragment thereof, or for the presence of the in vitro-assembled insoluble aggregate, in the system of said animal. In some aspects, the monitoring comprises detecting with a device the presence of the in vitro assembled insoluble aggregate or the in vitro assembled multi-subunit complex, or fragment thereof, in the system of said animal. In one embodiment, the in vitro assembled insoluble aggregate or the in vitro assembled multi-subunit complex, or fragment thereof, is or has been labeled with a fluorophore, magnetic resonance imaging contrast reagent, positron emitting reagent, X-ray contrast reagent, radionuclide, or luminescent molecule; and wherein the monitoring comprises detecting the presence of the labeled in vitro assembled insoluble aggregate or the labeled in vitro assembled multi-subunit complex, or fragment thereof. In another embodiment, the fluorophore is a near infrared fluorophore or an infrared fluorophore; and the device is a fluorometer, a magnetic resonance imaging machine, a positron emission tomography machine, an X-ray machine, a computerized tomography machine, a gamma counter, or a luminescent imager. In other embodiments, the method also comprises testing blood or tissue sample for antibodies against the in vitro assembled insoluble aggregate or the in vitro assembled multi-subunit complex, or fragment thereof, or testing blood or tissue samples for markers (e.g., cytokines) of plaque induced chronic inflammation. In further embodiments, the method comprises histochemical analysis of tissue, such as cardiovascular tissue; and, in some aspects, the histochemical analysis comprises staining the tissue with orange red, hemotoxilin, eosin, Von Kosa stain, or alizarin red.

The present invention also embodies an animal for drug development, wherein the animal has previously been treated with (1) an in vitro assembled complex or insoluble aggregate comprising two or more: cholesterol, lipid and calcium; or (2) an in vitro-assembled multi-subunit complex described herein. In some aspects, the in vitro assembled insoluble aggregate comprises a hybrid insoluble aggregate that was generated by mixing a lipid aggregate or cholesterol aggregate with a calcium-containing aggregate. In some aspects, the calcium-containing aggregate comprises calcium phosphate, calcium pyrophosphate, calcium chloride, or calcium oxalate. In some aspects, the calcium-containing aggregate comprises one or more: calcium phosphate (CP), calcium pyrophosphate (CPP), calcium chloride (CC), or calcium oxalate (CO). In some aspects, the hybrid-insoluble aggregate comprises CP, cholesterol (Chl) and lipid. In other aspects the hybrid insoluble aggregate comprises two or more: CP, cholesterol and lipid, e.g., CP and lipid, CO and lipid, CP and Chl, CO and Chl, Chl and lipid, and the like. In some aspects, the disclosure provides an animal for drug development in which the treatment with the in vitro assembled multi-subunit complex results in, or contributes to, the formation or deposition of a plaque or plaque-like complex in the system of the animal. In one embodiment, the in vitro assembled multi-subunit complex introduced to the animal, or developed in the animal, resembles an atherosclerotic plaque. In another embodiment, the in vitro assembled multi-subunit complex introduced to the animal, or developed in the animal, resembles an amyloid plaque. In some embodiments, this disclosure provides an animal for drug development, wherein the in vitro assembled multi-subunit complex is introduced to the system of the animal via intra-peritoneal, subcutaneous, or intravenous routes. In further embodiments, the animal exhibits one or more signs or symptoms of a plaque-related disease. In some aspects, the treatment with the in vitro assembled multi-subunit complex results in, or contributes to, the development of one or more signs or pathological symptoms associated with a plaque-related disease including but not limited to atherosclerosis, atherothrombosis, coronary artery disease, Alzheimer's disease, Parkinson's disease, mad cow disease or spongiform encephalopathy, Huntington's disease, cerebral hemorrhage with amyloidosis, atrial amyloidosis, hemodialysis-related amyloidosis, senile systemic amyloidosis, systemic amyloidosis, primary systemic amyloidosis, secondary systemic amyloidosis, fibrinogen α-chain amyloidosis, lysozyme amyloidosis, dialysis-related amyloidosis, lysozyme amyloidosis, insulin-related amyloidosis, familial amyloidotic polyneuropathy II, Type II diabetes, dementia, medullary carcinoma of the thyroid, or amyotrophic lateral sclerosis, in the animal for drug development. The animal used in the present invention may be a mouse, rat, pig, horse, non-human primate, guinea pig, hamster, chicken, frog, cat, dog, sheep, or cow.

V. Method of Use

A. Screening for Anti-Plaque Agents that Prevent, Reduce, or Inhibit Formation of Multi-Subunit Complex or Promote Disruption or Elimination of the Multi-Subunit Complex In Vitro and In Vivo The present invention provides screening the in vitro assembled complexes described herein for drug, chemical, or biological compounds that prevent, reduce, or inhibit formation of multi-subunit complex or promote disruption or elimination of the multi-subunit complex in vitro and in vivo.

In one embodiment, the invention involves the use of the method disclosed herein to screen agents for the inhibition or stimulation of the in vitro formation of the atherosclerotic plaque or plaque-like complexes. The present invention describes a simple and noninvasive diagnosis method developed based on the detection and profiling of antibodies as serum markers of atherosclerosis. This multiplexing method involves assembly of different types of in vitro atherosclerotic plaques followed by screening of biological samples such as human plasma and serum samples for identification and measurement of plaques specific antibody titers.

In another embodiment, the invention involves the use of the method disclosed herein to screen agents for the inhibition or stimulation of the in vitro formation of the amyloid plaque or plaque-like complexes. As such, agents including but not limited to chemical compounds, small molecule compounds, therapeutic drugs, biological molecules, oligomers, ligands, proteins, antibodies or other components, capable of binding the in vitro assembled atherosclerotic or amyloid plaque-like complexes, preventing their assembly, disassembling these complexes once already formed, or reducing their pathogenic properties, are tested for their potential as therapeutic leads for diagnosing, preventing, treating, and/or curing amyloid plaque diseases. Since the methods or processes disclosed herein are capable of isolating the steps of plaque assembly, anti-plaque agents targeting different stages of plaque development are also capable of being identified. The term "anti-plaque agents" and "anti-plaque therapeutics are used interchangeably herein and refer to compounds or drugs which are effective in a) dissolving, inhibiting or disrupting the architecture, or structure of a multi-subunit complex described herein, and/or b) inhibiting, preventing, or alleviating the detrimental effects that the complex or plaque may have on other cells, tissues or organs.

In one embodiment, the multi-subunit complexes or insoluble components thereof are labeled. Appropriate labeling agents include, but are not limited to, a radiolabel, an enzyme label, a fluorescent label, a chemiluminescent label, or an antigen label. Such screening methods can be employed using liquid phase and/or solid phase assays as described herein and appropriate detection systems such as a scintillation counter, gamma counter, spectrophotometer, fluorometer or nephelometer.

In another embodiment, to utilize multi-subunit complexes resembling atherosclerotic plaques or amyloid plaques for screening methods to identify anti-plaque therapeutic agents in vitro, agents which inhibit, disrupt or eliminate the complexes can be identified utilizing polarization microscopy. In one example, multi-subunit complexes resembling amyloid plaque will first be formed in vitro which demonstrate a typical maltese-cross pattern following staining with Congo red and when viewed under polarized light. Following incubation with a test compound (at the appropriate dosage and incubation time to be determined empirically), the complexes will be viewed under polarization microscopy to determine if a given compound or agent is capable of inhibition, disruption or elimination of the multi-subunit complex resembling an amyloid plaque such that there is a loss of congophilia and/or maltese-cross formation. Such compounds initially identified by such polarization microscopy techniques can be further analyzed in secondary or tertiary assays utilizing transmission and/or scanning electron microscopy methods to confirm plaque inhibition, disruption or elimination.

In yet another preferred embodiment, agents which inhibit, disrupt the structure (i.e. size and/or diameter) of the spherical amyloid plaques can be identified using methodologies involving a cell sorter. In such assays, multi-subunit complexes resembling amyloid plaques formed in vitro can be placed through a cell sorter to determine the average diameter (and range of diameters) of such plaques. These plaques can then be incubated with a variety of compounds or agents (at a given dosage and incubation time to be determined empirically) and then be placed through the cell sorter again to determine if the given compound was effective in breaking apart to disrupting the size (and hence diameter) of such complexes/plaques.

In one embodiment, the agent is an antibody-based molecule including antibody, any fragment thereof, or a labeled antibody. In another embodiment, the agent is a small molecule. In another embodiment, the agent is an RNA-based molecule including but not limited to siRNA, shRNA, and microRNA. The agent may be useful to inhibit a plaque-related disease or disease-like process. In one embodiment, the disease is atherosclerosis or atherothrombosis. In another embodiment, the disease is an amyloid disease including but not limited to Alzheimer's disease, Parkinson's disease, mad cow disease or spongiform encephalopathy, Huntington's disease, atrial amyloidosis, systemic amyloidosis, dialysis-related amyloidosis, hemodialysis-related amyloidosis, fibrinogen α-chain amyloidosis, lysozyme amyloidosis, insulin-related amyloidosis, amyotrophic lateral sclerosis, or familial amyloidotic polyneuropathy II. In some embodiments, the agent is tetracycline hydrochloride (PGN27) or any derivative or conjugates or analog thereof. In other embodiments, PGN27 is modified for optimal efficiency. In further embodiments, such agent is u-PA (PGN54) and its variants, a component of the plasminogen cascade. The tetracycline derivative is selected from 6-demethyltetracycline, bromotetracycline, chlorotetracycline, clomocycline, demeclocycline, doxycycline, lymecycline, meclocycline, methacycline, minocycline, oxytetracycline, rolitetracycline, tetracycline, sancycline, 5a,6-anhydrotetracycline, DDA-tetracycline, dactylocyclinone and 8-methoxychlorotetracycline. The tetracycline derivative also includes the optical isomers of the compounds mentioned above. More preferably, the tetracycline derivative is selected from doxycycline, methacycline, sancycline and minocycline or any tetracycline derivative or analog or tetracycline conjugated to anti-coagulants (e.g, warfarin, acenocoumarol, clopidogrel). Even more preferably, the tetracycline derivative is selected from 7-halosancycline, 9-halosancycline and minocycline. Most preferably, the tetracycline derivative is minocycline.

The term "prevent" or its grammatical equivalents as used herein is not intended to require complete reduction of the formation of the multi-subunit complexes. Such reduction is preferably by at least about 50%, at least about 75%, at least about 90%, or at least about 95% of the multi-subunit complex in the presence of the agent. The phrase "promote disruption or elimination of" is not intended to require complete destruction of the multi-subunit complexes. Such destruction is preferably by at least about 50%, at least about 75%, at least about 90%, or at least about 95% of the multi-subunit complex in the presence of the agent.

In one aspect, the present invention comprises a method for screening anti-plaque agents in vitro using in vitro assembled multisubunit complexes such as insoluble aggregates, plaque-like complexes, or thrombotic-like complexes in a cell-culture system, comprising contacting cells with one or more multi-subunit complex or an insoluble component thereof as described herein to cause the cells to express morphologic changes, produce cytokines, cell death or pathological symptoms; then contacting the same cells with an agent and selecting agent that prevents, reduces or destabilizes assembly of the multi-subunit complex, or promotes disruption or elimination of the multi-subunit complex, or prevents or lessens the formation of pathological symptoms, cell death or morphological changes in the cells. In one embodiment, the multi-subunit complex is an insoluble aggregate. In another embodiment, such complex is a hybrid insoluble aggregate. In other embodiments, the hybrid insoluble aggregate is CP-Chl-lipids, CP-Chl, Chl-lipids, CP-lipids, CO-lipids or CO-cholesterol. In another embodiment, the multi-subunit complex resembles an atherosclerotic plaque. In yet another embodiment, the multi-subunit complex resembles an amyloid plaque.

In another aspect, the disclosure provides a method for screening anti-plaque therapeutics in vivo comprising contacting an animal for drug development described herein (e.g., an animal that has been treated with an in vitro-assembled multi-subunit complex as described herein or an insoluble component thereof) with an agent, chemical or biological compound (including a library of inorganic or organic molecules; also including antibodies and enzymes to the in vitro assembled multi-subunit complex) and monitoring the animal for the development of pathological symptoms, death, morphological changes, or phenotypic changes. In one embodiment, such methods include, but are not limited to, the injection, infusion or placement by other means, of the assembled multi-subunit complex formed in vitro, into brain or other tissues of an animal. In one embodiment, an agent is screened for its effect on preventing or alleviating the signs or symptoms associated with an atherosclerotic plaque in the animal. In another embodiment, an agent is screened for its effect on preventing or alleviating the signs or symptoms associated with an amyloid plaque in the animal.

B. Pharmaceutical Composition of Anti-plaque Agents

Compounds of the invention may be administered as pharmaceutical formulations including those suitable for oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some embodiments, the pharmaceutical preparation is substantially free of preservatives. In other embodiments, the pharmaceutical preparation may contain at least one preservative. General methodology on pharmaceutical dosage forms is found in Ansel et al., Pharmaceutical Dosage Forms and Drug Delivery Systems (Lippencott Williams & Wilkins, Baltimore Md. (1999)). It will be recognized that, while any suitable carrier known to those of ordinary skill in the art may be employed to administer the compositions of this invention, the type of carrier will vary depending on the mode of administration.

Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug may be adjusted, the pH of the solution buffered and the isotonicity adjusted to be compatible with intravenous injection, as is well known in the art.

The compounds of the invention may be formulated as a sterile solution or suspension, in suitable vehicles, well known in the art. The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration. Suitable formulations and additional carriers are described in Remington "The Science and Practice of Pharmacy" (20th Ed., Lippincott Williams & Wilkins, Baltimore Md.), the teachings of which are incorporated by reference in their entirety herein.

The agents or their pharmaceutically acceptable salts may be provided alone or in combination with one or more other agents or with one or more other forms. For example a formulation may comprise one or more agents in particular proportions, depending on the relative potencies of each agent and the intended indication. For example, in compositions for targeting two different host targets and where potencies are similar, about a 1:1 ratio of agents may be used. The two forms may be formulated together, in the same dosage unit e.g., in one cream, suppository, tablet, capsule, aerosol spray, or packet of powder to be dissolved in a beverage; or each form may be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of the agents used in the present invention, and which are not biologically or otherwise undesirable. For example, a pharmaceutically acceptable salt does not interfere with the effect of an agent of the invention in preventing, reducing, or destabilizing the formation of a multi-subunit complex, or promoting the disruption of a multi-subunit complex.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents used in the present invention, and which are not biologically or otherwise undesirable. For example, the ester or amide does not interfere with the beneficial effect of an agent of the invention in preventing, reducing or destabilizing assembly of the multi-subunit complex, or promoting disruption or elimination of the multi-subunit complex in the cells, or preventing or alleviating one or more signs or pathological symptoms associated with exposure to one or more multisubunit complexes or insoluble components in a subject. Typical esters include ethyl, methyl, isobutyl, ethylene glycol, and the like. Typical amides include unsubstituted amides, alkyl amides, dialkyl amides, and the like.

C. Method of Profiling and Categorizing Pathogenicity

The present invention further provides a method of profiling or categorizing the pathogenicity of insoluble aggregates or nanomaterials or plaque-like complexes. In some embodiments, one or more of the in vitro assembled complexes described herein are evaluated to determine pathogenicity.

In one embodiment, the present invention provides a method for profiling or categorizing the pathogenicity of nanomaterials, insoluble aggregates, plaque-like complexes or thrombotic complexes in a cell culture system, and the method comprising: adding an in vitro-assembled insoluble aggregate, plaque-like complex, thrombotic-like complex, or a mixture thereof, to cultured mammalian cells; culturing mammalian cells with the insoluble aggregates, plaque-like complexes or thrombotic-like complexes or a mixture thereof; and evaluating the cultured mammalian cells, wherein expression of morphologic changes, expression of cytokines, pathological symptoms or cell death indicate the pathogenicity of the insoluble aggregates, plaque-like complexes or thrombotic-like complexes. The term "pathogenic" or its grammatical equivalents such as "pathogenicity" as used herein, means causing, capable of causing or tendency to cause diseases. In some instances the term "pathogenic" or its grammatical equivalents as used herein means causing, capable of causing, or tendency to cause an amyloid-related disease.

In another embodiment, the invention further provides a method for profiling or categorizing the pathogenicity of atherosclerotic plaque-like complexes comprising the in-vitro assembly of such complexes followed by evaluation of their pathogenicity. In yet another embodiment, the invention provides a method for profiling or categorizing the pathogenicity of amyloid plaque-like complexes comprising the in-vitro assembly of such complexes followed by evaluation of their pathogenicity. In one aspect, the amyloid plaque-like complexes are already formed. In a further embodiment, the present invention comprises adding one or more amyloid plaque-like complexes to mammalian cells. In a preferred embodiment, such mammalian cells are human umbilical vein endothethial cells (HUVECs). In preferred embodiments, the amyloid-plaque-like complexes resemble any one or more of the complexes described herein.

D. Method of Diagnosing and Predicting a Plaque-Related Disease

The present invention also encompasses a method for diagnosing, categorizing, evaluating, or predicting a plaque-related disease or disease-like-processes in a subject, preferably a human. The method includes (a) obtaining a correlation between plaque-forming potential (PFP) and the quantity or density of calcium present in a panel of one or more calcium-containing aggregates; and (b) determining the PFP of calcium deposition within a subject by referring to the correlation in step (a). The plaque-related diseases that may be diagnosed or predicted using the method described herein include but are not limited to atherosclerosis, atherothrombosis, Alzheimer's disease, Parkinson's disease, osteoarthritis, mad cow disease or spongiform encephalopathy, Huntington's disease, type II diabetes, dementia, atrial amyloidosis, systemic amyloidosis, dialysis-related amyloidosis, hemodialysis-related amyloidosis, fibrinogen α-chain amyloidosis, lysozyme amyloidosis, insulin-related amyloidosis, amyotrophic lateral sclerosis, familial amyloidotic polyneuropathy II, medullary carcinoma of the thyroid, kidney stone, gall bladder stone, pancreatic stone, or a calcification-related disease.

In some embodiments, the calcium deposition may be detected by a device capable of detecting calcium density or deposition. In some embodiments, the device comprises one or more of the following: electron beam computer tomography (EBCT) scan, computer assisted tomography (CAT) scan; computer tomography (CT) scan, magnetic resonance imaging (MRI), magnetic resonance multi-contrast plaque imaging, ex vivo magnetic resonance plaque studies, in vivo MRI experimental studies, X-ray angiography, IVUS, angioscopy, thermography, ultrasound (US), intravascular ultrasound (IVUS), optical coherence tomography (OCT), Raman spectroscopy, near-infrared spectroscopy (NIR), ultrafast computer tomography (UFCT), histological study, nuclear scintigraphy, or other scanning or imaging technology capable of detecting calcium deposition. The soluble molecules may be one or more of the following: proteins, lipids or carbohydrates In certain embodiments, the calcium-containing insoluble aggregate comprise any multi-subunit complex described herein.

In certain embodiments, the method may comprise: (a) contacting a biological sample including but not limited to blood, plasma, serum, urine or tissue of a test subject with a panel of one or more in vitro-assembled plaque-like complexes or aggregates; and detecting the binding of antibodies present in the biological sample to the plaque-like complexes or aggregates. Such complexes may be one or more of the multi-subunit complexes described herein. In certain embodiments, the antibodies are detected using a multiplexing immunological assay. The immunologic assay may be an immunoprecipitation assay. In some embodiments, the immunologic assay is an Enzyme-Linked Immunosorbent Assay (ELISA).

In further embodiments, the method further comprises the preparation of a binding profile of the test subject's antibodies to the panel of in-vitro-assembled plaque-like complexes or aggregates. The method may also include obtaining or generating a designation of the pathogenic potential of each constituent of the panel of plaque-like complexes or aggregates. In still further embodiments, the method comprises comparing the binding profile with the designation of pathogenic potential in order to diagnose, categorize, evaluate, quantitate or predict a plaque-related disease or disease-like processes in a test subject.

In one aspect, the present invention provides a method of diagnosing, detecting, analyzing, evaluating or quantitating advanced atherosclerotic plaques, aortic calcifications, and/or coronary calcifications, comprising administrating a therapeutically effective dose of a drug, biological compound or chemical compound to a subject, preferably a human, wherein the drug, biological compound, or chemical compound has been previously screened for its ability to bind, penetrate, disassemble, disrupt, or prevent in vitro assembled insoluble aggregates, in vitro assembled atherosclerotic plaques, in vitro assembled atherosclerotic plaque-like complexes or in vitro assembled thromboses. In some embodiments, the drug, biological compound, or chemical compound is coupled to a fluorogenic or other marker, which aids or effects diagnosis, detection, analysis, evaluation, or quantitation of advanced atherosclerotic plaques. In certain embodiments, the agent is PGN27 or any derivative or analog of tetracycline. The tetracycline derivative is selected from 6-demethyltetracycline, bromotetracycline, chlorotetracycline, clomocycline, demeclocycline, doxycycline, lymecycline, meclocycline, methacycline, minocycline, oxytetracycline, rolitetracycline, tetracycline, sancycline, 5a,6-anhydrotetracycline, DDA-tetracycline, dactylocyclinone and 8-methoxychlorotetracycline. The tetracycline derivative also includes the optical isomers of the compounds mentioned above. More preferably, the tetracycline derivative is selected from doxycycline, methacycline, sancycline and minocycline. Even more preferably, the tetracycline derivative is selected from 7-halosancycline, 9-halosancycline and minocycline. Most preferably, the tetracycline derivative is minocycline or any tetracycline derivative or analog or tetracycline conjugated to anti-coagulants (e.g, warfarin, acenocoumarol, clopidogrel). In some embodiments, the agent is able to penetrate the atherosclerotic plaque, aortic calcification or coronary calcification via a mechanism independent of binding to the proteins bound to the templates. In another aspect, the present invention provides a method of diagnosing, detecting, analyzing, evaluating or quantitating an amyloid plaque.

Another embodiment of the invention includes a method of using the in vitro complexes to evaluate the putative role of the plasminogen cascade in regulating the growth of the amyloid plaque-like complexes, thereby facilitating the use of plasminogen and/or its activators to reduce the amyloid plaque build-up in patients with advanced Alzheimer's disease and other amyloid diseases. Likewise, the method aids in the identification of activators of plasminogen that act either directly or by inhibiting known plasminogen inhibitors.

In some embodiments, such method comprises the addition of in vitro-assembled amyloid plaque-like complexes described above to a patient's serum and using the degree or quantity of binding or the specificity of the binding of the patient's antibodies to such complexes in order to diagnose, categorize, predict, or evaluate the patient's amyloid disease or disease-like process or risk of same. In addition, several features of the present invention support the development of diagnostics or methods of diagnosing a subject, e.g. a patient. In one example, the pathogenicity of in-vitro assembled amyloid plaque-like complexes of varying compositions is determined and such information aids in evaluating the pathogenicity of a patient's plaque-like complexes of similar composition. In another example, the antibodies present in a patient's bloodstream are combined with in vitro assembled amyloid plaque-like complexes of varying compositions and the degree of binding or specificity between them aids diagnoses or treatment.

VI. Method of Treatment

In some embodiments, the present invention comprises therapeutics or methods of therapeutic treatments of a subject, preferably a human, more preferably a patient. The invention encompasses both prophylactic and therapeutic treatment of a plaque-related or plaque-induced disease. The term "patient" refers to a warm-blooded mammal, preferably a human, who is healthy or who is afflicted with, at risk of being afflicted with, or suspected to be afflicted with, an underlying disease. For example, such therapeutics may prevent or disrupt the formation of atherosclerotic plaques, plaque-like complexes, or thromboses. The method may comprise administering to a patient or a test subject or animal a therapeutically-effective amount of an agent identified in a screen described herein. In some embodiments, the chemical compound is tetracycline hydrochloride (PGN27) or any derivative or conjugates or analog of tetracycline. In certain embodiments, the PGN27 is modified for optimal efficiency. The tetracycline derivative is selected from 6-demethyltetracycline, bromotetracycline, chlorotetracycline, clomocycline, demeclocycline, doxycycline, lymecycline, meclocycline, methacycline, minocycline, oxytetracycline, rolitetracycline, tetracycline, sancycline, 5a,6-anhydrotetracycline, DDA-tetracycline, dactylocyclinone and 8-methoxychlorotetracycline. The tetracycline derivative also includes the optical isomers of the compounds mentioned above. More preferably, the tetracycline derivative is selected from doxycycline, methacycline, sancycline and minocycline. Even more preferably, the tetracycline derivative is selected from 7-halosancycline, 9-halosancycline and minocycline. Most preferably, the tetracycline derivative is minocycline or any tetracycline derivative or analog or tetracycline conjugated to anti-coagulants (e.g, warfarin, acenocoumarol, clopidogrel). In other embodiments of the present invention, the agent, uPA (PGN54), is a component of the plasminogen cascade, for example plasminogen activator.

The term "treat" or its grammatical equivalents as used herein, means providing a therapeutic benefit and/or a prophylactic benefit. A therapeutic benefit refers to the eradication or amelioration of the underlying disorder being treated. Also, a therapeutic benefit is achieved when an improvement is observed in the patient, notwithstanding that the patient may still be afflicted with the underlying disorder. The term "disorder" is used interchangeably with the term "disease" herein. A prophylactic benefit arises when the compositions are administered to a patient at risk of developing a particular disease, or to a patient reporting one or more of the physiological symptoms of a disease, even without a diagnosis.

In some embodiments, the present invention comprises methods of treating, or protecting against, a plaque-related disease including but not limited to atherosclerosis, atherothrombosis, Alzheimer's disease, Parkinson's disease, osteoarthritis, mad cow disease or spongiform encephalopathy, Huntington's disease, type II diabetes, dementia, atrial amyloidosis, systemic amyloidosis, dialysis-related amyloidosis, hemodialysis-related amyloidosis, fibrinogen α-chain amyloidosis, lysozyme amyloidosis, insulin-related amyloidosis, amyotrophic lateral sclerosis, familial amyloidotic polyneuropathy II, medullary carcinoma of the thyroid, kidney stone, gall bladder stone, pancreatic stone, or a calcification-related disease in a subject. In a preferred embodiment, the subject is a human suffering from amyloid diseases or disease-like processes or at risk of same. In another preferred embodiment, the subject is a human suffering from atherosclerotic diseases or disease-like processes or at risk of same. In another embodiment, the subject is healthy.

In some embodiments, the present invention provides administering to a subject in need thereof a therapeutically effective amount of an agent that binds, penetrates, disassembles, prevents or disrupts a plaque involved in the disease, wherein the plaque resembles the in vitro assembled multi-subunit complex or an insoluble component thereof. In one embodiment, the agent is an antibody-based molecule. The antibody-based agent in any suitable form of an antibody e.g., monoclonal, polyclonal, or synthetic, can be utilized in the therapeutic methods disclosed herein. The antibody-based agents include any target-binding fragment of an antibody and also peptibodies, which are engineered therapeutic molecules that can bind to human drug targets and contain peptides linked to the constant domains of antibodies. In one embodiment, the antibodies used are humanized antibodies. In another embodiment, the therapeutic antibodies comprise an antibody generated against a component of the multi-subunit complex described in the present invention, wherein the antibody is conjugated to another agent, for example, and a cytotoxic agent. The present invention also embodies the use of any pharmacologic agent (e.g, PGN27) that can be conjugated to an antibody or an antibody binding fragment or a small molecule, and delivered in active form. Examples of such agents include cytotoxins, radioisotopes, hormones such as a steroid, anti-metabolites such as cytokines, and chemotherapeutic agents. Other embodiments can include agents such as a anti-coagulant, a cytokine, growth factor, bacterial endotoxin or a moiety of bacterial endotoxin. The targeting antibody-based agent directs the toxin to, and thereby selectively modulates the cell expressing the targeted surface receptor. In some embodiments, therapeutic antibodies employ cross-linkers that provide high in vivo stability (Thorpe et al., Cancer Res., 48:6396, 1988). In any event, it is proposed that agents such as these can, if desired, be successfully conjugated to an antibody or an antibody binding fragment, in a manner that will allow their targeting, internalization, release or presentation at the site of the targeted cells expressing the enzyme as required using known conjugation technology.

In another embodiment, the anti-plaque agent is an RNA-based molecule including but not limited to double stranded oligonucleotides such as siRNA, or single molecule that folds on itself to form a double stranded structure (e.g., shRNA or short hairpin RNA), or microRNA. The use of RNA-based molecules for gene silencing is well known in the art.

In another embodiment, the agent is a small molecule of any form which is capable of binding, penetrating, disassembling, preventing or disrupting a plaque involved in a plaque-related disease. In one preferred embodiment, the agent is tetracycline hydrochloride (PGN27) or any tetracycline derivative or analog or tetracycline conjugated to anti-coagulants (e.g, warfarin, acenocoumarol, clopidogrel) thereof. In another embodiment, PGN27 is modified for optimal efficiency. The tetracycline derivative that may be used in this invention is selected from 6-demethyltetracycline, bromotetracycline, chlorotetracycline, clomocycline, demeclocycline, doxycycline, lymecycline, meclocycline, methacycline, minocycline, oxytetracycline, rolitetracycline, tetracycline, sancycline, 5a,6-anhydrotetracycline, DDA-tetracycline, dactylocyclinone and 8-methoxychlorotetracycline. The tetracycline derivative also includes the optical isomers of the compounds mentioned above. More preferably, the tetracycline derivative is selected from doxycycline, methacycline, sancycline and minocycline. Even more preferably, the tetracycline derivative is selected from 7-halosancycline, 9-halosancycline and minocycline. Most preferably, the tetracycline derivative is minocycline. In another preferred embodiment, the agent is one or more members of the plasminogen (PLG) cascade or an activator of PLG including but not limited to urokinase plasminogen activator (uPA, i.e. PGN54). In other preferred embodiments, such agent is able to inhibit PLG activator inhibitors.

For embodiments where a prophylactic benefit is desired, a pharmaceutical composition of the invention may be administered to a patient at risk of developing a plaque-related disease, or to a patient reporting one or more of the physiological symptoms of a plaque-related disease, even though a diagnosis of the condition may not have been made. Administration may prevent the plaque from developing, or it may reduce, lessen, shorten and/or otherwise ameliorate the plaque that develops. The pharmaceutical composition may modulate a plaque activity or stability. Wherein, the term modulate includes inhibition or alternatively activation of a molecule that affects the plaque.

In further embodiments, atherosclerotic plaque or amyloid plaque-like complexes described herein are introduced into the system of a subject, including a human or a non-human animal. Antibodies elicited upon exposure to such complexes are collected, and a therapeutically-effective dose of such antibodies is administered to a subject, preferably a patient. In one preferred embodiment, such complexes are pre-screened for their ability to treat, reduce, or prevent atherosclerotic disease or disease-like processes. In another preferred embodiment, such complexes are pre-screened for their ability to treat, reduce, or prevent amyloid disease or disease-like processes. In another preferred embodiment, such antibodies, which have been elicited after iterative versions of atherosclerotic or amyloid plaque-like complexes, are sequentially or contemporaneously introduced into the system of a live non-human animal or a human in order to protect against various stages of a plaque-related disease.

Administration of the Agent:

In the method of the invention, the subject is administered an amount of an anti-plaque agent in one or several dosages. The dosage depends upon the purity and chemical form of the anti-plaque agent and the degree of absorption expected. Suitable amounts per dose are typically greater than about 0.5 mg/kg of body weight, preferably in the range of from about 0.5 to 5.0 mg/kg per dose, and most preferably are about 0.5 to 2.0 mg/kg per dose. These dosage ranges are intended to be suggestive and should not necessarily be considered as limiting, since the individual reactions of particular subjects will vary. Adjustment of the dosage ranges in accordance with individual variations is routine among practitioners.

Similarly, no single protocol appears to be desirable for all cases at this time. However, typical protocols will include either a single dose or an initial dose followed by 1-4 additional doses at weekly, biweekly or monthly intervals. A particularly preferred protocol calls for 3 doses about two weeks apart. Again, these protocols are not intended to be limiting in view of the wide variation permitted in protocol design.

The anti-plaque agent of the invention may be administered as a single compound, or as a mixture of various anti-plaque agents. Suitable formulations include those appropriate for systemic administration, including preparations for parenteral injection, transmucosal or transdermal administration, or oral administration. A particularly preferred means of formulating the anti-plaque agent of the invention for this use is in the form of a solution or as liposomes suitable for injection into a peripheral vein. The anti-plaque agent may be included within the liposomes, attached to their surface, or both. Suitable methods for preparing liposomes are well-known in the art.

When injected intravenously, the solution or liposome formulation disseminates throughout the vascular system and thus comes into direct contact with the arterial plaques being targeted, where the anti-plaque agent is selectively absorbed, with peak concentration typically occurring within about 24 hours. The presence of the anti-plaque agent in the plaque may be detected within a few hours after injection and may persist for as long as several days to two weeks.

In one embodiment, the absorption of anti-plaque agents by atheromatous plaques may be enhanced by binding to the anti-plaque agent some antibody specific to a component of the plaque. Monoclonal antibodies may be particularly useful due to their extreme specificity. Components of plaque that can serve as antigenic targets include elastic elements, collagen, and lipid constituents.

In the methods of the invention, the anti-plaque agents, formulated into pharmaceutical compositions, are administered without the need to irradiate invasively at the site of the potential or growing arterial plaque with light that is absorbed by the anti-plaque agent. The expression "in the absence of irradiation with light absorbed by the anti-plaque agent" is intended to mean that no such deliberate irradiation is administered. The phrase does not, of course, exclude inadvertent, coincidental, or normal exposure of the affected tissues to ambient light.

VII. Vaccination

In certain embodiments, the present invention comprises a method of generating a vaccine to an assembled multi-subunit complex or any insoluble component thereof. In some embodiments, the method comprises introducing one or more in vitro assembled complexes described herein into an animal or human in order to elicit an immune response. In certain embodiments, the invention comprises the antibodies elicited in response to the introduction of such complexes into the animal or human. In other embodiments, the invention comprises a method of treatment wherein such antibodies are administered to a test subject in order to disrupt or prevent the assembly of a plaque including an atherosclerotic plaque or an amyloid plaque or any plaque-like complexes. In certain embodiments, the antibodies are screened for their ability to treat, reduce, or prevent atherosclerosis or atherosclerosis disease-like processes. In further embodiments, the multi-subunit complex resembles atherosclerotic plaque subtypes. In some embodiments, such sub-types comprise pre-atheroma (type I or III) or atheroma (type IV or Va). In certain embodiments, the antibodies recognize one or more of the in vitro assembled plaques, plaque-like complexes or aggregates described herein. In further embodiments, the antibodies recognize oxidized low density lipoprotein (oxLDL), antigenic epitopes expressed on the walls of pathogens, epitopes expressed on the walls of *Streptococcus pneumonia* or are T15 antibodies.

In other embodiments, the disclosure provides a method of vaccinating an animal against a plaque-related disease by introducing in vitro assembled multi-subunit complexes (or complex) containing combinations of insoluble aggregates of proteins, lipids and other components into the animal. In one embodiment, the animal is vaccinated with a multi-subunit complex resembling an atherosclerotic plaque to generate immunity against an atherosclerotic disease. In another embodiment, the animal is vaccinated with a multi-subunit complex resembling an amyloid plaque to generate immunity against an amyloid plaque-related or induced disease. In another embodiment, the method further includes introducing an additional antigen into the animal. The animal may be a mouse, a rat, a pig, a horse, a non human primate, a guinea pig, a hamster, a chicken, a frog, a dog, a sheep, a cow, or a human.

In other embodiments, the present invention provides a method of generating vaccines wherein the in-vitro-assembled plaque-like complexes themselves are administered to a human, e.g. a patient. Such plaque-like complexes are administered to a patient in order to boost or elicit an immune response in the patient that counteracts an atherosclerotic disease or amyloid-related disease or process, or protects against such disease or disease-like process. In a preferred embodiment, such plaque-like complexes are iterative versions of amyloid plaque-like complexes and are sequentially or contemporaneously introduced into a subject, including a human or a non-human animal, in order to protect against various stages of disease. In another preferred embodiment, such plaque-like complexes are iterative versions of atherosclerotic plaque-like complexes and are sequentially or contemporaneously introduced into a subject, including a human or a non-human animal, in order to protect the subject against various stages of a plaque-associated disease.

In some embodiments, the present invention provides a method for the identification and profiling of antibodies from a biological sample including but not limited to human blood, plasma, serum, urine and tissue samples. Examples of detection methods include but are not limited to ELISA, fluorocenic and non-radioactive methods, which are all well known to one skilled in the art. In one embodiment, the invention further provides quantitatively detecting antibodies reacting to the in vitro assembled plaque complexes that facilitate in diagnosing and predicting atherosclerosis in asymptomatic high risk individuals. In another embodiment, the invention provides quantitatively detecting antibodies reacting to the in vitro assembled plaque complexes that facilitate in diagnosing and predicting amyloid-related diseases in asymptomatic high risk individuals.

VIII. Kit

The present invention also embodies a kit to aid in the diagnosis, prediction, prognosis, or detection of a plaque-related disease or disease-like process. In some embodiments, the kit comprises one or more multi-subunit complexes and/or insoluble components thereof as described herein. In other embodiments, the kit includes a pharmaceutical composition of one or more multi-subunit complexes with a pharmaceutically acceptable carrier, e.g. salt, adjuvant, booster and the like. The kit may provide components of a vaccine described herein. In other embodiments, the kit further includes reagents of an immunologic assay. In some embodiments, such immunologic assay is an ELISA.

The present invention also includes kits that can be used to treat a plaque-related disease. These kits comprise an agent or combination of agents that bind, penetrate, disassemble, inhibit, disrupt, or eliminate a plaque involved in a disease. In some embodiments instructions teaching the use of the kit according to the various methods and approaches described herein are provided. Such kits may also include information, such as scientific literature references, package insert materials, clinical trial results, and/or summaries of these and the like, which indicate or establish the activities and/or advantages of the agent. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like.

EXAMPLES

The following non-limiting examples further illustrate the invention disclosed herein:

Example 1

Overview of the Assembly of Atherosclerotic Plaque-Like Complexes

The example illustrated by FIG. 1 includes both a schematic diagram showing the steps of cyclic plaque assembly (CPA) leading to the assembly of atherosclerotic plaque-like complexes (top panels) and images of actual results representing different steps of the process. In Step 1, soluble organic and inorganic molecules are converted into insoluble aggregates and then are used as templates for "cyclic plaque assembly" In Step 2, CPA enables insoluble aggregates to contact a number of proteins through an iterative binding process. Step 3, involves the thrombosis of the in vitro assembled plaque like complexes occurs. In Step 4, dissolution of the thrombus generated from the in vitro assembled plaques like complexes occurs as a result of the addition of thrombolytic/fibrinolytic proteins.

Example 2

Preparation of Insoluble Aggregates (Templates)

Figure 2:
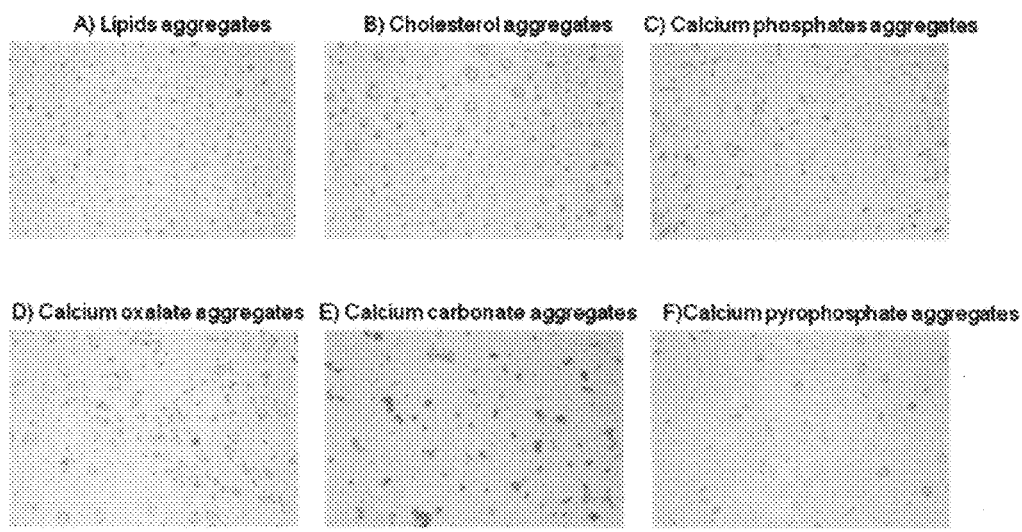
FIG. 2. Microscopic analysis of the different insoluble aggregates.

The example depicted in FIG. 2 illustrates the preparation of insoluble aggregates, or template complexes. Images of lipid aggregates (FIG. 2A), cholesterol aggregates (FIG. 2B), calcium phosphate (CP) aggregates (FIG. 2C), calcium oxalate aggregates (CO) (FIG. 2D), calcium carbonate (CC) (FIG. 2E) and calcium pyrophosphate (FIG. 2F) are provided.

To generate lipid aggregates, powders (10 mg) of atherogenic lipids are first solubilized in 2 ml of alcohol (100%) and then the resulting samples containing soluble lipids (100 µl) are used for preparation of insoluble aggregates. Further, these aggregate-containing samples are centrifuged (Effendorf 5417R, NY USA) at 3000 rpm for 5 min. It is observed that after centrifugation of the samples, the cholesterol containing aggregates are collected at the bottom of the tube by sedimentation process whereas the lipid containing aggregates do not form sedimentation. The insoluble cholesterol aggregates are suspended in 100 µl of the PBS and used for plaque assembly experiments. The lipid containing aggregates are directly used for binding with the proteins, calcium containing aggregates and plaques like complex assembly experiments.

To generate the cholesterol aggregates, powders of cholesterol (10 mg) are solublized in 2 ml of alcohol (100%) by incubating at 37° C. for 2 hrs. After their solubilization, 100 µl of the sample is used for formation of insoluble cholesterol aggregates. Exposure of esterified cholesterol molecules from organic medium (alcohol) to PBS buffer causes the transformation of these molecules into unesterified insoluble aggregates. Next, these aggregates are used for binding with the protein, calcium-containing aggregates and plaque assembly experiments.

For preparation of the CP aggregates, calcium chloride (4 mM, pH 6.0) is mixed with sodium phosphate dibasic (4 mM, pH 7.4) in 2 ml volume and incubated at room temperature for 1 hr. For calcium pyrophosphate (CaPPD) aggregates formation, calcium chloride (4 mM) is mixed with sodium pyrophosphate (4 mM, pH 7.4) in 2 ml volume and incubated at room temperature for 1 hr. Similarly, for calcium oxalate (CO) aggregates formation, calcium chloride (4 mM) is mixed with oxalic acid (4 mM, pH 6.3) and incubated at RT for 1 hr. For preparation of calcium bicarbonate (CC) aggregates, sodium bicarbonate (14 mM, pH 8.6) is mixed with calcium chloride (7 mM) and incubated at RT for 3 minutes. Finally, all these samples are centrifuged (2700 rpm, 3 min, 20° C.) and the supernatants are discarded. The aggregates are suspended in 200 µl of PBS buffer and later used for CPA and plaques assembly.

For preparing iron-phosphate aggregates, 2 ml of 2 mM $Fe(SO_4)_3$ solution is mixed with 2 ml of sodium phosphate dibasic (4 mM, pH 7.4) and incubated at 37° C. for 1 hr. The samples are centrifuged (7000 rpm, 5 min, 20° C.) and after discarding the supernatant, the pellet containing iron-phosphate aggregates are suspended in 200 µl of PBS. These templates are later used for the CPA and plaques assembly experiments.

Results: The insoluble aggregates are suspended in the PBS are used for examination using microscope (Olympus CK40-SL, Japan). Each aggregate (20 µl) is smeared on a glass microscopic slide and dried at RT for 5 min is used for examination (1000×) and the results are documented (FIG. 2). Although, all of these aggregates appear colorless visually, microscopic examination reveals heterogeneous structure and composition.

Example 3

Preparation of Hybrid Templates Containing Calcium, Cholesterol and Lipid Aggregates The example described here illustrates the preparation of hybrid aggregates containing cholesterol, calcium and lipids. In order to examine association between the lipid, cholesterol and calcium containing aggregates during the atherosclerotic plaque assembly processes, the lipids and cholesterol aggregates are individually mixed (50:50 v/v) with calcium containing aggregates (CP, CO and CC) and incubated at 37° C. for 30 min. This resulted in the formation of hybrid aggregates of CP-Lipids, CP-Chl-lipids, CO-Lipids and CC-Lipids as evidenced by sedimentation of both the lipids and the calcium aggregates. After centrifugation at 3000 rpm for 3 min, the supernatant is discarded and the hybrid aggregates are suspended in PBS for use in the CPA and plaques assembly experiments. Secondly, to prepare the mixture of the lipids, cholesterol, and CP aggregates, all these three aggregates are mixed together (cholesterol 25%, lipids 25% and CP 50% v/v). After incubation at 37° C. for 30 min followed by centrifugation, the resultant aggregates are suspended in PBS and later used for the CPA and plaques assembly experiments.

Example 4

Binding of Proteins with Insoluble Lipid Aggregates

Figure 3:
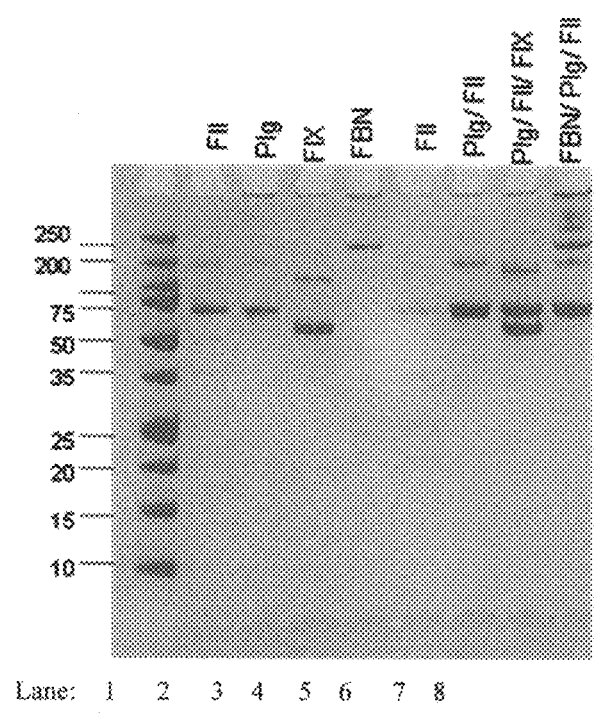
FIG. 3 SDS-PAGE analysis of the interaction of proteins with the lipids aggregates. The lanes 1 to 4 indicate binding of proteins individually with the lipid aggregates and lanes 5 to 8 indicate binding of more than one protein with the insoluble lipid aggregates. The proteins used for the binding with the lipid aggregates are indicated on top of each lane.

The example illustrated in FIG. 3 show a gel analysis of proteins that bind to the lipid aggregates. Unlike the binding of proteins with calcium containing or cholesterol templates, the lipids-proteins complexes do not result in the sedimentation of aggregates-protein complexes. To analyze interaction between the proteins and lipids aggregates, 50 µl of the aggregates is mixed with 2 µg of each protein individually or in combination with other proteins. For negative control experiment, the protein/s are mixed with buffer without aggregates and treated similar to binding with aggregates. After 1 hr incubation at 37° C., 25 µl of the complexes are directly used for SDS-PAGE analysis under reducing condition. The complexes are mixed with 5 µl of 5×SDS sample solubilzation buffer containing reducing agent (beta-mercaptoethonl) and boiled for 10 min before loading into 4-20% gradient gel (Cambrex Bio Sci, ME, USA). After staining with coomassie blue stain R-250 (Sigma MI), the proteins detected for interaction with the lipid aggregates are documented. Gel analysis of the lipid-protein complexes showed oligomerization of some of the proteins such as the PLG and FII upon binding to the lipids aggregates (FIG. 3). The oligomerization of proteins might occur due to lipid mediated oxidation that results in the cross-linking of proteins. Lipids are known to induce cross-linking of proteins through oxidation mechanism (Jayaraman S et al, 2007) causing aggregation of proteins that could contribute to their accumulation in the plaques assembly processes.

Example 5

Identification of Proteins Binding to the Templates

Figure 4:
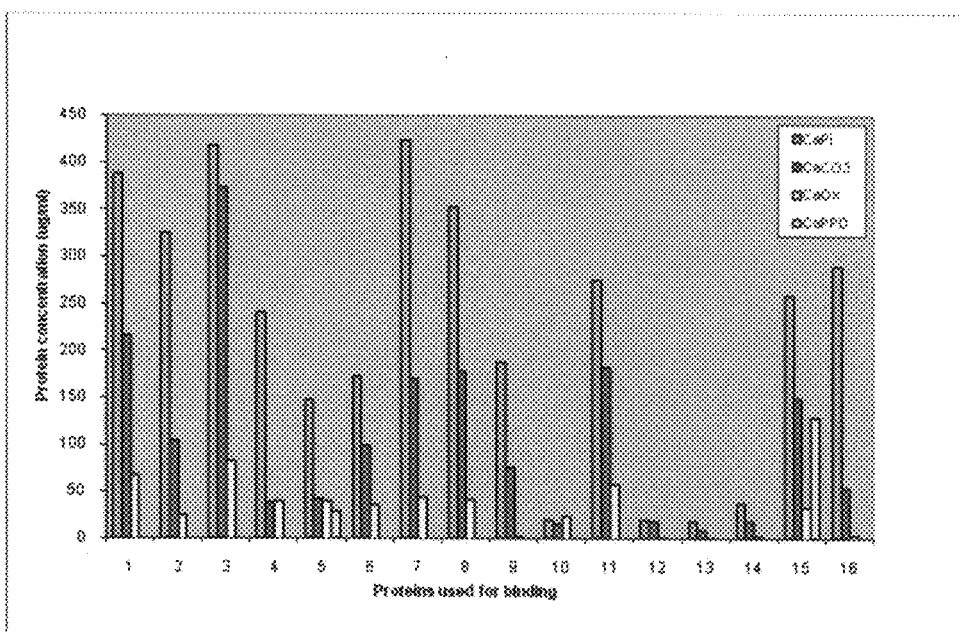
FIG. 4 Identification of proteins binding to the calcium containing aggregates. The proteins screened for binding are: 1, coagulation factor II (FII); 2, anti-thrombin III (AT III); 3, coagulation factor IX (FIX); 4, plasminogen activator inhibitor 1 (PAI-1); 5, complement factor 1 (C1); 6, complement factor 3 (C3); 7, complement factor 4 (C4); 8, complement factor H (FH); 9, complement factor 5 (C5); 10, plasminogen (PLG); 11, human fibrinogen (FBN); 12, horse radish peroxidase (HRP); 13, carbonic anhydrase (CAH); 14, human insulin (HINS); 15, human serum albumin (HAS) and 16, protein S (ProS).

The example illustrated in FIG. 4 depicts the various proteins that bind to templates. The proteins screened for binding are: 1, coagulation factor II (FII); 2, anti-thrombin III (AT III); 3, coagulation factor IX (FIX); 4, plasminogen activator inhibitor 1 (PAI-1); 5, complement factor 1 (C1); 6, complement factor 3 (C3); 7, complement factor 4 (C4); 8, complement factor H (FH); 9, complement factor 5 (C5); 10, plasminogen (PLG); 11, human fibrinogen (FBN); 12, horse radish peroxidase (HRP); 13, carbonic anhydrase (CAH); 14, human insulin (HINS); 15, human serum albumin (HAS) and 16, protein S (ProS). The templates used for these experiments are either CP, CC, CO, or CaPPD.

The Proteins used for binding with the aggregates are diluted first in the PBS to make 1 mg/ml concentration and then stored at −20° C. as 50 µl aliquots. These samples are then thawed on ice and centrifuged (10,000 rpm, 10 min, 4° C.) to remove any precipitation and the supernatant containing only the soluble proteins are used for binding studies. To start with, for identification of proteins binding with calcium containing aggregates, a number of proteins are screened individually with the aggregates. Binding experiment is performed in 100 µl reaction (50 µl PBS buffer and 50 µl of individual aggregates) containing 2 µg of protein and the mixtures are incubated at 37° C. for 1 hr. For control experiments, protein (2 µg) is mixed in 100 µl PBS without aggregates. After the binding, the mixture is centrifuged (2500 rpm, 2 min, 20° C.) and the pellet is washed four times with 200 µl PBST (Tween 20, 0.05%). After each wash the supernatant is discarded and the complexes are transferred to a new microfuge tube to avoid any carry-over of the proteins. The calcium containing aggregates-protein complexes are suspended in 20 µl of PBS to which 5 µl of EDTA (25 mM final concentration) is added for solubilization of the complexes. Finally, the solublized samples are used for protein quantitation using protein estimation kit (Pierce, Ill.) and the data are used in the Microsoft Excel program to generate Graph 1 (FIG. 4). All the binding experiments and subsequent CPA experiments are carried out in low protein bind 1.7 ml centrifuge tubes (Effentorf, Calif.). For all the following binding experiments the same buffer, centrifugation and washing conditions are used.

For analyzing binding of the proteins with the calcium containing aggregates, a number of proteins involved in the blood coagulation, fibrinolysis and complement activation pathways are screened individually with the CP, CC, CO, and CaPPD aggregates. Among sixteen proteins screened for binding, thirteen proteins show detectable binding with the CP aggregates. They are FII, AT III, FH, C5, FIX, C3, ProS, C4, PAI-1, PLG, FBN, HSA and C1. Except AT III, the remaining twelve proteins that shows binding to the CP aggregates also show binding with the CC aggregates. Besides, only FII and FIX proteins are detected for binding with the CO aggregates and no significant binding of proteins is observed with the CaPPD aggregates. In addition, proteins such as HRP, HIN and CAH show no detectable binding with any of these aggregates. Previous studies have found that proteins such as FII, AT III, FBN, C4 and C3 showed binding with the CP (Klein C P et al 1980; Tsortos A et al, 1996; Dornheim G et al, 1982). Similarly, the FII and its derivatives are known to binding with the CO crystals (Stapleton A M et al, 1996).

Example 6

Development of a Novel Cyclic Plaque Assembly Method (CPA)

To probe the role of lipids, cholesterol and calcium containing aggregates for in vitro atherosclerotic plaques assembly processes these insoluble aggregates are used as templates to analyze their iterative binding with the proteins. The method for identification of protein/s binding to the aggregates is based on the observation that the insoluble aggregates tend to precipitate or sediment in solution and soluble protein/s that have binding affinity to the aggregates could be co-precipitated as protein-aggregates complex. Further, in order to determine the contribution of lipids, cholesterol and calcium containing aggregates towards in vitro atherosclerotic processes, these aggregates are used as templates in the CPA method. As lipid aggregates are resistant to sedimentation, first, calcium containing templates are used for the CPA. Second, we observed that the cholesterol, calcium and lipid aggregates bind to each other and the resulting hybrid aggregates or plaque initiation complex form sedimentation in the solution. The protocol for the CPA method is described herein.

Example 7

Assembly of the Atherosclerotic Plaques Like Complexes Using Calcium-Containing Aggregates The example depicted in FIG. 5 illustrates the assembly of atherosclerotic plaque-like complexes using calcium-containing templates. Four calcium-containing templates (CP, CaPPD, CO and CC) are used individually to assemble the plaque like complexes. For each cycle of binding, 50 µl of the templates are used and when the number of binding cycle is increased the templates concentration are also increased, additional 50 µl of templates for every cycle. Iterative binding of the proteins with the templates is performed for six cycles and depending upon the number of cycles to be performed, the starting volumes of reactions are adjusted. For example, to perform six cycles of binding, the starting volume of reaction mixture during first cycle of the binding is 300 µl of templates (obtained from 2 ml reactions) to which FII and AT III (6 µg each) are added. For control experiment, the reaction is carried out in 300 µl of the PBS buffer containing FII and AT III (6 µg each) without any templates. The reaction mixture is incubated at 37° C. for 30 min followed by washing of the resultant complexes for four times with PBST (PBS with Tween 20, 0.05%). As described above, after each wash the complexes are transferred to new microfuge to avoid any carry-over of the proteins. For second cycle of binding, the complexes that underwent first round of binding are suspended in 300 µl of PBS, out of which 50 µl is removed to monitor the growth of the complexes later, and for remaining 250 µl of the complexes both C5 and FH (5 µg of each) are added. For control experiment performed without templates, since there is no templates or complexes present in the tube, the tube is just washed with 300 µl of PBS, out of which 50 µl is removed for later analysis and for remaining 250 µl of the sample, both C5 (5 µg) and FH (5 µg) are added. For all the following cycles of binding the control experiments are performed similar to protein binding with the templates. After second cycle of binding and washing, the resultant complexes are suspended in 250 µl of PBS from which 50 µl of the complexes are removed for later analysis and for remaining 200 µl complexes both 4 µg of C3 and FIX (4 µg) are added for third cycle of binding.

After incubation and washing, the resultant complexes are suspended in 200 µl of PBS and 50 µl are removed from that for later analysis and for remaining 150 µl of the complexes both 3 µg of C4, and 3 µg ProS are added and continued for fourth cycle of binding. After binding and washing, the complexes are used for fifth cycle of binding. Again, the complexes are suspended in 150 µl of PBS from that 50 µl of the complexes are removed and for remaining 100 µl of the complexes both 2 µg PAI-1 and FBN (2.0 µg) are added. As performed earlier, after binding and washing, the resultant complexes are suspended in 100 µl of PBS out of which 50 µl is removed and for remaining 50 µl of the complexes both C1 (1 µg) and HSA (1 µg) are added. After binding and washing, the final complexes are suspended in 50 µl of PBS. Finally, all the complexes that are collected after each cycle of binding are centrifuged at 3000 rpm for 3 min. The supernatants are discarded and the complexes are dissolved in 2 µl of solublizatation buffer (PBS with 25 mM EDTA) by incubating them at RT for 1 hr. The dissolved complexes are then used both for gel analysis and protein estimation using protein estimation kit (Pierce, Ill.). Samples containing the dissolved complexes are used to determine protein concentration utilizing reagents and protocols supplied by the manufacturer and final reading are taken using spectrophotometer (Molecular Devices, CA, USA). For gel analysis, the dissolved complexes are mixed with 5 µl of SX SDS sample solublizing buffer and the mixtures are boiled for 10 minutes before loading them in to the 4-20% gradient polyacrylamide gels. After running the gels under reducing conditions they are stained with coomassie stain R250 (Sigma, MI) to detect the proteins and the results are documented.

The gel analysis of the resultant complexes showed differential binding of the proteins with the calcium containing templates. For example, stable binding is observed for all the proteins that are used in the complex formation with the CP templates (FIG. 5a). Likewise, it is found that except AT III, the remaining twelve proteins formed stable complexes with the CC templates. Conversely, FII and FIX are the only two proteins that formed stable complexes with the CO template (FIGS. 5b, c). There is no significant binding or complex formation observed with either the CaPPD templates or in the negative control experiments performed without any templates (FIG. 5d, e).

Example 8

Progressive Binding of Proteins to Templates

Figure 6:
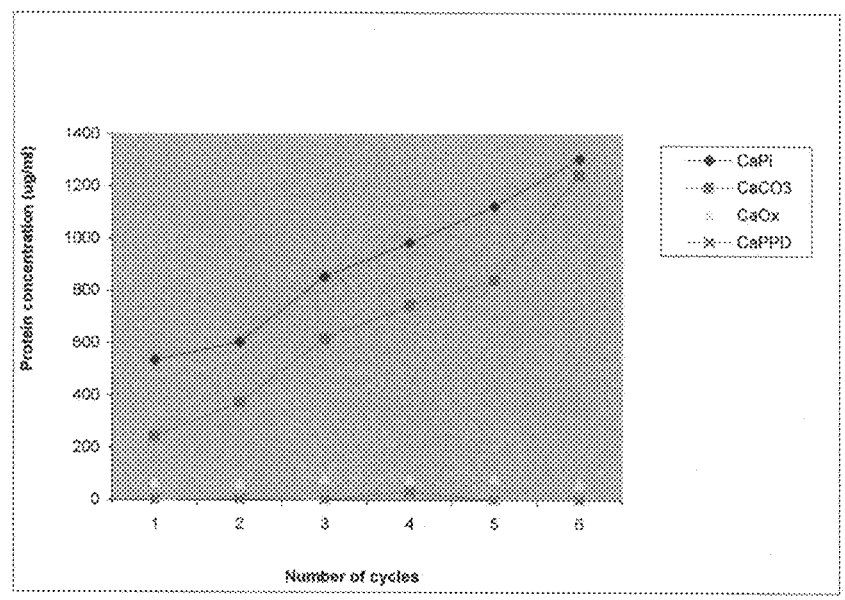
FIG. 6 Analysis of plaques like complexes assembled using calcium-containing aggregates. Cycle 1, binding of FII and AT III to the templates; cycle 2, binding of FH and C5 proteins to the complexes-1; cycle 3, binding of FIX and C3 proteins to the complexes-2; cycle 4, binding of ProS and C4 proteins to the complexes-3; cycle 5, binding of PAI-1 and FBN proteins to the complexes-4 and cycle 6, binding of HAS and C1 proteins to the complexes-5. Note: CaPPD refers to calcium pyrophosphate.

The example depicted in FIG. 6 demonstrates the progressive binding of proteins to calcium-containing aggregates. Cycle 1, binding of FII and AT III to the templates; cycle 2, binding of FH and C5 proteins to the complexes-1; cycle 3, binding of FIX and C3 proteins to the complexes-2; cycle 4, binding of ProS and C4 proteins to the complexes-3; cycle 5, binding of PAI-1 and FBN proteins to the complexes-4 and cycle 6, binding of HAS and C1 proteins to the complexes-5.

Figure 7:
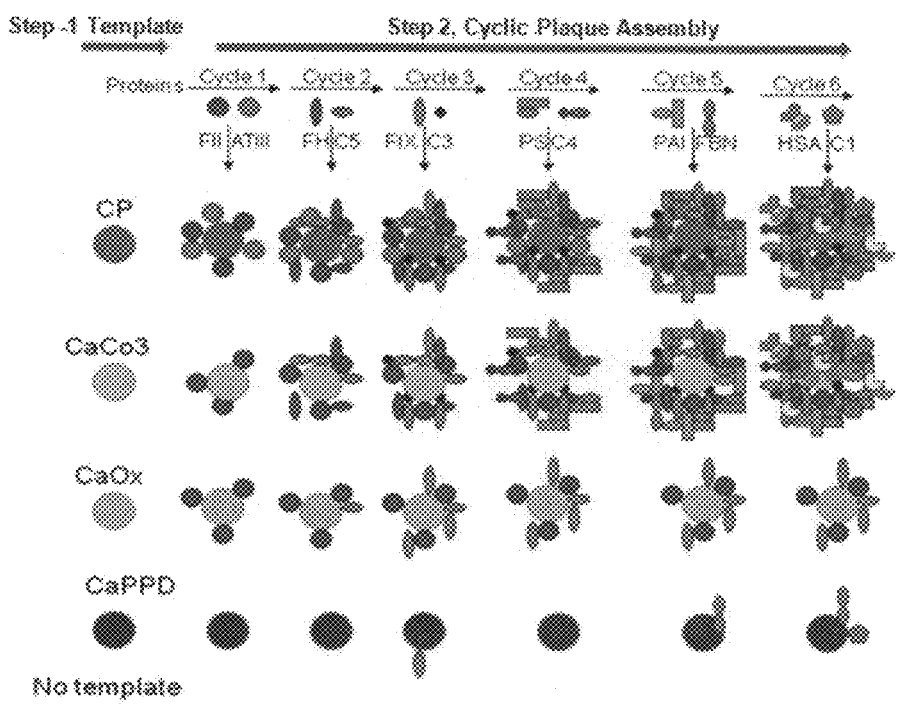
FIG. 7 Diagram showing analysis of the CPA performed using four different calcium based templates. CaPPD refers to calcium pyrophosphate.

The protein concentrations obtained for the complexes after assembly from the CP and CC templates show progressive binding of proteins with the templates after every cycle of complex formation. However, a significantly low level binding of proteins is found for complexes assembled on the CO templates and no significant binding is observed with either CaPPD templates or the proteins processed without any templates (FIG. 6). These results are in perfect agreement with our gel analysis data for complexes assembled using these templates. Interestingly, the complex formation profiles suggest that both the CP and CC templates appear to be highly pathogenic whereas the CO and CaPPD templates appear to be less pathogenic. The results are shown diagrammatically (FIG. 7).

These results suggest that using the CPA method the biochemical profiles of the CP, CC, CO and CaPPD could be determined. Besides, the complex formation profiles indicate that the pathogenic properties of the calcium-based templates could be determined by their morphology and conformations of the insoluble aggregates. The conformation/s of the CP and CC aggregates appears to be more favorable for binding with a wide range of the proteins involved in critical biochemical pathways such as blood coagulation, fibrinolysis and complement activation. Previous studies have shown that binding of proteins to the CO crystals led to changes in crystal morphology (Royal R L et al, 2005; Sheng X et al, 2005). The complex formation between the proteins and the templates might be mediated by non-covalent interactions and it is predictable that over the period of time these complexes could evolve into compact plaques under in vivo conditions. Also, continuous sequestering of vital proteins by the pathogenic aggregates might eventually lead to compromise on normal functions of the related biochemical pathways.

Example 9

CPA Using Hybrid Lipid Cholesterol and Calcium Templates

The example depicted in FIG. 8 illustrates the interrogation of whether the conformation of hybrid templates is modified by interaction with other templates. Cholesterol and calcium based crystals are two major pathogenic materials present in the atherosclerotic plaques. Specifically, vulnerable atherosclerotic plaques (type-IV, Va) contain significant accumulation of cholesterol, lipids and calcified crystals. However, co-localization of the calcium, lipid and cholesterol crystals in the atherosclerotic plaques takes place by unknown mechanism. Interestingly, these inorganic and organic molecules are not binding partners when exist in soluble forms whereas when they transform into the insoluble aggregates they bind to each other as described above. In the present study, we observed that the calcium and lipid aggregates have affinity to each other and their binding leading to the formation of the hybrid aggregates with new properties. It is likely that such interaction between organic and inorganic aggregates might be mediated by novel confirmations acquired by these aggregates during the process of their structural transition from soluble to insoluble states.

To further probe whether the conformational states of the hybrid templates are modified due to interaction with the other templates, CP-Chl-Lipids and CO-Lipids templates are used for the CPA. As described herein, the hybrid templates are subjected to the CPA. For control experiment, CP and CO templates are individually used for CPA simultaneously. Gel analysis of the resultant complexes revealed that the profiles of both the CP-Lipid and CO-Lipid hybrid aggregates are similar to the CP and CO aggregates respectively (FIGS. 8a and b). These results suggest that the lipid aggregates might be less pathogenic and its binding with the calcium aggregates did not affect the original affinity of the CP and CO aggregates with the proteins as demonstrated below (FIG. 8c).

Example 10

CPA Using Hybrid Templates Containing Cholesterol-CP-Lipids

The example depicted in FIG. 9 illustrates the complex formation of a mixture of hybrid templates containing cholesterol, CP and lipids, prepared as described herein. In these experiments, hybrid templates are subjected to CPA. As a control, the CP template is used for CPA simultaneously. Gel analysis of the resultant complexes show that the profile of the hybrid templates is similar to the control CP template (FIGS. 9a and b). These results are in agreement with the preceding observation that binding of the lipid aggregates with the CP did not affect the interaction of the CP with the proteins. However, it is found that the hybrid templates and the plaques like complexes assembled on them are resistant to dissolution in solubilization buffer (PBS with 25 mM EDTA) compared to the complexes assembled only with the CP template. Importantly, these results suggest that calcium and lipid containing hybrid templates are more stable material that could be difficult to eliminate from the body. As a result, their progressive accumulation could contribute to the build-up of plaque complexes in the artery walls leading to the narrowing of the arteries and reduced blood flow.

Example 11

Blood-Platelet Independent Thrombosis of the Plaques Like Complexes

Figure 10:
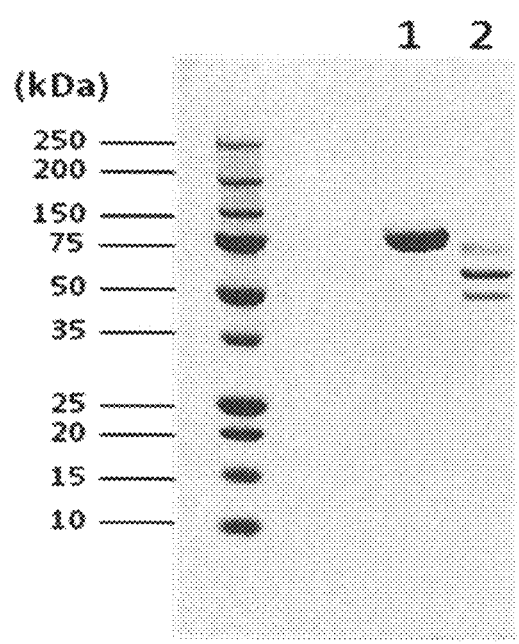
FIG. 10 SDS-PAGE analysis of the degradation products of FII treated with trypsin-agarose beads. Lane 1, shows FII untreated and lane 2, shows degradation products of the FII generated after trypsin-agarose treatment.

The example depicted in FIG. 10 shows SDS-PAGE analysis of the degradation products of FII treated with trypsin-agarose beads and its use for inducing thrombosis of plaque complexes.

The third step of the PET platform involves demonstration of the biochemical consequences of exposing the calcium, cholesterol and lipid containing aggregates and their plaques like complexes to the blood coagulation factors. This step is to mimic the rupture of in vivo vulnerable atherosclerotic plaques that results in the release of its contents into the blood circulation. To start with, five different insoluble aggregates of CP, CO, lipids, cholesterol and iron-phosphate are prepared, as described above, and then examined individually for their clot formation in the presence and absence of FBN and FII. Typically, the blood coagulation cascade is initiated at the site of injury by exposure of tissue factor that binds to FVII or FVIIa and then they together activate inactive factor FX into active FXa. Next, the active FXa converts the inactive FII into active α-thrombin that in turn activates soluble human FBN into insoluble fibrin mesh (Chang FY, 1986).

With relevant to atherothrombosis, the rupture of unstable plaques followed by release of its contents into the blood circulation and the possible interaction of them with the hemostasis factors are not completely understood. However, it is recognized that the rupture of unstable atherosclerotic plaques lead to the release of its soluble and insoluble contents like lipids, cell debris, calcified crystal, proteases and tissue factor (TF) (Annex B H et al, 1999). In general, the rupture of vulnerable plaques accompany the release of one or more of the following contents: higher concentration of lipids, tissue factor, proteolytic enzymes, calcified nodules, inflammatory cells, superficial platelet aggregate, fibrin deposition etc (Naghavi M et al, 2003). The plaque contents containing TF and proteases play role in the initiation of the classical blood coagulation cascade leading to the blood platelets dependent intra-vascular thrombosis. Besides, it is highly likely that the interactions of the insoluble plaques components with the plasma proteins, particularly with coagulation factors, might lead to thrombosis of the plaques contents itself in a blood platelets independent thrombosis mechanism. The thrombosis of the plaque contents together with the blood platelets dependent thrombosis could cause life-threatening conditions such as myocardial infarction, thrombogenesis, stroke, thromboembolism and atherogenesis. Microscopic examinations of the lipids and CP aggregates showed that their shape appear heterogeneous and suggest that they might be susceptible for thrombosis when exposed to coagulation factors. Hence, it is imperative to better understand the consequences of exposing the in vitro assembled plaque complexes containing insoluble calcium, cholesterol and lipid containing complexes to the coagulation factors to examine blood platelets independent thrombosis. Methods: Thrombosis of the Calcium and Lipid Containing Insoluble Aggregates and Their Complexes To test the hypothesis of blood platelets independent thrombus formation of the in vitro assembled plaque complexes, the insoluble aggregates and their complexes are used for a series of clot formation experiments. The clotting assay is carried out in 1.5 ml microfuge tube containing 100 µl of the aggregates/complexes in assay buffer (PBS with 1 mM sodium citrate) and 3 µg of FII (prothrombin) or its derivatives (PTD) and 4 µg of FBN. The reaction mixture is incubated for 30 to 60 min at 37° C. For control experiment, the aggregates/complexes are incubated with either FII or FBN. The tubes are gently tapped after every 15 minutes and visually examined for the clot formation. After 1 hr incubation, 1 ml of PBS is added to each assay tube to confirm the thrombosis of the plaque complexes by visual and then by microscopic examination. The assay tube with visible clot present in the buffer is treated as positive for thrombosis whereas the tube without such visible clot presence is considered negative.

The PTD are prepared by treating 1 ml of prothrombin (FII) (1 mg/mL) with 25 µl of trypsin-agarose beads (Sigma, MI). After incubation at 37° C. shaker (Environ Shaker, Labline, Calif.) at 150 rpm for 1 hr, the samples are centrifuged at 3000 rpm for 5 min. The supernatant is carefully removed to separate from the beads. After repeating the centrifugation step for three times, the supernatant containing PTD is used for protein estimation and later for the clotting assays. Gel analysis of the PTD show partial degradation of the FII and its lower molecular weight proteins (FIG. 10). All the clotting experiments are carried out using the PTD instead of its individual purified components.

To address whether the FII in the presence or absence of FBN could cause the clot formation of the aggregates, CP, CO, lipid and cholesterol aggregates are mixed individually with the FII alone or together with the FBN. Visual examination of the clotting assay containing the aggregates showed no thrombosis. In the next experiment, the FII is freeze-thawed for ten cycles (−70° C. for 30 min followed by 37° C. for 30 min) and added to the aggregates in the presence and absence of the FBN to examine thrombosis.

Results: The assays containing both the freeze-thawed FII and the FBN indicate partial clot formation (thrombosis of ~50% of the aggregates) with the CP, CO, cholesterol and lipid aggregates. Conversely, there is no clot formation observed when iron-phosphate complexes are mixed with both freeze thawed FII and FBN. In addition, the clot formation is not observed when the aggregates are impregnated only with the freeze-thawed FII. These results suggest that the degradation product/s of the FII could induce FBN dependent thrombosis. To further probe the effect of PTD on clotting process of the aggregates, the PTD generated after treating with trypsin-agarose beads is mixed with aggregates in the presence of FBN. It is found that the CP, CO, CC and CaPPD aggregates showed thrombosis whereas iron-phosphate aggregates did not show clot formation (FIG. 11a). In addition, the plaque complexes assembled in vitro were subjected to binding with various stains that are commonly used to identify human atherosclerotic plaques (FIG. 11b). Interestingly, stains such as Alizarin red, Von Kosa, orange O red and hemotoxilin and eosin, that are commonly used to detect human atherosclerotic plaques, bind to the plaque complexes/ thromboses thereby confirm that in vitro assembled plaque-like complexes resemble human plaque.

Example 12

Microscopic Examination of Thrombus Formation

Figure 12:
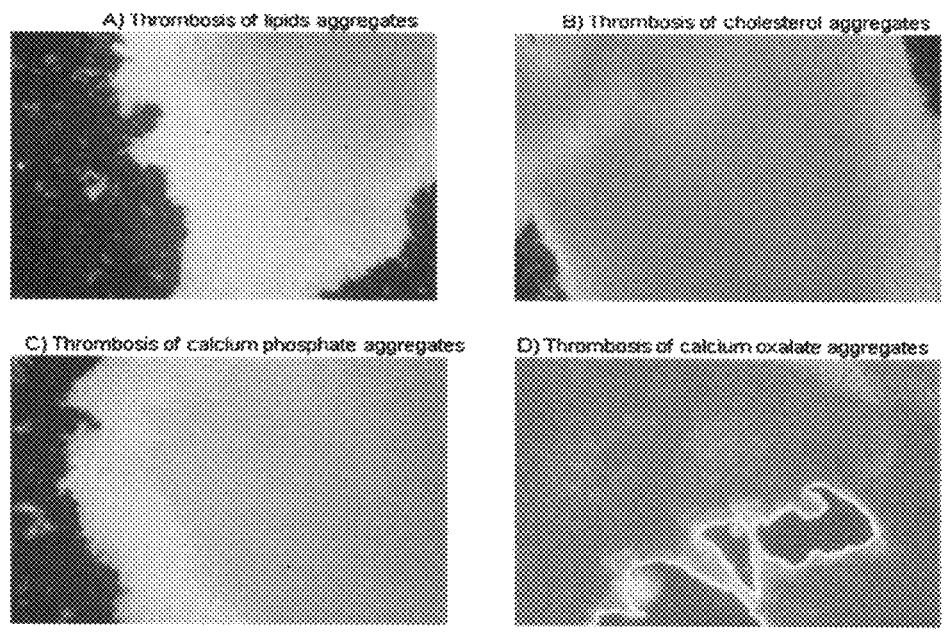
FIG. 12 Microscopic examination of the thrombi generated from insoluble aggregates. Labels on top of the each picture indicate the insoluble aggregates used for thrombus generation.

The example depicted in FIG. 12 illustrates the microscopic examination of thrombus formation. In order to further analyze the thrombus formation of the calcium, lipid and cholesterol aggregates, the clots generated from these aggregates are used for microscopic examination (Olympus CK40-SL, Japan). Interestingly, it is found that the clots contained dense packing of the aggregates that are possibly entangled with the fibrin mesh (FIGS. 12a, b, c and d): These results reveal that degradation of the FII by specific or non-specific proteolysis could cause FBN dependent thrombosis of the aggregates and their plaque complexes. The clotting experiments are intentionally performed with the PTD, rather than with purified components, to demonstrate that even simple proteolysis of the prothrombin during the plaque rupture could lead to blood platelets independent atherothrombosis. Also, these experiments suggest that the FII present in the plasma and urine could be degraded by non-specific proteases released from host tissues under pathological conditions or by bacteria.

These experiments suggest that the lipids, cholesterol and calcium containing aggregates are susceptible to thrombosis when exposed to both the PTD and FBN, whereas the iron-phosphate aggregates exhibited resistance to the thrombus formation. As described earlier, the calcified plaques/nodules are implicated in the development of diverse diseases including atherosclerosis, kidney stone diseases, valvular calcification, vascular calcification and CaPPD crystal diseases. It is likely that under the pathological conditions the thrombosis could occur because of exposure of these aggregates or their complexes to the coagulation factors. Being a multifunctional enzyme α-thrombin not only act on FBN but also activates platelets and induces their aggregation at the site of the injury (Vu T K et al, 1991; Monroe D M et al, 2005). Thrombin also activates other types of cells such as monocytes, endothelial cells, epithelial cells, smooth muscle. cells and lymphocytes (Ofosu F A, 2002). In addition to activating various cells, thrombin found to be involved in effecting morphological changes on the calcium containing crystals enabling their adhesion (Grover P K et al, 1999). The present study also suggests that the calcium and lipids containing plaques like complexes might play a role, similar to the platelets during blood coagulation, leading to their adhesion and clot formation in a blood platelets independent process. Further, it is likely that thrombosis of the aggregates and their plaque like complexes would cause serious life threatening events comparable to in vivo blood platelet dependent atherothrombosis.

Example 13

Thrombosis of the Plaque Complexes in Biological Samples

Figure 13:
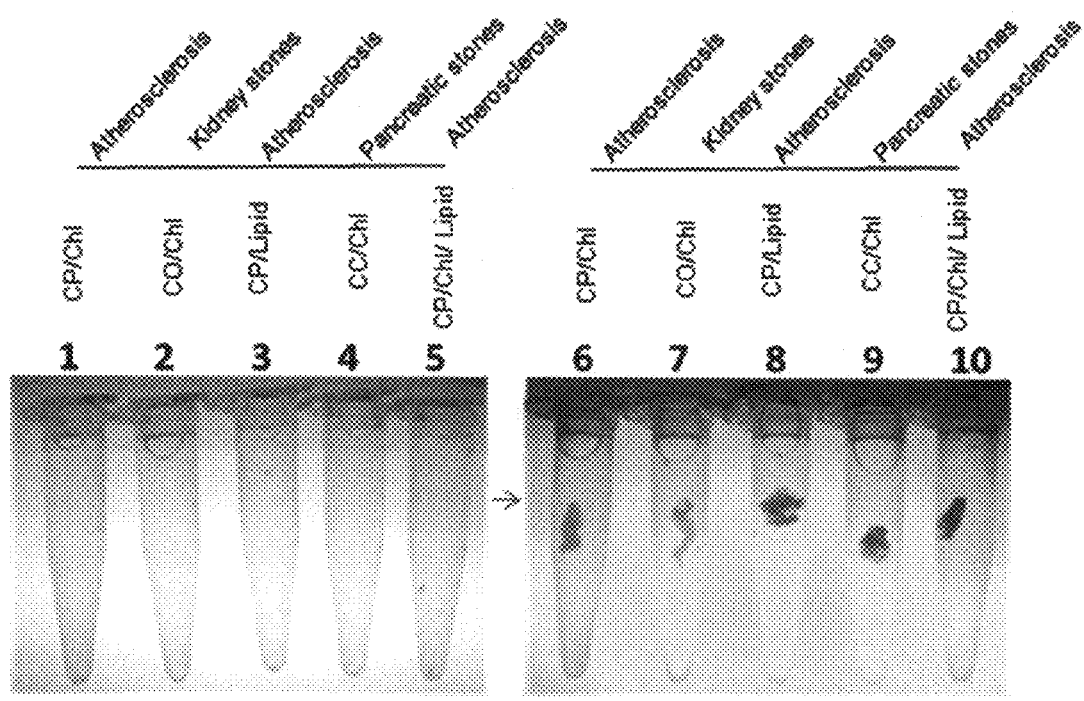
FIG. 13 Thrombosis of the in vitro assembled plaques like complexes using CP-Cholesterol, CP-lipids, CC-Cholesterol, CO-Cholesterol and CO-lipids aggregates. The label on top of the each tube indicate the aggregates used for assembly of the complexes and then for thrombus generation associated to various diseases.

FIG. 13 is an example illustrating thrombosis when the hybrid templates are incubated with biological samples such as human plasma or serum. To further explore the relevance of these in vitro findings to the clinical milieu, the following experiments are carried out to test the thrombosis of the in vitro assembled plaques complexes in the biological samples such as human serum, human plasma and human urine. The plasma and urine are the two major extra-cellular aqueous environments wherein majority of the insoluble aggregates and plaque initiation complex formation occur by either active or passive interaction with the organic and inorganic molecules. Initially, the plaque like complexes assembled using hybrid templates and the CPA method are incubated with diluted (25%) human plasma and human serum (25%) separately to examine the thrombosis and the results showed that there is no thrombus formation. In the next experiment, the complexes are pre-incubated with the PTD for 10 minutes followed by the addition of the diluted (2.5%) plasma or serum. Interestingly, thrombosis is observed for the complexes of the CP-Cholesterol, CP-Lipids, CO-Cholesterol, CO-Lipids and CC-Cholesterol (Chl) that are impregnated with both the PTD and plasma (FIG. 13).

Example 14

Thrombosis when Supplemented with FBN and PTD

Figure 14:
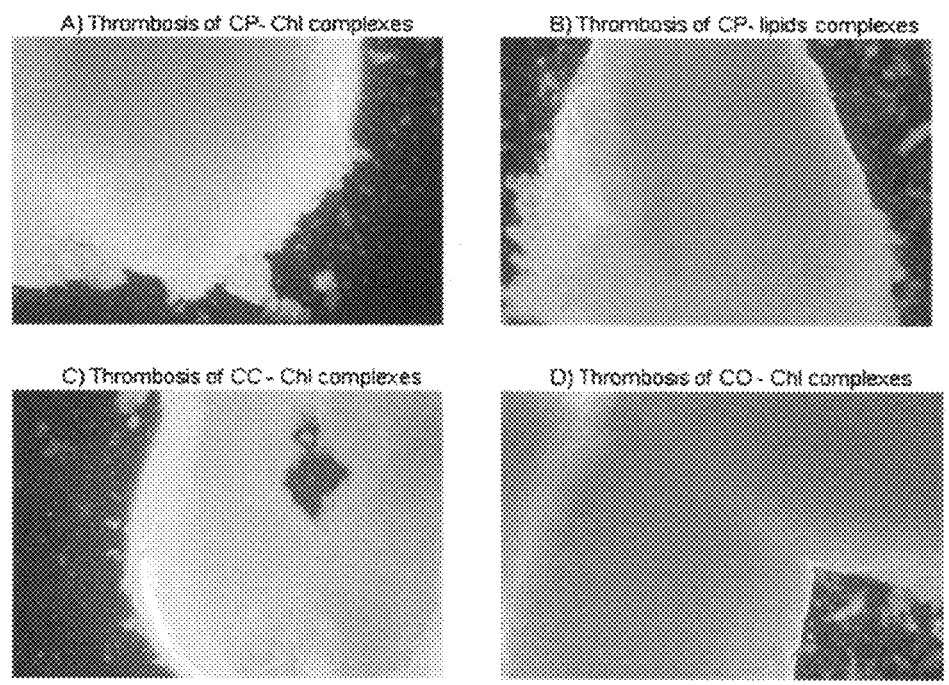
FIG. 14 Microscopic examination of the thrombi generated from insoluble aggregates. Labels on top of the each picture indicate the insoluble aggregates used for thrombus generation.

The example depicted in FIG. 14 illustrates experiments similar to those in the preceding example, except that here the complexes are contacted with FBN or PTD. Thrombosis is not observed when these PTD pre-treated complexes are mixed with the human serum (5%). However, these complexes showed thrombus formation when the serum is supplemented with both the FBN and PTD and the results are further confirmed by microscopic observation of the thrombus (FIGS. 14a, b, c and d).

Example 15

Clot Formation when Urine Sample is Supplemented with Both FBN and PTD

Figure 15:
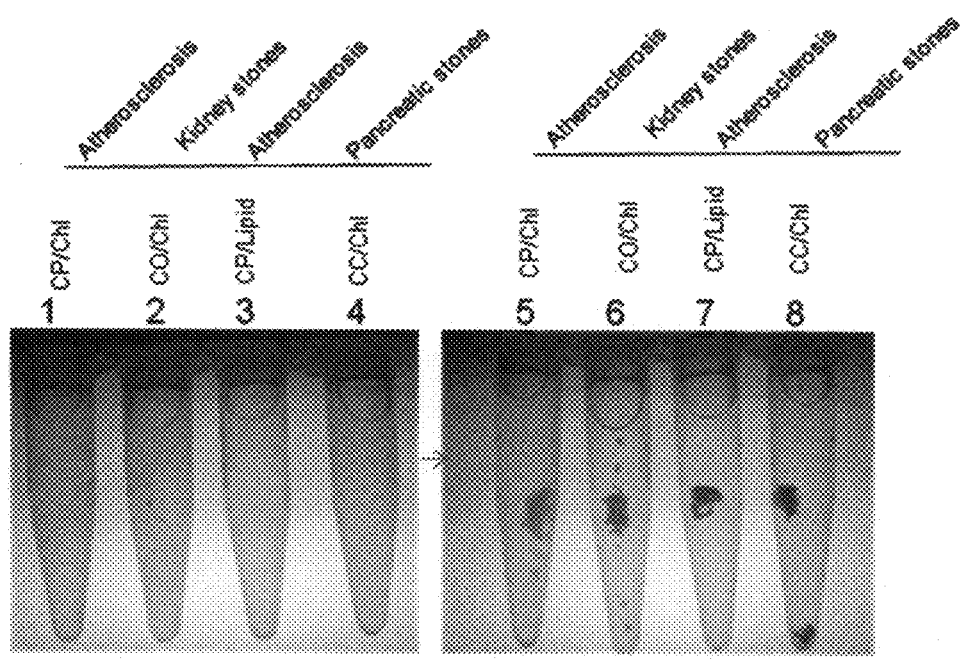
FIG. 15 Thrombosis of the in vitro assembled plaques like complexes using CP-Cholesterol (Chl), CO-Chl, CC-Chl, and CO-lipids aggregates. The label on top of the each tube indicate the aggregates used for assembly of the complexes and then for thrombus generation.

The example depicted in FIG. 15 illustrates clot formation of hybrid complexes when contacted with urine supplemented with both FBN and PTD. It is notable that since human serum lacks FBN, thrombus formation does not occur although the complexes are pre-incubated with the PTD, suggesting absolute requirement of both the PTD and FBN for the thrombosis of the plaque like complexes. Substantial amount of FBN and fibrin degradation products found coexisting with calcified nodules and cholesterol crystals in the atherosclerotic plaques (Bini, A et al, 1995). In the next experiment, the thrombus formation of the plaque complexes is studied in the urine sample. The clotting assay is modified for this experiment. The assays are performed in the presence of urine samples substituting the clotting assay buffer. For example, after CPA, the complexes are centrifuged and the pellet containing the complexes are suspended in 100 μl of human urine samples (pH 6.5 to 7.4), collected from healthy individual, and tested for thrombosis. It is found that when the plaques complexes of the CP-Cholesterol, CP-Lipids, CO-Cholesterol, and CC-Cholesterol are incubated in the urine sample, there is no clot formation. As observed in the preceding clotting experiments performed with human serum, the clot formation of these plaque complexes occurred only when the urine samples are supplemented with both the PTD and FBN (FIG. 15).

In addition, thrombi prepared from the aggregates and their complexes exhibit resistance to dissolution when incubated with metal chelators such as sodium citrate or EDTA (25 mM) for 6 to 12 hrs. Besides, the thrombus is stable for weeks when stored in the PBS supplemented with 5% human serum. Advanced imaging techniques have shown that the highly calcified nodule of plaques are often intermingled and superimposed with fibrin (Schaar J A et al, 2004). In addition, histopathological studies have shown that plaques containing high calcium depositions are considered to have matured from asymptomatic stage to highly advanced stage of atherosclerosis (Ehara S et al, 2005). And, the highly calcified regions of plaques with loss of fibrous cap are particularly susceptible for rupture (Burke A P et al, 2001). The present study showed that interactions among the PTD, FBN, aggregates and their complexes led to the formation of the clots that exhibited resistance to solubility with EDTA or sodium citrate. It is likely that the clots thus formed could occlude intra-vascular blood vessels and could potentially cause serious clinical consequences comparable to the events of atherothrombosis. These results also indicate that the calcified plaques deposited in the soft tissues, vascular beds, kidney stones, implanted calcium-based materials and atherosclerotic plaques are susceptible for the clot formation when exposed to the coagulation factors. It is appropriate to mention that the components such as insoluble aggregates of the cholesterol, lipids, CP and FBN that are used for in vitro assembly of atherosclerotic plaque like complexes have been identified in the in vivo vulnerable atherosclerotic plaques isolated from the patients.

The clinical consequences of the atherothrombosis are mainly unstable angina, acute myocardial infarction, ischemic stroke, peripheral arterial disease and ischemic cerebrovascular disease (Leys D, 2001; Munger M A et al, 2004). Our present study reveals that exposure of the lipid, cholesterol and calcium containing aggregates and their plaque complexes to the components of the coagulation factors mimic rupture of the unstable atherosclerotic plaques. Previous studies have identified calcium containing mobile thrombus, as a new risk factor among patients with chronic kidney diseases, which could cause cerebrovascular, cardiovascular and pulmonary thromboembolism related mortalities (Tsuchihashi K et al, 1999; Willens H J et al, 2003).

The present study demonstrates that the derivatives of FII might contribute for crystals adhesion and PTD, FBN dependent clot formation. Bleeding is an accompanying event commonly noticed while the kidney stones are passing through the lumen especially in kidney stone diseases. It is possible that during such process the kidney stones are exposed to interaction with the FII and FBN that might cause stones related clot formation. However, degradation of the FII might take place during pathological conditions and infections leading to non-specific activation of the FII and crystals related clot formation. This argument is supported by previous studies suggesting kidney tissues under various pathological conditions such as renal injuries, bleeding, infections and dysfunction promote retention of urinary stones and plaques formation (Khan S R, 2006). Furthermore, thrombosis of the calcium containing materials have wide clinical implications, for example, implantation of CP based biomaterials frequently identified as a source of undesired clot formation. Similarly, nanoparticles entering into the body from environment or formed due to various pathological conditions could also contribute to thrombosis related serious health complications.

Example 16

Dissolution of the Clots by Thrombolytic Proteins

Figure 16:
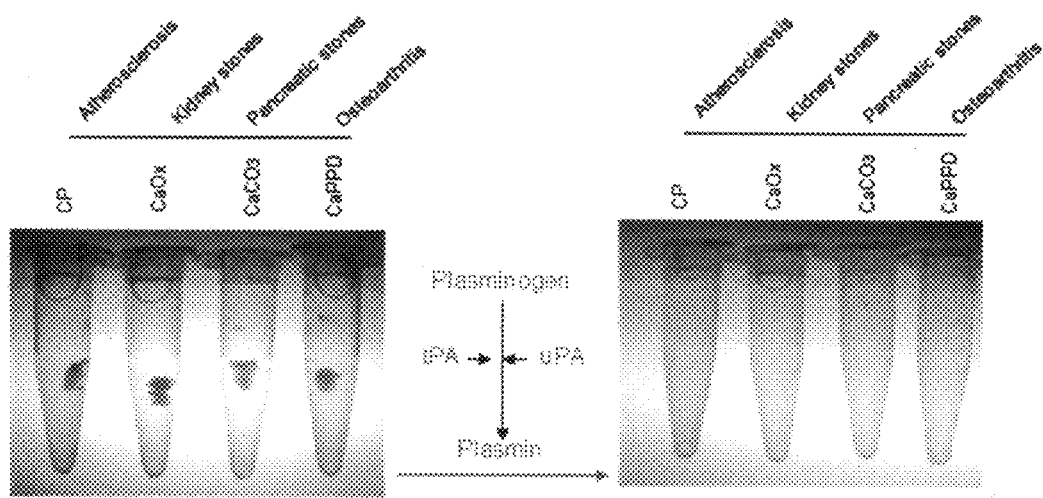
FIGS. 16a and b. Fibrinolysis of the thrombi generated from calcium containing aggregates. The label on top of the each tube indicates the aggregates used for assembly of the plaque complexes and then for thrombus generation associated to various diseases.

The example depicted in FIG. 16 illustrates the dissolution of thrombi upon incubation with thrombolytic proteins such as PLG and t-PA or u-PA.

Blood coagulation and fibrinolysis are two essential components of the hemostasis system that under normal circumstances operate in a harmonized way to maintain uninterrupted blood flow in the blood vessels (Dahlback B, 2000). In addition, both impaired blood coagulation and fibrinolysis considered important factor linked to atherosclerosis and other coagulation related mortalities. Under normal circumstances the components of vascular hemostasis system is capable of successfully neutralizing the blood clots by recruiting fibrinolytic factors at the site of fibrin clot thereby maintaining normal blood flow. The fibrinolytic cascade system consists of PLG, u-PA, t-PA, PAI-1 and PAI-2.

The fourth step of the PET technology development is to demonstrate the effect of PLG cascade system on dissolution of the thrombus generated from the in vitro assembled plaques complexes. To examine this, both PLG and PLG activators are used to target these clots. Thrombolytic assays are carried out in 100 µl reaction containing thrombus, generated from 100 µl of aggregates or plaque complexes, 1 µg of PLG and 20 ng of u-PA or t-PA in PBS buffer. The reactions are incubated at 37° C. for 1 hr and after every 15 min the tubes are gently tapped to mix the contents. After 1 hr incubation, 1 ml of PBS is added to all the tubes and the samples are visually examined for dissolution of the thrombus.

The thrombus generated from the cholesterol, lipids, CP, and CO complexes are incubated separately with PLG, u-PA and t-PA to examine whether these proteins individually could dissolve the clots. As expected, all the thrombus remained stable and did not show any dissolution suggesting these proteins have no individual effects on the clots. Conversely, when the thrombus is incubated with both PLG and t-PA, complete dissolution of the thrombus is observed (FIGS. 16a and b).

Figure 17:
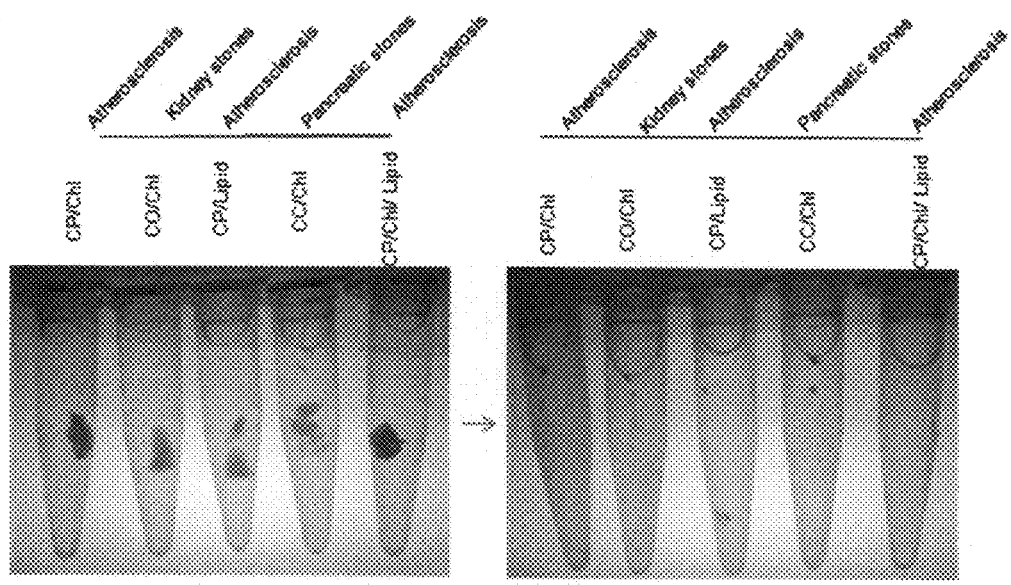
FIGS. 17a and b. Fibrinolysis of the thrombi generated from plaques complexes. The label on top of the each tube indicates the aggregates used for assembly of the plaque complexes and then for thrombus generation associated to various diseases.

The dissolution of the thrombus could be due to the activation of the inactive PLG into active plasmin by u-PA or t-PA that in turn cleaved the fibrin leading to the release of plaque contents from the fibrin mesh by a mechanism similar to the in vivo fibrinolysis of blood clot. As expected, when the clots are incubated with PAI-1 (25 ng), in addition to the PLG and u-PA, there is no dissolution of the clots. This could be due to the inhibition of u-PA by the PAI-1 thereby preventing the activation of the PLG. In the next experiment, the aggregates of CP-Cholesterol, CP-Lipids, CP-Cholesterol-Lipids, Cholesterol-Lipids, CO-Cholesterol and CO-Lipids are individually used in CPA for five cycles to assemble complexes followed by their thrombus generation. Incubation of these clots with the PLG and u-PA proteins led to their dissolution as shown in FIGS. 17a and b.

Example 17

Dissolution of Clots by PLG and u-PA

Figure 18:
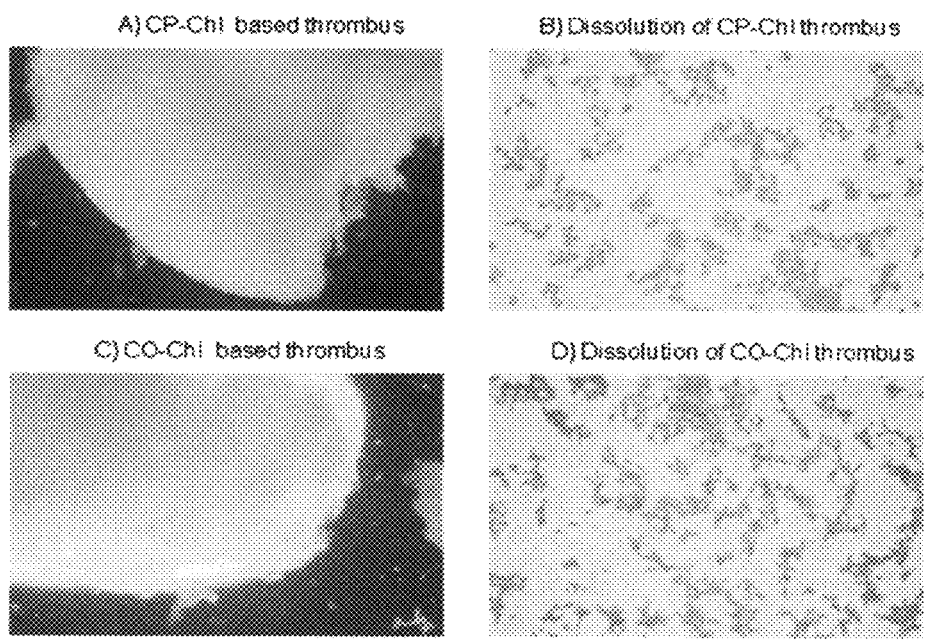
FIG. 18 Microscopic examination of the plaque complexes degraded by plasminogen cascade system. Labels on top of the each picture indicate the insoluble aggregates used for thrombus generation and their dissolution.

The example depicted in FIG. 18 illustrates the dissolution of thrombi by PLG and u-PA. Besides, the thrombus generated from the plaque complexes in the presence of plasma (2.5%) followed by their incubation with both PLG and u-PA results in their dissolution. Both the clots and the dissolved complexes are further examined under microscope to confirm the visual examination (FIGS. 18a, b, c and d). The thrombus formed in the urine is also dissolved by the action of PLG and u-PA. These results suggest that both the coagulation and fibrinolytic factors could interplay with the in vitro assembled plaque complexes leading to thrombosis and thrombolysis respectively mimicking the in vivo blood clot formation and thrombolysis mechanisms.

The presence of PLG activators particularly the u-PA in both the plasma and urine could play role in dissolving not only blood clots but also the clots formed from these aggregates and their complexes. The findings of this study shed new light on our understanding of blood platelets independent thrombosis of plaque complexes. Both the coagulation and fibrinolytic proteins play important role in this process by a novel mechanism homologous to blood coagulation and blood clot dissolution. The results obtained from this study would tremendously aid to identify novel therapeutic candidates for effectively targeting atherosclerosis and atherothrombosis.

Example 18

In Vitro Plaque Assembly in the Presence of Bacteria (*E. coli*)

Figure 19:
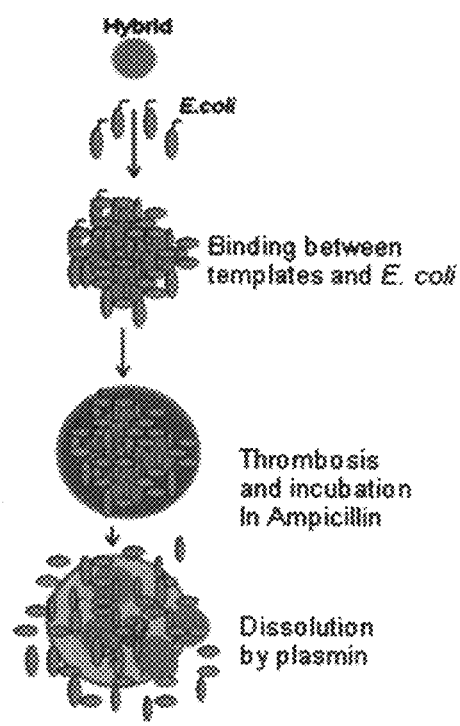
FIG. 19 Diagram showing sequences of plaques assembly process in the presence of E. coli.
Figure 20:
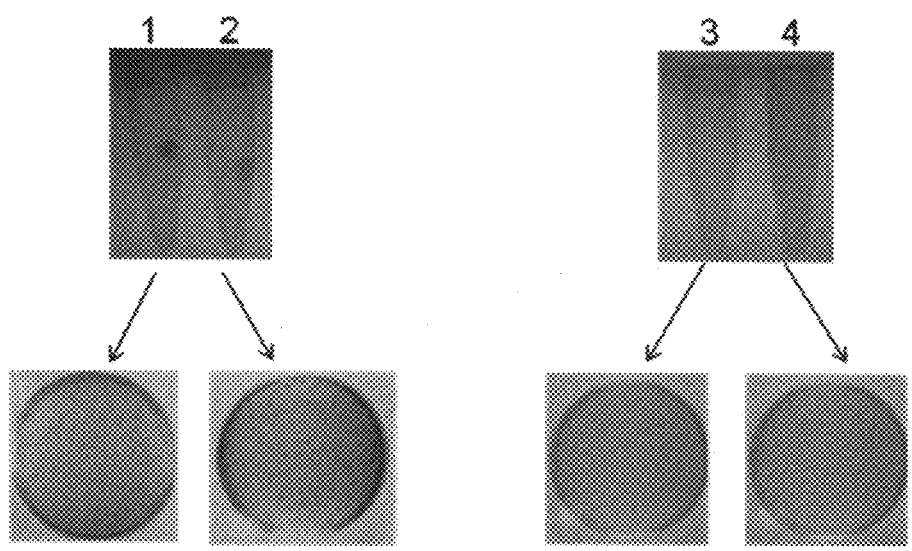
FIG. 20 Examination of bacterial growth after dissolution of the plaque complexes. Tubes 1 and 2 indicate plaque complexes assembled in the presence of both E. coli and, insoluble aggregates of CP and CO respectively. Tubes 3 and 4 indicate E. coli cells processed without the aggregates. The bottom of the picture shows E. coli growth on LB agar plates.

The examples depicted in FIGS. 19 and 20 illustrate in vitro plaque assembly in the presence of bacteria. Bacteria and virus debris have been identified from in vivo plaque contents suggesting they might play a role in the atherosclerotic processes (Shah, P K, 2001; Libby P et al, 1997). To understand the implication of association of bacteria with the plaques components, the in vitro plaque assembly is carried out in the presence of *E. coli* (XL-1 Blue) as shown below (FIG. 19). A single colony of the *E. coli* is inoculated in 2 ml of Luria Broth (LB) medium and grown overnight at 37° C. shaker at 220 rpm. Next day, 20 µl of the overnight culture is inoculated into fresh 2 ml LB medium and the culture is grown at 37° C. shaker at 220 rpm until it reaches the density of 0.5-0.6 (OD at 560 nm).

The plaque assembly is carried out in duplicate sterile 1.5 ml microfuge tubes using CP-Cholesterol and CO-Cholesterol aggregates that are prepared as described above. First, *E. coli* ($5.0 \times 10^8$ CFU) is mixed with 100 µl of the CP-Cholesterol and CO-Cholesterol hybrid aggregates separately and incubated at 37° C. for 30 min. For control experiment, *E. coli* ($5.0 \times 10^8$ CFU) is mixed with 100 µl of PBS. Next, 3 µg of the PTD and 4 µg of FBN or human plasma (2.5%) is added to both the samples containing the *E. coli* and aggregates and for control experiments. Following 1 hr incubation at 37° C., 1 ml of LB medium supplemented with ampicillin (100 µg/ml) is added to all the tubes. As expected, the tubes containing both the aggregates/complexes and *E. coli* showed thrombus formation whereas the control experiment without aggregates did not show visible thrombus formation. After this, the tubes are closed tightly and sealed with parafilm (Fisher, Calif.) followed by their incubation at 37° C. for 48 hrs.

After incubation, 2 µg of the PLG is added to all tubes and incubated for 30 min at 37° C. followed by the addition of 20 ng of u-PA to activate the PLG. After incubation for another 1 hr, 1 ml of sterile PBS is added to all the tubes and it is observed that the thrombus is dissolved in tubes containing both aggregates and *E. coli*. The samples are processed further to examine bacterial growth. The samples from both positive (*E. coli* and aggregates) and negative control (only *E. coli*) are serially diluted and plated on both LB agar and LB agar plate supplemented with ampicillin (50 µg/ml). After overnight incubation at 37° C. the plates are used to count colonies. Interestingly, it is found that the LB plates with samples spread from tubes containing the *E. coli* and CP-Cholesterol aggregates showed *E. coli* growth (~$3 \times 10^4$ CFU) (FIG. 20) and surprisingly few colonies (~$0.7 \times 10^2$ CFU) are also seen on ampicillin plates. Similarly, the samples plated from CO-Cholesterol and *E. coli* complex tubes showed colonies ($9.0 \times 10^3$ CFU) on both LB (FIG. 20) and ampicillin plates (~$0.2 \times 10^2$ CFU). Conversely, no colony is seen on both the LB and ampicillin plates for samples plated from control tubes processed for *E. coli* without the aggregates.

These experiments suggest that the insoluble aggregates act as building blocks for plaque like complexes assembly and the *E. coli* residing inside the complexes evade from antibiotic action. During this incubation time a tiny population of *E. coli* living inside the thrombus under anaerobic condition evolves resistant to ampicillin. This result indicates that by manipulating the selection conditions, similar to antibiotic selection, one could evolve microorganisms to perform novel functions using plaques assembling technology. In addition, these results reveal that the plaque assembly processes with bacterial cells could be used to develop, modify and improve the properties of the microorganisms. Bacterial infections and particularly *E. coli* infection is a common medical problem associated with kidney stones and urinary tract infections (Mysorekar I U et al, 2006). Also, it is relevant to compare these results to in vivo pathological conditions often observed with biomaterial implantation that cause bacterial infection, thrombosis, biofilm formation and antibiotic resistance (Gilbert P et al, 2002). Finally, these experiments validate the in vitro plaque assembly process that mimic in vivo pathological conditions and provide a powerful tool both for drug discovery and carrying out basic research.

Example 19

Assembly of Atherosclerotic Plaque Like Complexes with Human Endothelial Cells

Figure 21:
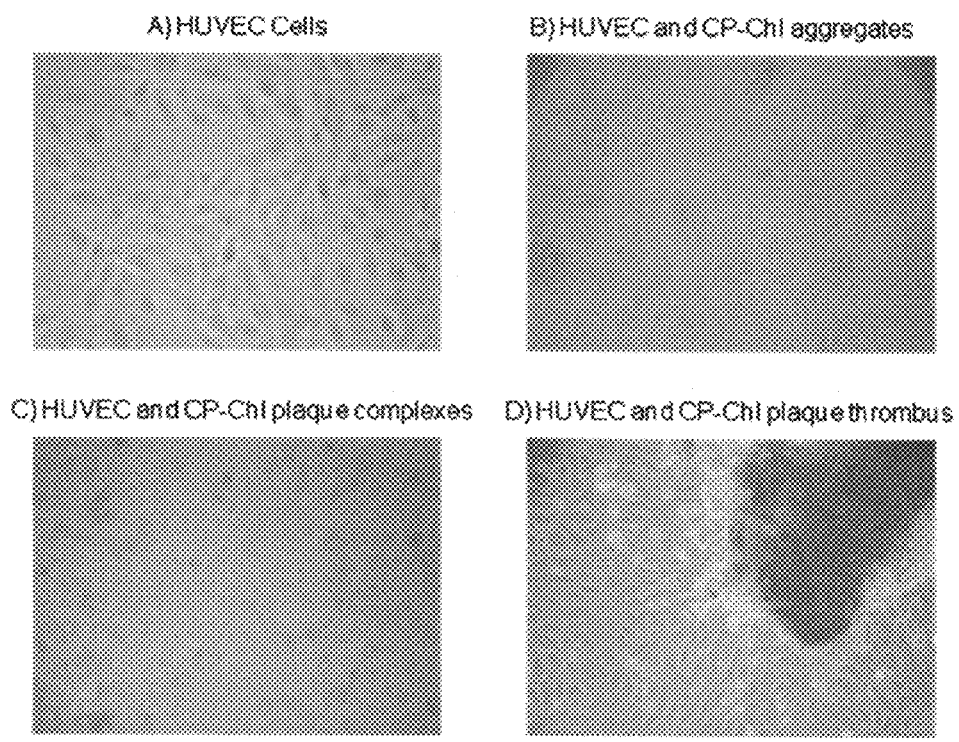
FIG. 21a to d. Microscopic observation (400×) of HUVECs after 48 hrs growth. a) HUVECs growth, control without aggregates; b) HUVECs growth with CP-Chl aggregates; (c) HUVECs growth with CP-Chl plaque like complexes and d) HUVECs growth with thrombus.

The example depicted in FIG. 21 illustrates the assembly of atherosclerotic plaque like complexes with human endothelial cells. The preceding two sections described the development of PET platform to mimic in vivo atherosclerotic plaque assembly. In the next step to develop a cell culture based atherosclerotic plaque model system, human endothelial cells are used in the plaque assembly experiments. The vascular bed of the arteries is covered with endothelial cells and their dysfunction is one of the key early events contributing to the initiation of the atherosclerotic plaques development (Gerhard, A T et al, 1995; Davignon, J et al, 2004). The plaques built up on the walls of the arteries occur as an extracellular process due to progressive deposition of various components such as cholesterol, lipids, calcium, minerals and blood clots These components remain physically associated with the endothelial cells and the pathogenic effect of such assembly on these cells is not completely understood. In order to determine the interplay among the plaque components and endothelial cells, the in vitro plaque like complexes assembly is carried out in the presence of endothelial cells. To achieve this, human umbilical vein endothelial cells (HUVECs) and endothelial cell growth medium (ECGM) are purchased (Cell applications, CA). The cells are grown to confluence in 75 cm2 culture flasks containing 20 ml of ECGM. After removing the medium, the cells are treated with trypsin-EDTA solution and scraped off the plate. Then the cells are harvested by centrifugation at 2000 rpm for 5 min (Beckman GS-6, CA), washed once with sterile PBS followed by their suspension in 2 ml ECGM. After cell count, the HUVECs (6000 per well) are seeded into 6 well tissue culture plates containing 3 ml of ECGM and grown with and without plaque complexes. After 48 and 72 hours incubation, the cell viability is determined by microscopic examination (Olympus CK40, Japan).

A series of experiments are performed with HUVECs to examine the effect of different aggregates, plaque like complexes and thrombus on cell viability. First, the hybrid aggregates of CP-Chl, CO-Chl and Chl-Lipids are prepared as described above and directly used for binding with HUVECs. For binding, 50 µl of the aggregates are mixed with the cells (6000) for 10 min in a sterile 1.5 ml microfuge and then the cells-complexes are transferred to 3 ml ECGM medium and incubated for 72 hrs. Second, for binding of plaques like complexes with the HUVECs, the hybrid aggregates are used for four cycles of CPA and then the resultant complexes (50 µl) are mixed with the cells (6000) for 10 min and then the cell-complexes are transferred to 3 ml ECGM medium for 72 hrs growth. Third, for generation of thrombus in the presence of both the plaque complexes and HUVECs, the plaque complexes (50 µl) prepared after four cycles of CPA are mixed with the cells (6000) to which 3 µg of the PTD and 4 µg of FBN or 2.5% of human plasma are added. After 30 min incubation at 37° C., the samples are examined for thrombus formation by visual examination. After confirming the thrombosis, the cells-thrombus combinations are transferred to the 3 ml ECGM in 6 well cell culture plates for 72 hrs incubation. For control experiments, the HUVECs (6000) are grown in 3 ml ECGM without any aggregates or plaque complexes. The cells are then analyzed for viability by microscopic examination and the results are documented for further analysis.

After 48 hrs, the microscopic observation of the HUVECs incubated with the CP-Chl aggregates showed only 10% viable HUVECs and, compared to the control HUVECs, these cells showed pathological symptoms as evidenced by extensive morphological changes. Similarly, the HUVECs incubated with CP-Chl plaque complexes showed 30% viability with extensive morphological changes. However, the HUVECs grown with the thrombus showed 60% of the viability and only the cells that remain attached to the thrombus showed morphological changes whereas cells that are not attached to the thrombus appeared normal, similar to control HUVECs (FIG. 21a to d). These results suggest that the binding of the aggregates and plaque complexes directly to the HUVECs cause severe pathological symptoms to the cells. The cells that are attached to the thrombus also showed similar symptoms although the effect is localized to thrombus. In this case, since most of the CP-Chl aggregates are accumulated in the thrombus a large number of the cells did not show pathological symptoms. These results suggest that the CP-Chl aggregates and their complexes are highly pathogenic to HUVECs and in good agreement with our biochemical experiments performed using the CPA.

Example 20

HUVECs in Contact with CO-Chl

Figure 22:
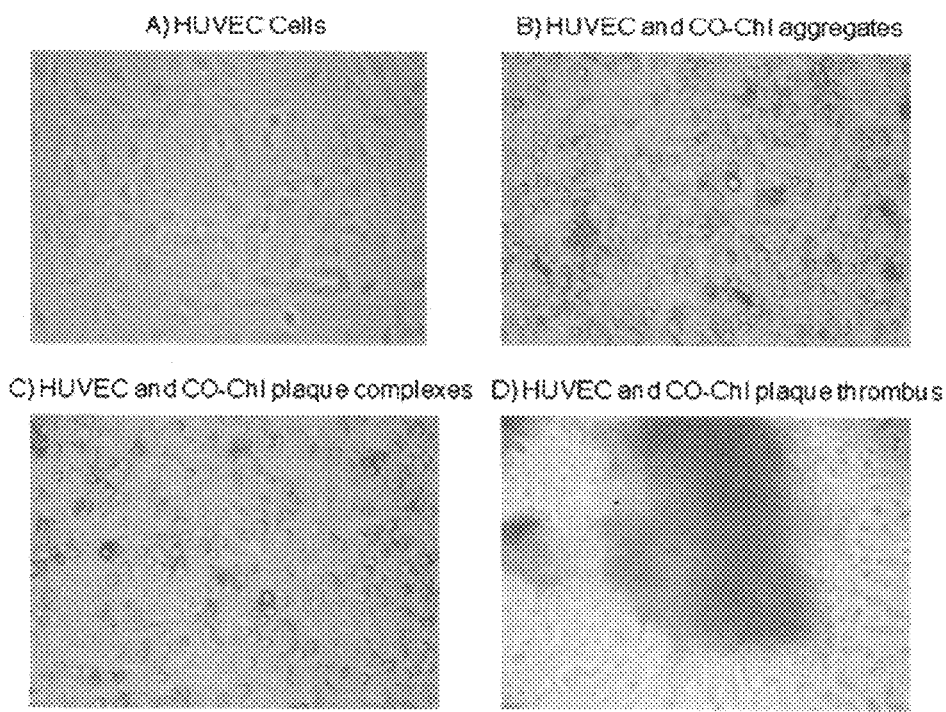
FIG. 22a to d. Microscopic observation (400×) of HUVECs after 48 hrs growth. a) HUVECs growth, control without aggregates; b) HUVECs growth with CO-Chl aggregates; (c) HUVECs growth with CO-Chl plaque like complexes and d) HUVECs growth with thrombus.

The example depicted in FIG. 22 illustrates the results when HUVECs are incubated with CO-cholesterol. In identical experiments performed with the CO based aggregates, the microscopic observation of the HUVECs cultured with the CO-Chl aggregates showed approximately 90% cells viability. However, 60% of those cells showed significant pathological symptoms compared to the control HUVECs. In addition, the HUVECs growth with the CO-Chl plaque like complexes also showed approximately 90% viability and 50% of them with morphological changes. The HUVECs growth with the CO-Chl thrombus showed 70% viable cells and again only the cells that are attached to the thrombus showed morphological changes (FIG. 22a to d). These results suggest that the CO-Chl aggregates and their plaque like complexes are also pathogenic to the HUVECs thus further confirming our results obtained using the CPA method.

Example 21

HUVECs in Contact with Chl-Lipids

Figure 23:
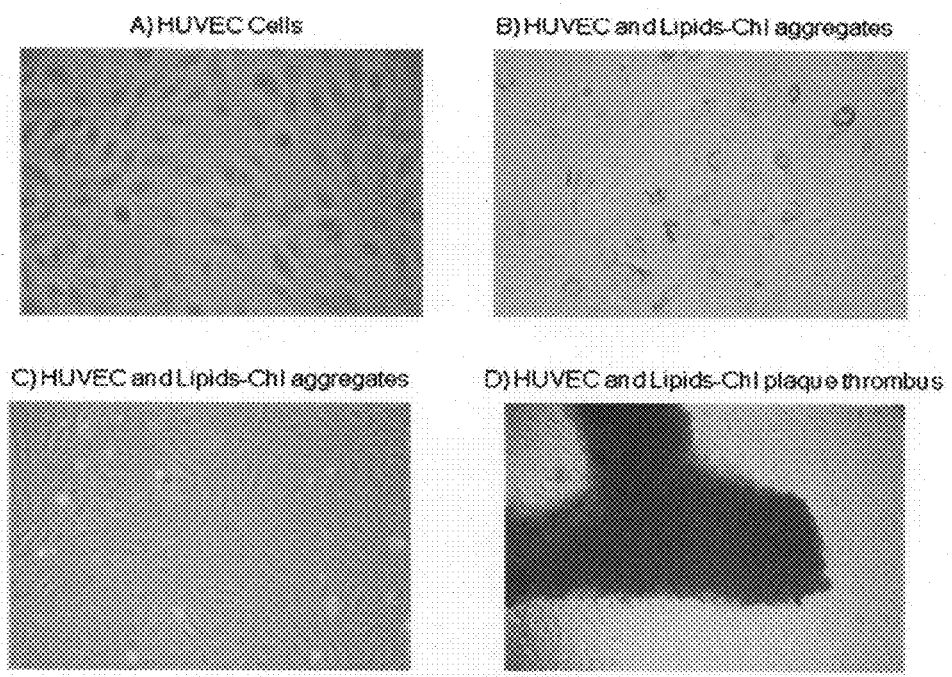
FIG. 23a to d. Microscopic observation (400×) of HUVECs after 48 hrs growth. a) HUVECs growth, control without aggregates; b) HUVECs growth with Chl-Lipid aggregates; (c) HUVECs growth with Chl-Lipid based plaque like complexes and d) HUVECs growth with the Chl-Lipids thrombus.

The example depicted in FIG. 23 illustrates HUVECs that are in contact with Chl-Lipids. Microscopic examinations of the HUVECs growth with the Chi-Lipids aggregates show that approximately 90% of the cells are viable and 50% of them showed morphological changes as observed with the other aggregates. However, with the Chl-Lipids plaque complexes around 90% of the HUVECs are viable with less pathological symptoms. Similar to previous observations with CP-Chl and CO-Chl based thrombus, described herein, the HUVECs growth with Chl-Lipids thrombus showed 90% of viable and normal cells (FIG. 23a to d).

Example 22

Morphologic Changes in HUVECS in Contact With Plaque Complexes

Figure 24:
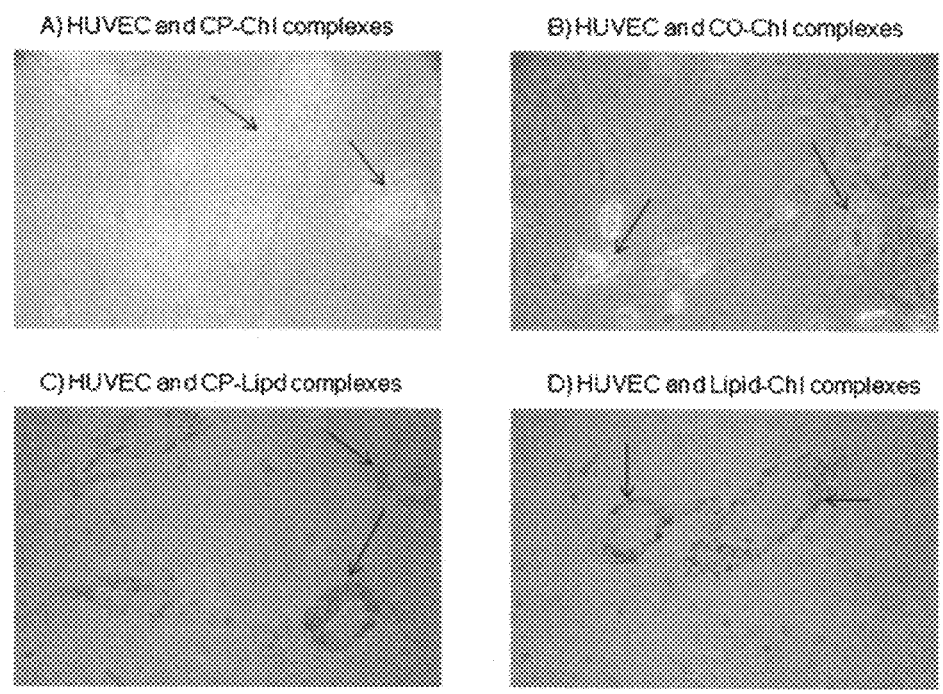
FIG. 24a to d, Microscopic observation of the plaque complexes attached to the surface of the HUVECs. The plaque like complexes used for binding are indicated at the top of each picture (a, b, c and d) and the arrows indicate localization of the plaque complexes and pathological symptoms of the HUVECs.

The example depicted in FIG. 24 shows morphological changes in HUVECs in contact with plaque complexes. The microscopic observation of the plaque complexes with the HUVECs grown for 72 hrs show the localization of plaque complexes on the surface of the cells. The cells attached to these complexes show extensive morphological symptoms compared to the controls (FIG. 24a to d). These results strongly suggest that the in vivo binding of atherosclerotic plaque complexes to the endothelial cells could lead to their dysfunction and eventually death, one of the early events in the development of atherosclerotic plaques. In addition, apoptosis mediated endothelial cell death and their morphological changes facilitate adhesion of monocytes and macrophages in the arteries. The infiltration of monocytes into the atherosclerotic plaque leads to release of pro-inflammatory cytokines causing chronic plaque inflammation.

However, the thrombosis of the plaque complexes and their progressive accumulations with the endothelial cells could cause narrowing of the blood vessels, chronic inflammation, cardiovascular complications and reduced blood flow. Finally, the detachment of the plaque complexes or thrombus from the endothelium, due to rupture or other pathological conditions, would generate serious medical conditions such as Myocardial infarction, stroke and other thromboembolic events (Rauch U et al, 2001).

Taken together, these results reveal that the pathogenic level of these aggregates on HUVECs varies and are in the order of >CP-Chl>CO-Chl and Chl-Lipid, thus confirming the biochemical predictions obtained using the CPA method. Importantly, the HUVECs based atherosclerotic model system is a novel method suitable for accelerated drug discovery targeting atherosclerosis, kidney stone and gall stone diseases. This system also enables assembly of different plaque sub types to mimic atherosclerotic plaques sub types such as pre-atheroma (type I to III), containing high lipids content and atheroma type (type IV and Va) containing CP, Chl, lipids and fibrin clots. In addition, the HUVEC based cell culture model system could be used to test efficacy and safety of the lead molecules identified from the biochemical PET platform. Identification of drug or drug like leads that prevent or inhibit the pathogenic effect of insoluble aggregates and/or their plaque like complexes on HUVECs could be successful therapeutic candidates for treating atherosclerosis and other plaques related diseases.

Example 23

Figure 25:
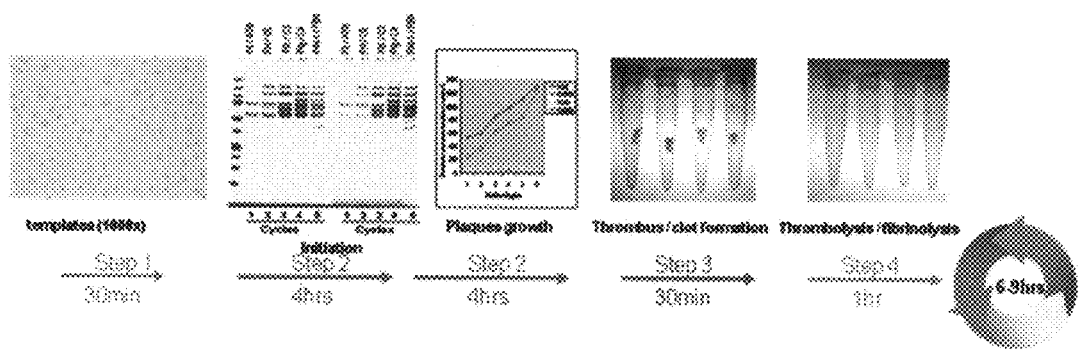
FIG. 25 Four steps of the in vitro plaque like complexes assembly and times schedule for completion of drug discovery cycle.

Integration of the Four Steps of In Vitro Plaques Assembly Processes for Development of Pet Platform and its Application for Drug Discovery The example illustrated in FIG. 25 depicts the four steps of the PET platform and includes images demonstrating the time course.

The development of PET platform involves a chain of biochemical interactions among soluble and insoluble components that are carried out in the following sequences: a) begins with the insoluble aggregates formation prepared from homogeneous molecules or by product of interaction between inorganic molecules; b) interfacing of the insoluble aggregates with the soluble molecules by iterative binding leading to the progressive growth of the complexes; c) interplay of insoluble aggregates and their complexes with the coagulation and fibrinolytic proteins; d) interaction of insoluble aggregates and their complexes with the micro-organism and 5) assembly of plaque like complexes with HUVECs and determining the pathogenic effects of the complexes on the cell viability. The novel interactions among various organic and inorganic components that contribute to the in vitro plaque assembly process are potential targets for drug discovery. Any drug or drug like molecules that would be identified for disrupting these processes or interactions would be a novel therapeutic candidate for treatment of atherosclerotic plaques related diseases. Strikingly, the biochemical process of plaques assembly process could be completed in 6-9 hrs that mimic decades of in vivo atherosclerotic plaques development stages (FIG. 25).

Example 24

Identification of Lead Molecules that Prevent Formation of Plaque Complexes

Figure 26:
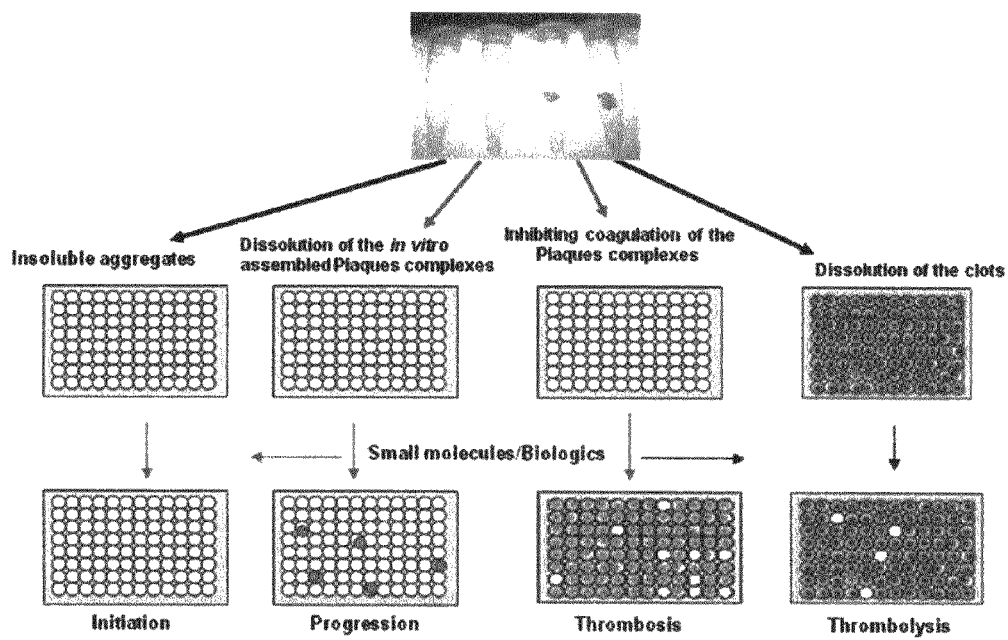
FIG. 26 Diagram showing format for high throughput drug discovery targeting four steps of the PET platform.

Assembly of hybrid templates shows novel interaction among Chl, lipids and CP aggregates to form plaque initiation complexes during plaque assembly. More specifically, the CP aggregates play important role in such initial complex formation of these aggregates and the resulting complexes act as template for progressive plaque growth. The example depicted in FIG. 26 depicts the identification of lead molecules that prevent formation of CP aggregates and plaque initiation complex formation. To validate this innovative PET drug discovery platform, the CP, CP-Lipids and CP-Chl-lipids complex formations and their thrombosis processes are identified as primary targets for current drug discovery. Besides, based on our biochemical and cell culture model systems it is evident that the CP, CP-Lipids and CP-Chl insoluble aggregates and their complexes are the most pathogenic factors that could play important role in the advanced atherosclerotic plaque formation. The first objective of the drug discovery efforts is to identify a molecule to inhibit the CP aggregates formation so that the initiation of the atherosclerotic process could be suppressed. To achieve this goal, screening is carried out in 96 wells assay plates with 100 μreaction volumes to identify a known or unknown drug molecule effective to disrupt one or more of the CP mediated initial plaques assembly processes as shown below (FIG. 26). Initially, a number of known drug molecules are screened in the assays containing 5 mM sodium phosphate dibasic and 5 mM experimental drug compound, to which 5 mM calcium chloride is added to examine whether the drug molecule could prevent the CP aggregates formation. For control, both calcium chloride and sodium phosphate dibasic (5 mM each) are mixed and treated similar to other samples. After 30 min incubation at 37° C., the assay plates are centrifuged at 3000 rpm for 3 min (Beckman GS-6, CA) and examined for insoluble aggregates formation by both visual and microscopic examinations.

Example 25

Figure 27:
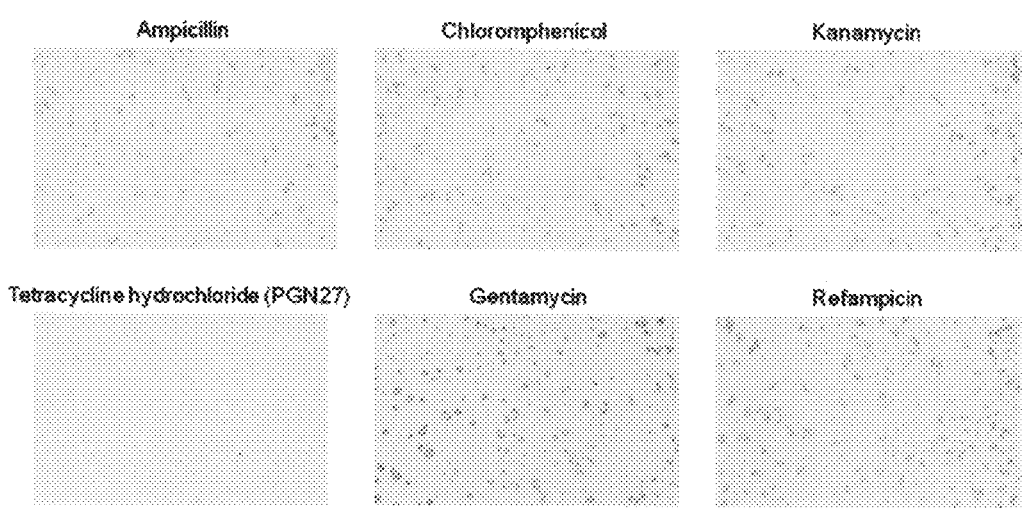
FIG. 27 Microscopic examination of the aggregates formation in the presence of different antibiotics. The legends on top of the each picture shows the antibiotic used in the assay.

Identification of Tetracycline Chloride as an Inhibitor of Plaque Initiation Complex Formation The example depicted in FIG. 27 illustrates the identification of tetracycline hydrochloride as an inhibitor of CP aggregate formation. In one of the screenings carried out to probe whether antibiotics could be effective to prevent the CP aggregates formation, antibiotics such as ampicillin, chloromphenical, kanamycin, tetracycline hydrochloride, rifampicin and gentamycin are used with sodium phosphate dibasic, and calcium chloride. Surprisingly, among these six antibiotics tested, tetracycline hydrochloride prevented the CP aggregates formation (FIG. 27a to e). The experiments are repeated many times and the results consistently showed that the tetracycline hydrochloride effectively prevented the CP aggregates formation that in turn resulted in the prevention of plaque initiation complex formation.

Example 26

Structure of Tetracylcine Hydrochloride

Figure 28:
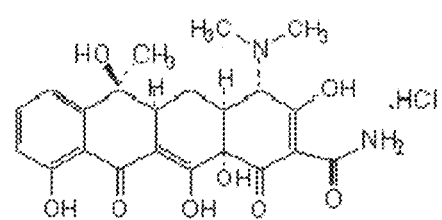
FIG. 28 Molecular formula of tetracycline hydrochloride (PGN27).

The example depicted in FIG. 28 is a schematic illustrating the structure of tetracycline hydrochloride. Tetracycline hydrochloride ($C_{22}H_{24}N_2O_8$), (FIG. 28) is a known antibiotic used to treat a spectrum of bacteria and it inhibits bacterial protein synthesis. It binds to 30S ribosomal unit and prevents the binding of aminoacyl t-RNA to the A-site of the ribosome leading to the inhibition of the bacterial protein synthesis (Maniatis T et al, 1989).

Example 27

Inhibition of Thrombosis of Plaque Complexes by Tetracycline Hydrochloride (PGN27)

Figure 29:
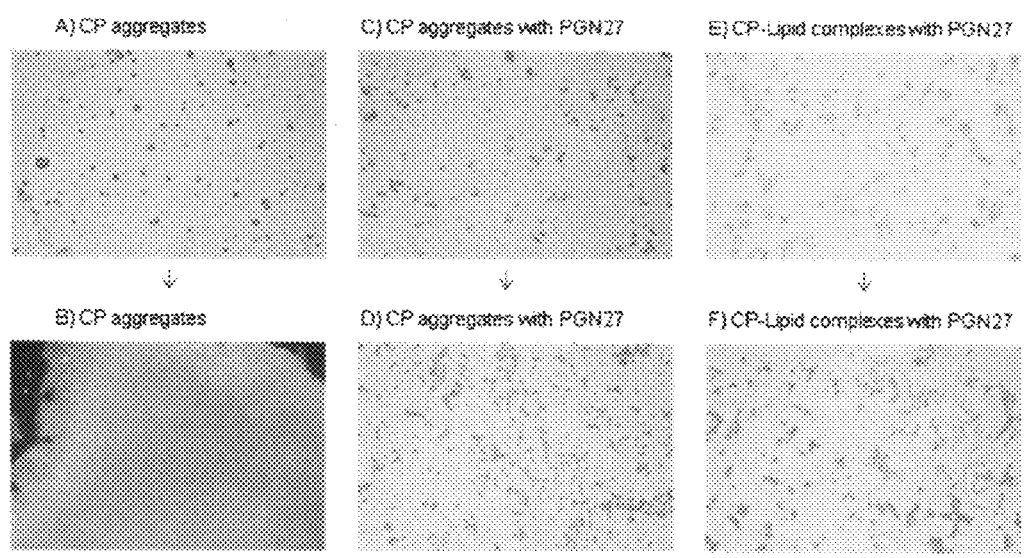
FIG. 29 Microscopic analysis of thrombosis of plaque like complexes in the presence and absence of the PGN27.

The example depicted in FIG. 29 illustrates the inhibition of thrombosis of aggregates/plaque complexes by tetracycline hydrochloride (PGN27). The tetracycline chloride is now named as PGN27 and further used to examine its effect on other steps of the in vitro plaque assembly processes. More specifically, here CP-containing aggregates are studied.

It is reported earlier that the tetracycline has affinity binding with calcium under in vitro conditions (Finerman G M et al, 1963). However, in the current study, we have discovered that the tetracycline hydrochloride has novel property of inhibiting binding of the calcium with inorganic phosphate thereby preventing the CP aggregates formation and assembly of plaque initiation complex. Next, to examine the dose dependent inhibition of the CP aggregates formation by PGN27, the concentrations of the both sodium phosphate dibasic and calcium chloride are fixed (4 mM each) whereas the PGN27 concentration is varied (4, 2, 1, 0.5 and 0.25 mM) in the assays. After 30 min incubation at 37° C. followed by centrifugation, the examination of the assays showed that the CP aggregates formation occurred only with 0.5 and 0.25 mM of PGN27 whereas the rest of the assays containing 4, 2 and 1 mM tetracycline did not show the CP aggregates formation. Notably, it is observed that the PGN27 did not inhibit CO, lipid and cholesterol aggregates formations suggesting it is specific to inhibition of the CP aggregates formation.

A series of experiments are performed with the PGN27 to probe its effect on cyclic plaque assembly, thrombosis and thrombolysis. The CP aggregates (200 μl) prepared, as described herein, are mixed with the 2 mM PGN27 and incubated at 37° C. for 30 min. After centrifugation at 3000 rpm, 3 min, the supernatants are discarded and the CP-PGN27 complexes are suspended in 200 µl of PBS. It is observed that the CP aggregates treated with the PGN27 turned from colorless to yellow color indicating specific and stable binding of the PGN27 with the CP aggregates. Further, these CP-PGN27 complexes are subjected to four cycles in CPA. For control experiments, the CP aggregates without PGN27 treatment are simultaneously used for the CPA. Gel analysis of the complexes showed the profile of CP-PGN27 complex is similar to the CP aggregates. These results suggest that binding of the PGN27 to the CP is an independent process and it did not compete or affect binding of the proteins with the CP aggregates.

Next, in order to probe whether the PGN27 could have effect on the thrombosis, the CP based plaque like complexes are used in the thrombosis assay as described in the section 2.4.1. The CP, CP-Chl, and CP-Lipids based plaque complexes (100 µl), generated after four cycles of CPA, and then treated with 2 mM PGN27 at 37° C. for 30 min followed by centrifugation. After discarding the supernatant, the CP-PGN27, CP-Chl-PGN27 and CP-Lipids-PGN complexes are used for thrombosis using the PTD (3 µg) and FBN (4 µg) or 2.5% human plasma. For control experiment, the CP without PGN27 treatment is used for thrombosis. Interestingly, the results showed that the CP based plaque complexes treated with the PGN27 did not form thrombus and, as expected, thrombosis is observed in the control experiment. These experiments strongly suggest that, in addition to inhibiting assembly of plaque initiation complex, the PGN27 has potential to inhibit thrombosis of the plaque like complexes (FIG. 29a to f). It is our hypothesis that (1) the PGN27 might modulate conformational changes on plaque complexes leading to the inhibition of their aggregation and (2) the PGN27 bound plaque complexes might inhibit the activity of the thrombin, a member of serine protease, thereby inhibiting the coagulation of plaque complexes. Previous studies have shown that Tetracycline is a potent inhibitor of collagenase, a serine protease, and matrix metallo protease (MMP).

Example 28

PGN27 Inhibition of the Thrombosis of CO and CO-Lipid Plaque-like Complexes

Figure 30:
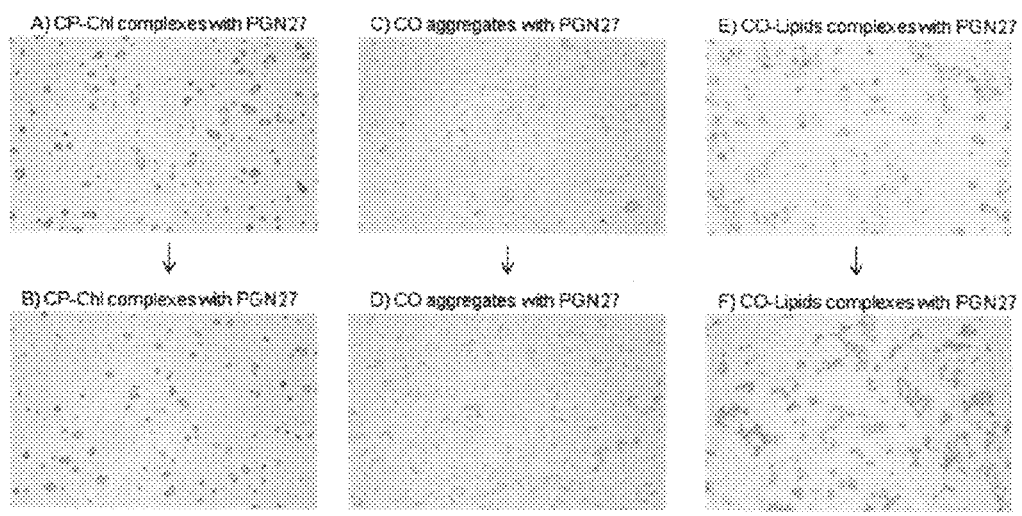
FIG. 30 Microscopic analysis of thrombosis of plaque like complexes in the presence and absence of the PGN27.

The example depicted in FIG. 30 illustrates PGN27 inhibiting the thrombosis of CO and CO-Lipid plaque-like complexes. (FIG. 30a to f). Together, these results reveal that the PGN27 has novel property to inhibit blood platelet independent thrombosis of the plaque like complexes. To examine whether the PGN27 has any effect on dissolution of the thrombus, generated from the CP-Chl aggregates, it is incubated with 2 mM PGN27 for 1 hr. It is observed that there is no dissolution of the thrombus by the PGN27. However, it is found that after treating with the PGN27, the thrombus turned from colorless to yellow indicating PGN27 could pass through the thrombus and stably bind with the plaque components.

5.2 Therapeutic Potential of the PGN27 for Treating Patients with Advanced Atherosclerosis and Atherothrombosis The above described results clearly indicate that the PET is a powerful drug discovery platform for accelerated drug discovery. By applying this platform we could rapidly identify a known drug, tetracycline hydrochloride, and discovered novel anti-atherosclerotic mechanism of actions for this drug. Its novel properties both for inhibiting new atherosclerotic plaque formation and the thrombosis of the pre-formed atherosclerotic plaques by binding to the calcified component have interesting therapeutic applications for treating patients with advanced atherosclerotic plaque burden, vascular calcification, aortic valvular calcification, chronic kidney diseases, end stage renal disease, kidney stone diseases. Specifically, by stably binding to the calcium component of the advanced calcified atherosclerotic plaques, the PGN27 could effectively reduce the risk associated with the atherothrombosis due to the rupture of vulnerable atherosclerotic plaques. Our biochemical studies have repeatedly demonstrated the susceptibility of these plaque contents for thrombosis in a blood platelet independent mechanism. These results strongly suggest that preventing the coagulation of these plaque complexes would significantly reduce the risks and mortalities of patients who are diagnosed with advanced atherosclerotic plaques and likely to develop atherothrombosis. As reviewed above, the CP based pathologies are associated with numerous human diseases, particularly, 82% of the patients with advanced atherosclerosis have higher accumulation of the CP with co-localized lipids and cholesterol crystals. In addition, the coronary calcification associated with aortic valve calcification is the third leading cause of the heart diseases in adults (Garg V el al 2005) and approximately 40-50% of mortalities of patients with chronic kidney disease are due to atherosclerosis, valvular calcification, myocardial infarction etc (Campean V et al, 2005). We believe that treating patients diagnosed for advanced atherosclerosis with the PGN27 would significantly reduce the risks associated with atherosclerosis and atherothrombosis, a life threatening medical condition responsible for millions of annual fatalities worldwide.

Finally, the nanotechnology based PET drug discovery platform has applications in cross-therapeutic areas. Using the PET platform it is possible to assemble other plaque complexes that mimic amyloid, Parkinson's, kidney stone and gall stone diseases. As disclosed herein in connection with targeting atherosclerosis like in vitro plaque assembly processes, it is now possible to screen drug or drug like compound libraries to discover novel molecules that block these plaques assembly processes. Also, the PET platform enables one to screen more drugs like molecule libraries to identify a second-generation lead compounds that would effectively disrupt multiple novel interactions contributing to in vitro atherosclerotic plaque assembly processes. Because of its unique and innovative nature, the PET drug discovery platform makes it possible to revolutionize the drug discovery and development processes and tremendously aid to rapidly discover novel therapeutic modalities to prevent or cure atherosclerosis and other plaques related diseases.

Example 29

Figure 31:
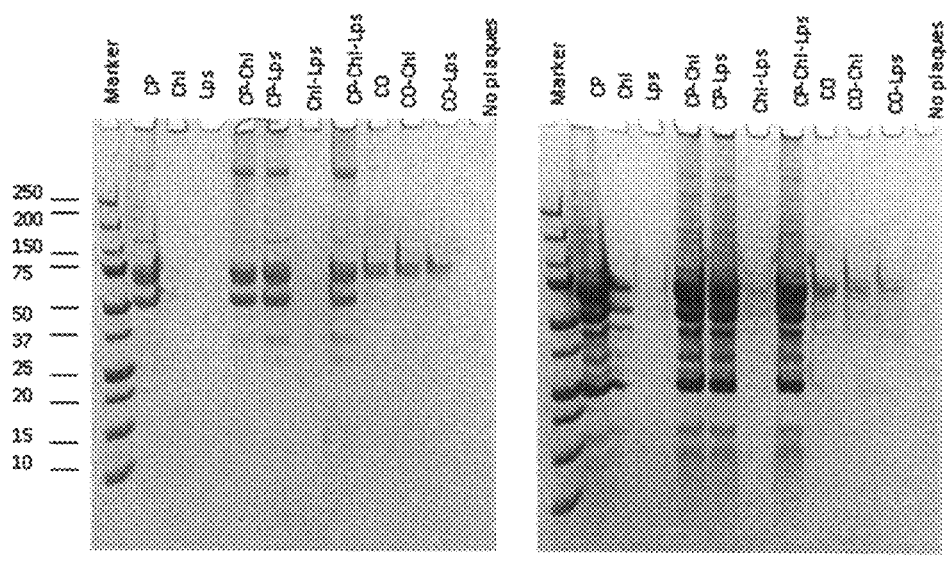
FIGS. 31a and b. SDS-PAGE analysis of the binding of the human serum and plasma proteins with the in vitro assembled plaque complexes or aggregates. 31a, binding of human plasma proteins to the different types of the plaque complexes. The plaque complexes used for the binding are indicated on top of each lane. 31b, binding of human serum proteins to the different types of the plaque complexes. The plaque complexes used for the binding are indicated on top of each lane.

Binding of Human Serum and Plasma Proteins to In-Vitro-Assembled Plaque Complexes or Aggregates The example depicted in FIG. 31 illustrates the binding of human serum and plasma proteins to in-vitro-assembled plaque complexes.

Methods: Preparation of Insoluble Plaque Forming Aggregates

The cholesterol (Chl), lipid (Lipids), calcium phosphate (CP) and calcium oxalate (CO) aggregates are prepared as described in example 2.

Preparation of hybrid templates containing cholesterol, calcium and lipid aggregates as described in example 3.

It is interesting to note that formation of Chl-lipids-CP hybrid complexes, major compositions identified in advanced calcified atherosclerotic plaques of human, mimic advanced plaque complexes.

7. Identification of Serum and Plasma Proteins Binding to the Plaque Complexes

For binding with the plaque complexes, the human plasma and serum samples are first centrifuged at 10,000 rpm for 10 min and the supernatants containing soluble proteins are transferred to new centrifuge tubes. Next, the supernatants are diluted in PBS to make 10% of the serum and plasma samples that are centrifuged again at 10,000 rpm for 10 min. The supernatants are removed and used for binding with the aggregates or plaque complexes. Nine different plaque complexes or aggregates are individually used for binding with the diluted serum and plasma samples. Each binding experiment is performed in a 600 µl reaction (4001 of 10% plasma or serum and 200 µl of the complexes/aggregates) and the mixtures are incubated at 37° C. for 1 hr. For control experiments, 400 µl of the 10% plasma or serum is mixed with 200 µl PBS without the aggregates or complexes. After the binding, the mixture is centrifuged (2500 rpm, 5 min, 20° C.) and the pellets containing complexes are washed two times with 5 ml PBST (Tween 20, 0.05%). After each wash, the supernatant is discarded and the complexes are transferred to a new 15 ml centrifuge tube to avoid any carry-over of the proteins. The lipids containing complexes are centrifuged at 7000 rpm for 5 min and washed carefully, since their sedimentation is observed on the sides of the centrifuge tubes, unlike other complexes that formed sedimentation at the bottom of the centrifuge tubes. Finally, the complexes are incubated in 200 µl of PBS containing EDTA (25 mM final concentration). After 1 hr incubation at 37° C., the samples are centrifuged at 5000 rpm for 5 min and the supernatant containing proteins eluted from plaque complexes are used for further analysis. For gel analysis, 25 µl of the each sample is mixed with 5 µl of 5×SDS sample solublization buffer containing reducing agent (beta-mercaptoethonl) and boiled for 10 min before loading into 4-20% gradient gel (Cambrex Bio Sci, ME, USA). After staining the gels with coomassie blue stain R-250 (Sigma MI), the proteins detected for interaction with the various types of the plaque complexes are documented. Unless otherwise mentioned, all the following binding experiments are carried out using the same buffer, centrifugation and washing conditions.

Results: The SDS-PAGE analysis shows that a number of proteins from the human plasma and serum samples bind to the plaque complexes. Notably, identification of nontraditional serum markers might help to predict the atherosclerosis related coronary events and complement other diagnostic methods described in Table 2. Some of the proteins binding to these in vitro plaque complexes could be specific and indicative of atherosclerotic plaque development. However, proteomic analysis of these binding proteins would help to identify the atherosclerosis specific serum markers. In addition, the profile of proteins binding to these complexes appears to be varying among them (FIG. 31a b). The human serum or plasma is a complex biological fluid containing approximately 289 proteins and $10^7$ variants of circulating immunoglobulins at a given point of time (Molina H et al, 2005; Anderson N L et al 2002). The present results indicate that various serum and plasma proteins differentially bind to the plaque complexes and functional significance of such interactions and their role in the in vivo atherosclerotic plaque development is yet to be understood. In the next step, in order to identify the presence of antibodies from these binding proteins, efforts are made to purify them.

Example 30

Figure 32:
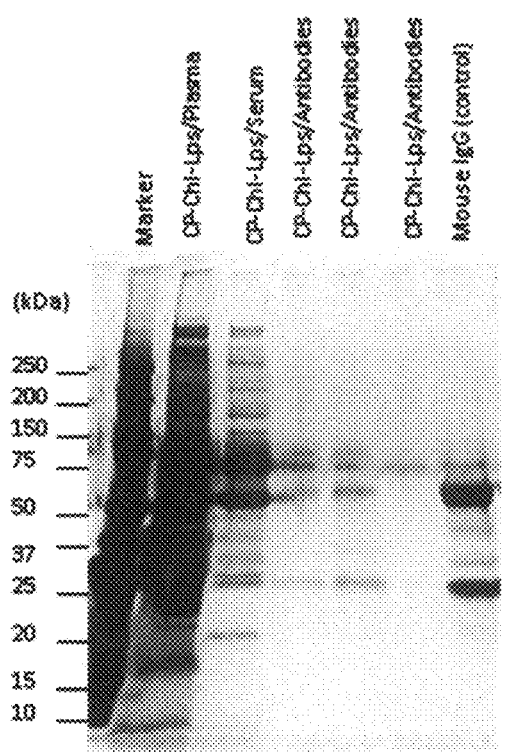
FIG. 32 SDS-PAGE analysis of the binding of human serum and plasma proteins with the in vitro assembled plaque complexes and purification of antibodies. Lane 1, Marker; lane 2, plasma proteins binding to the plaque complexes; lane 3, serum protein binding to the plaque complexes; lane 4, purified antibodies from plasma; lane 5, antibodies purified from serum samples; lane 6, antibodies purified from plasma and lane 7, mouse control IgG. The plaque complexes used for the binding are indicated on top of each lane.

Purification of Antibodies Binding to the In Vitro Atherosclerotic Plaque Complexes The example depicted in FIG. 32 illustrates the purification of antibodies binding to the in vitro atherosclerotic plaque complexes.

Methods: In order to purify antibodies binding to the plaque complexes, the experiments are carried out in two steps. First, the CP-Chl-Lipids plaque complexes, that are major components in the in vivo later stage atherosclerotic plaques, are used for binding with the serum and plasma samples and second the dissolved complexes containing bound proteins are used for purification of the antibodies using Protein A-Agarose beads (Biovision, CA).

*Staphylococcus aureus* Protein A is a cell wall constituent that is characterized by its binding affinity to the Fc portion of immunoglobulins, especially the IgG class. The protein A is a 42 kDa protein and its IgG binding domain (domain B) consists of three antiparallel alpha-helices, the third of which is disrupted when the protein A bind to the Fc region of the IgG (Okmari H K et al, 2007). As described in the preceding experiment, the 10% human serum and plasma samples are prepared and used for the binding with the plaque complexes in 1.5 ml reaction (1 ml of 10% plasma or serum and 500 µl of CP-Chl-Lipids complexes). The mixtures are incubated at 37° C. for 1 hr. For control experiments, 1 ml of the 10% plasma or serum is mixed with 500 µl PBS without complexes. After the binding, the mixture is centrifuged (2500 rpm, 5 min, 20° C.) and the pellets containing the plaque complexes are washed two times with 10 ml PBST (Tween 20, 0.05%). After each wash, the supernatant is discarded and the complexes are transferred to a new 15 ml centrifuge tube to avoid any carry-over of the proteins. The complexes are finally suspended in 3 ml of elution buffer (PBS with 12 mM EDTA, pH 8.0 or 0.1M Citric acid, pH 2.0) and incubated at 37° C. shaker at 150 rpm for 1 hr. After centrifugation at 300 rpm for 5 min, the supernatants are removed for purification of antibodies. An aliquot of the eluted proteins are saved for later analysis and the remaining samples are used for purification of antibodies.

To the supernatants containing eluted proteins, 150 µl of Protein A-Agarose beads are added and incubated at 37° C. shaker at 150 rpm for 1 hr. After binding, the beads are washed three times with PBST to remove unbound proteins and finally the antibodies bound to the protein A beads are eluted (0.1M citric acid, pH 2.0) in 100 µl. Next, after neutralizing the samples with Tris-buffer (1M Tris pH 8.0), 25 µl of the each sample is mixed with 5 µl of 5×SDS sample solublization buffer containing reducing agent (beta-mercaptoethonl) and boiled for 10 min before loading into 4-20% gradient gel (Cambrex Bio Sci, ME, USA). For verification, 25 µl of the pre-protein A treated samples are used for gel analysis. After staining the gels with silver stain (Pierce, Ill.), the antibodies are detected for interaction with the CP-Chl-Lipids complexes.

Results:

Many proteins from the plasma and serum are binding with the CP-Chl-Lipids complexes. Interestingly, the SDS-PAGE analysis revealed that there are antibodies present in the human plasma and serum samples recognizing the in vitro assembled atherosclerotic plaque complexes (FIG. 32). In addition, the presence of more than one high molecular weight antibody heavy chains suggests they could be immunoglobulin isotypes such as IgG, IgA, IgE and IgM. The identification of antibodies for the in vitro plaque complexes is a significant observation because they could be used as a serum marker for the detection of individuals without overt symptoms of atherosclerosis. These results also suggest the antibodies particularly IgG could be produced in response to the in vivo formation of atherosclerotic plaque originated from the traditional risk factors such as lipids, cholesterol and calcium. Production of the antibodies against the plaque complexes could be both specific against individual aggregates and their complexes forms. In addition, it is likely that these antibodies might interfere with the in vivo atherosclerotic plaque assembly processes at different stages.

These results further validate that the in vitro plaque assembly processes mimic in vivo atherosclerotic plaque development and the antibodies generated against this might interfere with the atherosclerosis related pathogenesis. In addition, these functional antibodies could be detected from the asymptomatic atherosclerotic patients by screening their sera against in vitro assembled atherosclerotic plaque complexes. In general, atherosclerotic plaques are isolated from patients cadavers for experimental and histochemical analysis and those samples are contaminated with adjoining tissues or cells contents. Conversely, the in vitro generated plaque complexes are intermediate forms between their soluble and crystalline forms and such complexes could be predictably used to screen sera from suspected patients to diagnose atherosclerosis.

Example 31

Differential Binding to In Vitro Atherosclerotic Plaque Complexes by Antibodies Isolated from Human Sera and Plasma The example depicted in FIG. 32 illustrates the differential binding to in vitro atherosclerotic plaque complexes by antibodies isolated from human sera and plasma.

To further confirm the preceding results, different combinations of the in vitro atherosclerotic plaque forming aggregates/complexes are prepared to mimic various stages of atherosclerosis (I to III) and (IV to Va) and used for screening against the diluted human serum and plasma samples. Eight different aggregates or complexes (CP, Chl, Lipids, CP-Chl, CP-Lipids, CP-Chl-Lipids, CO-Chl and Chl-Lipids) are individually mixed with the 10% serum and plasma for binding. As described earlier, each binding experiment is performed in 600 µl reaction (400 µl of 10% plasma or serum and 200 µl of the complexes) and the mixtures are incubated at 37° C. for 1 hr. After the binding, the mixture is centrifuged (2500 rpm, 5 min, 20° C.) and the pellets containing the complexes are washed two times with 5 ml PBST (Tween 20, 0.05%). The Lipids containing complexes are centrifuged at 7000 rpm for 5 min and washed carefully since their sedimentation is observed on the sides of the centrifuge tubes. After each wash, the supernatant is discarded and the complexes are transferred to a new 15 ml centrifuge tube to avoid any carry-over of the proteins. Finally, the complexes are suspended in 3 ml of elution buffer (PBS with 12 mM EDTA, pH 8.0) and incubated at 37° C. shaker at 150 rpm for 1 hr. After centrifugation at 300 rpm for 5 min, the supernatants are removed for purification of antibodies. Next, to the supernatants containing eluted proteins, 100 µl of Protein A-Agarose beads are added and incubated at 37° C. shaker at 150 rpm for additional 1 hr. After binding, the beads are washed three times with the PBST to remove unbound proteins and finally the antibodies bound to the protein A beads are eluted (0.1M citric acid, pH 2.0) in 100 µl. In addition, the samples containing the antibodies are neutralized with Tris-buffer (1M Tris pH 8.0) and 25 µl of the each sample is mixed with 5 µl of 5×SDS sample solublization buffer and boiled for 10 min before loading into 4-20% gradient gel (Cambrex Bio Sci, ME, USA). After staining the gels with silver stain (Pierce, Ill.), the antibodies are detected for binding with the plaque complexes.

Figure 33:
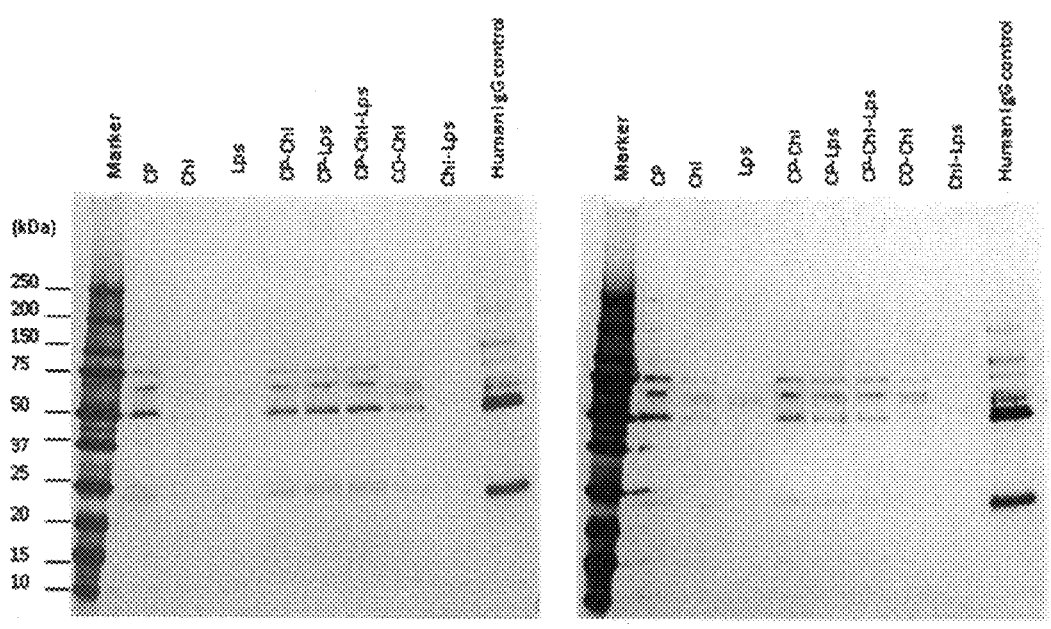
FIG. 33 SDS-PAGE analysis of the antibodies purified using protein A sepharose beads. 33a, antibodies purified from human serum and the plaque complexes used for the binding are indicated on top of each lane. 33b, antibodies purified from human plasma and the plaque complexes used for the binding are indicated on top of each lane.

The SDS-PAGE analysis showed differential binding of the antibodies isolated from the human serum and plasma samples to the in vitro atherosclerotic plaque complexes (FIGS. 33a and b). Similar to the preceding results, three different higher molecular weight proteins (~50, 60 and 75 kDa) are observed suggesting that they may be heavy chains of IgG, IgA and IgE immunoglobulin isotypes. Considering the fact that the human serum and plasma used in this study are commercially purchased pooled samples obtained from individuals whose medical history is unknown, it is assumed that there might be a low level of circulating antibodies for the atherosclerosis is present in the serum. It is also likely since the atherosclerotic plaque formation is a long process spanning form years to decades those individuals could have been exposed to the plaque forming components earlier. In addition, the profiling of the antibodies binding to the various plaque sub types indicate that their binding could be complex specific as a result the antibody titers might vary from one individual to another depending upon the severity of the atherosclerosis. Serological measurements of the antibodies titer for different plaque complexes would help to diagnose asymptomatic high risk patients for adverse coronary heart diseases. Detecting the asymptomatic individuals using this non-invasive antibody profiling method would help in risk stratification and appropriate therapy.

Example 32

Quantitation of Antibodies Binding to the Plaques using ELISA Method

The example depicted in FIG. 34 illustrates the quantitation of antibodies binding to the plaques using ELISA method. In order to determine the titer of IgG binding to the different plaque complexes, ELISA method is used. First, the human serum and plasma proteins binding to the plaque complexes are isolated and second the eluted proteins are used for determining the antibody concentrations by ELISA method as described below (FIGS. 34a and b). In the first step, eight different aggregates or complexes (CP, Chl, Lipids, CP-Chl, CP-Lipids, CP-Chl-Lipids, CO-Chl and Chl-Lipids) are individually mixed with the 10% serum and plasma for binding. Each binding experiment is performed in a 600 µl reaction (400 µl of 10% plasma or serum and 200 µl of the complexes) and the mixtures are incubated at 37° C. for 1 hr. After the binding, the mixture is centrifuged (2500 rpm, 5 min, 20° C.) and the pellets containing the complexes are washed two times with 5 ml PBST (Tween 20, 0.05%). After each wash, the supernatant is discarded and the complexes are transferred to a new 15 ml centrifuge tube to avoid any carry-over of the proteins. Finally, the complexes are suspended in 200 µl of elution buffer (PBS with 12 mM EDTA, pH 8.0) and incubated at 37° C. shaker at 150 rpm for 1 hr. After centrifugation at 3000 rpm for 5 min, the supernatants are removed for determination of the antibodies concentrations.

In the second step, the Protein A coated microtitre stripes are used for capturing the antibodies followed by their quantitation. The protein A coated ELISA method is suitable to accurately detect the human IgG from other proteins present in the eluted samples. In the following experiments, to the protein-A pre-coated and pre-blocked microtitre strips, 100 µl of the eluted samples are added in duplicate wells and incubated for 1 hr at RT shaking (shaker). For positive control, purified human IgG is serially diluted in PBS (5, 2.5, 1.25, 0.625, 0.312, 0.16, 0.08 and 0.04 µg/ml) and 100 µl of them are added in duplicate well for the binding. For negative control, four wells in the strip are added with bovine serum albumin (BSA, 1 µg/mL). After binding, the samples are discarded and the stripes are washed 6×PBST (Tween 20, 0.05%). The stripes are blocked with 5% skim milk (Bio Rad, CA) for 1 hr followed by addition of chicken anti-Human-IgG-Fab-HRP conjugate (Callus Immunotech, Canada) for detecting the captured human IgG. After the binding, the stripes are washed 6×PBST (Tween 20, 0.05%) and used for detection using One-Step Microwell tetramethylbenzidine (TMB) solution (Pierce, Ill.). After adding 100 µl of the TMB solution, the reaction is allowed until the color development is observed that occur due to conversion of the substrate by the HRP conjugate. Next, 100 µl of stop solution (1.5M sulphuric acid, pH 2.0) is added to stop the enzyme reaction (the blue reaction mixture turns yellow). A positive result is indicated as a color change which is read by a micro plate photometer (Molecular Devices, CA). Absorbance of the samples and standard references are read at 450 nm within 30 minutes after adding the stop reagent. The absorbance values for each unknown test sample and standard references are used to calculate the concentration of antibodies binding to the each plaque complexes.

Example 33

Figure 35:
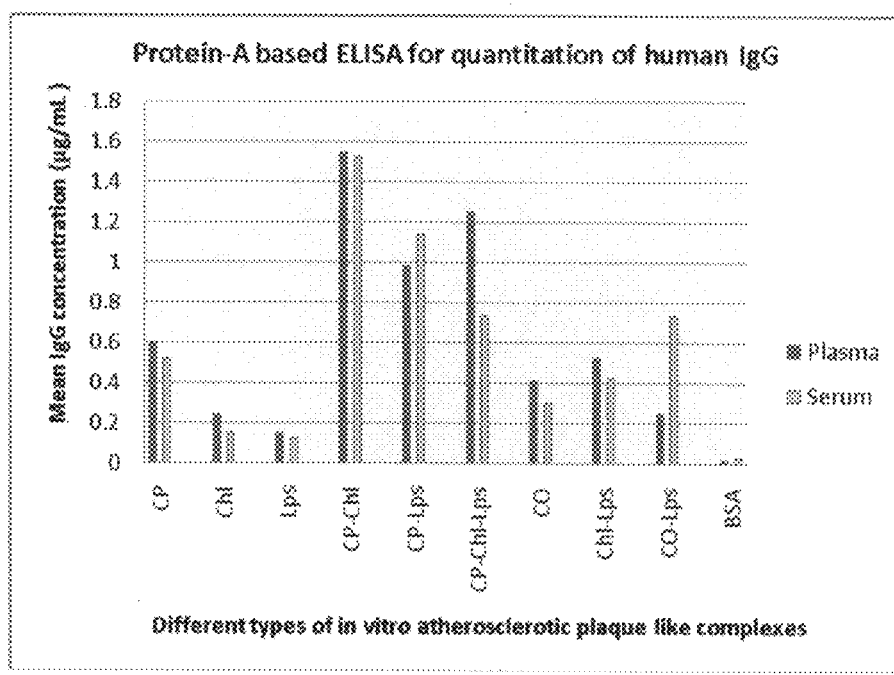
FIG. 35 Measurement of human IgG identified for binding with different sub-types of the in vitro assembled atherosclerotic plaque like complexes. Detection and profiling of the human IgG molecules using conventional ELISA method.

Measurement of Human IgG Identified for Binding with Different Sub-Types of the In Vitro Assembled Atherosclerotic Plaque Like Complexes The example depicted in FIG. 35 illustrates the measurement of human IgG identified for binding with different sub-types of the in vitro assembled atherosclerotic plaque like complexes. As observed with the SDS-PAGE analysis of purified antibodies, the concentration of IgG molecules binding to the different plaque sub-types are varying (FIG. 35). This also suggests that the calcified plaque complexes might be more immunogenic/pathogenic therefore elicit higher titer of antibody production in vivo. It is notable, advanced atherosclerotic plaques contain higher accumulation of calcified plaques. In addition, the IgG binding profile from both the human plasma and serum samples appeared similar against all plaque complexes suggesting any one of those samples could be used to predict atherosclerosis. The minimum detection limit of IgG molecules from the samples using this method is in the range of 10-30 ng/mL.

The combination of a unique and highly specific Protein A based antibody capturing ELISA method is a sensitive assay suitable to accurately detect the in vitro atherosclerotic plaque specific human antibodies.

Example 34

Figure 36:
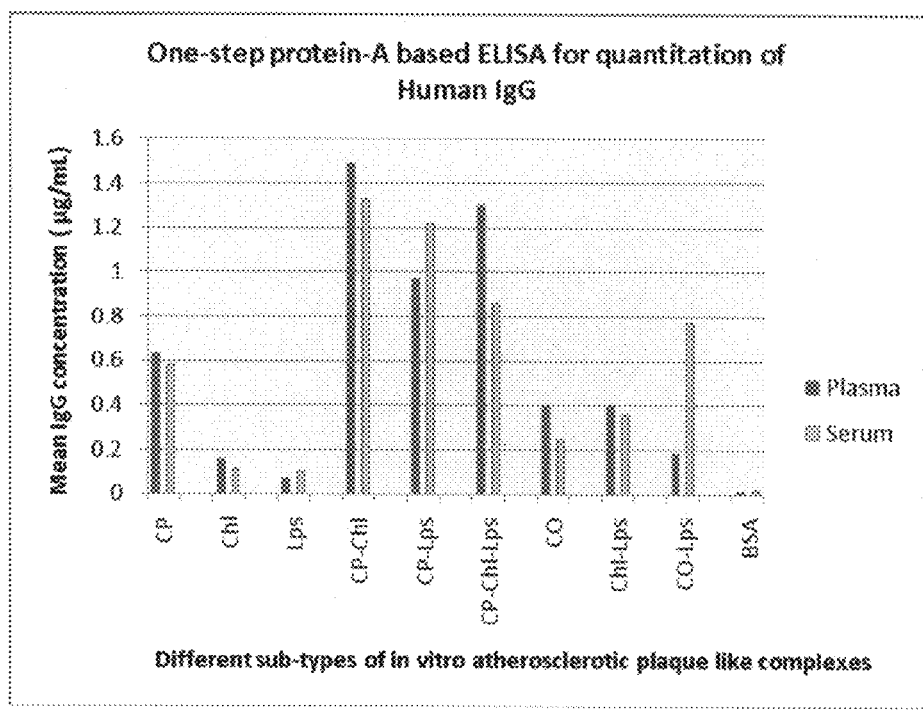
FIG. 36 Measurement of human IgG identified for binding with different sub-types of the in vitro assembled atherosclerotic plaque like complexes. Detection and profiling of the human IgG molecules using one-step ELISA method.

Measurement of Human IgG Binding with Different Sub-Types of In-Vitro Assembled Atherosclerotic Plaque-Like Complexes The example depicted in FIG. 36 illustrates the measurement of human IgG binding with different sub-types of in-vitro assembled atherosclerotic plaque-like complexes.

To further improve the ELISA method for rapid diagnosis of the high risk asymptomatic individuals of atherosclerosis, this method is modified in the second step. Unlike the above described conventional ELISA method, both the eluted proteins from plaque complexes and the chicken anti-Human-IgG-Fab-HRP conjugate (Callus Immunotech, Canada) are added together to the protein A coated and pre-blocked microtitre strips. This allowed simultaneous binding of Fc region of the human IgG to the protein A and detection of its Fab region by the chicken anti-Human-IgG-Fab-HRP conjugate. Since chicken anti-Human-IgG-Fab-HRP conjugate does not bind to the protein A, there is a little background in the assays. Also, the modified one-step ELISA method requires approximately 2 hrs to measure the titer of the antibodies present in the samples compared to 4-5 hrs required for conventional ELISA method. For example, to the protein-A pre-coated and pre-blocked microtitre strips, 100 µl of the eluted samples combined with the chicken anti-Human-IgG-Fab-HRP conjugate are added in duplicate wells followed by incubation for 30-45 mins at RT shaking (shaker). For positive control, purified human IgG is serially diluted in PBS (5, 2.5, 1.25, 0.625, 0.312, 0.16, 0.08 and 0.04 µg/ml) and 100 µl of them are added in duplicate wells for binding. For negative control, four wells in the strip are added with BSA (1 µg/mL). After binding, the samples are discarded and the stripes are washed 6×PBST (Tween 20, 0.05%). For detection, 100 µl of the TMB solution is added to each well and the reaction is allowed until the color development. Finally, 100 µl of stop solution (1.5M sulphuric acid, pH 2.0) is added to stop the enzyme reaction (the blue reaction mixture turns yellow). A positive result is indicated as a color change which is read by a micro plate photometer (Molecular Devices. CA). Absorbance of the samples and standard references are read at 450 nm within 30 minutes after adding the stop reagent. The absorbance values for each unknown test sample and standard references are used to calculate the concentration of antibodies binding to each plaque complexes.

In general, the one-step ELISA results of IgG measurement is in consistence with the preceding conventional ELISA data and could be suitable for serological testing of samples from suspected individuals of atherosclerosis (FIG. 36). The minimum detection limit to determine antibody titers using this method is in the range of 10-30 ng/mL that would be sensitive enough to screen clinical samples. It is anticipated that the profile of antibody titers against different plaque complexes would vary from normal individual to suspected individuals and comparing the antibody profiles would help to diagnose patients and severity of the atherosclerotic plaque development non-invasively. For example, individuals showing higher titers of antibodies for Lipids-Chl complexes would be low/medium at risk category compared to the individuals showing higher antibodies titer for CP-Chl-Lipids complexes. Screening of clinical samples from both normal and confirmed or suspected clinical population of atherosclerosis using this method would help to better evaluate this novel method. For testing the clinical samples, at least six different plaque complexes (CP, Chl, CP-Chl, CP-Lipids, CP-Chl-Lipids, and CO-Chl-Lipids) could be used to analyze antibody profiles to predict atherosclerosis and differentiate low, medium and high risk individuals.

The titer of antibodies binding to the different plaque complexes appears to be diverse. This suggests some of the antibodies may be complex specific and some might recognize both the calcium and non-calcium containing plaque complexes. Serological tests might help to measure the antibody titers that would possess unique patterns of rise and fall during the longer window period of the atherosclerotic plaque developments. To further discriminate the individuals carrying silent atherosclerosis, it might be useful not only to profile the in vitro atherosclerotic plaque specific antibodies present in the serum but also profiling the isotypes of the immunoglobulins. In the present study, the SDS-PAGE analysis of the purified antibodies showed presence of multiple Ig heavy chains binding to the protein A beads. However, the ELISA method detected only human IgG captured by the protein A and other isotypes like IgA, IgE, IgD and IgM are not detected since the detection antibody is specific for the IgG. Performing IgA, IgM, IgE and IgD specific ELISA experiments to further determine their titer using the specific detection antibodies might help to differentiate vulnerable atherosclerotic plaque from early stage atherosclerotic plaques. Also, the half life and persistence of immunoglobulin sub types are widely variable. Finally, applying this one-step ELISA method to identify atherosclerosis specific serum antibodies would significantly help to rapidly diagnose asymptomatic individuals and take appropriate preventive measures.

Example 35

Development of Microchip Based Multiplex Technology for Diagnosis of Atherosclerosis This example illustrates the development of microchip based multiplex technology for the diagnosis of atherosclerosis. The studies described herein may provide new insights on binding of antibodies to the in vitro assembled plaque complexes and may move us one step closer to the development of a microchip based multiplex detection technology for early diagnosis of atherosclerosis. It is possible to design microchips using nanostructure surfaces with biocompatible characteristics and resulting in sensitive detection of atherosclerosis. In this method, different types of in vitro assembled complexes could be spotted in small volumes (5 to 10 µL) onto the biocompatible surfaces. These microchips may be tested to screen diluted (5%) human plasma or serum samples (100 to 200 µL) of suspected individuals of atherosclerosis. After washing the microchip to remove unbound serum proteins, the antibodies bound to the different to plaque complexes may be detected using protein A-HRP conjugates and chemiluminescence substrate following the protocol supplied by vendor (GE Healthcare, CA). Finally, the light emitting from the spots due to the action of the HRP on chemiluminescence substrate may be detected using CCT camera, a method routinely used in the labs for detection of proteins from western-blot and dot-blot experiments. The quantitative analysis of the signal detected for test samples may be compared to the control sample to predict the severity of the atherosclerosis. The advantage of this approach is that using a very low quantity of blood sample for testing against a panel of plaque complexes at the same time may enable specific binding of antibodies to the complexes. The microchip based miniaturized and highly parallel immunoassays can greatly improve efficiency of diagnosis by increasing the amount of information acquired with a single examination and reduces costs by decreasing reagent consumption.

Example 36

Analysis of Protective Effect of the Purified Antibodies

Figure 37:
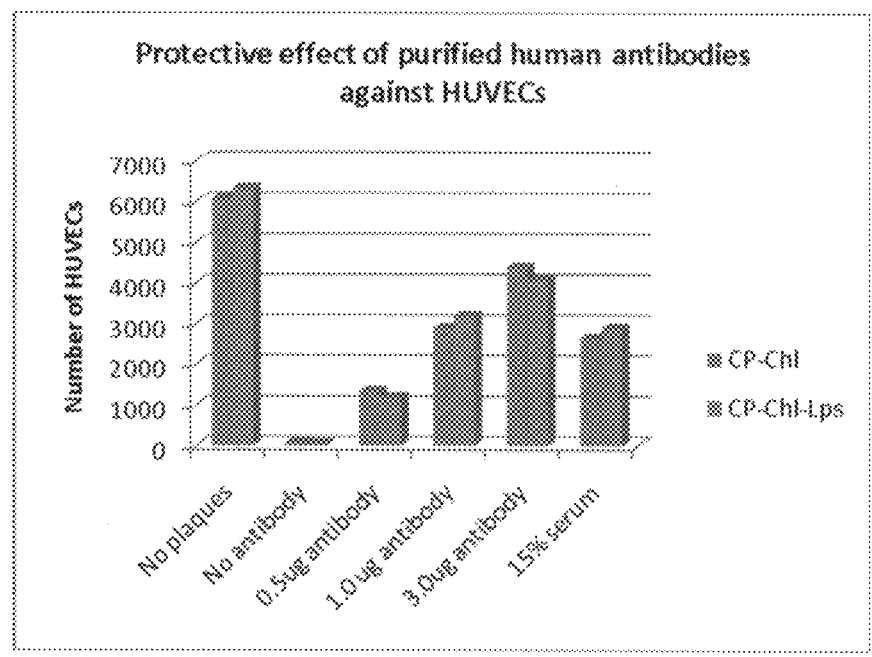
FIG. 37 Examining neutralizing property of the plaques specific antibodies in tissue culture model of atherosclerosis. Dose dependent efficacy of the antibodies against pathogenic effect of in vitro assembled atherosclerotic plaque like complexes.

The example depicted in FIG. 37 illustrates the analysis of the protective effect of the purified antibodies.

For evaluating the functional significance of binding of the human antibodies to the in vitro assembled plaque complexes, the purified antibodies are concentrated using centricon 30 filters (Millipore, Calif.) and may be used to examine its protective effect in the cell culture model of atherosclerosis. The in vitro assembled atherosclerotic plaque complexes may be pathogenic to human umbilical vein endothelial cells (HUVECs) (example 22). More specifically, CP, CP-Chl, CP-Lipids and CP-Chl-Lipids complexes may be highly pathogenic to the HUVECs since these complexes cause severe morphological and pathological symptoms to these cells. In the present study to test the protective effect of the human antibodies, first, the antibodies are purified from the human serum samples and after neutralizing the samples with the Tris-Hcl buffer the samples they are quantitated using ELISA. Second, the CP-Chl, CP-Chl-Lipids complexes may be used for binding with the antibodies. Third, the HUVECs and endothelial cell growth medium (ECGM) are purchased (Cell applications, CA). The cells are grown to confluence in 75 cm2 culture flasks containing 20 ml of ECGM. After removing the medium, the cells are treated with trypsin-EDTA solution and scraped off the plate. Then the cells are harvested by centrifugation at 2000 rpm for 5 min (Beckman GS-6, CA), washed once with sterile PBS followed by their suspension in 2 ml ECGM. After cell count, the HUVECs (6000 per well) are seeded into 12 wells tissue culture plates containing 3 ml of ECGM and grown with and without the plaque complexes. After 48 and 72 hours incubation, the cell viability is determined by microscopic examination (Olympus CK40, Japan).

Example 37

Evaluation of the Pathogenicity of the Atherosclerotic Plaque-like Complexes

This example illustrates the evaluation of the pathogenicity of in vitro assembled atherosclerotic plaque-like complexes in the presence and absence of the purified antibodies by combining such complexes with HUVECs. The CP-Chl, CP-Chl-Lipids complexes (25 µl each) are mixed with three different concentrations of the antibodies (0.2, 1.0 and 3 µg) and incubated at 37° C. for 1 hr. For control experiments, the CP-Chl, CP-Chl-Lipids complexes are incubated with 50 µl of the 10% serum and for negative control the CP-Chl, CP-Chl-Lipids complexes with 50 µl PBS. After incubation at 37° C., the mixtures are washed with PBST for three times and the final complexes are suspended in 50 µl PBS. All the complexes are individually mixed with HUVECs (6000 per well) for 5 min and then added to 2 ml ECGM medium. As a control, the HUVECs (6000) are grown in 2 ml ECGM without any plaque complexes. After 48-72 hrs incubation, the cells are analyzed for viability by microscopic examination and the results are then documented.

After 48 hrs, microscopic observation of the HUVECs incubated with the plaque complexes, that are pre-treated with the purified antibodies, showed dose dependent effect (20-70%) on cell viability compared to the control cells grown without plaque complexes (FIG. 37). Similarly, the cells incubated with the plaque complexes that are treated with the 15% serum showed 30-40% of viable cells compared to control grown without any plaque complexes. Conversely, only 5-10% of the HUVECs are viable when grown with these two complexes that are neither treated with the antibodies nor serum and these cells showed pathological symptoms as evidenced by extensive morphological changes. These results together suggest that the binding of the purified antibodies or serum proteins to the plaque complexes inhibit pathogenic effect of plaque complexes towards HUVECs.

Interestingly, the interaction of antibodies with the plaque complexes might block or modulate the conformations of the CP-Chl and CP-Chl-Lipids complexes thereby protecting the HUVECs from pathogenicity mediated by in vitro atherosclerotic plaque like complexes. Together, these results suggest that the in vitro assembled plaque complexes are pathogenic/immunogenic and their administration into animals might elicit antibody production that would interfere with the in vivo atherosclerotic plaques development. Next, this novel approach of developing therapeutic antibodies for treatment of the atherosclerosis would be demonstrated in the animal studies.

Example 38

Identification of Anti-Atherosclerotic Antibodies from Phage Display Antibody Libraries Phage display technology is a powerful molecular biological tool being widely used to display peptides and proteins including antibodies. In the phage display technology, bacteriophage is engineered to express antibody fragments which then are displayed on their surfaces. A large collection of recombinant phage libraries (1-10 billion), each displaying a single and unique antibody fragment is now commercially available. The phage antibody libraries may be purchased from different vendors and may be used for selection against plaque complexes. In this method, as we found that there are antibodies present in the human blood samples reacting to the in vitro assembled plaque complexes, we may perform panning of these antibody phage libraries against different plaque complexes as described earlier (O'Brian, P M et al, 2002). After repeated selection and screening, the phage clones showing specific binding to the plaque complexes can be characterized using our proprietary atherosclerotic biochemical and cell culture assays to further confirm their specificity and sensitivity. In addition, the cDNA of phage clones identified for binding with the plaque complexes can be cloned into E. coli expression vectors for expression and purification of the antibodies as soluble proteins. These functional antibodies may be again tested in the atherosclerotic screening assays to determine their efficiency for diagnosis and or as therapeutics to target atherosclerosis.

Example 39

Sources of Reagents for Studies

This example illustrates the sources of reagents for many of the studies described herein. The following reagents may be purchased from Sigma (MI, USA); carbonic anhydrase (CAH), human insulin (HIN), horseradish peroxidase (HRP), human serum albumin (HSA), sodium phosphate dibasic, bovine serum albumin (BSA), cholesterol, ampicillin, chloromphenicol, tetracycline chloride, rifampicin, gentamycin, phospholipids, olive oil, calcium chloride, oxalic acid, sodium pyrophosphate dihydrate, sodium bicarbonate, EDTA, Fe(SO4)3, sodium citrate and phosphate buffered saline (PBS) tablets. Complement factors C1 (C1), C3 (C3), C4 (C4), C5 (C5) and Factor H (FH) may be purchased from Quidel (CA, USA). Lys-plasminogen (PLG), urokinase (u-PA), tissue PLG activator (t-PA) and human FBN (FBN) are purchased from American Diagnostics Inc (CT, USA). Human blood coagulation factor prothrombin (FII), IX (FIX), antithrombin III (AT III), human plasma, human serum and Protein S (ProS) are available from Enzyme Research Laboratories (IN, USA). PLG Activator inhibitor 1 (PAI-1) is purchased from Molecular innovation Inc (MI, USA). All the reagents and buffers may be prepared with MilliQ purified water. Unless otherwise noted, the rest of the chemicals herein may be procured from Sigma.

Example 40

Sources of Reagents for the Antibody Studies

This example illustrates the sources of reagents for the antibody studies described herein. The following reagents may be purchased from Sigma (MI, USA); cholesterol, lipids, calcium chloride, oxalic acid, sodium bicarbonate, EDTA, and phosphate buffered saline (PBS) tablets. Human plasma, purified human IgG and human serum are purchased from Innovative Research (MI, USA). Protein A beads are purchased from Biovision (CA, USA). Protein A coated strip plates, one-step TMB (substrate for HRP) are purchased from Pierce (IL, USA). Chicken anti-human IgG-Fab-HRP antibody is purchased from Callus Immunotech (Canada).

Example 41

Development of Asymptomatic Induced Animal Models of Atherosclerosis for Drug Discovery The insoluble lipid, Chl, CP and CO aggregates were prepared as described in example 2. The hybrid aggregates containing lipid, cholesterol and calcium containing aggregates were prepared as described in example 3. To accelerate in vivo atherosclerotic plaque development CP-Lipids-Cholesterol plaque complexes are used because they induce in vivo plaques resembling late stage Atherosclerotic plaques in human. Mice (C57BL/6 or Apo-E) are widely used as a small animal model for the atherosclerotic studies (Nachtigal P, et al, 2006). Mice weighing 20-40 g are purchased from Charles River Laboratories or Taconic (Piedrahhita J A, et al 1992). Before the dosing of plaque complexes, they are acclimatized for 2-3 days with a 12-hour light-dark cycle at a temperature of 20-23° C. with free access to standard rodent chow and water ad libitum. They are fasted overnight when being used in the study. For developing asymptomatic atherosclerotic plaque development, the plaque complexes (100 µl) are injected by tail vein route as described below for the development of induced atherosclerotic mice model (Johnston T P et al, 1999; 2000). Following administration of these plaque complexes at different concentrations, the mice are monitored for changes in respiration and salivation. If any abnormal behavior/symptom is observed in the mice then the concentration of the plaque complexes are reduced to a tolerable level. After testing different concentrations of plaque complexes ranging from 50-500 µl per mouse it is determined that 100 µl of plaque complexes are near the tolerable limit per mouse. Different combinations of plaque complexes are used to identify the appropriate plaque complexes to induce in vivo plaque formation. Blood samples are collected periodically from the mice for biochemical analysis. Also, histochemical studies are carried out to determine plaque formation in the blood vessels of the mice.

For each experiment, out of 14 mice two are treated as controls and remaining twelve are divided into four groups. 100 µl of plaque complexes are dosed via tail vein route per mouse to induce plaque formation. Dosing of plaque complexes is repeated after every week as shown in the table 4. Mice are fed with atherogenic diet for eight weeks. Blood is collected after every week from group 1 mice for determining plasma lipid concentrations. Four mice (one from each group) are euthanized for collection of blood, arteries and heart tissues for examining plaque growth by histo-chemical methods. Remaining mice are maintained and fed with atherogenic diet. Plaque growth from heart tissue samples is confirmed by histochemical methods and groups showing plaque deposition are selected for testing tetracycline hydrochloride (PGN27) and ovavastin drugs. Drugs are administrated orally (5-10 mg/kg/day) and the mice are fed with a regular diet. Drugs are administrated for 8 weeks followed by euthanization of mice to isolate arteries and heart tissues. Tissue samples are used to examine regression of atherosclerotic plaques by histo-chemical methods. The above described animal experiments were repeated for two more times for confirmation of anti-atherosclerotic effect of the drugs.

TABLE 4

Intra-vascular Administration of plaque forming components to induce Atherosclerosis

| Groups | First week | Second week | Third week | Fourth week |
|---|---|---|---|---|
| Group 1 | + | + | + | + |
| Group 2 | + | + | + | − |
| Group 3 | + | + | − | − |
| Group 4 | + | − | − | − |
| # of mice used | 3 | 6 | 9 | 12 |

Results: The mice dosed with plaque complexes one or more times do not show any morphological symptoms after 4-6 weeks compared to control mice that are not dosed with the plaque complexes. However, despite the outward asymptomatic nature of the mice, the histochemical analysis of heart tissues of mice dosed with plaque complexes show accumulation of plaque complexes in the heart tissues. Three different stains are used to localize the presence of plaque complexes in the heart and arteries isolated from normal and plaque induced mice. Compared to the control, the heart tissues isolated from mice induced for plaque formation show positive staining for plaque complexes (FIGS. 38A, B, C and D; FIGS. 39A, B, C and D). Further analysis of tissue samples by Van Kosa and Alizarin Red stains identifies the plaque accumulation in the heart tissues. Both the Van Kosa stain and Alizarin Red stains are commonly used to identify advanced calcified plaques because of their specific binding with calcium component of the plaques (FIGS. 40A, B, C and D). Together, these experiments confirm the induction of Atherosclerotic plaque developments in mice dosed with in vitro assembled plaque complexes.

Example 42

Development of Mice Models with Plaque Induced Chronic Inflammation

The objective of the present study is to develop animal models that show morphological symptoms of plaque induced chronic inflammation. It is increasingly understood that chronic inflammation plays an important role in atherogenesis, plaque progression and unstable plaque rupture (Peter, L et al 2002). However, the underlying factors or plaque components that trigger plaque inflammation are largely unknown.

Methods: 12 of 14 mice (C57BL/6 or Apo-E) are divided into four groups, and the remaining two are used as controls. 300 µl of plaque complex (PGN32, cholesterol-lipids-calcium phosphate) are dosed via intra-peritoneal route per mouse to induce plaque formation. Dosing of plaque complexes is repeated after every week as shown in the table 5. Mice were fed with atherogenic diet for eight weeks. Blood is collected after every week from group 1 mice for determining plasma lipid concentrations. Mice showing plaques induced chronic inflammation are selected for testing tetracycline hydrochloride (PGN27) and ovastatin drugs. Drugs are administrated orally (5-10 mg/kg/day) and the mice are fed with a regular diet. Drugs are administered for 8 weeks followed by visual examination of mice for showing reduction in plaque induced chronic inflammatory symptoms such as regrowing of hairs, healing of skin redness, and reduced itching rate of the mice. The experiments were repeated for two more time to confirm therapeutic effect of drugs.

TABLE 5

Intra-peritoneal Administration of plaque forming components to induce Atherosclerosis

| Groups | First week | Second week | Third week | Fourth week |
|---|---|---|---|---|
| Group 1 | + | + | + | + |
| Group 2 | + | + | + | − |
| Group 3 | + | + | − | − |
| Group 4 | + | − | − | − |
| # of mice used | 3 | 6 | 9 | 12 |

Mice dosed with the plaque complexes develop chronic inflammation after 6 to 8 weeks. By dosing the plaque complexes containing Chl-Lipids-CP aggregates through intra-peritoneal route asymptomatic atherosclerotic plaque development transforms into a symptomatic process in mice. These mice show morphological symptoms of plaque induced chronic inflammation (FIGS. 41A and B). The symptoms of hair loss, skin redness and frequent scratching of skin by the mice are related to chronic inflammation. Chronic inflammation plays important role in the pathogenesis, progression and rupture of vulnerable atherosclerotic plaques. However, the enigmatic causative agent/s that triggers the plaque built up and/or chronic inflammation is largely unknown. We now have successfully identified a transient plaque complex that accelerates both in vivo atherosclerotic plaque formation and chronic plaque inflammation. Targeting the plaque complex is expected to provide more effective drugs to treat atherosclerosis and chronic plaque inflammation indications.

Example 43

Validation of Induced Mouse Models of Atherosclerosis

The preceding examples 41 and 42 have shown inducing Atherosclerotic plaque development in the mice. In the next step, these mice models are used for testing two drug candidates to determine their efficacy both on reducing progression of plaque development and symptoms of chronic inflammation. Mice purchased from vendors are used for in vivo atherosclerotic plaque development by multiple doses of plaque complexes by intra-peritoneal and intravenous routes as described in examples 41 and 42. After confirming plaque growth in the heart tissue and chronic inflammatory symptoms the mice are used to screen against Ovastatin and PGN27 drugs. The investigational anti-atherosclerotic test drug, PGN27, is a generic molecule and clinically proven to be safe for use in animals and human. Ovastatin, an established anti-atherosclerotic drug (Schwartz et al, 2001) is used for control purposes in these studies and administered by oral route at 5-10 mg/kg per day of body weight.

Both ovastatin and PGN27 (5-10 mg/kg per day) are orally administrated to the symptomatic and asymptomatic atherosclerotic mice models for 8 weeks. Following administration of the drugs, mice with asymptomatic plaque development are euthanized and blood collected via cardiac puncture. In addition, heart and arteries are isolated from these mice and used for biochemical and histochemical analysis to confirm the efficacy of these drugs on atherosclerotic plaque development.

Figures 42, 42A, 42B, 42C:
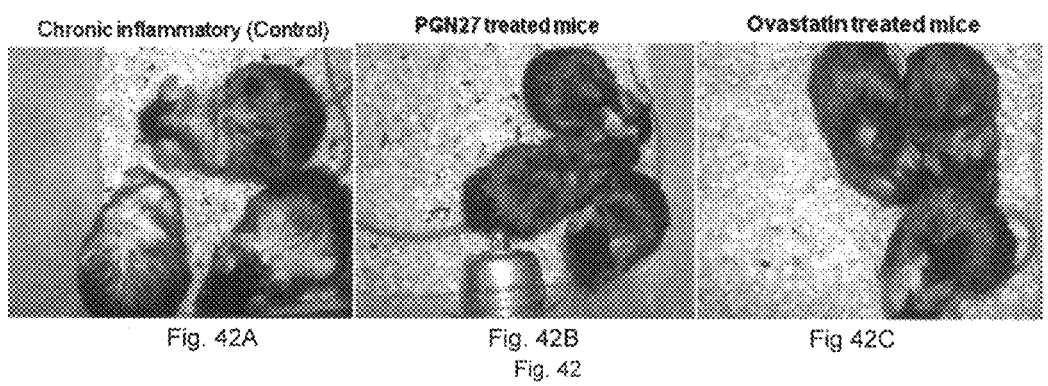
Figure 43:
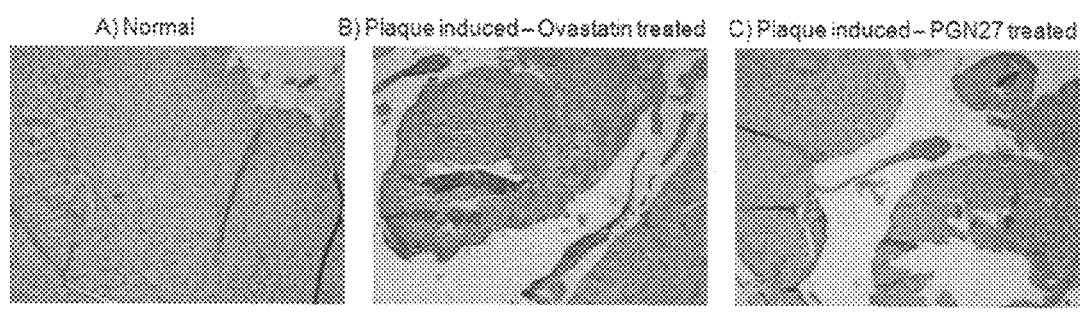
Figures 44, 44A, 44B, 44C:
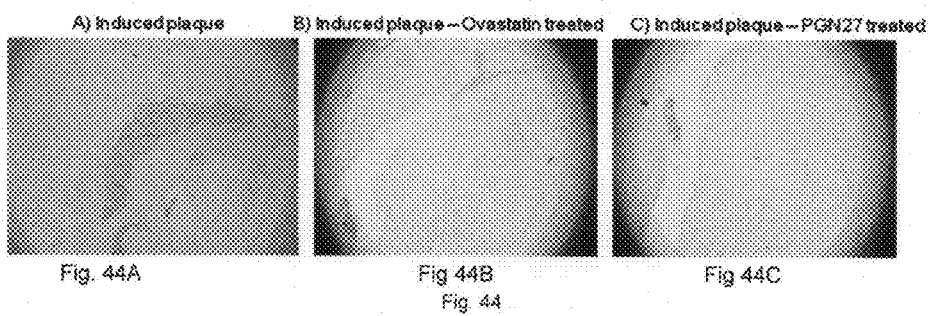

Mice showing morphological plaque induced chronic inflammation are monitored after treatment with drugs for reduction in the symptoms such as healing of skin redness, reduced scratching, re-growing of hairs and improved activity compared to control mice without drug treatment. The mice treated with ovastatin or PGN27 show reduced symptoms of plaque inflammation compared to the control animal (FIGS. 42A, B and C). In addition, histochemical analysis of the heart tissues isolated from asymptomatic mice model show reduced plaque accumulation after treating with both ovastatin and PGN27 (FIGS. 43A, B, and C; FIGS. 44A, B, and C).

The Atherosclerotic mouse models developed in this study mimic advanced atherosclerotic plaques development and suitable for testing efficacy of anti-atherosclerotic drug candidates on both plaque regression and chronic plaque inflammation. Drugs showing efficacy on both plaque regression and plaque inflammation are expected to be more effective to treat patients with Atherosclerosis. Also, transient plaque complexes identified for triggering chronic inflammation may be used to induce atherosclerotic plaque formation and chronic plaque inflammation in higher animal models. The animal models are used for testing anti-atherosclerotic drugs to test their efficacy.

For analyzing PK/PD parameters of drugs: Induced mice weighing 20-40 g are acclimatized for 2-3 days with a 12-hour light-dark cycle at a temperature of 20-23° C. with free access to standard rodent chow and water ad libitum. Drug is administered by oral (op), intravenous (iv), intraperitoneal (ip) and/or subcutaneous (sc) routes. Following administration of the drugs, blood samples are collected at various time points and used for biochemical analysis to determine their efficacy towards atherosclerotic plaque development. Each mouse is euthanized by carbon-dioxide inhalation and blood collected by cardiac puncture and/or other tissues will be removed. In addition, histological studies are carried out to determine plaque regression in the drug administrated animal models. Based on the PK results the compounds are chemically modified for improved PK characteristics, or the dose and dosing frequency is selected for efficacy studies in animal models.

Example 44

Preparation of Insoluble Iron-Loaded Amyloid Aggregates

To prepare insoluble aggregates, lyophilized powders of amyloid peptides abeta40, abeta42 and/or prion peptides are first resuspended in MilliQ purified water to make a stock of 1 mg/mL and then store them at −70° C. as 100 µl aliquots. For iron-loaded aggregates preparation, 50 µg of peptides is diluted in 200 µl of PBS (pH 6.8 to 7.3) to which 250 µM of $Fe_2(SO_4)_3$ is added. After 3 hrs of incubation at 37° C., the suspension is centrifuged (Eppentorf, 5417R, CA) at 9000 rpm, 9 min, 4° C. and the supernatant is used for protein estimation to determine the amount of peptides precipitated by iron. Protein estimation is carried out using Micro BCA protein assays kit (Pierce, Ill., USA). The suspension of the insoluble aggregates is washed once with 500 µl of PBS and after centrifugation the final aggregates are suspended in 200 µl of PBS for complex formation with various proteins (FIGS. 46a and b).

Example 45

Preparation of Self-Formed Insoluble Amyloid Aggregates

Lyophilized powders of amyloid peptides abeta40, abeta42 and/or prion peptides are first resuspended in MilliQ purified water to make a stock of 1 mg/mL and then store them at −70° C. as 100 µl aliquots. For preparing self-formed insoluble amyloid aggregates, an aliquot of abeta42 peptides taken from the stock and diluted in 2×PBS buffer to make a final concentration of 0.5 mg/mL. The dilution is incubated at 37° C. for 3 to 5 days. After centrifugation of the suspension (7000 rpm, 9 min, 15° C.) the supernatant is used to determine amount of insoluble aggregates formation and the final aggregates are suspended in PBS buffer for plaques assembly.

Example 46

Preparation of Iron-Phosphate Aggregates

Iron-phosphate aggregates are prepared by mixing 250 µM of $Fe_2(SO_4)_3$ with 1 mL of PBS (pH 7.3). After 3 hrs of incubation at 37° C., the suspension is centrifuged (9000 rpm, 9 min, 15° C.) and the aggregates are suspended in PBS (200 µL) for use in the plaques complex formation.

Example 47

Preparation of Amyloid Template Complexes Using Cyclic Plaque Assembly

Figure 45:
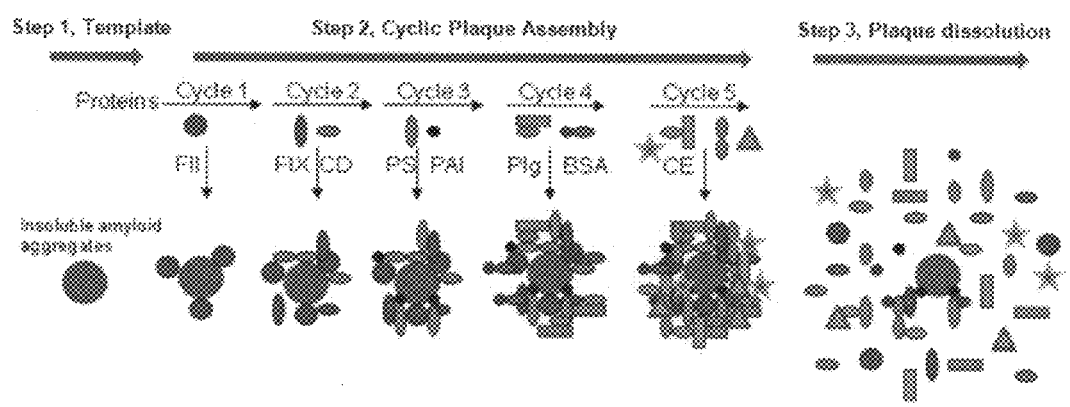

The insoluble aggregates are used as templates to initiate Cyclic plaque assembly (CPA) as shown in the diagram (FIG. 45), which involves several cycles of binding with proteins, lipids, or carbohydrates. In an example of five-cycle complex formation, the first cycle begins with a starting volume of reaction mixture of 250 µl (150 µl of chemical obtained from 1 ml of solutions and 100 µl PBS) and 5.0 µg of BSA. The reaction mixture is incubated at 37° C. for 1 hr followed by washing the complexes by repeated centrifugation (5×5000 rpm, 5 min). In the second cycle, the resulting template complexes are suspended in 250 µl of PBS out of which 50 µl is removed to monitor the growth of complex formation. Factor IX (4.0 µg) is added to the remaining 200 µl of suspension. As earlier, after incubation and washing the resulting complexes are suspended in 200 µl of PBS and 50 µl of the complexes are removed for later analysis. Plasminogen (PLG) (3.0 µg) is then added to the remaining 150 µl and continued for a third cycle of complex formation. After incubation and washing, the complexes are suspended in 150 µl of PBS and 50 µl are removed from that for later analysis. To the remaining 100 µl, 2.0 µg of PAI-1 is added for a fourth cycle of binding. After binding and washing, the complexes are used for a fifth round of binding. The complexes are suspended in 100 µl of PBS and 50 µl of the aggregates are removed. To the remaining 50 µl, 1.0 µg of protein S is added. After binding and washing the final complex is suspended in 20 µl of elution buffer (PBS with 100 mM EDTA). All the other complexes that are collected after every cycle of binding are centrifuged and are then suspended in 20 µl of elution buffer. After two hours of incubation the samples are centrifuged (9000 rpm, 10 min) and the supernatant is used for protein estimation using Micro BCA protein assays reagent (Pierce, Ill., USA). Protein estimation is carried out in a microtiter plate following information supplied with the kit and readings are taken using a spectrophotometer (Molecular Dynamics, CA, USA).

Example 48

Identification of Proteins that Bind to Insoluble Amyloid Aggregates

FIG. 46 illustrates an example involving the identification of proteins that bind to iron-loaded abeta42 templates. The iron-loaded abeta42 templates are combined with known and unknown cell extracts (CE) and subjected to CPA, as described herein. To determine which proteins successfully bind the templates, the final template complexes are suspended in denaturing sample buffer, boiled, and loaded into SDS-PAGE gel. The gels are then stained with coomassie blue or silver stain in order to visualize the binding proteins. FIGS. 46a and b illustrate an example wherein the proteins that bind with the templates include plasminogen (PLG), bovine serum albumin (BSA), plasminogen activator inhibitor 1 (PAI-1), blood coagulation factor II (FII), Factor IX (FIX), protein S (ProS), complement factor D (CD), complement factor B (CB), recombinant human hepatocyte growth factor (rhHGF) as well as unknown proteins from cytoplasmic extracts (CE). Proteins such as human insulin, chicken ovalbumin, horseradish peroxidase and carbonic anhydrase show no detectable binding with the templates. In the negative control, no significant binding is observed when the proteins are incubated in the absence of the templates.

In experiments such as these, known and unknown cell extract proteins that are used for the complex formation with the aggregates are diluted in PBS to a 1 mg/ml concentration and stored at −70° C. as 50 µl aliquots. These samples are thawed on ice and centrifuged (13000 rpm, 15 min, 4° C.) to remove any precipitation. The supernatant containing soluble proteins is used to form complexes with the aggregates. Various proteins are screened against the iron loaded abeta42 aggregates for examining their binding. Binding experiments are performed in PBS (50 µl, pH 7.3) containing 6.0 µg of iron loaded abeta 42 aggregates and 1.0 µg of each protein. The mixture is incubated at 37° C. for 1 hr. After that, the samples are centrifuged (9000 rpm, 9 min, 15° C.) and the complexes are washed five times with 100 µl PBST (PBS containing 0.05% of Tween 20). After each wash, the supernatant is discarded and the complexes are transferred to a new tube to avoid any carry-over of the proteins. The final complexes are suspended in 20 µl of PBS to which 5.0 µl of denaturing sample solublising buffer (Bio Rad, CA, USA) is added. After boiling the samples for 10 min they are loaded into 4-20% SDS-PAGE (Cambrex Bio Sci, ME, USA). The proteins in the gels are detected using coomassie blue or silver stain (Owl silver stain, Pierce, Ill., USA). All the binding and the CPA experiments are carried out in low protein bind 1.7 ml centrifuge tubes (Effentorf, Calif.).

For many of the example experiments described herein, the same buffer, centrifugation and washing conditions are used.

Example 49

Assembly Of Amyloid Complexes Using Cyclic Plaque Assembly (CPA)

This example illustrates the process of assembling complexes in vitro using the iterative process of Cyclic plaque assembly (CPA). In one example of this method, proteins capable of binding to an iron-loaded abeta42 template are added step-wise to the templates for up to five cycles. The resulting in vitro amyloid plaque-like complexes obtained after successive cycles reveal progressive binding of these proteins with the templates (FIGS. 47a, b). CPA is also repeated using the abeta42 templates with new combinations of the proteins to examine whether the binding of proteins to the templates is an ordered versus a random process. Proteins such as complement factor B, complement factor D, recombinant human hepatocyte growth factor (rhHGF), PAI-1, ProS, PLG, BSA and from CE are able to progressively bind to the templates (FIGS. 47c and d). In addition, these results suggest that protein binding to the templates is a random process and not limited to a particular order of protein binding.

Templates for CPA include insoluble aggregates of abeta42, abeta40, prion, self-formed abeta42 and/or iron-inorganic phosphate. The in vitro amyloid plaques formation experiments are performed in four or five cycles and depending upon the number of cycles to be performed, the starting volume of reactions would be adjusted. Typically, the reaction volume for each cycle of binding would be 50 µl of PBS containing 5.0 µg of the amyloid aggregates or 25 µl of the iron-phosphate aggregates and 0.5 µg of each protein. For complex formation through multiple cycles, the experiment would be started with higher volume of reagents and after every cycle of binding the reaction volumes would be gradually reduced. For example, in five-cycle complex formation, the starting volume of the reaction mixture in the first cycle would be 250 µl containing 25.0 µg of the amyloid aggregates and 2.5 µg of Factor II. The reaction mixture would be incubated at 37° C. for 1 hr followed by washing of the complexes as mentioned above. For the second cycle of binding, the complexes-1 are suspended in 250 µl of PBS out of which 50 µl is removed for monitoring the growth of the complex and for remaining 200 µl of the complexes Factor IX (2.0 µg) and complement factor D (2.0 µg) proteins are added together. As performed earlier, after the second cycle of binding and washing the complexes-2 are suspended in 200 µl of PBS from which 50 µl of the complexes are removed for later analysis and for remaining 150 µl both 1.5 µg of Protein 5 and 1.5 µg of PAI-1 proteins are added and continued for third cycle of binding. After binding and washing, the complexes-3 are be suspended in 150 µl of PBS and 50 µl is removed from that for later analysis and for remaining 100 µl of complexes both 1.0 µg of PLG and 1.0 µg of BSA proteins are added and proceed to a fourth cycle of binding. After binding and washing, the complexes-4 are used for a fifth cycle of binding. The complexes are suspended in 100 µl of PBS from which 50 µl is removed and for remaining 50 µl 6.0 µg of CE proteins is added. The final complexes-5, after washing, are suspended in 50 µl of PBS. All the complexes collected after successive cycles of complex formation are centrifuged (9000 rpm, 9 min, 15° C.) and suspended in 20 µl PBS. To each these suspensions 5 µl of 5×SDS sample solublishing buffer containing beta-mercapto ethanol (BME) is added and the mixtures is boiled for 10 minutes before loading them into 4-20% gradient polyacrylamide gels (Cambrex Biosciences, ME, USA). After running the gels under reducing conditions they are stained with silver reagent to detect proteins (Owl silver stain, Pierce, Ill., USA) and the results are documented. For control experiments, the reactions are carried out using only proteins without the templates following the above described experimental conditions. After each cycle of binding, the tubes are washed with PBS (250, 200, 150, 100 µl) and 50 µl is removed after every cycle for later analysis. All the samples collected after each cycle of binding are centrifuged (9000 rpm, 9 min, 15° C.) and finally are resuspended in 20 µl PBS, even though no apparent complex formation of the proteins is observed. To each of these suspensions, 5 µl of 5×SDS sample solubilishing buffer is added and the mixtures are boiled for 10 minutes before loading them into 4-20% gradient polyacrylamide gels (Cambrex Biosciences, ME, USA). After running the gels under reducing conditions they are stained with silver reagent to detect proteins and the results are documented.

Example 50

Determination of Whether Metals are Required for Plaque Assembly

In a further example, the present invention is used to determine whether the presence of iron, or other metals, is necessary for amyloid-plaque formation. In this example, the self-formed abeta42 templates are used as a template for CPA in the absence of iron, or other metals. Analysis of complexes resulting from every cycle of complex-formation reveals progressive binding of proteins with self-formed abeta42 templates (FIG. 48a). As a result, it is possible to conclude that iron is not essential for complex formation. Since inorganic phosphate buffered saline (PBS) is used to prepare iron loaded amyloid templates, it is conceivable that iron, in addition to binding with amyloid peptides, might react with phosphate and co-precipitates with iron-loaded amyloid templates. Hence, to determine whether iron-phosphate templates alone are a suitable template for complex formation, the CPA experiment is carried using these templates. Analysis of the resulting plaque complexes shows complex formation of proteins with these templates as well (FIG. 48b). As a negative control, when the proteins that are used in the complex formation are processed in the absence of the templates no complex formation is observed (FIGS. 48c and d). Together, such results indicate that all the templates (metals loaded amyloid templates, self-formed abeta42 templates and iron-phosphate templates) are suitable for plaques complex formation.

Example 51

Assembly of Plaque Complexes Using Various Iron-loaded Complexes

Figures 49, 49A, 49B:
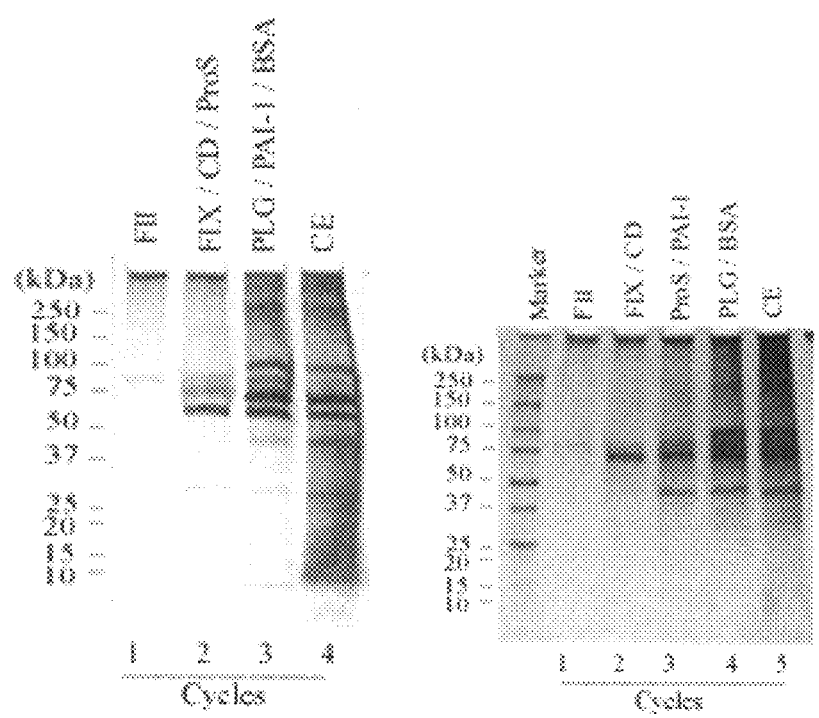
FIG. 49. SDS-PAGE analysis of the plaque complexes assembled using various iron-loaded amyloid templates. 49a, cycle 1, binding of FII to the amyloid templates; cycle 2, binding of FIX, CD and ProS proteins to the complexes-1; cycle 3, binding of PLG, PAI-1 and BSA proteins to the complexes-2 and cycle 4, binding of CE proteins to the complexes-3. 49b, cycle 1, binding of FII with the amyloid templates; cycle 2, binding of FIX and CD proteins to the complexes-1; cycle 3, binding of ProS and PAI-1 proteins to the complexes-2; cycle 4, binding of PLG and BSA proteins to the complexes-3 and cycle 5, binding of CE proteins to the complexes-4.

To determine whether the complex formation is a property unique to abeta42 templates or whether it is a feature common among amyloid templates, the CPA studies are conducted with abeta40 and prion (106-126) templates. The iron-loaded templates of these peptides are used for the CPA in four or five cycles. Resulting complexes show progressive binding of proteins in plaque formations (FIGS. 49a, b). These results reveal that generally all the iron loaded amyloid aggregates that are studied are suitable templates for in vitro amyloid plaque formation. As is the case with the abeta42 aggregates, there is no detectable binding of proteins like carbonic anhydrase, STI and HRP with the iron loaded prion or abeta40 templates. Proteins binding to abeta42 templates also bind to other amyloid templates. Likewise proteins that do not bind to the abeta42 aggregates appear not to bind to other templates.

These findings suggest that selective binding of proteins with the aggregates determined by presence of a specific or common structure among these aggregates. Previous studies have indicated the presence of a common structure or conformation among insoluble amyloid fibrils or their soluble oligomers (Bucciantini, M et al, 2002; O Nuallaian B, 2002; Kayed R et al, 2003; Nelson R et al, 2005).

Example 52

Determination of the Vulnerability of Amyloid-Plaque-like Complexes to Proteolytic Degradation This example illustrates the use of the invention to evaluate the proteolytic degradation of the amyloid complexes. For example, iron loaded abeta42 aggregates are mixed with CE proteins, and the resulting template complexes are treated with five different serine proteases. More specifically, nine independent reactions are carried out with each containing 5.0 µg of the iron-loaded aggregates of abeta42 and 6.0 µg of the CE proteins. After incubation and washing, the complexes are suspended in 50 µl of PBS. The nine complexes are sub-divided into two groups, with six individual complexes comprising Group I and three complexes comprising Group II. In order to interrogate the role of the plasminogen (PLG) activation system, which is implicated in the catabolism of amyloid peptides as well as the pathobiology of amyloid diseases (Melchor J P et al, 2003; Van Nostrand W E et al, 1999; Kranenburg O, 2005), the Group II complexes are subjected to another cycle of binding with both PLG (0.5 µg) and BSA (0.5 µg) proteins. After binding and washing, the PLG and BSA bound plaques complexes are suspended in 50 µl of PBS.

For proteolysis analysis, five of the six Group I template complexes are incubated with 20 ng of each protease (plasnin, chymotrypsin, trypsin, proteinase K and urokinase). The remaining complex is used as a control without protease treatment. Among three complexes of the Group II containing PLG attached to them, one is treated with u-PA (20 ng), a second is treated with t-PA (20 ng) and the third complex is used as a control without protease treatment. All these plaque complexes are incubated at 37° C. for 1 hr and after every 15 min, the tubes are gently tapped in order to encourage mixing. After washing, both the proteases-treated and control plaque complexes are suspended in 20 µl PBS. The complexes are boiled for 10 min with sample solubilizing buffer and loaded in to 4-20% gradient SDS-PAGE. Further, the gels are processed for silver staining and the results are documented for further analysis.

In this example, proteins bound to the aggregates are degraded when the complexes are treated with the plasmin, chymotrypsin, trypsin and proteinase K, all of which are known to cleave a broad range of peptide sequences (FIGS. 50a, b). As expected, no significant degradation of the proteins is observed when the plaque complex is treated with urokinase (u-PA), a serine protease known to cleave selective protein sequences. In another example, in a two-step amyloid plaque complex formation sequence, cytoplasmic extract (CE) proteins are mixed with the iron loaded abeta42 aggregates followed by another cycle of binding of the resulting complexes with both the PLG and BSA proteins. Interestingly, when the PLG/BSA-attached complexes are treated with either u-PA or t-PA, the inactive PLG is converted into active plasmin that, in turn, degrades other proteins attached to the complexes, a novel mechanism of amyloid plaque degradation similar to the fibrinolysis of the blood clot (FIGS. 50a, b).

Example 53

Determination of the Vulnerability of Iron-loaded Amyloid-Plaque-like Complexes to Proteolytic Degradation In order to verify the preceding results, such experiments are repeated using iron-loaded abeta40 templates for plaque complex formation. Proteins binding to the abeta40 templates appear to be cleared when they are treated with the same proteases. Both u-PA and t-PA activate the PLG-bound complex, which leads to the generation of active plasmin that in turn degrades other proteins in the complexes (FIGS. 51a, b).

Example 54

Evaluation of the Functionality and Conformation of PLG Attached to Template Complexes This example illustrates a method of evaluating the conformation and functionality of PLG attached to template complexes. Three groups of experiments are carried out to add the PLG at different layers of plaque complex formation. Group I includes three independent reactions containing both the PLG and BSA (0.5 μg each) that are added in the first cycle of the complex formation with the templates (5.0 μg). Group II includes three reactions to which both the PLG and BSA (0.5 μg each) are added in the first cycle of complex formation followed by another cycle of binding of the resulting complexes with the CE proteins (6.0 μg). Similarly, Group III includes three reactions each containing 5.0 μg of CE proteins and 5.0 μg of the abeta42 templates for complex formation in the first cycle of binding. The resulting complexes are subjected to another cycle of binding with both the PLG and BSA (0.5 μg each). To examine activation of the PLG attached to these complexes by the PLG activators, one complex from each group is treated with u-PA (20 ng), second complex is treated with t-PA (20 μg) and the remaining one complex is used as control. After treating with the PLG activators, all the complexes are washed and finally suspended in 20 μl of PBS. After boiling the complexes for 10 min in sample solublizing buffer they are loaded into 4-20% gradient SDS-PAGE. Further, the gel is processed for silver staining and the results are documented for analysis.

These three complexes are treated with either u-PA or t-PA to examine activation of the PLG attached to these complexes. Analysis of the u-PA or t-PA treated complexes reveals that the PLG binding to the complex during the first cycle of binding exhibits a detectable level of resistance to activation compared to the PLG binding to the complex in the second cycle of binding (FIGS. 52a, b).

Example 55

Evaluation of the Activation of Complex-bound PLG by u-PA (PGN54)

This example illustrates the evaluation of the activation of complex-bound PLG against increasing concentrations of u-PA and involves the assembly of two different groups of molecules. The groups involve sandwiching PLG between layers of molecules. Group I includes four independent reactions to which both the PLG and BSA (0.5 μg each) are added in the first cycle of the complex formation with the iron loaded abeta42 aggregates (5.0 μg). Group II includes four reactions of complex formation with the aggregates. In the first cycle of complex formation, the CE proteins (6.0 μg) are mixed with the aggregates followed by another cycle of binding of the resulting complexes with both the PLG and BSA (0.5 μg each). After incubation and washing, all these complexes are used for the PLG activation by u-PA. To examine activation of the PLG attached to the complexes three different concentrations of u-PA are used. One complex from each group is treated with 25 ng, second complex is treated with 50 ng and the third complex is treated with 100 ng of u-PA. The remaining one complex from each group is used as a control. After activation with u-PA, all the complexes are washed and finally suspended in 20 μl of PBS. After boiling the complexes for 10 min in sample solublizing buffer they are loaded into 4-20% gradient SDS-PAGE. Further, the gel is processed for silver staining and the results are documented for analysis. Analysis of the different template complexes includes that the PLG attached to aggregates during the first cycle of binding exhibits resistance even when incubated with increased concentrations of the u-PA compared to the PLG that is attached to the complexes in the second cycle of binding (FIGS. 53a, b).

Example 56

Evaluation of the Conformational and Functional States of Complex-bound PAI-1

This example illustrates a method of further understanding the conformational state of complex-bound PAI-1 proteins. Here, two groups of complexes are assembled with PAI-1 and the iron-loaded abeta42 or abeta40 aggregates. The first group comprises four independent reactions containing the abeta42 aggregates (5.0 μg each) and 5.0 μg of CE proteins. These reactions are performed in 50 μl of PBS. Among these four, three of the resulting complexes are subjected to another cycle of binding with both the PLG and BSA (0.5 μg of each) and different concentrations of PAI-1 (0.1, 0.2 and 0.5 μg) proteins. The second group comprises three independent reactions containing the iron-loaded abeta40 aggregates (6.0 μg) and 5.0 μg of CE proteins. The resulting complexes are subjected to another cycle of complex formation with both the PLG and BSA (0.5 μg of each) and different concentrations of PAI-1 (0.1, 0.2 and 0.5 μg) proteins. Following the complex formation and washing, they are suspended in 50 μl of PBS to which 20 ng of u-PA is added to activate the complex bound PLG. After u-PA treatment, the complexes are washed as earlier and finally suspended in 20 μl of PBS.

At lower concentrations, the complex-bound PAI-1 does not inhibit u-PA activity and, therefore, PLG becomes activated. However, at higher concentrations, the complex-bound PAI-1 proteins efficiently inhibit the u-PA activity and prevent the activation of complex-bound PLG (FIGS. 54a and b).

Example 57

In another example of the use of the present invention, PAI-1 is separated from PLG and BSA in a further effort to determine the conformational or functional properties of PAI-1 bound to complexes. These molecules are used in different cycles of CPA or multi-layered protein formation. The resulting complexes should then contain PAI-1 separated from PLG by a layer of proteins.

Two groups of complexes are assembled with PAI-1 and the iron-loaded abeta42 or abeta40 aggregates. The complexes are assembled in three cycles and out of five individual complexes four is assembled between the iron-loaded abeta42 aggregates (5.0 μg) and four different concentrations of PAI-1 (0.05, 0.1, 0.2 and 0.5 μg). The remaining one reaction is used as control without the PAI-1. For the second cycle of binding the resultant four complexes and control is subjected to another cycle of binding with 5.0 μg of CE proteins. In the third cycle of complex formation, the PLG and BSA (0.5 μg each) proteins are added to all resultant complexes for binding. Finally, all the complexes containing the bound PLG, BSA and PAI-1 proteins are treated with 20 ng of u-PA to activate PLG. After u-PA treatment, the complexes are washed and suspended in 20 μl of PBS. Sample solubilizing buffer is added to these complexes and after boiling for 10 min they are loaded in 4-20% gradient SDS-PAGE. Further, the gel is processed for silver staining and the results are documented for analysis.

Figures 55, 55A, 55B:
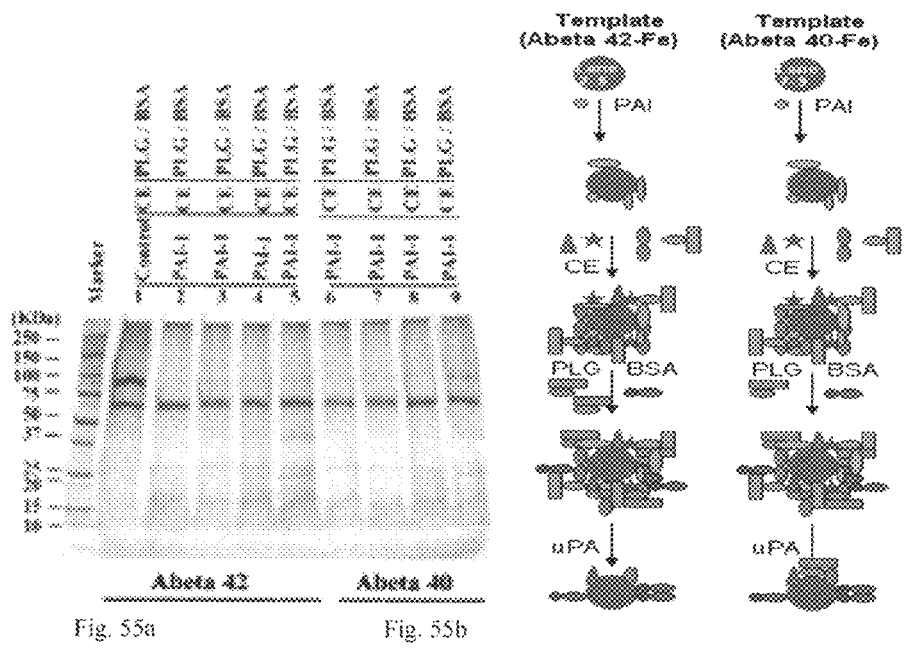
FIG. 55 Treatment of the complexes containing PAI-1 and PLG proteins that were bound to complexes in the first and third cycles respectively. 55a, Lane 1, the control complex without PAI-1 and u-PA treatment; lanes 2 and 6 are the complexes attached with the PLG and PAI-1 (20 ng) proteins and treated with u-PA (20 ng); lanes 3 and 7 are the complexes attached with the PLG and PAI-1 (50 ng) proteins and treated with u-PA (20 ng); lanes 4 and 8 are the complexes attached with PLG and PAI-1 (100 ng) proteins and treated with u-PA (20 ng) and lanes 5 and 9 are the complexes attached with PLG and PAI-1 (200 ng) proteins treated with u-PA (20 ng). 55b, Diagram showing probing the functional and conformational states of PAI-1 sandwiched between layers of proteins.
Figure 56:
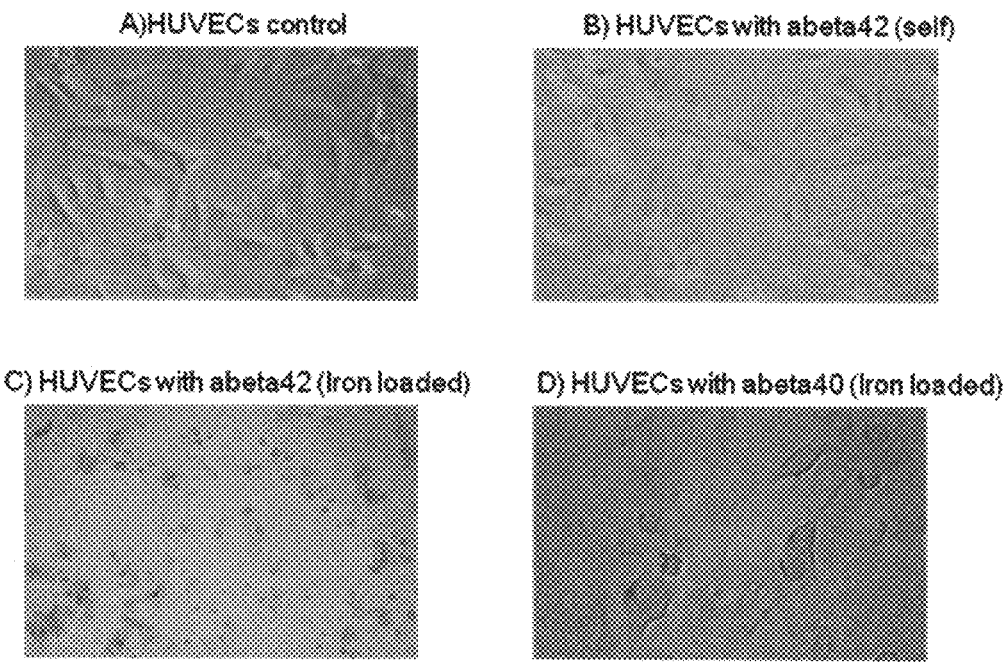
FIG. 56a to d. Microscopic observation (400×) of HUVECs treated with abeta templates. a) HUVECs growth, control without aggregates; b) HUVECs growth with abeta42 templates (10 μg); (c) HUVECs growth with iron-loaded abeta42 templates (10 μg) and d) HUVECs growth with iron-loaded abeta40 templates (10 μg).

Incubation of such complexes with u-PA reveals significant activation of PLG even in the presence of higher concentrations of complex-attached PAI-1 (FIGS. 55a, b). These results suggest that direct interaction of the PAI-1 with the templates might cause excessive conformational changes in their structure including its reactive center loop thereby affecting their normal binding with the u-PA.

Example 58

Evaluation of In Vitro Assembled Amyloid Plaque-like Complexes for Pathogenicity This example illustrates the evaluation of the pathogenicity of in vitro assembled amyloid plaque-like complexes by combining such complexes with HUVECs. In this example, the templates of abeta42 self assembled, iron-loaded abeta42 and iron-loaded abeta40 are prepared as described herein and then added to the HUVECs.

The human umbilical vein endothelial cells (HUVEC) are grown as described in example 36. For binding, 50 μl of the insoluble templates that are obtained from 10 μg of the soluble amyloid peptides, are mixed with the cells (2000) for 10 min in a sterile 1.5 ml microfuge and then the cells-complexes are transferred to 2 ml ECGM medium for 72 hrs. Second, for binding of the amyloid plaques like complexes with the HUVECs, the iron-loaded abeta42 and iron-loaded abeta40 templates are used individually for binding with the CE (10 μg) followed by the binding of the resulting complexes with the PLG and BSA in the second cycle of binding. Then the resulting complexes (50 μl) are mixed with the cells (2000) for 10 min and the cell-complexes are transferred to 2 ml ECGM medium for 72 hrs. As a control, the HUVECs (2000) are grown in 2 ml ECGM without any templates or plaque complexes. The cells are then analyzed for viability by microscopic examination and the results are then documented.

After 48 hrs, microscopic observation of the HUVECs incubated with the self assembled abeta42 templates shows 90% viable HUVECs compared to the control. Conversely, only 10% of the HUVECs are viable when grown with the iron-laded abeta42 templates and these cells showed pathological symptoms as evidenced by extensive morphological changes. Similarly, only 20% of the HUVECs are viable when grown with the iron-loaded abeta40 templates (FIG. 56a to d).

Example 59

Evaluation of In Vitro Assembled Amyloid Plaque-like Complexes for Pathogenicity This example illustrates an experiment that is similar to that described in the preceding example, except that it illustrates the use of a different set of plaque-like complexes.

Figure 57:
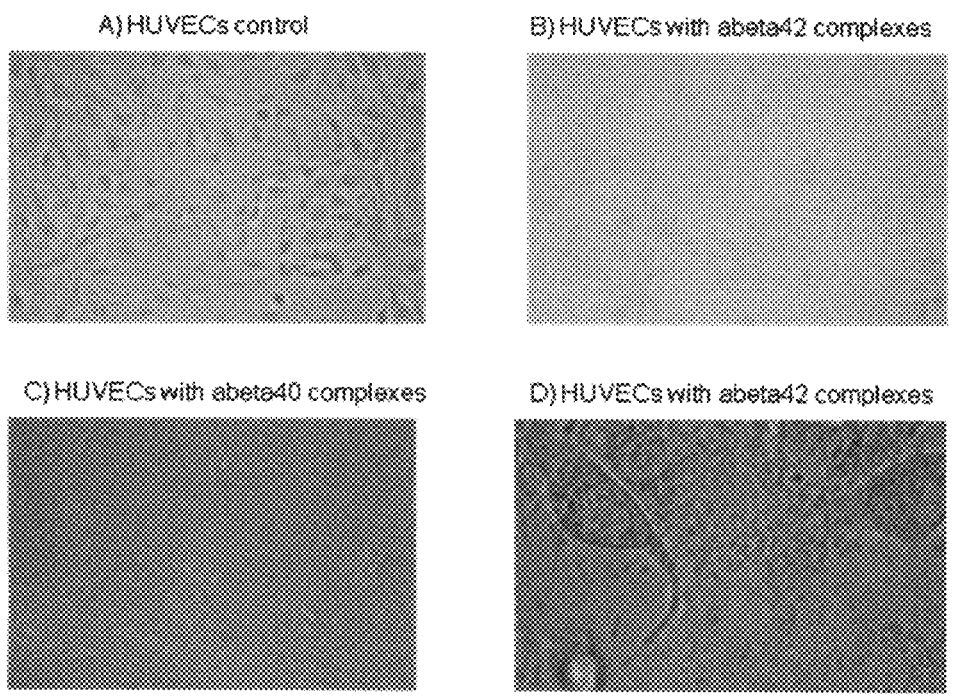
FIG. 57a to d. Microscopic observation (400×) of HUVECs treated with amyloid like plaque complexes. a) HUVECs growth, control without complexes; b) HUVECs growth with plaque complexes assembled using iron loaded abeta42 (10 μg); (c) HUVECs growth with plaque complexes assembled using iron-loaded abeta40 templates (100 μg) and d) HUVECs grown with abeta42 complexes showing pathological symptoms and accumulation of plaque complexes on cell surface as indicated by arrows.

Here, HUVECs are incubated with the abeta40 and abeta42 derived amyloid plaque complexes and show approximately 10% viability with extensive pathological symptoms. Microscopic examination of the HUVEC morphological symptoms reveal binding of the plaque-like complexes, apparently to cell surfaces (FIGS. 57a, b, c and d).

These results together suggest that the binding of the amyloid templates and their plaque complexes directly to the HUVECs cause pathological symptoms to the cells. Particularly, the iron-loaded abeta42 and their plaque complexes appear to be highly pathogenic to the HUVECs.

Example 60

Figure 58:
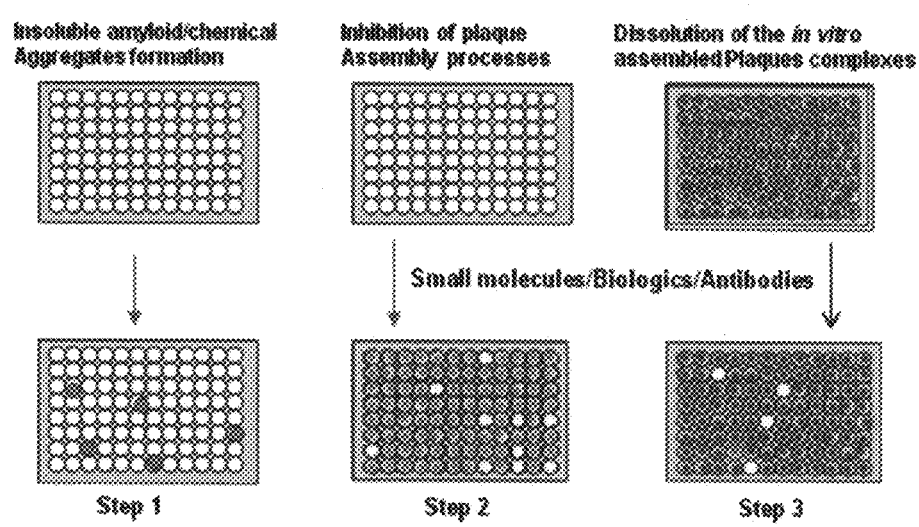
FIG. 58 Sequences showing in vitro amyloid plaque assembly and particularly targeting steps 2 and 3 for drug discovery.

Identification of Drugs capable of Preventing the Assembly of or Promoting the Disassembly of Amyloid Plaque-like Complexes FIG. 58 illustrates an example of a method of identifying lead compounds capable of preventing assembly of amyloid plaque-like complexes or of promoting disassembly of amyloid plaque-like complexes (FIG. 58). Such lead compounds could be precursors to therapeutics for the treatment of amyloid diseases in humans. The amyloid plaque assembly processes are carried out in 96 well microtitre plates with 100 μl reaction volume containing 15 μg of iron-loaded abeta42 or other amyloid templates and test compound/s. For identification of molecule/s that disrupts or interferes with the step 2 of the plaques assembly process, in the first cycle of complex formation, the templates are mixed with both FII (3 μg) and test compound/s (10 μg) and followed by washing the complexes are transferred to new microtitre plate. For second cycle of binding, the complexes-1 are subjected to the binding with both the CE (10 μg) and test compound (10 μg) and followed by incubation and washing, the complexes-2 are subjected to third round of binding with both the PLG and BSA (3 μg each) in the presence of the test compound/s. After binding and washing, the complexes are suspended in 50 μl PBS, out of which 25 μl is used for solubilization in PBS/EDTA (20 mM). After 30 min incubation at 37° C., the samples are centrifuged at 300 rpm for 10 min and the supernatants are used for protein estimation using Micro BCA protein assay kit (Pierce, Ill.). The remaining 25 μl of the assembled complexes are used for SDS-PAGE analysis as described above. Simultaneously, for control experiment the amyloid plaque assembly experiment is carried out without the test compound. Analysis of protein estimation and gel analysis of the complexes assembled in the presence of test compound/s would reveal the efficacy of these compounds for disrupting the complex formation, as evidenced by reduction in the protein concentration compared to the control experiments. Molecules showing efficacy for preventing the in vitro amyloid plaques like complex assembly would be considered as "hits" and would be subjected for further analysis.

In order to identify lead compounds able to dissolve the pre-assembled amyloid plaque like complexes, the preceding experiments are repeated to assemble complexes in three cycles using the iron-loaded abeta42 templates. Then, 50 μl of the resulting complexes is incubated with test compound/s (50 ng to 1 μg) for 1 hr at 37° C. followed by washing and analysis of the complexes for their dissolution. For example, 50 μl of the pre-assembled complexes is mixed with u-PA or t-PA (20 ng) at 37° C. for 1 hr followed by washing and protein estimation or gel analysis of the resultant complexes. As observed in example 12, the complexes incubated with the u-PA and t-PA show reduction in the protein concentration. Further, gel analysis of these complexes shows degradation of complex bound PLG suggesting the activated plasmin may be responsible for degradation of other proteins attached to the plaque complexes. This approach is also useful to optimize u-PA (PGN54) molecule for use as a therapeutic lead to treat patients with advanced amyloid diseases such as Alzheimer. Reducing the amyloid plaque burden or plaque build-up in the cerebral arteries would greatly improve or reverse the pathological symptoms associated with the amyloid diseases. In addition, to test the hypothesis of amyloid plaque burden reduction as an effective strategy, optimized u-PA or other plasminogen activators are used in the animal models of Alzheimer's disease. After demonstrating the efficacy of the optimized PGN54 for reducing amyloid plaque build up in animal models, it will be tested in a small population of patients with advanced Alzheimer's disease.

Example 61

Identification of Drugs capable of Preventing the Pathogenic Effects of Amyloid-Plaque-Like Complexes This example illustrates a method of identifying drugs capable of preventing the pathogenic effects of amyloid plaque-like complexes. In this example, amyloid plaque-like complexes would be generated using the methods described herein or otherwise obtained. In addition, mammalian cells such as HUVECs would be prepared as described herein, except that they would be seeded into multi-well plates suitable for high-throughput screening. The amlyoid plaque-like complexes would be incubated with the mammalian cells over a period of time so as to enable morphogenic changes in the cells and cytokine expression that are consistent with pathogenic effects. A library of lead compounds would be added to the multi-well plates either before, contemporaneously, or after the plating of the mammalian cells, or after the addition of the amyloid plaque-like complexes. The wells would then be evaluated by a technology capable of detecting changes in cellular morphology such as by microscopy. The lead compounds corresponding to wells demonstrating diminished cellular morphological changes would be isolated and further evaluated as potential therapies for amyloid diseases.

Example 62

Treating or Protecting Against Amyloid Diseases or Disease-Like Processes in Patients Using Wild-Type or PAI-1 Resistant Urokinase Plasminogen Activator (PGN54)

This example illustrates a method of preventing or treating amyloid disease-like processes in patients using wild-type or PAI-1 resistant urokinase plasminogen activator (PGN54). Wild type and PAI-1 inhibitor resistant PGN54 (optimized) would be introduced intravenously into animal models of Alzheimer's disease using different doses of u-PA (0.1 to 1 mg/Kg) at 12, 24 and 48 hrs, followed by pharmokinetic and pharmodynamic analysis. The animals would be evaluated for indications of in vivo plaque regression, and improvement of disease related. The data generated from Alzheimer's animal model would be used to treat Alzheimer's disease patients in clinical studies.

Example 63

Examples of Buffers, Reagents, and Other Procedures for Experiments

The following chemicals and proteins may be purchased from Sigma (MI, USA): Prion peptide (106-126), Abeta 40, Abeta 42, plasmin, trypsin, chymotrypsin and Proteinase K, carbonic anhydrase, Horseradish peroxidase, chicken ovalbumin, soybean trypsin inhibitor, $Fe_2(SO_4)_3$, BSA and EDTA. Lys-Plasminogen (PLG), Coagulation factors II, IX, and Protein S may be purchased from Enzyme Research Laboratories (IN, USA). High molecular weight urokinase plasminogen activator (u-PA), two chain tissue plasminogen activator (t-PA) and Plasminogen Activator inhibitor 1 (PAI-1) may be purchased from Molecular Innovation Inc (MI, USA). Complement factors B and D may be purchased from Advanced Research Technologies (CA, USA). Recombinant human hepatocyte growth factor may be procured from SBH Sciences (MA, USA). All buffers and reagents may be prepared using MilliQ purified water. The human umbilical vein endothelial cells may be purchased from Cell applications, Inc (CA, USA). Unless otherwise mentioned all other chemicals used in this study may be purchased from Sigma (MI, USA).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

OTHER PUBLICATIONS

1. Fayad, Z. A., Fuster, V. Clinical imaging of the high-risk or vulnerable atherosclerotic plaque. *Circ. Res.* 89, 305-316 (2001).
2. Selkoe, D. J. Folding proteins in fatal ways. *Nature.* 426, 900-4 (2004).
3. Evan, A., Lingeman, J., Coe, F. L., Worcester, E. Randall's plaque: pathogenesis and role in calcium oxalate nephrolithiasis. *Kidney Int,* 69, 1313-8 (2006).
4. Lalla, E., Lamster, I. B., Hofman, M. A., Bucciarelli, L., Jerun, A. P., Tucker, S., Lu, Y., Papanou, P. N., Schmidt, A. N. Oral infection with a periodontal pathogen accelerates early atherosclerosis in apolipoprotein E-null mice. *Arterioscler Thromb Vasc Biol.* 23, 1405-1411 (2003).
5. Viles-Gonzalez, M. J., Fuster, V., Badimon, J. J. Atherothrombosis: A widespread disease with unpredictable and life-threatening consequences. *Eur. Heart Journal,* 25, 1197-1207 (2004).
6. Serfaty, J. M., Chaabane, L., Tabid, A., Chevallier, J. M., Briguet, A., Douek, P. C. Atherosclerotic plaques: Classification and characterization with T2-weighted high-spacial-resolution MR imaging-an in vitro study. *Radiology,* 219, 403-410 (2001).
7. Corti, R., Hutter R., Badimon, J. J., Fuster, V. Evolving concepts in the triad of atherosclerosis, inflammation and thrombosis. *J Thromb Thrombolysis.* 17. 35-44 (2005).
8. Rauch, U., Osende, J. I., Fuster, V., Badimon, J. J., Fayad, Z., Chesebro, J. H. Thrombus formation on atherosclerotic plaques: pathogenesis and clinical consequences. *Ann. Intern. Med,* 134, 224-238 (2001).
9. Doherty, T. M., Fitzpatrick, L. A., Inoue, D., et al, Molecular, endocrine and genetic mechanisms of arterial calcification. *Endocrine reviews.* 25, 629-672 (2003).

10. Mykkanen, L., Kuusisto, J., Haffner, S. M., Laakso, M., Austin, M. A. LDL size and risk of coronary heart disease in elderly men and women. *Arterioscler Thromb Vasc Biol.* 19, 2742-2748 (1999).
11. Carmena, R., Duriez, P., Fruchart, J. C. Atherogenic lipoprotein particles in atherosclerosis. *Circulation.* 109, (suppl III-2-III-7) (2004).
12. Hirona, T., Ito, Y., Koba, S., Toyoda, M., Ikejiri, A., Saegusa, H., Yamazaki, J., Yoshino, G. Clinical significance of small dense low-density lipoprotein cholesterol levels determined by the simple precipitation method. *Arterioscler Thromb Vasc Biol.* 24, 558-563 (2004).
13. Festa, A., Agostino, R. D., Mykkanen, L., Tracy, R., Howard, B. V., Haffner, S. V. Low-density lipoprotein particle size is inversely related to plasminogen inhibitor-1 levels. *Arterioscler Thromb Vasc Biol.* 19, 605-610 (1998).
14. Peng, S., Guo, W., Morrisett, J. D., Johnstone, M. T., Hamilton, J. A. Quantification of cholesteryl esters in human and rabbit atherosclerotic plaques by magic-angle spinning. *Arterioscler Thromb Vasc Biol.* 12. 2682-8 (2000).
15. Sarig, S., Utian, W. H., Sheean, L. A., Gorodeski, G. I. Distribution of unesterified cholesterol-containing particles in human atherosclerotic lesions. *Am. J. Pathol.* 146, 139-147 (1994a).
16. Small, D. M., Progression, and regression of atherosclerotic lesions: insights from lipid physical biochemistry. *Arteriosclerosis,* 8, 103-129 (1988).
17. Guyton, J. R., Klemp, K. F. Development of the lipid-rich core in human atherosclerosis. *Arterioscler Thromb Vasc Biol.* 16, 4-11 (1996).
18. Sarig, S., Weiss, T. A., Katz, I, Kahana, F., Azoury, R., Okon, E., Kruth, H. S. Detection of cholesterol associated with calcium mineral using confocal fluorescence microscopy. *Lab Invest,* 71, 782-787 (1994b).
19. Kruth, H. S., Filipin-positive, oil red O-negative particles in atherosclerotic lesions induced by cholesterol feeding. *Lab invest.* 50, 87-93 (1984).
20. Hirsch, D., Azoury, R., Sarig, S., Kruth, H. S. Colocalization of cholesterol and hydroxyapatite in human atherosclerotic lesions. *Calcif Tissue Int.* 52, 94-98 (1993).
21. Guo, W., Morrisett, J. D., DeBakey, M. E., Lawrie, G. M., Hamilton, J. A. Quantitation in situ of crystalline cholesterol and calcium phosphate hydroxyapatite in human atherosclerotic plaques by solid state magic angle spinning NMR. *Arterioscler Thromb Vasc Biol.* 20, 1630-1636 (2000).
22. Brancaccio, D., Cozzolino, M. The mechanism of calcium deposition in soft tissues. *Contrib Nephrol.* 149, 279-86 (2005).
23. McCullough, P. A., Sandberg, K. R., Dumier, F., Yanez, J. E. Determinants of coronary vascular calcification in patients with chronic kidney disease and end-stage renal disease: a systemic review. *J. Nephrol.* 17, 205-15 (2004).
24. Higgins, C. L., Marvel, S. A., Morrisett, J. D. Quantification of calcification in atherosclerotic lesions. *Arterioscler Thromb Vasc Biol.* 25, 1567-76 (2005).
25. Young, E. W., Albert, J., M., Satayathum, S., Goodkin, D. A., Pisoni, R. L., Akiba, T., Kurokawa, K., Bommer, J., Piera, L., Poit, F. K. Predictors and consequences of altered mineral metabolism: the dialysis outcomes and practice patterns study. *Kidney Int.* 67, 1179-87 (2005).
26. Wang, A. Y., Woo, J., Wang, M., Sea, M. M., Li, P. K., Lui, S. F., Sanderson, J. E. Association of inflammation and malnutrition with cardiac valve calcification in continuous ambulatory peritoneal dialysis patients. *J Am Soc Nephrol.* 12, 1927-36 (2001).
27. Schmiedl, A., Schwille, P. O., Bonucci, E., Erben, R. G., Grayczyk, A., Sharma, V. Nephrocalcinosis and hyperlipidemia in rats fed a cholesterol and fat-rich diet: association with hyperoxaluria, altered kidney and bone minerals, and renal tissue phospholipid-calcium interaction. *Urol Res.* 28, 404-15 (2000).
28. Carson, D. A. An infectious origin of extraskeletal calcification. *Proc Natl Acad. Sci.* 95, 7846-7847 (1998).
29. Bini, A., Mann, K. G., Kudryk, B. J., Schoen, F. J. Non-collagenous bone matrix proteins, calcification, and thrombosis in carotid artery atherosclerosis. *Arterioscler Thromb Vasc Biol.* 19. 1852-61 (1999).
30. Thompson, G. R., Naoumova, R., Sidhu, P., Underwood, R. Predicting coronary heart disease. *Lancet.* 343. 670-71 (1994).
31. Garg, V., Muth, A. N., Ransom, J. F., Schluterman, M. K., Barnes, R., King, I. N., Grossfeld, P. D., Srivastava, D. Mutations in NOTCH1 cause aortic valve disease, *Nature.* 437, 270-273 (2005).
32. Campean, V., Neureiter, D., Varga, I., Runk, F., Reiman, A., Garlichs, C., Achenbach, S., Normast-Daniel, B., Amann, K. Atherosclerosis and vascular calcification in chronic renal failure. *Kidney Blood Press Res.* 28. 280-9 (2005).
33. Cullen, P., Rauterberg, J., Lorkowski, S. The pathogenesis of atherosclerosis. *Handb Exp Pharmacol.* 170. 3-70 (2005).
34. Ribeiro, S., Ramos, A., Brandao, A., Rebelo, J. R., Guerra, A., Resina, C., Vila-Lobos, A., Carvalho, F., Remedio, F., Ribeiro, F. Cardiac valve calcification in haemodialysis patients: role of calcium-phosphate metabolism. *Nephrol Dial Transplant.* 8. 2037-40 (1998).
35. Lomashvili, K. A., Cobbs, S., Hennigar, R. A., Hardcastle, K. I., O'Neil, W. C. Phosphate-induced vascular calcification: Role of pyrophosphate and osteopontin. *J Am Soc Nephrol.* 15, 1392-1401 (2004).
36. Raggi, P., Boulay, A., Chasen-Taber, S., Amin, N., Dillon, M., Burke, S. K., Chertow, G. M. Cardiac calcification in adult hemodialysis patients. *J. Amer. Col. Cardiology,* 39, 695-701 (2002).
37. Margolis, J. R., Chen, J. T., Kong, Y., Peter, R. H., Behar, V. S., Kisslo, J. A. The diagnostic and prognostic significance of coronary artery calcification: a report of 800 cases. *Radiology,* 137, 609-16 (1980).
38. Jono, S., Shioi, A., Ikari, Y., Nishizawa, Y. Vascular calcification in chronic kidney disease. *J Bone Miner Metab.* 24, 176-81 (2006).
39. Ferramosca, E., Bellasi, A., Ratti, C., Raggi, P. Ethiopathogenesis, diagnosis and prevention of vascular calcification in end stage renal disease. *Curr Med Chem Cardiovasc Hematol Agents.* 3, 165-71 (2005).
40. Goodman, W. G. Vascular calcification in end-stage renal disease. *J. Nephrol.* 6, 82-85 (2002).
41. Xiao, Q., Danton, M. J., Witte, D. P., Kowala, M. C., Valentine, M. T., Degen, J. L. Fibrinogen deficiency is compatible with the development of atherosclerosis in mice. *J Clin Invest.* 101. 1184-94 (1998).
42. McAllister, C., Karymov, M. A., Kawano, Y., Lushnikov, A. Y., Mikheikin, A., Uversky, V. N., Lyubchenko, Y. L. Protein interactions and misfolding analyzed by AFM force spectroscopy. *J Mol. Biol.* 354, 1028-42 (2005).
43. Jayaraman, S., Gantz, D. L., Gursky, O. Effects of oxidation on the structure and stability of human low-density lipoprotein. *Biochemistry.* 46, 5790-7 (2007).

44. Klein, C. P., De Groot, K., Vermeiden, J. P., Van Kamp, G. Interaction of some serum proteins with hydroxylapatite and other materials. *J Biomed Mater Res.* 14, 705-12 (1980).
45. Tsortos, A., Ohki, S., Zieba, A., Baier, R. E., Nancollas, G. H. The dual role of FBN as inhibitor and nucleator of CP phases: The importance of structure. *J Colloid Interface Sci.* 177, 257-262 (1996).
46. Dornheim, G., Schon, R. Preparation and characterization of an antithrombin III concentrate. *Folia Haematol Int Mag Klin Morphol Blutforsch.* 109, 870-7 (1982).
47. Stapleton, A. M., Dawson, C. J., Grover, P. K., Hohmann, A., Comacchio, R., Boswarva, V., Tang, Y., Ryall, R. L. Further evidence linking urolithiasis and blood coagulation: urinary FII fragment 1 is present in stone matrix. *Kidney Int.* 49, 880-8 (1996).
48. Royal, R. L., Chauvin, M. L., Grover, P. K. Intracrystalline proteins and urolithiasis: a comparison of the protein content and ultrastructure of urinary CO monohydrate and dihydrate crystals. *Br J. Urol.* 96, 654-663 (2005).
49. Sheng, X., Ward, M. D., Wesson, J. A. Crystal surface adhesion explains the pathological activity of calcium oxalate hydrates in kidney stone formation. *J Am Soc Nephrol.* 16, 1904-8 (2005).
50. Chang, J. Y. The structures and proteolytic specificities of autolysed human thrombin. *Biochem. J.* 240, 797-802 (1986).
51. Annex, B. H., Denning, S. M., Channon, K. M et al, Differential expression of tissue factor protein in directional atherectomy specimens from patients with stable and unstable coronary syndromes. *Circulation.* 91, 619-22 (1995).
52. Vu, T. K., Wheaton, V. I., Hung, D. T., Charo, I., Coughlin, S. R. Domains specifying thrombin-receptor interaction. *Nature,* 353, 674-7 (1991).
53. Monroe, D. M., Hoffman, M. What does it take to make the perfect clot? *Arterioscler Thromb Vasc Biol.* 26, 41-8 (2005).
54. Ofosu, F. A. The blood platelet as a model for regulating blood coagulation on cell surfaces and its consequences. *Biochemistry* (Mosc). 67, 47-55 (2002).
55. Grover, P. K., Ryall, R. L. Inhibition of CO crystal growth and aggregation by FII and its fragments in vitro. *Eur. J. Biochem.* 263, 50-56 (1999).
56. Schaar, J. A., Muller, J. E., Falk, E., Virmani, R., Fuster, V., Serruys, P. W., Colombo, A., Stefanadis, C., Ward., Casscells, S., Moreno, P. R., Maseri, A., van der Steen, A. F. Terminology for high-risk and vulnerable coronary artery plaques. *Eur Heart J* 25, 1077-82 (2004).
57. Ehara, S., Kobayashi, Y., Yoshiyama, M., Shimada, K., Shimada, Y., Fukuda, D., Nakamura, Y., Yamashita, H., Yamagishi, H., Takeuchi, K., Naruko, T., Haze, K., Becker, A. E., Yoshikawa, J., Ueda M. Spotty calcification typifies the culprit plaque in patients with acute myocardial infarction: an intravascular ultrasound study. *Circulation.* 30, 3424-9 (2004).
58. Burke, A. P., Kolodgie, F. D., Farb, A et al. Healed plaque ruptures and sudden coronary death: evidence that subclinical rupture has a role in plaque progression. *Circulation.* 103, 934-940 (2001).
59. Naghavi, M., Libby, P., Falk, E., Casscells, S. W., Litovsky, S et al. From vulnerable plaque to vulnerable patient: A call for new definitions and risk assessment strategies: part I. *Circulation.* 108, 1664-1672 (2003). Vu, T. K., Wheaton, V. I., Hung, D. T., Charo, I., Coughlin, S. R. Domains specifying thrombin-receptor interaction. *Nature,* 353, 674-7 (1991).
60. Leys, D. Atherothrombosis: a major health burden. *Cerebrovasc Dis.* 11, Suppl 2:1-4 (2001).
61. Munger, M. A., Hawkins, D. W. Atherothrombosis: epidemiology, pathophysiology, and prevention. *J Am Pharm Assoc.* 44, (2 Suppl 1):S5-12 (2004).
62. Tsuchihashi, K., Nozawa, A., Marusaki, S., Moniwa, N., Oh-numa, Y., Kuno, A., Takagi, S., Takizawa, H., Ura, N., Shimamoto, K. Mobile intracardiac calcinosis: a new risk of thromboembolism in patients with haemodialysed end stage renal disease. *Heart.* 82, 638-40 (1999).
63. Willens, H. J., Ferreira, A. C., Gallagher, A. J., Morytko, J. A. Mobile components associated with rapidly developing mitral annulus calcification in patients with chronic renal failure: review of mobile elements associated with mitral annulus calcification. *Echocardiography.* 20, 363-7 (2003).
64. Khan, S. R. Renal tubular damage/dysfunction: key to the formation of kidney stones. *Urol Res.* 11, 1-6 (2006).
65. Dahlback, B. Blood coagulation. *Lancet,* 355, 1627-32 (2000).
66. Shah, P. K. Link between infection and atherosclerosis: who are the culprits: viruses, bacteria, both or neither? *Circulation,* 102, 2335-2340 (2000).
67. Libby, P., Eagan, D., Skarlatos, S. Roles of infectious agents in atherosclerosis and restinosis. *Circulation,* 96, 4095-4103 (1997).
68. Mysorekar, I. U., Hultgren, S. J. Mechanisms of uropathogenic *Escherichia coli* persistence and eradication from the urinary tract. *Proc. Natl. Acad. Sci. USA.* 103, 14170-14175 (2006).
69. Gilbert, P., Allison, D. G., McBain, A. J. Biofilsm in vitro and in vivo: do singular mechanisms imply cross-resistance? *J. Appl. Microbiol.* 92, 98-110 (2002).
70. Calenoff E. Atherosclerotic plaque specific antigens and antibodies thereto and uses thereof. U.S. Pat. No. 6,025, 477 (2000).
71. Mathu, S., Kant, S. Preclinical evaluation of atherosclerosis. *Int J Diab Dev Ctries.* 26, 105-111.
72. Greenland, P et al. ACCF/AHA 2007 Clinical expert consensus document on coronary artery calcium scoring by computed tomography in global cardiovascular risk assessment and in evaluation of patients with chest pain. *J. Amer. Col. Cardiology.* 49: 378-402 (2007).
73. Gerhard, A. T., Meredith, I. T., Charbonneau, F., Delagrange, D., Creager, M. A., Selwyn, A. P., Ganz, P. Systemic nature of endothelial dysfunction in atherosclerosis. *Am J. Cardiol.* 75, 71B-74 (1995).
74. Davignon, J., Ganz, P. Role of Endothelial Dysfunction in Atherosclerosis. *Circulation.* 109, III-27-III-32 (2004).
75. Hollander, W et al. *Atherosclerosis.* 34, 391-405 (1979).
76. Parums, E et al. *Atherosclerosis.* 38, 211-216 (1981).
77. Hannson, G et al. *Experimental and Mol. Pathol.* 34, 264-280 (1981).
78. Hannson, G et al. *Acta Path Microbiol Immunol Scan. Sec A.* 92, 429-435 (1984).
79. Anderson, N. H., Anderson, N. G. The human plasma proteome. *Mol Cell Proteomics.* 1.11, 845-867 (2002).
80. Molina, H., Bunkenborg, J., Hanumanthu Reddy. G., Muthusamy, B., Scheel. P. J., Pandey, A. A Proteomic Analysis of Human Hemodialysis Fluid. *Mole Cell Proteomics* 4.5, 637-650 (2005).
81. Ohmori, H. K., Hirao, M., Nishiyama, M. Concentration dependence of IgG-protein A affinity studied by wireless-electrodeless QCM. *Biosens Bioelectron.* 153238-42 2007.
82. O'Brian, P. M., Aitken, R. Antibody phage display. *Methods and protocols.* Humana press. 1-416 (2002).

83. Nachtigal P, Jamborova G, Pospisilova N, Pospechova K, Solichova D, Zdansky P, Vladimir Semecky (2006) Atorvastatin has distinct effects on endothelial markers in different mouse models of atherosclerosis. J Pharm Pharmaceut Sci, 9(2):222-230.
84. Piedrahita J A, Zhang S H, Hagaman J R, Oliver P M, Maeda N. (1992) Generation of mice carrying a mutant apolipoprotein E gene inactivated by gene targeting in embryonic stem cells. Proc Natl Acad Sci USA,
85. Schwartz, G. G., Olsson, A. G., Ezekowitz, M. D., Ganz, P., Oliver, M. F., Waters, D., Zeiher, A., Chaitman, P. R., Leslie, S., Stem, T. (2001) Effects of Atorvastatin on Early Recurrent Ischemic Events in Acute Coronary Syndromes. JAMA, 285:1711-1718
86. Johnston, T. P., Baker, J. C., Jamal, A. S., Hall, D., Emerson, E. E., Palmer, W. K. (1999) Potential downregulation of HMG-CoA reductase after prolonged administration of P-407 in C57BL/6 mice. J Cardovasc Pharmacol, 34: 831-42.
87. Johnston, T. P., Baker, J. C., Hall, D., Jamal, A. S., Palmer, W. K., Emerson, E. E. (2000) Regression of poloxamer 407-induced atherosclerotic lesions in C57BL/6 mice using atorvastatin. Atherosclerosis. 149: 303-13.
88. Peter, L., Ridker, P. M., Maseri, A. Inflammation and Atherosclerosis. Circulation. 105, 1135 (2002)
89. Uversky, V. N., Li, J, and A. L. Fink (2001) Metal-triggered structural transformations, aggregation, and fibrillation of human alpha-synuclein. A possible molecular NK between Parkinson's disease and heavy metal exposure. J Biol. Chem. 276, 44284-96.
90. Purdey, M (2004) Elevated levels of ferromagnetic metals in food chains supporting the Guam cluster of neurodegeneration: do metal nucleated crystal contaminants evoke magnetic fields that initiate the progressive pathogenesis of neurodegeneration?. Med. Hypothesis. 63, 793-809.
91. Selkoe, D. J (2003) Folding proteins in fatal ways. Nature 426, 900-904.
92. Garzon-Rodriguez, W., Yatsimirsky, A. K, and C. G. Glabe (1999) Binding of Zn(II), Cu(II), and Fe(II) ions to Alzheimer's Abeta peptide studied by fluorescence. Bioorg Med Chem. Lett. 9, 2243-8.
93. Smith, M. A., Harris, P. L., Sayre, L. M, and G. Perry (1997) Iron accumulation in Alzheimer disease is a source of redox-generated free radicals. Proc Natl Acad Sci USA 94, 9866-9868.
94. Lovell, M. A., Robertson, J. D., Teesdale, W. J., Campbell, J. L, and W. R. Markesbery (1998) Copper, iron and zinc in Alzheimer's disease senile plaques. J Neurol Sci. 158, 47-52.
95. Jennette, K. W (1981) The role of metals in carcinogenesis: biochemistry and metabolism. Environ Health Prospect. 40, 233-52.
96. Huang, X., Atwood, C. S., Moir, R. D., Hartshorn, M. A., Tanzi, R. E, and A. I. Bush (2004) Trace metal contamination initiates the apparent auto-aggregation, amyloidosis, and oligomerization of Alzheimer's abeta peptides. J Biol Inorg Chem. 9, 954-60.
97. Maynard, C. J., Bush, A. I., Masters, C. L., Cappai, R, and Q. X. Li (2005) Metals and amyloid-beta in Alzheimer's disease. Int J Exp Pathol. 86, 147-59.
98. Gaggelli, E., Bemardi, F., Molteni, E., Pogni, R., Valensin, D., Ramelli, M., Luczkowski, M, and H. Kozlowski (2005) Interaction of human prion PrP (106-126) sequence with copper(II), manganese(II) and zinc(II): NMR and EPR studies. J Am Chem. Soc. 127, 996-1006.
99. Roy, C. N, and N. C. Andrews (2001) Recent advances in disorders of iron metabolism: mutations, mechanisms and modifiers. Human Mol. Genetics. 10, 2181-2186.
100. Richardson, D. R (2004) Novel chelators for central nervous system disorders that involve alterations in the metabolism of iron and other metal ions. Ann. N.Y. Acad. Sci. 1012, 326-341.
101. Stadler, N., Lindner, R. A, and M. J. Davies (2004) Direct detection and quantification of transition metal ions in human atherosclerosis plaques: Evidence for the presence of elevated levels of iron and copper. Arterioscler Thromb Vasc Biol. 24, 949-54.
102. Ong, W. Y and B. Halliwell (2004) Iron, atherosclerosis, and neurodegeneration: a key role for cholesterol in promoting iron-dependent oxidative damage?. Ann N Y Acad Sci. 1012, 51-64.
103. Ong, W. Y and A. A. Farooqui (2005) Iron, neuroinflammation, and Alzheimer's disease. JAlzheimers Dis. 8, 183-200.
104. Mandel, S., Maor, G, and M. B. Youdim (2004) Iron and alpha-synuclein in the substantia nigra of MPTP treated mice: effect of neuroprotective drugs R-apomorphine and green tea polyphenol(−)-epigallocatechin-3-gailate. J Mol. Neurosci. 24, 401-16.
105. Tannir, E. L., Tayara, N., Delatour, B., Le Cudennec, C., Guegan, M., Volk, A and M. Dhenain (2005). Age-related evolution of amyloid burden, iron load, and MR relaxation times in a transgenic mouse model of Alzheimer's disease. Neurobiol Dis.
106. Burgermeister, P., Calhoun, M. E., Winkler, D. T, and M. Jucker (2000) Mechanisms of cerebrovascular amyloid deposition. Lessons from mouse models. Ann N Y Acad. Sci. 903, 307-16.
107. Walker, L. C, and R. A. Durham (1999) Cerebrovascular amyloidosis: experimental analysis in vitro and in vivo. Histol Histopathol. 14, 827-37.
108. de la Torre, J. C (2004) Alzheimer's disease is a vasocognopathy: a new term to describe its nature. Neurol Res. 26, 517-24.
109. Miao, J., Xu, F., Davis, J., Otte-Holler, I., Verbeek, M. M, and W. E. Van Nostrand (2005) Cerebral micro vascular amyloid (beta) protein deposition induces vascular degeneration and neuroinflammation in transgenic mice expression human vasculotropic mutant amyloid (beta) precursor protein. Am J. Pathol. 167, 505-15.
110. Kimchi, E. Y., Kajdasz, S., Baeskai, B. J, and B. T. Hyman (2001) Analysis of cerebral amyloid angiopathy in a transgenic mouse model of Alzheimer's disease using in vivo multiphoton microscopy. J Neuropathol Exp Neurol. 60, 274-9.
111. Beckmann, N., Schuler, A., Mueggler, T., Meyer, E. P., Wiederhold, K. H., Staufenbiel, M, and T. Krucker (2003) Age-dependent cerebrovascular abnormalities and blood flow disturbances in APP23 mice modeling Alzheimer's disease. J. Neurosci. 23, 8453-9.
112. Haas, C., Aludo, J., Cazorla, P., Bullido, M. J., de Miguel, C., Vazquez, J, and F. Valdivieso (1997) Proteolysis of Alzheimer's disease beta-amyloid precursor protein by factor Xa. Biochim Biophys Acta. 1343, 85-94.
113. Grammas, P., Samany, P. G and L. Thirumangalakudi (2006) Thrombin and inflammatory proteins are elevated in Alzheimer's disease micro vessels: Implications for disease pathogenesis. J Alzheimers Dis. 9, 51-58.
114. Purandare, N., Burns, A., Daly, K. J., Haricre, J., Morris, J., Macfarlane, G and C. McCollum (2006) Cerebral emboli as potential cause of Alzheimer's disease and vascular dementia: case-control study. B M J. 332, 1119-1124.

115. Kalaria, R. N (1999) The blood-brain barrier and cerebrovascular pathology in Alzheimer's disease. Ann N Y Acad. Sci. 893, 113-25.
116. Beeri, M. S., Rapp, M., Silverman, J. M., Schmeidler, J., Grossman, H. T., Fallon, J. T., Purohit, D. P., Perl, D. P., Siddiqui, A., Lesser, G., Rosendorff, C and V. Haroutunian (2006) Coronary artery disease is associated with Alzheimer disease neuropathology in APOE4 carriers. *Neurology.* 66, 1399-404.
117. Bose, M., Gestwicki, J. E., Devasthali, V., Crabtree, G. R, and I. A. Graef (2005) "Nature-inspired" drug-protein complexes as inhibitors of Abeta aggregation. Biochem Soc Trans. 33, 543-7.
118. Hersh, L. B (2003) Peptidases, proteases and amyloid beta-peptide catabolism. Curr Pharm Des. 9, 449-54.
119. Higuchi, M., Iwata, N, and T. C. Saido (2005) Understanding molecular mechanisms of proteolysis in Alzheimer's disease: Progress toward therapeutic interventions. Biochim Biophys Acta. 175, 60-67.
120. Fuster, L. O., Galindo, M. F., Cena, V, and J. Jordan (2004) The serine proteases and their function in neuronal death process. Rev Neurol. 38, 449-57.
121. Molinari, F., Meskanaite, V., Munnich, A., Sonderegger, P, and L. Colleaux (2003) Extracellular proteases and their inhibitors in genetic diseases of the central nervous system. Human Mol. Gen. 12, 195-200.
122. Angles-Cano, E (1994) Overview on fibrinolysis: Plasminogen activation pathways on fibrin and cell surfaces. Chem Phys Lipids. 68, 353-62.
123. Syrovets, T, and T. Simmet (2004) Novel aspects and new roles for the serine protease plasmin. Cell Mol Life Sci. 8, 873-85.
124. Nicholl, S. M., Roztocil, E and M. G. Davies (2006) Plasminogen activator system and vascular disease. *Curr Vasc Pharmacol.* 4, 101-116.
125. Miao, J., Vitek, M. P., Xu, F., Previti, M. L., Davis, J and W. E. Van Nostrand (2005) Reducing cerebral micro vascular amyloid-beta protein deposition diminishes regional neuroinflammation in vasculotrophic mutant amyloid precursor protein transgenic mice. *J. Neurosci.* 25, 6271-77.
126. Melchor, J. P., Pawlak, R, and S. Strickland (2003) The tissue plasminogen activator-plasminogen proteolytic cascade accelerates amyloid-beta (Abeta) degradation and inhibits abeta-induced neurodegeneration. J. Neurosci. 23, 8867-71.
127. Sim, R. B, and S. A. Tsiftsoglou (2004) Proteases of complement system. Biochem Soc Trans. 32, 21-7.
128. Casserly, I, and E. Topol (2004) Convergence of atherosclerosis and Alzheimer's disease: inflammation, cholesterol, and misfolded proteins. Lancet. 363, 1139-46.
129. McGeer, P. L., Klegeris, A., Walker, D. G., Yasuhara, 0, and E. G. McGeer (1994) Pathological proteins in senile plaques. Tohoku J Exp Med. 174, 269-77.
130. Eikelenboom, P., Rozemuller, J. M., Kraal, G., Stam, F. C., McBride, P. A., Bruce, M. E, and H. Fraser (1991) Cerebral amyloid plaques in Alzheimer's disease but not in scrapie-affected mice are closely associated with a local inflammatory process. Virchows Arch B Cell Pathol Inci Mol. Pathol. 60, 329-36.
131. Sarkar, D, and P. B. Fisher (2005) Molecular mechanisms of aging-associated inflammation. Cancer Lett. In press.
132. McGeer, P. L, and E. G. McGeer (2004) Inflammation and degenerative disease of aging. Ann N Y Acad. Sci. 1033, 104-16.
133. Tanskanen, M., Lindsberg, P. J., Tienari, P. J., Polyikoski, T., Sulkava, R., Verkkoniemi, A., Rastas, S., Paetau, A, and S, Kiuru-Enari (2005) Cerebral amyloid angiopathy in a 95+ cohort: complement activation and apolipoprotein E (ApoE) genotype. Neuropathol Appl Neurobiol. 31, 589-99.
134. Finehout, E. J., Franck, Z, and K. H, Lee (2005) Complement protein isoforms in CSF as possible biomarkers for neurodegenerative disease. Dis Markers. 21, 93-101.
135. Bonifati, D. M and U. Kishore (2006) Role of complement and neurodegeneration. Mol. Immunol.
136. Gandy, S (2005) The role of cerebral amyloid β accumulation in common forms of Alzheimer's disease. J Clin Invest. 115, 1121-1129.
137. Barrow, C. J, and M. G. Zagorski (1995) Solution structures of β-peptide and its constituent fragments: Relation to amyloid deposition. Science 253, 173-182.
138. Lansbury, P. T (1995) In pursuit of the molecular structure of amyloid plaque: New technology provides unexpected and critical information. Biochemistry 31, 6865-6870.
139. Esler, W. P., Stimson, E. R., Ghilardi, J. R., Vinders, H. V., Lee, J. P., Mantyh, P. W, and J. E. Maggio (1996) In vitro growth of Alzheimer's disease β-amyloid plaques displays first-order kinetics. Biochemistry 23, 749-757.
140. Atwood, C. S., Moir, R. D., Huang, X., Scarpa, R. C., Bacarra, N. M., Romano, D. M., Hartshorn, M. A., Tanzi, R. E, and A. I. Bush (1998) Dramatic aggregation of Alzheimer AB by Cu (II) is induced by conditions representing physiological acidosis. J Biol. Chem. 273, 12817-12826.
141. Huang, X., Atwood, C. S., Hartshorn, M. A., Multhaup, G., Goldstein, L. E., Scarpa, R. C., Cuajungco, M. P., Gray, D. N., Lim, J., Moir, R. D., Tanzi, R. E, and A. I. Bush (1999) The Aβ peptide of Alzheimer's disease directly produces hydrogen peroxide through metal ion reduction. Biochemistry. 38, 7609-7616.
142. Kayed, R., Head, E., Thompson, J. L., McIntire, T. M., Milton, S. C., Cotman, C. W, and C. G. Glabe (2003) Common structure of soluble amyloid oligomers implies common mechanism of pathogenesis. Science 300, 486-489.
143. Trojanowski, J. Q and V. M. Lee (2000) 'Fatal attractions' of proteins. A comprehensive hypothetical mechanism underlying Alzheimer's disease and other neurodegenerative disorders. Ann N Y Acad Sci. 924, 62-7.
144. Dobson, C. M (2003) Protein folding and misfolding. Nature 426, 884-890.
145. Brown, R. C., Lockwood, A. H and B. R. Sonawane (2005) Neurodegenerative diseases: an overview of environmental risk factors. *Environ Health Perspect.* 113, 1250-56.
146. White, A. R., Barnham, K. J and A. I. Bush (2006) Metal homeostasis in Alzheimer's disease. *Expert Rev Neurother.* 6, 711-22.
147. Liu, G., Huang, W., Moir, R. D., Vanderburg, C. R., Lai, B., Peng, Z., Tanzi, R. E., Roger, J. T and X. Huang (2006). Metal exposure and Alzheimer's pathogenesis. *J Struct Biol.*
148. Gaeta, A and R. C. Hider (2005) The crucial role of metal ions in neurodegeneration: the basis for a promising therapeutic strategy. Br J. Pharmacol.
149. Allen, L. T., Tosetto, M., Miller, I. S., O'Connor, D. P., Penny, S. C., Lynch, I., Keen, A. K., Pennington, S. R., Dawson, K. A and W. M. Gallagher (2006) Surface-induced changes in protein adsorption and implications for cellular phenotypic responses to surface interaction. *Biomaterials.* 27, 3096-3108.

150. Engel, M. F., Visser, A. J and C. P. Van Mierlo (2004) Conformation and orientation of a protein folding intermediate trapped by adsorption. *Proc Natl Acad Sci USA*. 101, 11316-11321.

151. Lindersson, E., Beedholm, R., Hojrup, P., Moos, T., Gai, W., Hendil, K. B, and P. H. Jensen (2004) Proteasomal inhibition by α-synuclein filaments and oligomers. J Biol. Chem. 279, 12924-12934.

152. Fenton, H., Finch, P. W., Rubin, J. S., Rosenberg, J. M., Taylor, W. G., Kuo-Leblane, V., Rodiguez-Wolf, M., Baird, A., Schipper, H. M, and E. G. Stopa (1998) Hepatocyte growth factor (HGF/SF) in Alzheimer's disease. Brain Res. 779, 262-70.

153. Strohmeyer, R., Shen, Y, and J. Rogers (2000) Detection of complement alternative pathway mRNA and proteins in the Alzheimer's disease brain. Brain Res Mol Brain Res. 81, 7-18.

154. Hino, H., Akiyama, H., Iseki, E., Kato, M., Kondo, H., Ikeda, K, and K. Kosaka (2001) Immunohistochemical localization of plasminogen activator inhibitor-1 in rat and human brain tissues. Neurosci Lett. 297, 105-08.

155. Bucciantini, M., Giannoni, E., Chiti, F., Boroni, F., Formigli, L., Zurdo, J., Taddei, N., Ramponi, G., Dobson, C. M, and M. Stefani (2002) Inherent cytotoxicity of aggregates implies a common origin for protein misfolding diseases. Nature 416, 507-511.

156. O'Nuallain, B, and R. Wetzel (2002) Conformational Abs recognizing a generic amyloid fibril epitope. Proc Natl Acad Sci USA 99, 1485-1490.

157. Nelson, R., Sawaya, M. R., Balbirnie, M., Madsen, A. O., Reikel, C., Grothe, R, and D. Eisenberg (2005) Structure of the cross-beta spine of amyloid-like fibrils. Nature 435, 773-778.

158. Castilla, J., Saa, P., Hetz, C, and C. Soto (2005) In vitro generation of infectious scrapie prions. Cell 121, 195-206.

159. Murphy, R. M (2002) Peptide aggregation in neurodegenerative disease. Annu Rev Biomed Eng. 4, 155-174.

160. Melchor, J. P., Pawlak, R, and S. Strickland (2003) The tissue plasminogen activator-plasminogen proteolytic cascade accelerates amyloid-beta (Abeta) degradation and inhibits Abeta-induced neurodegeneration. J. Neurosci. 32, 8867-8871 (2003).

161. Van Nostrand, W. E, and M. Porter (1999) Plasmin cleavage of the amyloid beta protein: alteration of secondary structure and stimulation of tissue plasminogen activator activity. Biochemistry. 38, 11570-6.

162. Kranenburg, O., Gent, Y. Y., Romijin, E. P., Voest, E. E., Heck, A. J, and M. F. Gebbink (2005) Amyloid-beta-stimulated plasminogen activation by tissue-type plasminogen activator results in processing of neuroendocrine factors. Neuroscience. 131, 877-886.

163. Ke, S. H., Coombs, G. S., Tachias, K., Corey, D. R, and E. L. Madison (1997) Optimal subsite occupancy and design of a selective inhibitor of urokinase. J Biol. Chem. 272, 20456-20462.

164. Silverman, G. A., Bird, P. I., Carrell, R. W., Church, F. C., Coughlin, P. B., Gettins, P. G., Irving, J. A., Lomas, D. A., Luke, C. J., Moyer, R. W., Pemberton, P. A., Remold-O'Donnel, E., Salvesen, G. S., Travis, J, and J. C. Whisstock (2001) The serpins are an expanding superfamily of structurally similar but functionally diverse proteins. J Biol Chem 276, 33293-33296.

165. Elliott, P. R., Lomas, D. A., Carrell, R. W, and R. L. Abrahams (1996) Inhibitory conformation of the reactive loop of alpha 1-antitrypsin. Nat Sturct Biol. 8, 676-681.

166. Reilly, C. F, and J. E. Hutzelmann (1992) Plasminogen activator inhibitor-1 binds to fibrin and inhibits tissue-type plasminogen activator-mediated fibrin dissolution. J Biol. Chem. 267, 17128-17135.

167. Silverstein, R. L., Friedlender, R. J., Nicholas, R. L, and R. L. Nachman (1988) Binding of Lys-Plasminogen to Monocytes/Macrophages. J Clin Invest. 82, 1948-1955.

168. Kuusela, P, and O, Saksela (1990) Binding and activation of plasminogen at the surface of *Staphylococcus aureus*. Increase in affinity after conversion to the Lys form of the ligand. Eur J. Biochem. 193, 759-65.

169. Angles-Cano, E., Hervio, L., Rouy, D., Fournier, C., Chapman, J. M., Laplaud, M and M. L. Koschinsky (1994) Effects of lipoprotein (a) on the binding of plasminogen to fibrin and its activation by fibrin-bound tissue-type plasminogen activator. Chem Phys Lipids. 67-68, 369-80.

170. Lynch, I., Dawson, K. A and S. Linse (2006) Detecting cryptic epitopes created by Nanoparticles. Sci STKE. 327, 14.

171. Quintana, C., Bellefqih, S., Laval, J. Y., Guerquin-Kern, J. L., Wu, T. D., Avila, J., Ferrer, I., Arranz, R and C. Patino (2006) Study of the localization of iron, ferritin, and hemosderin in the Alzheimer's disease hippocampus by analytical microscopy at the sub cellular level. *J Struct Biol*. 153, 42-54.

172. Connor, J. R., Menzies, S. L., Martin, S. M, and E. J. Mufson (1992) A histochemical study of iron, transferring, and ferritin in Alzheimer's diseased brain. J Neurosci Res. 31, 75-83.

173. Connar, J. R., Milward, E. A., Moalem, S., Sampietro, M., Boyer, P., Percy, M. E., Vergani, C., Scott, R. J and M. Chorney (2001) Is hemochromatosis a risk factor for Alzheimer's disease?. *J Alzheimers Dis*. 3, 471-477.

174. Le Vine, S. M (1997) Iron deposits in multiple sclerosis and Alzheimer's disease brains. Brain Res. 760, 298-303.

175. Falangola, M. F., Lee, S. P., Nixon, R. A., Duff, K and J. A. Helpern (2005) Histological co-localization of iron in Abeta plaques of PS/APP transgenic mice. *Neurochem Res*. 30, 201-205.

176. Collingwood, J. F., Mikhaylova, A., Davidson, M., Batich, C., Streit, W. J., Terry, J and J. Dobson (2005) In situ characterization and mapping of iron compounds in Alzheimer's disease tissue. *J Alzheimers Dis*. 7, 267-72.

177. Liao, L., Cheng, D., Wang, J., Duong, D. M., Losik, T. G., Gearing, M., Rees, H. D., Lah, J. J., Levey, A. I, and J. Peng (2004) Proteomic characterization of postmortem amyloid plaques isolated by laser capture micro dissection. J Biol. Chem. 279, 37061-37068.

178. McAllister, C., Karymov, M., Kawano, Y., Lushnikov, A. Y., Mikheikin, A., Uversky, V. N and Y. L. Lyubchenko (2005) Protein interactions and misfolding analyzed by AFM force spectroscopy. *J Mol. Biol*. 354, 1028-1042.

179. Lockhart, A., Ye, L., Judd, D. B., Merrit, A. T., Lowe, P. N., Morgenstern, J. L., Hong, G., Gee, A. D and J. Brown (2005) Evidence for the presence of three distinct binding sites for the thioflavin T class of Alzheimer's disease PET imaging agents on the beta-amyloid peptides fibrils. *J Biol. Chem*. 280, 7677-84.

180. Meredith, S. C (2006) Protein denaturation and aggregation: cellular responses to denatured and aggregated proteins. *Ann N Y Acad Sci*. 1066, 181-221.

What is claimed is:

1. A multi-subunit complex formed by a process comprising the steps of:

(a) converting a mixture of soluble molecules into an insoluble aggregate to form a template, wherein the mixture of soluble molecules consists essentially of (a1)

cholesterol with calcium; or (a2) phospholipid with calcium; wherein the aggregate binds to themselves and or to soluble molecules to form a template or plaque initiation complex;

(b) adding a cell extract or substantially purified protein, lipid or carbohydrate to the template or plaque initiation complex, wherein the substantially purified one protein, lipid or carbohydrate binds to the template or plaque initiation complex to form a template complex;

(c) removing unbound substantially purified protein, lipid or carbohydrate from the template complex;

(d) repeating the addition of the substantially purified protein or lipid or carbohydrate to the template complex, wherein the additional substantially purified protein, lipid or carbohydrate binds to the template complex to form a multi-subunit complex; and (e) obtaining a purified multi-subunit complex after cyclic plaque assembly (CPA) by removing unbound protein, lipid or carbohydrate from the multi-subunit complex of step (d).

2. The multi-subunit complex of claim 1, wherein the adding of step (b) comprises adding at least one substantially purified protein that is selected from the group consisting of human blood coagulation factor prothrombin, antithrombin III, factor H, a complement factor, protein S, plasminogen activator inhibitor I(PAI-1), plasminogen (PLG), human fibrinogen (FBN), serum albumin, blood coagulation factor II (FII), factor IX (FIX), and recombinant human hepatocyte growth factor.

3. The multi-subunit complex of claim 1, wherein the substantially purified protein of step (b) is selected from the group consisting of alpha-synuclein, amyloid β peptide, atrial natiuretic factor, abeta 40-42, serum amyloid A protein, β micro globulin, iron-beta 40, iron-beta 42 and transthyretin.

4. The multi-subunit complex of claim 1, wherein the multi-subunit complex formed is an atherosclerotic plaque, atherothrombosis plaque and Alzheimer's disease plaque.

5. The multi-subunit complex of claim 1, further comprises a physiologically acceptable carrier to form a pharmaceutical composition.

6. The multi-subunit complex of claim 1, wherein in step (b) the lipid is cholesterol.

7. The multi-subunit complex of claim 1, wherein the multi-subunit complex is formed after repeating steps (d) and (e) at least two additional times.

8. The multi-subunit complex of claim 1, wherein the multi-subunit complex is formed after repeating steps (d) and (e) at least ten additional times.

* * * * *